(12) United States Patent
Agulnick et al.

(10) Patent No.: US 10,376,545 B2
(45) Date of Patent: *Aug. 13, 2019

(54) METHODS FOR PRODUCING HORMONE SECRETING CELLS IN A SUBJECT

(71) Applicant: ViaCyte, Inc., San Diego, CA (US)

(72) Inventors: Alan D. Agulnick, San Diego, CA (US); Kevin Allen D'Amour, San Diego, CA (US)

(73) Assignee: ViaCyte, Inc., San Diego, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 15/478,094

(22) Filed: Apr. 3, 2017

(65) Prior Publication Data

US 2017/0202885 A1    Jul. 20, 2017

Related U.S. Application Data

(63) Continuation of application No. 14/455,059, filed on Aug. 8, 2014, now Pat. No. 9,650,610, which is a continuation of application No. 14/106,330, filed on Dec. 13, 2013, now Pat. No. 8,859,286.

(60) Provisional application No. 61/781,005, filed on Mar. 14, 2013.

(51) Int. Cl.
| | |
|---|---|
| *A61K 35/39* | (2015.01) |
| *C12N 5/071* | (2010.01) |
| *A61K 35/545* | (2015.01) |
| *G01N 33/68* | (2006.01) |

(52) U.S. Cl.
CPC ............ *A61K 35/39* (2013.01); *A61K 35/545* (2013.01); *C12N 5/0676* (2013.01); *C12N 5/0678* (2013.01); *C12N 2500/25* (2013.01); *C12N 2501/115* (2013.01); *C12N 2501/117* (2013.01); *C12N 2501/119* (2013.01); *C12N 2501/15* (2013.01); *C12N 2501/155* (2013.01); *C12N 2501/16* (2013.01); *C12N 2501/195* (2013.01); *C12N 2501/385* (2013.01); *C12N 2501/415* (2013.01); *C12N 2501/727* (2013.01); *C12N 2501/998* (2013.01); *C12N 2501/999* (2013.01); *C12N 2506/02* (2013.01); *C12N 2506/45* (2013.01); *C12N 2533/90* (2013.01)

(58) Field of Classification Search
CPC ..... A61K 35/39; C12N 5/0676; C12N 5/6078
See application file for complete search history.

(56) References Cited

U.S. PATENT DOCUMENTS

| | | | |
|---|---|---|---|
| 5,453,357 A | 9/1995 | Hogan | |
| 5,478,838 A | 12/1995 | Arita et al. | |
| 5,529,914 A | 6/1996 | Hubbell et al. | |
| 5,670,372 A | 9/1997 | Hogan | |
| 5,690,926 A | 11/1997 | Hogan | |
| 5,801,033 A | 9/1998 | Hubbell et al. | |
| 5,843,780 A | 12/1998 | Thomson | |
| 6,075,007 A | 6/2000 | Economides et al. | |
| 6,200,806 B1 | 3/2001 | Thomson | |
| 6,251,671 B1 | 6/2001 | Hogan et al. | |
| 6,258,870 B1 | 7/2001 | Hubbell et al. | |
| 6,800,480 B1 | 10/2004 | Bodnar et al. | |
| 6,911,227 B2 | 6/2005 | Hubbell et al. | |
| 7,005,252 B1 | 2/2006 | Thomson et al. | |
| 7,427,415 B2 | 9/2008 | Scharp et al. | |
| 7,432,104 B2 | 10/2008 | Mitalipova et al. | |
| 7,510,876 B2 | 3/2009 | D'Amour et al. | |
| 7,534,608 B2 | 5/2009 | Martinson et al. | |
| 7,541,185 B2 | 6/2009 | D'Amour et al. | |
| 7,695,963 B2 | 4/2010 | Agulnick et al. | |
| 7,695,965 B2 | 4/2010 | Martinson et al. | |
| 2002/0072117 A1 | 6/2002 | Xu et al. | |
| 2003/0087919 A1 | 5/2003 | Nagarathnam et al. | |
| 2003/0125344 A1 | 7/2003 | Nagarathnam et al. | |
| 2003/0175956 A1 | 9/2003 | Bodnar et al. | |
| 2004/0002507 A1 | 1/2004 | Nagarathnam et al. | |
| 2004/0002508 A1 | 1/2004 | Nagarathnam et al. | |
| 2004/0014755 A1 | 1/2004 | Nagarathnam et al. | |
| 2005/0192304 A1 | 9/2005 | Nagarathnam et al. | |
| 2005/0209261 A1 | 9/2005 | Nagarathnam et al. | |
| 2005/0266554 A1 | 12/2005 | D'Amour et al. | |
| 2007/0122905 A1 | 5/2007 | D'Amour et al. | |
| 2007/0259421 A1 | 11/2007 | D'Amour et al. | |
| 2008/0233610 A1 | 9/2008 | Thomson et al. | |
| 2009/0047263 A1 | 2/2009 | Yamanaka | |
| 2009/0104696 A1 | 4/2009 | Robins et al. | |

(Continued)

FOREIGN PATENT DOCUMENTS

| | | |
|---|---|---|
| WO | WO02076976 | 10/2002 |
| WO | WO03059913 | 7/2003 |

(Continued)

OTHER PUBLICATIONS

Agarwal et al., "Efficient differentiation of functional hepatocytes from human embryonic stemcells", Stem Cells, (2008) 26:1117-1127.

(Continued)

*Primary Examiner* — Allison M Fox
(74) *Attorney, Agent, or Firm* — Klarquist Sparkman, LLP

(57) ABSTRACT

A human immature endocrine cell population and methods for making an immature endocrine cell population are provided. Specifically, immature beta cells and methods for production of immature beta cells are described. Immature beta cells co-express INS and NKX6.1 and are uni-potent and thereby develop into mature beta cells when implanted in vivo. The mature beta cells in vivo are capable of producing insulin in response to glucose stimulation.

18 Claims, 82 Drawing Sheets

(56) References Cited

U.S. PATENT DOCUMENTS

| | | |
|---|---|---|
| 2009/0263896 A1 | 10/2009 | Kelly et al. |
| 2009/0298178 A1 | 12/2009 | D'Amour |
| 2010/0003757 A1 | 1/2010 | Mack et al. |
| 2010/0112691 A1 | 5/2010 | Green et al. |
| 2010/0124564 A1 | 5/2010 | Martinson et al. |
| 2011/0014702 A1 | 1/2011 | Xu |
| 2011/0151560 A1 | 6/2011 | Xu |
| 2011/0151561 A1 | 6/2011 | Davis et al. |
| 2012/0141436 A1 | 6/2012 | Bonner-Weir |
| 2012/0270890 A1 | 10/2012 | Chung et al. |
| 2013/0330823 A1 | 12/2013 | Rezania |

FOREIGN PATENT DOCUMENTS

| | | |
|---|---|---|
| WO | WO03062225 | 7/2003 |
| WO | WO03062227 | 7/2003 |
| WO | WO03051753 | 6/2005 |
| WO | WO2005080598 | 9/2005 |
| WO | WO2007101130 | 9/2007 |
| WO | 2007143193 A1 | 12/2007 |
| WO | WO2008011882 | 1/2008 |
| WO | WO2008013664 | 1/2008 |
| WO | WO2009052505 | 4/2009 |
| WO | WO2009117439 | 9/2009 |
| WO | WO2009154606 | 12/2009 |
| WO | 2010057039 A2 | 5/2010 |
| WO | WO2010053472 | 5/2010 |
| WO | 2010124142 A2 | 10/2010 |

OTHER PUBLICATIONS

Application as Filed in U.S. Appl. No. 11/993,399, filed Dec. 20, 2007.
Application as Filed in U.S. Appl. No. 12/839,041, filed Jul. 19, 2010.
Attisano et al., "Activation of signalling by the activin receptor complex", Mol. Cell Biol., (1996) 16(3):1066-1073.
Aye et al., "Identification of Markers for Newly Formed Beta-Cells in the Perinatal Period: A Time of Recognized Beta-Cell Immaturity." Journal of Histochemistry & Cytochemistry. 2010, vol. 58, No. 4, pp. 369-376.
Bonner Wier et al Proc Nat Acad Sci 97: 7999-8004, 2000.
Borowiak et al., "Small molecules efficiently direct endodermal differentiation of mouse and human embryonic stem cells", Cell Stem Cell, (2009) 4:348-358.
Bruin et al., "Characterization of polyhormonal insulin-producing cells derived in vitro from human embryonic stem cells," Stem Cell Research 12: 194-208 (2014).
Bruin et al., Maturation and function of human embryonic stem cell-derived pancreatic progenitors in macroencapsulation devices following transplant into mice,: Diabetalogia 56: 1987-1998 (2013).
Brunner et al., "Distinct DNA methylation patterns characterize differentiated human embryonic stem cells and developing human fetal liver", Genome Res., (2009) 19:1044-1056.
Chang et al., "Rho Kinases Regulate the Renewal and Neural Differentiation of Embryonic Stem Cells in Cell Plating Density-Dependent Manner" PLoS One (2010) 5(2) (e9187):1-9.
Chang et al., Genetic analysis of the mammalian transforming growth factor-beta superfamily, Endocrine Review, (2002) 23(6):787-823.
Chen et al., "Improved production and purification of minicircle DNA vector free of plasmid bacterial sequences and capable of persistent transgene expression in vivo", Hum. Gene Ther., (2005) 16:126-131.
Chen et al., "Minicircle DNA vectors devoid of bacterial DNA result in persistent and high-level transgene expression in vivo", Mol. Ther., (2003) 8:495-500.
D'Amour et al. "Production of Pancreatic Hormone-Expressiing Endocrine Cells From Human Embryonic Stem Cells" (Nov. 1, 2006) Nature Biotechnology 24, 1392-1401.
D'Amour et al., "Efficient differentiation of human embryonic stem cells to definitive endoderm." Nature Biotechnology, Dec. 2005, vol. 23, No. 12, pp. 1534-1541.
Derynck et al., Cell, "Smads: transcriptional activators of TGF-beta responses", (1998) 95(6):737-740.
Dimos et al., "Induced pluripotent stem cells generated from patients with ALS can be differentiated into motor neurons", Science, (2008) 321:1218-21.
Ebert et al., "Induced pluripotent stem cells from a spinal muscular atrophy patient", Nature, (2009) 457:277-80.
Foster et al., "Induction of KLF4 in basal keratinocytes blocks the proliferation-differentiation switch and initiates squamous epithelial dysplasia", Oncogene, (2005) 24:1491-1500.
Guilluy et al., "Rho protein crosstalk: another social network?" Trends in Cell Biology, (2011) 21(12): 718-726.
Hammar, et al., Role of the Rho-Rock (Rho-Associated Kinase) signaling pathway in the regulation of pancreatic cell function., Endocrinology, 2009, vol. 150, No. 5, 2072-2079.
Higuchi et al., "In vitro models of pancreatic differentiation using embryonic stem or induced pluripotent stem cells," Congenital Anomalies 51(1): 21-25 (Feb. 21, 2011).
Hochedlinger et al., "Ectopic expression of Oct-4 blocks progenitor-cell differentiation and causes dysplasia in epithelial tissues", Cell, (2005) 121:465-477.
Huangfu, et al., "Induction of Pluripotent Stem Cells from Primary Human Fibroblasts with only Oct4 and Sox2," Nature Biotechnology, 2008 vol. 26, No. 11, 1269-1275.
International Preliminary Report on Patentability from parent PCT Application No. PCT/US2014/026529, 10 pages (dated Sep. 15, 2015).
International Search Report and Written Opinion dated Jul. 24, 2014 for International Application No. PCT/US2014/026529, 16 pages.
Jia et al., "A nonviral minicircle vector for deriving human iPS cells", Nature Methods, (2010) 7(3):197-199.
Kaji et al., "Virus-free induction of pluripotency and subsequent excision of reprogramming factors", Nature, (2009) 458 (7239):771-5.
Kelly et al., "Cell-surface markers for the isolation of pancreatic cell types derived from human embryonic stem cells," Nature Biotechnology 29(8): 750-756 (Jul. 31, 2011).
Kim et al., "Generation of human induced pluripotent stem cells by direct delivery of reprogramming proteins", Cell Stem Cell, (2009) 4(6):472-6.
Kroon et al. Pancreatic endoderm derived from human embryonic stem cells generates glucose-responsive insulin-secreting cells in vivo. Nat Biotechnol. 26(4):443-52, 2008.
Maehr et al., "Generation of pluripotent stem cells from patients with type 1 diabetes", Proc. Natl. Acad. Sci. USA, (2009) 106(37):15768-73.
Massaque, "How cells read TGF-beta signals", Mol. Cell. Biol., (2000) 1(3):169-78.
Mathews, "Activin receptors and cellular signaling by the receptor serine kinase family", Endocr. Rev., (1994) 15 (3):310-325.
McLean et al., "Activin a efficiently specifies definitive endoderm from human embryonic stem cells only when phosphatidylinositol 3-kinase signaling is suppressed", Stem Cells, (2007) 25(1):29-38.
Nostro et al., "Stage-specific signaling through TGF.beta. family members and WNT regulates patterning and pancreatic specification of human pluripotent stem cells," Development and Stem Cells 138(5): 861-871 (Mar. 1, 2011).
Okita et al., "Generation of mouse induced pluripotent stem cells without viral vectors", Science, (2008) 322 (5903):949-53.
Park et al., "Disease-specific induced pluripotent stem cells", Cell, (2008) 134(5):877-86.
Park et al., "Reprogramming of human somatic cells to pluripotency with defined factors", Nature, (2008) 45 (7175):141-6.
Rezania et al., "Maturation of human embryonic stem cell-derived pancreatic progenitors into functional islets capable of treating pre-existing diabetes in mice," Diabetes 61: 2016-2029 (2012).
Segev et al., "Differentiation of human embryonic stem cells into insulin-producing clusters," Stem Cells (2004) 22:265-274.

(56) References Cited

OTHER PUBLICATIONS

Soldner et al., "Parkinson's disease patient-derived induced pluripotent stem cells free of viral reprogramming factors", Cell, (2009) 136:964-977.

Sosa-Pineda, B. "The Gene Pax4 is an Essential Regulator of Pancreatic .beta.-Cell Development," Molecules and Cells, 2004, vol. 18, No. 3, 289-294.

Stadtfeld et al., "Induced pluripotent stem cells generated without viral integration", Science, (2008) 322:945-949.

Takahashi et al., "Induction of pluripotent stem cells from adult human fibroblasts by defined factors", Cell (2007), 131 (5):861-872.

Thatava et al., "Intrapatient variations in type 1 diabetes-specific iPS cell differentiation into insulin-producing cellsI," Molecular Therapy 21(1): 228-239 (Nov. 27, 2012).

Uehata et al., Calcium sensitization of smooth muscle mediated by a Rho-associated protein kinase in hypertension, Nature 389: 990-994 (1997).

Van Hoof et al., "Derivation of insulin-producing cells from human embryonic stem cells," Stem Cell Research 3(2-3) 73-87 (Sep. 1, 2009).

Zhang, Donghui, Cell Research, Apr. 1, 2009, vol. 19, No. 4, pp. 429-438.

Wang et al., "Self-renewal of human embryonic stem cells requires insulin-like growth factor-1 receptor and ERBB2 receptor signaling," Blood 110(12): 4111-4119 (Aug. 29, 2007).

Watanabe et al., "A Rock inhibitor permits survival of dissociated human embryonic cells", Nature Biotechnology (2007), 25(6): 681-686.

Wernig et al., "In vitro reprogramming of fibroblasts into a pluripotent ES-cell-like state", Nature, (2007) 448:318-324.

Woltjen et al., "PiggyBac transposition reprograms fibroblasts to induced pluripotent stem cells", Nature, (2009) 458 (7239):766-770.

Yu et al. "Induced pluripotent stem cell lines derived from human somatic cells", Science, (2007), 318(5858):1917-20.

Yu et al., "Human induced pluripotent stem cells free of vector and transgene sequences", (2009), Science, 324 (5928):797-801.

Zhang et al., "Highly efficient differentiation of human ES cells and IPS cells into mature pancreatic insulin-producing cells," Cell Research (2009): 429-438.

Zhou et al., "Generation of induced pluripotent stem cells using recombinant proteins", Cell Stem Cell, (2009), 4 (5):381-384.

FIG. 3A  FIG. 3B
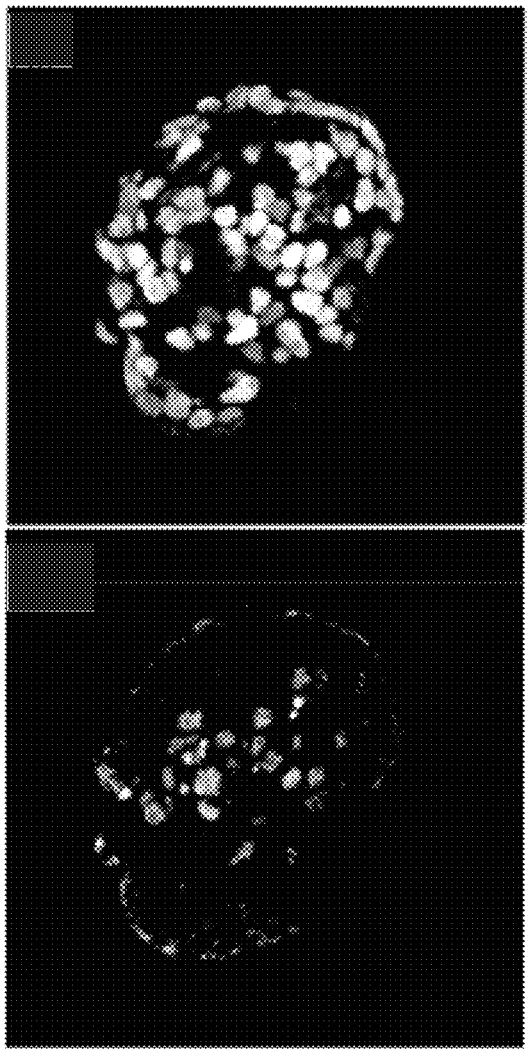 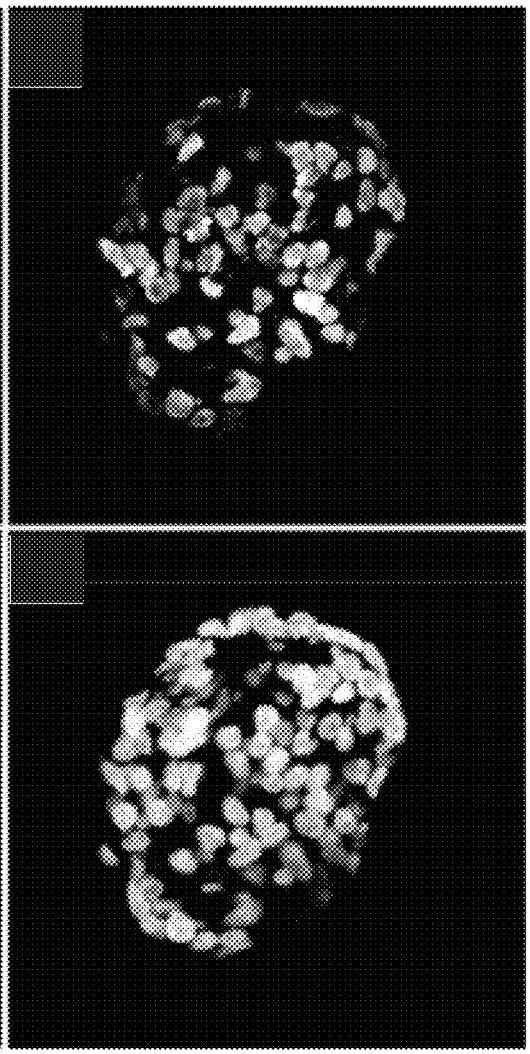
FIG. 3C  FIG. 3D
*E2021 using G4 hIPS cell line at Stage 4 differentiation (PDX1-positive pancreatic endoderm cells)*
  *A) Pdx1*
  *B) Nkx6.1*
  *C) Ptf1a*
  *D) Dapi*

FIG. 4A
FIG. 4B
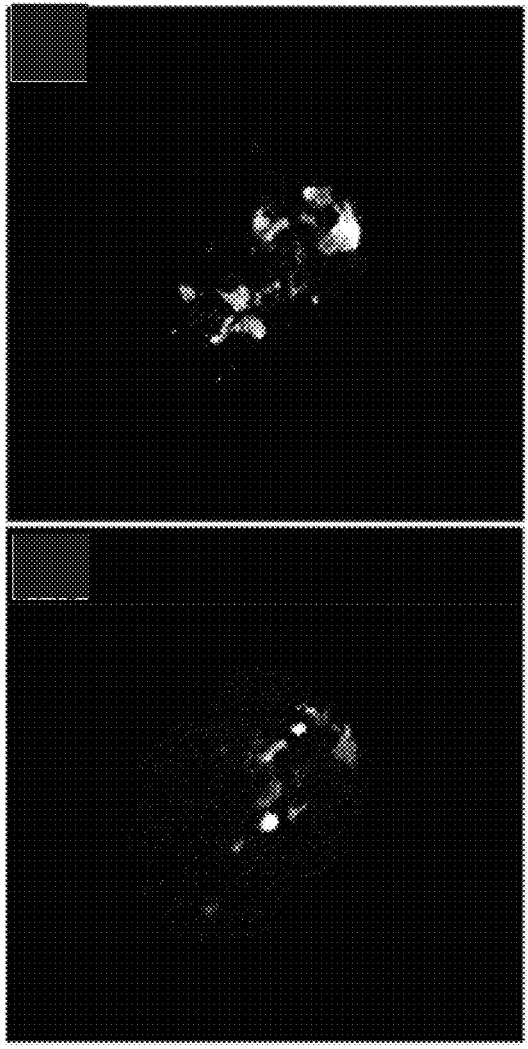
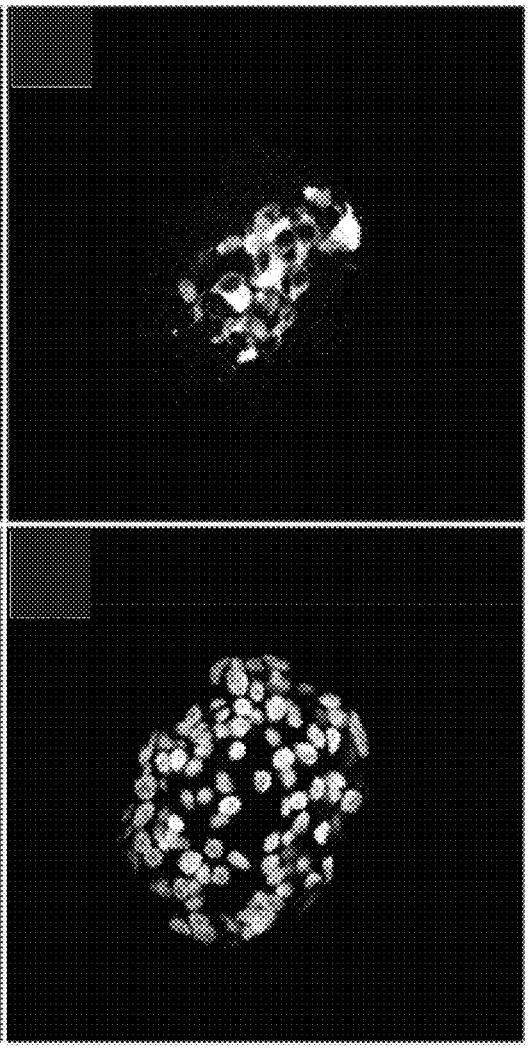
FIG. 4C
FIG. 4D
*E2021 G4 h1PS cell line at Stage 5*
  *A) Glucagon*
  *B) Insulin*
  *C) Somatostatin*
  *D) Dapi*

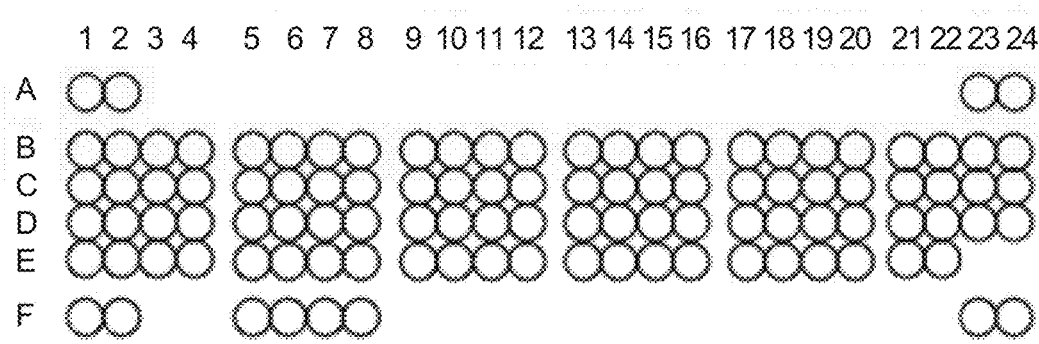

FIG. 5A

Phospho-RTK array key

| Coordinate | Family | RTK/Control | Coordinate | Family | RTK/Contrl |
|---|---|---|---|---|---|
| A1, A2 | Control (+) | PY-Control* | D1, D2 | Tie | TIE-2 |
| A23, A24 | Control (+) | PY-Control* | D3, D4 | NGFR | TRKA |
| B1, B2 | EGFR | EGFR | D5, D6 | NGFR | TRKB |
| B3, B4 | EGFR | ERBB2 | D7, D8 | NGFR | TRKC |
| B5, B6 | EGFR | ERBB3 | D9, D10 | VEGFR | VEGFR1 |
| B7, B8 | EGFR | ERBB4 | D11, D12 | VEGFR | VEGFR2 |
| B9, B10 | FGFR | FGFR1 | D13, D14 | VEGFR | VEGFR3 |
| B11, B12 | FGFR | FGFR2α | D15, D16 | MuSK | MuSK |
| B13, B14 | FGFR | FGR3 | D17, D18 | EphR | EPHA1 |
| B15, B16 | FGFR | FGFR4 | D19, D20 | EphR | EPHA2 |
| B17, B18 | Insulin R | IR | D21, D22 | EphR | EPHA3 |
| B19, B20 | Insulin R | IGF1R | D23, D24 | EphR | EPHA4 |
| B21, B22 | Axl | AXL | E1, E2 | EphR | EPHA6 |
| B23, B24 | Axl | DTK | E3, E4 | EphR | EPHA7 |
| C1, C2 | AXl | MER | E5, E6 | EphR | EPHB1 |
| C3, C4 | HGFR | HGFR | E7, E8 | EphR | EPHB2 |
| C5, C6 | HGFR | MSPR | E9, E10 | EphR | EPHB4 |
| C7, C8 | PDGFR | PDGFRα | E11, E12 | EphR | EPHB6 |
| C9, C10 | PDGFR | PDGFRβ | E13, E14 | Control (-) | Mouse IgG$_1$ |
| C11, C12 | PDGFR | SCFR | E15, E16 | Control (-) | Mouse IgG$_{2A}$ |
| C13, C14 | PDGFR | FLT-3 | E17, E18 | Control (-) | Mouse IgG$_{2B}$ |
| C15, C16 | PDGFR | M-CSFR | E19, E20 | Control (-) | Goat IgG |
| C17, C18 | RET | c-RET | E21, E22 | Control (-) | PBS |
| C19, C20 | ROR | ROR1 | F1, F2 | Control (+) | PY-CONTROL* |
| C21, C22 | ROR | ROR2 | F23, F24 | Control (+) | PYPY-CONTROL* |
| C23, C24 | Tie | TIE-1 | | | |

*Phospho-tyrosine positive control

FIG. 5B

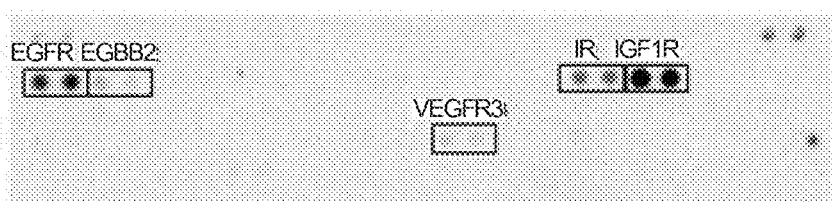
FIG. 6A Steady State
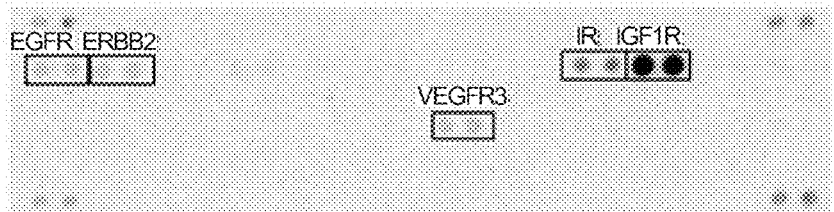
FIG. 6B Starved 24hrs
FIG. 6C Pulsed KE
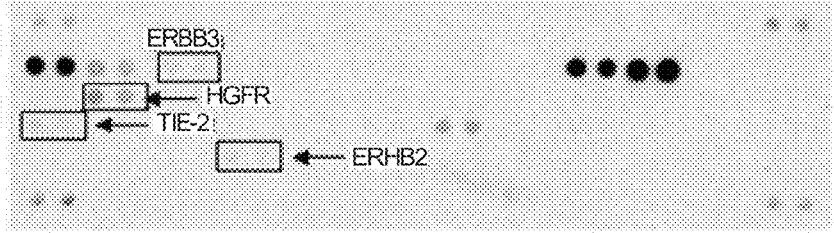
FIG. 6D Pulsed Serum

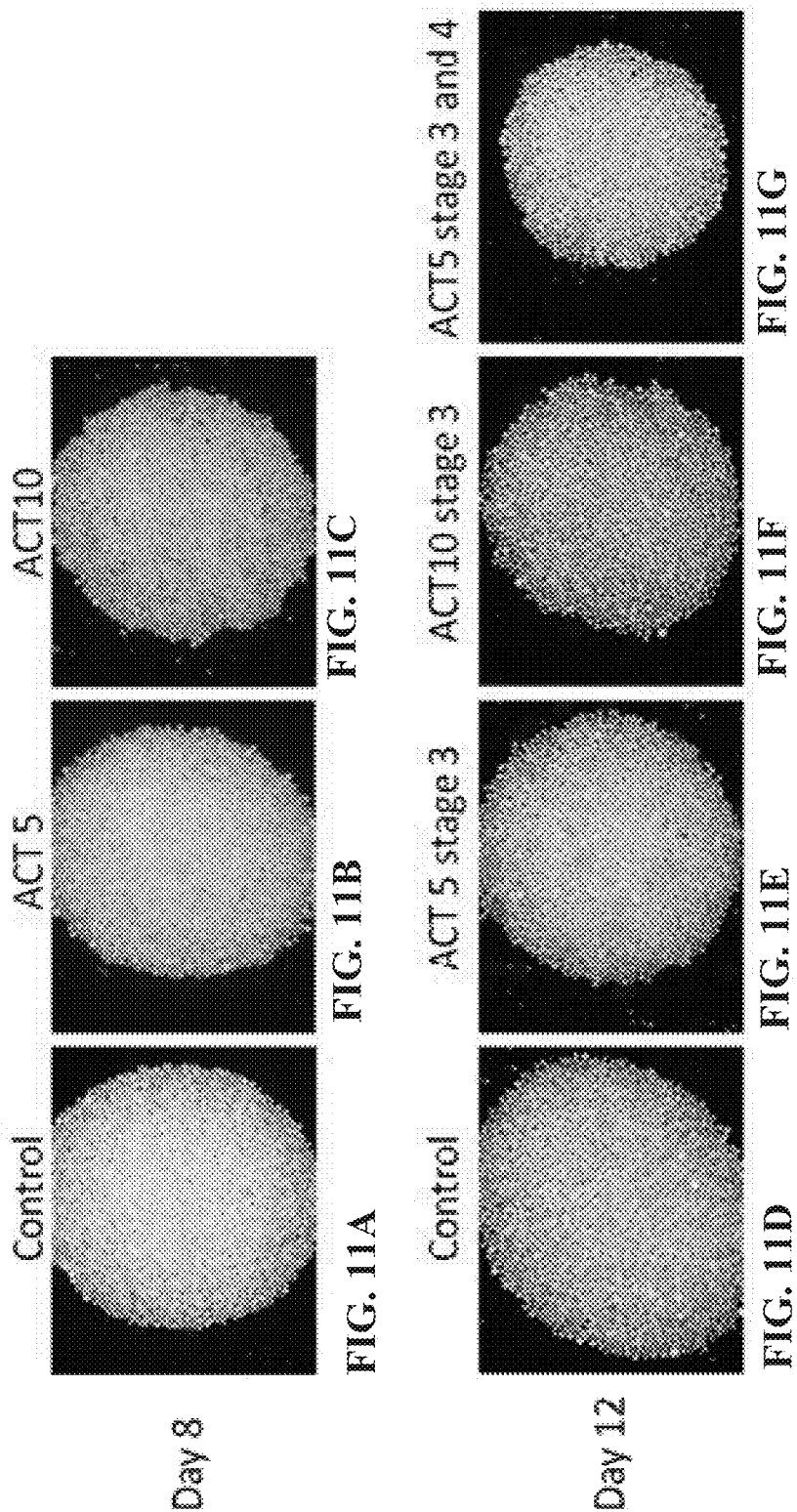

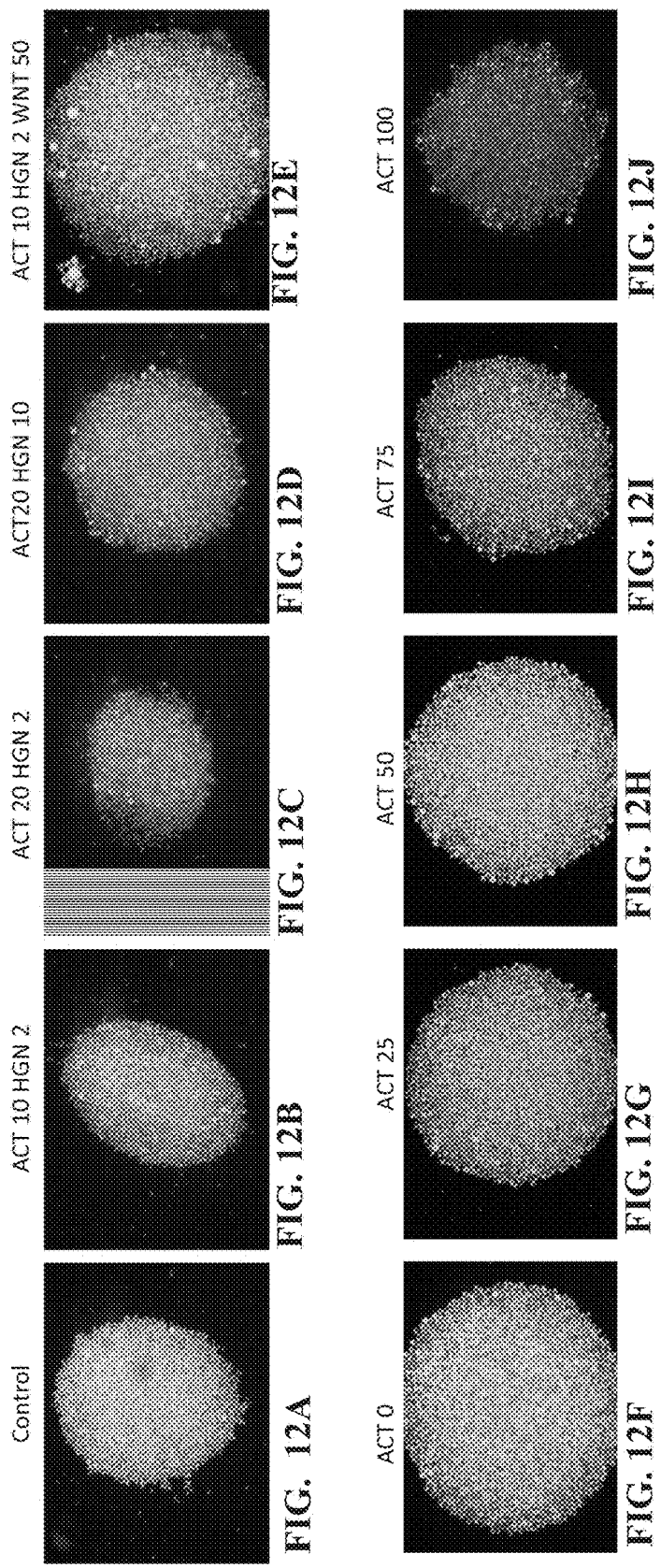

METHODS FOR PRODUCING HORMONE SECRETING CELLS IN A SUBJECT

CROSS REFERENCE TO RELATED APPLICATIONS

This is a continuation of U.S. patent application Ser. No. 14/455,059, filed Aug. 8, 2014, which is a continuation of U.S. patent application Ser. No. 14/106,330, filed Dec. 13, 2013, issued as U.S. Pat. No. 8,859,286, which claims the benefit of U.S. Provisional Patent Application No. 61/781,005, filed Mar. 14, 2013. The prior applications are incorporated herein by reference in their entirety.

STATEMENT OF GOVERNMENT SUPPORT

This research was made possible, in part, by an award from the California Institute for Regenerative Medicine (CIRM) (Award No. DRI-01423).

FIELD OF THE INVENTION

This invention relates generally to the isolation, maintenance, and use of cell cultures. More specifically, it relates to cell compositions and methods to differentiate pluripotent stem cells in vitro to pancreatic endoderm cell (PEC) cultures enriched for a non-endocrine multipotent pancreatic progenitor sub-population (CHGA−) but relatively replete of cells committed to the endocrine lineage (CHGA+). The specification also describes, for the first time, cell compositions and methods to differentiate pluripotent stem cells in vitro to endocrine cells which, after implantation into a mammal, produce insulin in response to glucose stimulation in vivo. The specification also describes, cell compositions and methods to differentiate pluripotent stem cells in vitro to endocrine cells which produce insulin in vitro.

BACKGROUND

The development of expanded populations of human pancreatic β-cells that can be used for cell transplantation is a major goal of diabetes research. In recent years attention has been focused on using pluripotent stem cells as a potential renewable source for β-cells. Because of the complex nature of pancreatic endocrine differentiation, which is presently not yet elucidated, differentiation of pluripotent stem cells to mature and functional β-cells has not been efficiently achieved in vitro. To date, only progenitor cells such as pancreatic endoderm cells (PEC) have been transplanted into rodents and after 8-12 weeks demonstrate human-specific β-cell function. PEC cell populations comprise at least two cell populations: a non-endocrine multipotent pancreatic progenitor sub-population (CHGA−) and cells committed to the endocrine lineage (CHGA+). It was discovered that upon implantation of PEC, it is the non-endocrine multipotent pancreatic progenitor sub-population (CHGA−) that matures and forms β-cells in vivo. Transplanting PEC cell populations require a long maturation time in vivo (8-12 weeks) which can be shortened or eliminated if: (a) in vitro PEC populations contain more of the cell type that matures into β-cells in vivo (i.e., non-endocrine multipotent pancreatic progenitor cells (CHGA−)), (b) terminal (β-cell) differentiation is achieved in vitro, or (c) an in vitro progenitor population that is further along the differentiation pathway than is currently used is identified, i.e., developmentally advanced cell population.

While not limiting this application to any one theory, a possible explanation as to why pluripotent stem cells do not mature into fully functional n-cells in vitro is that in vitro derived cells do not have the same marker expression at the same time points as during in vivo mammalian pancreatic development. For example, NGN3 expression during in vitro differentiation occurs earlier than in in vivo mammalian pancreatic development. Indeed, it has been observed that in traditional 4 stage differentiation protocols as described in Applicant's many publications and patents incorporated herein by reference in their entireties, PEC populations express NGN3 and NKX2.2. Thus, suppression or inhibition of NGN3 expression until after expression of PDX1/NKX6.1 co-positive non-endocrine multipotent pancreatic progenitor subpopulation differentiation is an important step in achieving in vitro differentiation of pluripotent stem cells to mature and functional β-cells or differentiation of PEC populations which contain more non-endocrine multipotent pancreatic progenitor cells (CHGA−) compared to cells committed to the endocrine lineage (CHGA+).

Identifying a protocol which delays the expression of NGN3 and NKX2.2 is non-obvious because the differentiation protocol should not disrupt, and preferably increases the formation of non-endocrine multipotent pancreatic progenitor sub-population (CHGA−) and should minimize cell loss; or at minimum maintain adequate cell mass and cell yield (i.e. micrograms, grams, kilograms of cells).

Additionally, since NGN3 expression is required for initiating endocrine cell differentiation, promoting islet cell maturation and maintaining islet function, stimulating or inducing NGN3 expression in cells committed to the endocrine lineage (CHGA+) is an important step in achieving in vitro differentiation of pluripotent stem cells to mature and functional n-cells.

SUMMARY OF THE INVENTION

In one aspect, an in vitro method of producing a cell population including human PDX1 positive pancreatic endoderm cells is provided. The method includes contacting a cell population including definitive endoderm lineage cells with a TGFβ superfamily growth factor and a Wnt family member, thereby generating the cell population including PDX1 positive pancreatic endoderm cells. In embodiments, the TGFβ superfamily growth factor is selected from the group consisting of Nodal, Activin A, Activin B, BMP2, BMP4, GDF8, GDF-10, GDF-11 and GDF-15. In embodiments, the method further includes contacting the cell population including definitive endoderm lineage cells with an ERBB receptor kinase activating agent. In embodiments, the TGFβ superfamily growth factor is Activin A. In embodiments, the Wnt family member is Wnt3a. In embodiments, the ERBB receptor kinase activating agent is Heregulin.

In embodiments, the cell population including PDX1 positive pancreatic endoderm cells is contacted with at least 25 ng/mL of the TGFβ superfamily growth factor. In embodiments, the cell population including PDX1 positive pancreatic endoderm cells is contacted with at least 50 ng/mL of the TGFβ superfamily growth factor. In embodiments, the cell population including PDX1 positive pancreatic endoderm cells is contacted with at least 75 ng/mL of the TGFβ superfamily growth factor.

In embodiments, the cell population including PDX1 positive pancreatic endoderm cells is contacted with at least 25 ng/mL of the Wnt family member. In embodiments, the cell population including PDX1 positive pancreatic endoderm cells is contacted with at least 50 ng/mL of the Wnt family member. In embodiments, the cell population including PDX1 positive pancreatic endoderm cells is contacted with at least 75 ng/mL of the Wnt family member.

In embodiments, the cell population is contacted with 5-15 fold less of the ERBB receptor kinase activating agent than each of the TGFβ superfamily growth factor and the Wnt family member. In embodiments, at least about 50% of said cell population including PDX1 positive pancreatic endoderm cells are PDX1-positive pancreatic endoderm cells. In embodiments, at least about 60% of the cell population including PDX1 positive pancreatic endoderm cells are PDX1-positive pancreatic endoderm cells. In embodiments, at least about 70% of the cell population including PDX1 positive pancreatic endoderm cells are PDX1-positive pancreatic endoderm cells. In embodiments, at least about 80% of the cell population including PDX1 positive pancreatic endoderm cells are PDX1-positive pancreatic endoderm cells. In embodiments, at least about 90% of the cell population including PDX1 positive pancreatic endoderm cells are PDX1-positive pancreatic endoderm cell.

In embodiments, the PDX1-positive pancreatic endoderm cells further express NKX6.1 and do not substantially express NGN3. In embodiments, the PDX1-positive pancreatic endoderm cells do not express CHGA. In embodiments, the PDX1-positive pancreatic endoderm cells further express NKX6.1 and PFT1A and do not substantially express NGN3. In embodiments, the PDX1-positive pancreatic endoderm cells are multipotent cells that can that can differentiate into unipotent immature beta cells.

In one aspect, a human pancreatic endoderm cell culture including a definitive endoderm linage cell and a TGFβ superfamily growth factor and a Wnt family member is provided. In embodiments, the TGFβ superfamily growth factor is selected from the group consisting of Nodal, Activin A, Activin B, BMP2, BMP4, GDF8, GDF-10, GDF-11 and GDF-15. In embodiments, the method further includes contacting the cell population including definitive endoderm lineage cells with an ERBB receptor kinase activating agent. In embodiments, the TGFβ superfamily growth factor is Activin A. In embodiments, the Wnt family member is Wnt3a. In embodiments, the ERBB receptor kinase activating agent is Heregulin.

In another aspect, an in vitro unipotent human immature beta cell is provided. In embodiments, the unipotent human immature beta cell expresses INS and NKX6.1 and does not substantially express NGN3. In embodiments, the unipotent human immature beta cell is capable of differentiating to a mature beta cell. In embodiments, the differentiating is in vivo. In embodiments, the unipotent human immature beta cell forms part of a cell population. In embodiments, at least 10% of the cell population are immature beta cells. In embodiments, at least 20% of the cell population are immature beta cells. In embodiments, at least 30% of the cell population are immature beta cells. In embodiments, at least 40% of the cell population are immature beta cells. In embodiments, at least 50% of the cell population are immature beta cells. In embodiments, at least 60% of the cell population are immature beta cells. In embodiments, at least 80% of the cell population are immature beta cells. In embodiments, at least 90% of the cell population are immature beta cells. In embodiments, at least 98% of the cell population are immature beta cells. In embodiments, the human immature beta cell is singly hormonal. In embodiments, the unipotent human cell expresses MAFB.

In one aspect, a method of producing a unipotent human immature beta cell is provided. The method includes contacting human definitive endoderm lineage cells in vitro with a TGFβ superfamily member and Wnt family member thereby generating immature beta cells. In embodiments, the unipotent human immature beta cell expresses INS, NKX6.1 and does not substantially express NGN3. In embodiments, the TGFβ superfamily member is selected from the group consisting of Nodal, Activin A, Activin B, BMP2, BMP4, GDF8, GDF-10, GDF-11 and GDF-15. In embodiments, the method further includes contacting the human definitive endoderm lineage cells in vitro with an ERBB receptor kinase activating agent. In embodiments, the TGFβ superfamily growth factor is Activin A. In embodiments, the Wnt family member is Wnt3a. In embodiments, the ERBB receptor kinase activating agent is Heregulin. In embodiments, the TGFβ superfamily growth factor is BMP.

In embodiments, the method further includes contacting the human definitive endoderm lineage cells in vitro with nicotinamide, a retinoic acid or retinoic acid analogue, a rho kinase inhibitor or a gamma secretase inhibitor. In embodiments, the retinoic acid is selected from the group consisting of all-trans-retinoic acid (RA), 13-cis-retinoic acid (13-cis-RA), and arotinoid acid (TTNPB). In embodiments, the retinoic acid is all-trans retinoic acid (RA). In embodiments, the retinoic acid is 13-cis-retinoic acid (13-cis-RA). In embodiments, the retinoic acid is arotinoid acid (TTNPB). In embodiments, the rho kinase inhibitor is selected from the group consisting of Y-27632, Fasudil, H-1152P, Wf-536 and Y-30141. In embodiments, the rho kinase inhibitor is Y-27632.

In embodiments, the gamma secretase inhibitor is selected from the group consisting of gamma secretase inhibitor I (GSI I), gamma secretase inhibitor II (GSI II), gamma secretase inhibitor III (GSI III), gamma secretase inhibitor IV (GSI IV), gamma secretase inhibitor V (GSI V), gamma secretase inhibitor VI (GSI VI), gamma secretase inhibitor VII (GSI VII), gamma secretase inhibitor IX (GSI IX), (DAPT), gamma secretase inhibitor XI (GSI XI), gamma secretase inhibitor XII, (GSI XII), gamma secretase inhibitor XIII (GSI XIII), gamma secretase inhibitor XIV (GSI XIV), gamma secretase inhibitor XVI (GSI XVI), gamma secretase inhibitor XVII (GSI XVII), gamma secretase inhibitor XIX (GSI XIX), gamma secretase inhibitor XX (GSI XX), gamma secretase inhibitor XXI (GSI XXI), gamma40 secretase inhibitor I, gamma40 secretase inhibitor II and RO4929097. In embodiments, the gamma secretase inhibitor is RO4929097. In embodiments, the gamma secretase inhibitor is GSI IV.

In another aspect, a method for producing mature beta cells in vivo is provided. The method includes, (a) contacting human definitive endoderm lineage cells in vitro with a TGFβ superfamily member and Wnt family member, thereby generating immature beta cells; (b) transplanting the immature beta cells of step (a) into a mammalian subject; and allowing the immature beta cells to differentiate in vivo to produce a population of cells including mature beta cells. In embodiments, the method further includes allowing the mature beta cells to produce insulin in response to glucose stimulation. In embodiments, the TGFβ superfamily growth factor is selected from the group consisting of Nodal, Activin A and Activin B, GDF-8, GDF-11 and GDF-15. In embodiments, the method further includes contacting the human definitive endoderm lineage cells in vitro with an ERBB receptor kinase activating agent. In embodiments, the TGFβ superfamily growth factor is Activin A. In embodiments, the Wnt family member is Wnt3a. In embodiments, the ERBB receptor kinase activating agent is Heregulin.

In embodiments, the human definitive endoderm lineage cells are contacted with at least 25 ng/mL of the TGFβ superfamily growth factor. In embodiments, human definitive endoderm lineage cells are contacted with at least 50 ng/mL of the TGFβ superfamily growth factor. In embodiments, the human definitive endoderm lineage cells are contacted with at least 75 ng/mL of the TGFβ superfamily growth factor.

In embodiments, the human definitive endoderm lineage cells are contacted with at least 25 ng/mL of the Wnt family member. In embodiments, the human definitive endoderm lineage cells are contacted with at least 50 ng/mL of the Wnt family member. In embodiments, the human definitive endoderm lineage cells are contacted with at least 75 ng/mL of the Wnt family member.

In embodiments, the human definitive endoderm lineage cells are contacted with 5-15 fold less of the ERBB receptor kinase activating agent than the TGFβ superfamily growth factor and the Wnt family member. In embodiments, at least 10% of the cell population are immature beta cells. In embodiments, at least 20% of the cell population are immature beta cells. In embodiments, at least 30% of the cell population are immature beta cells. In embodiments, at least 40% of the cell population are immature beta cells. In embodiments, at least 50% of the cell population are immature beta cells. In embodiments, at least 60% of the cell population are immature beta cells. In embodiments, at least 70% of the cell population are immature beta cells. In embodiments, at least 80% of the cell population are immature beta cells. In embodiments, at least 90% of the cell population are immature beta cells. In embodiments, the immature beta cells express INS and NKX6.1 and do not express substantially NGN3. In embodiments, the immature beta cells express INS, NKX6.1 and MAFB and do not express substantially NGN3.

In one aspect, an in vitro unipotent human immature beta cell is provided. In embodiments, the unipotent human immature beta cell expresses INS and NKX6.1 and does not substantially express NGN3. In embodiments, the unipotent human immature beta cell is capable of maturing to a mature beta cell.

In one aspect, a method for producing mature beta cells in vivo is provided. The method includes: a. contacting human definitive endoderm lineage cells in vitro with a TGFβ superfamily member and Wnt family member thereby generating immature beta cells; b. transplanting the immature beta cells of step (a) into a mammalian subject; and c. allowing the immature beta cells to mature in vivo to produce a population of cells including insulin secreting beta cells.

In one aspect, a unipotent human immature beta cell that expresses INS and NKX6.1 and does not substantially express NGN3 is provided. In embodiments, the unipotent human immature beta cell is capable of maturing to a mature beta cell. In embodiments, the unipotent human immature beta cell further expresses MAFB.

In one aspect, an in vitro unipotent human immature beta cell expressing INS and NKX6.1 and not substantially expressing NGN3 is provided. In embodiments, the unipotent human immature beta cell is capable of maturing to a mature beta cell. In embodiments, the unipotent human immature beta cell further expresses MAFB.

In one aspect a method of producing a unipotent human immature beta cell is provided. The method includes contacting human definitive endoderm lineage cells in vitro with a TGFβ superfamily member and a Wnt family member thereby producing a unipotent human immature beta cell. In embodiments, the unipotent human immature beta cell expresses INS, NKX6.1 and does not substantially express NGN3. In embodiments, the method further includes contacting the human definitive endoderm lineage cells in vitro with an ERBB receptor kinase activating agent. In embodiments, the TGFβ superfamily growth factor is Activin A. In embodiments, the Wnt family member is Wnt3a. In embodiments, the ERBB receptor kinase activating agent is Heregulin.

In one aspect, a method for producing mature beta cells in vivo is provided. The method includes: a. contacting human definitive endoderm lineage cells in vitro with a TGFβ superfamily member and Wnt family member thereby generating immature beta cells; b. transplanting the immature beta cells of step (a) into a mammalian subject; and c. allowing the immature beta cells to mature in vivo to produce a population of cells including insulin secreting beta cells. In embodiments, the method further includes contacting the human definitive endoderm lineage cells in vitro with an ERBB receptor kinase activating agent. In embodiments, the TGFβ superfamily growth factor is Activin A. In embodiments, the Wnt family member is Wnt3a. In embodiments, the ERBB receptor kinase activating agent is Heregulin. In embodiments, the human definitive endoderm cells are contacted with at least 50 ng/mL of the TGFβ superfamily growth factor. In embodiments, the human definitive endoderm lineage cells are contacted with at least 25 ng/mL of the Wnt family member. In embodiments, the human definitive endoderm lineage cells are contacted with 5-15 fold less of the ERBB receptor kinase activating agent than the TGFβ superfamily growth factor and the Wnt family member. In embodiments, the immature beta cells express INS and NKX6.1 and do not substantially express NGN3. In embodiments, the immature beta cells express INS, NKX6.1 and MAFB and do not substantially express NGN3.

One embodiment provides a composition and method for differentiating pluripotent stem cells or precursor cells derived from pluripotent stem cells to endocrine and non-endocrine populations. In one aspect, endocrine cells express at least CHGA (or CHGA+) and non-endocrine do not express CHGA (or CHGA−). In one aspect, these cell populations are referred to as endocrine (CHGA+) and non-endocrine (CHGA−) sub-populations, or just CHGA+ or CHGA− sub-populations, or simply endocrine and non-endocrine sub-populations. In another aspect, these endocrine and non-endocrine sub-populations may be multipotent progenitor/precursor sub-populations such as non-endocrine multipotent pancreatic progenitor sub-populations or endocrine multipotent pancreatic progenitor sub-populations; or they may be unipotent sub-populations such as immature endocrine cells, preferably immature beta cells, immature glucagon cells and the like.

One embodiment provides a composition and method for differentiating pluripotent stem cells in vitro to pancreatic endoderm cell (PEC) cultures comprising both endocrine and non-endocrine sub-populations, wherein expression of NGN3 is suppressed. In one aspect, expression of NKX2.2 is also suppressed in the PEC culture. In one aspect, expression of CHGA is also suppressed in the PEC culture. In one aspect, expression of PDX1 and NKX6.1 are co-expressed on a single cell in the PEC culture. In one aspect, less than 50% preferably less than 40%, 30%, more preferably less than 20%, 10%, 5%, 2%, 1% of the cells in the PEC culture express NGN3, NKX2.2 or CHGA. In one aspect, the PEC culture is enriched for non-endocrine multipotent pancreatic progenitor sub-population (CHGA−). In one aspect, the PEC culture expresses markers (PDX1 and/or NKX6.1) for the non-endocrine multipotent pancreatic progenitor sub-population (CHGA−). In one aspect, the PEC culture with abundant non-endocrine multipotent progenitor sub-population (CHGA−) is implanted in a mammalian host and the graft matures and produces insulin in vivo in response to glucose. In one aspect, the PEC culture with abundant non-endocrine multipotent pancreatic progenitor sub-population (CHGA−) matures in vivo at a faster rate than PEC cultures without an abundant non-endocrine multipotent progenitor sub-population (CHGA−). In one aspect, the implanted PEC culture with abundant non-endocrine multipotent progenitor sub-population (CHGA−) has at least a 2× improvement in in vivo function as measured by C-peptide (insulin) production in response to glucose stimulation at about 10 weeks or about 12 weeks post implant than implanted PEC cultures without an abundant non-endocrine multipotent pancreatic progenitor sub-population (CHGA−).

One embodiment provides a composition and method for differentiating pluripotent human stem cells in vitro wherein expression of genes typical of endocrine differentiation and development such as NGN3 and NKX2.2 are suppressed until after non-endocrine multipotent pancreatic progenitor (CHGA− and PDX1/NKX6.1 co-expression) production.

One embodiment provides a method for differentiating pluripotent stem cells in vitro to PEC cultures comprising the steps of: (a) obtaining a PDX1-negative foregut endoderm cell population; (b) contacting the cell population in step (a) with an agent that activates a TGFβ receptor family member thereby generating a cell culture comprising PEC wherein the PEC do not substantially express a marker selected from the group comprising CHGA, NGN3 or NKX2.2. In one aspect, the PEC comprises a sup-population of cells that co-expresses PDX1 and NKX6.1. In one aspect, the PEC comprises a sub-population of non-endocrine multipotent pancreatic progenitor (CHGA−) cells. In one aspect the agent that activates a TGFβ receptor family member is selected from the group consisting of Nodal, Activin A, Activin B, BMP2, BMP4, GDF8, GDF-10, GDF-11, GDF-15 and a mixture thereof. In one aspect, Activin A is added at 100 ng/mL, 75 ng/mL, 50 ng/mL, 25 ng/mL or 10 ng/mL at stage 3; and 15 ng/mL, 10 ng/mL or 5 ng/mL at stage 4. In one aspect, the PEC culture formed by adding Activin A to a PDX1-negative foregut endoderm cell population has at least a 2× improvement in vivo function as measured by C-peptide (insulin) production in response to glucose stimulation than PEC cultures without an abundant non-endocrine multipotent progenitor sub-population (CHGA−).

In one aspect, the PEC culture with a non-endocrine multipotent pancreatic progenitor sub-population (CHGA−) has at least a 2× improvement in in vivo function as measured by insulin production in response to glucose stimulation than PEC cell cultures without abundant non-endocrine multipotent progenitor sub-populations (CHGA−).

One embodiment provides a method for differentiating pluripotent stem cells in vitro to a cell population comprising PEC comprising the steps of: (a) obtaining a PDX1-negative foregut endoderm cell population (b) contacting the cell population in step (a) with an agent that activates a TGFβ receptor family member thereby generating a PEC population wherein the PEC population does not substantially express a marker selected from the group comprising CHGA, NGN3 or NKX2.2. In one aspect, the PEC population comprises cells that co-express PDX1 and NKX6.1. In one aspect, the PEC population comprises non-endocrine multipotent pancreatic progenitor cells (CHGA−). In one aspect the agent that activates a TGFβ receptor family member is selected from the group consisting of Nodal, Activin A, Activin B, BMP2, BMP4, GDF8, GDF-10, GDF-11, GDF-15 and a mixture thereof. In one aspect the agent that activates a TGFβ receptor family member is Activin A. In one aspect, Activin A is added at 100 ng/mL, 75 ng/mL, 50 ng/mL, 25 ng/mL or 10 ng/mL at stage 3; and 15 ng/mL, 10 ng/mL or 5 ng/mL at stage 4. In one aspect the EGF family ligand is selected from the group comprising Heregulin (also known as Neuregulin1 (NRG1)), Neuregulin2 (NRG2), Neuregulin3 (NRG3), Neuregulin4 (NRG4), EGF (epidermal growth factor) and betacellulin. In one aspect the EGF family ligand is Heregulin. In one aspect, Heregulin is added at 2 ng/mL, 5 ng/mL, 10 ng/mL, 20 ng/mL, 15 ng/mL, 30 ng/mL, 40 ng/mL, 50 ng/mL, 60 ng/mL, 70 ng/mL or 80 ng/mL. In one aspect, the PEC culture formed by adding Activin A and Heregulin to a PDX1-negative foregut endoderm cell population has at least a 2× improvement in vivo function as measured by C-peptide (insulin) production in response to glucose stimulation than PEC cultures without abundant non-endocrine multipotent progenitor sub-populations (CHGA−).

One embodiment provides a method for differentiating pluripotent stem cells in vitro to a cell culture comprising PEC comprising the steps of: (a) obtaining a PDX1-negative foregut endoderm cell population (b) contacting the cell population in step (a) with at least an agent that activates a TGFβ receptor family member, an EGF family ligand or an agent that activates a Wnt signaling pathway, alone or in combination, thereby generating a cell culture comprising PEC wherein the PEC do not substantially express a marker selected from the group comprising CHGA, NGN3 or NKX2.2. In one aspect, the PEC culture comprises cells that co-express PDX1 and NKX6.1. In one aspect, the PEC cell culture comprises a non-endocrine multipotent pancreatic progenitor sub-population (CHGA−). In one aspect the agent that activates a TGFβ receptor family member is selected from the group consisting of Nodal, Activin A, Activin B, BMP2, BMP4, GDF8, GDF-10, GDF-11, GDF-15 and a mixture thereof. In one aspect the agent that activates a TGFβ receptor family member is Activin A. In one aspect, an agent that activates a Wnt signaling pathway is a Wnt family member selected from the group comprising WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16 and Wnt3A. In one aspect, the Wnt family member is Wnt3A. In one aspect, Activin A is added at 100 ng/mL, 75 ng/mL, 50 ng/mL, 25 ng/mL or 10 ng/mL at stage 3; and 15 ng/mL, 10 ng/mL or 5 ng/mL at stage 4. In one aspect, Heregulin is added at 2 ng/mL, 5 ng/mL, long/mL, 20 ng/mL, 15 ng/mL, 30 ng/mL, 40 ng/mL, 50 ng/mL, 60 ng/mL, 70 ng/mL or 80 ng/mL. In one aspect, WNT is added at 5 ng/mL, 25 ng/mL, 50 ng/mL to 75 ng/mL more preferably at 50 ng/mL.

In one aspect, Activin A is added alone or combined with WNT at stage 3. In another aspect, Activin A is added with WNT or WNT and Heregulin at stage 3. In still one more aspect, Active A is added alone or combined with Heregulin at stage 4.

In one aspect, more than 10% preferably more than 20%, 30%, 40% and more preferably more than 50%, 60%, 70%, 80%, 90%, 95%, 98% or 100% of the cells in the cell population are the non-endocrine multipotent progenitor sub-population (CHGA−). In one aspect, the PEC cell culture formed by adding Activin A, Heregulin and WNT to a PDX1-negative foregut endoderm cell population has at least a 2× improvement in vivo function as measured by insulin production in response to glucose stimulation than PEC cell cultures without an abundant non-endocrine multipotent progenitor sub-population (CHGA−).

One embodiment provides a composition and method for differentiating pluripotent stem cells in vitro to PEC cultures comprising minimal cells committed to the endocrine lineage (CHGA+). In one aspect, the cells committed to the endocrine lineage are characterized by the expression of CHGA. In one aspect, less than 50%, preferably less than 40%, 30%, more preferably less than 20%, 10%, 5%, 2%, 1% of the cells in the cells in the PEC culture are cells committed to the endocrine lineage (CHGA+).

One embodiment provides a composition and method for differentiating pluripotent stem cells in vitro to substantially PEC cultures and further differentiating the PEC culture to endocrine cells in vitro. In one aspect, the endocrine cells express CHGA. In one aspect, the endocrine cells can produce insulin in vitro. In one aspect, the in vitro endocrine insulin secreting cells may produce insulin in response to glucose stimulation. In one aspect, more than 10% preferably more than 20%, 30%, 40% and more preferably more than 50%, 60%, 70%, 80%, 90%, 95%, 98% or 100% of the cells in the cells population are endocrine cells.

One embodiment provides a method for differentiating pluripotent stem cells in vitro to endocrine cells comprising the steps of: (a) obtaining a cell population comprising PEC (b) contacting the cell population in step (a) with growth factors selected from the group consisting of a bone morphogenetic protein (BMP), a hedgehog inhibitor, Platelet-derived growth factor (PDGF), member of the fibroblast growth factor family, a retinoid, insulin growth factor 1 and 2 (IGF1 and IGF2) and nicotinamide thereby generating endocrine cells. In one aspect the endocrine cells express CHGA. In one aspect, the endocrine cells are immature insulin-producing beta-cells in vitro. In one aspect, the endocrine cells are loaded into an implantable semipermeable encapsulation device, mature and are capable of producing insulin in response to glucose stimulation in vivo. In one aspect, more than 10% preferably more than 20%, 30%, 40% and more preferably more than 50%, 60%, 70%, 80%, 90%, 95%, 98% or 100% of the cells in the cell population are endocrine cells. In one aspect, SSH is added at 10 g/mL to 100 ng/mL. In one aspect, PDGF is added at 10 ng/mL to 100 ng/mL. In one aspect, BMP is added at 10 g/mL to 20 ng/mL. In one aspect, FGF2 is added at 2 ng/mL to 20 ng/mL. In one aspect, IGF1 or IGF2 are added at 25 ng/mL to 100 ng/mL. In one aspect, the above compounds are added in combination with each other. In one aspect the member of the fibroblast growth factor family is FGF2. In one aspect the retinoid is retinoic acid and/or retinoic acid analogs such as TTNPB or TT3, Insulin-like growth factor I (IGF-I or IGF1) and -II (IGF-II or IGF2). In one aspect the bone morphogenetic protein is BMP4. In one aspect the hedgehog inhibitor is sonic Hedgehog, KAAD-cyclopamine, KAAD-cyclopamine analogs, jervine, jervine analogs, hedgehog pathway blocking antibodies and any other inhibitors of hedgehog pathway function known to those of ordinary skill in the art.

One embodiment provides a method for differentiating pluripotent stem cells in vitro to endocrine cells comprising the steps of: (a) obtaining a cell population comprising PEC (b) contacting the cell population in step (a) with a gamma secretase inhibitor thereby making endocrine cells in vitro. In one aspect the endocrine cells express CHGA. In one aspect, the endocrine cells are immature insulin-producing beta-cells in vitro. In one aspect, the endocrine cells are insulin secreting cells that produce insulin in response to glucose stimulation in vitro. In one aspect, the endocrine cells are loaded into an implantable semipermeable encapsulation device, mature and are capable of producing insulin in response to glucose stimulation in vivo. In one aspect, the gamma secretase inhibitor is selected from the group comprising N—[N-(3,5-Diflurophenacetyl-L-alanyl)]-S-phenylglycine t-Butyl Ester (DAPT), RO44929097, 1-(S)-endo-N-(1,3,3)-Trimethylbicyclo[2.2.1]hept-2-yl)-4-fluorophenyl Sulfonamide, WPE-III31C, S-3-[N'-(3,5-difluorophenyl-alpha-hydroxyacetyl)-L-alanilyl]amino-2,3-dih-ydro-1-methyl-5-phenyl-1H-1,4-benzodiazepin-2-one, (N)—[(S)-2-hydroxy-3-methyl-butyryl]-1-(L-alaninyl)-(S)-1-amino-3-methyl-4,5,6,7-tetrahydro-2H-3-benzazepin-2-one, BMS-708163 (Avagacestat), BMS-708163, Semagacestat (LY450139), Semagacestat (LY450139), MK-0752, MK-0752, YO-01027, YO-01027 (Dibenzazepine, DBZ), LY-411575, LY-411575, or LY2811376. In some embodiments, the gamma secretase inhibitor is present in the cell culture or cell population at a concentration ranging from about 0.01 μM to about 1000 μM. In preferred embodiments, the gamma secretase inhibitor is present in the cell culture or cell population at a concentration ranging from about 0.1 μM to about 100 μM. In one aspect, the gamma secretase inhibitor is removed subsequent to its addition.

Embodiments described herein provide for compositions and methods of differentiating pluripotent human stem cells in vitro to endocrine cells. In one aspect, the endocrine cells express CHGA. In one aspect, the endocrine cells can produce insulin in vitro. In one aspect, the endocrine cells are immature endocrine cells such as immature beta cells. In one aspect, the in vitro insulin producing cells may produce insulin in response to glucose stimulation.

One embodiment provides a method for producing insulin in vivo in a mammal, said method comprising: (a) loading an endocrine cell population into an implantable semipermeable device; (b) implanting the device with the endocrine cell into a mammalian host; and (c) maturing the endocrine cell population in said device in vivo wherein at least some of the endocrine cells are insulin secreting cells that produce insulin in response to glucose stimulation in vivo, thereby producing insulin in vivo to the mammal. In one aspect the endocrine cell is derived from a cell composition comprising PEC with a higher non-endocrine multipotent pancreatic progenitor sub-population (CHGA−). In another aspect, the endocrine cell is derived from a cell composition comprising PEC with a reduced endocrine sub-population (CHGA+). In another aspect, the endocrine cell is an immature endocrine cell, preferably an immature beta cell.

In one aspect the endocrine cells made in vitro from pluripotent stem cells express more PDX1 and NKX6.1 as compared to PDX-1 positive pancreatic endoderm populations, or the non-endocrine (CHGA−) subpopulations which are PDX1/NKX6.1 positive. In one aspect, the endocrine cells made in vitro from pluripotent stem cells express PDX1 and NKX6.1 relatively more than the PEC non-endocrine multipotent pancreatic progenitor sub-population (CHGA−). In one aspect, a Bone Morphogenic Protein (BMP) and a retinoic acid (RA) analog alone or in combination are added to the cell culture to obtain endocrine cells with increased expression of PDX1 and NKX6.1 as compared to the PEC non-endocrine multipotent progenitor sub-population (CHGA−). In one aspect BMP is selected from the group comprising BMP2, BMP5, BMP6, BMP7, BMP8 and BMP4 and more preferably BMP4. In one aspect the retinoic acid analog is selected from the group comprising all-trans retinoic acid and TTNPB (4-[(E)-2-(5,6,7,8-Tetrahydro-5,5,8,8-tetramethyl-2-naphthalenyl)-1-propenyl]benzoic acid Arotinoid acid), or 0.1-10 μM AM-580 (4-[(5,6,7,8-Tetrahydro-5,5,8,8-tetramethyl-2-naphthalenyl) carboxamido]benzoic acid) and more preferably TTNPB.

One embodiment provides a method for differentiating pluripotent stem cells in vitro to endocrine and immature endocrine cells, preferably immature beta cells, comprising dissociating and re-associating the aggregates. In one aspect the dissociation and re-association occurs at stage 1, stage 2, stage 3, stage 4, stage 5, stage 6 or stage 7 or combinations thereof. In one aspect the definitive endoderm, PDX1-negative foregut endoderm, PDX1-positive foregut endoderm, PEC, and/or endocrine and endocrine progenitor/precursor cells are dissociated and re-associated. In one aspect, the stage 7 dissociated and re-aggregated cell aggregates consist of fewer non-endocrine (CHGA−) sub-populations as compared to endocrine (CHGA+) sub-populations. In one aspect, more than 10% preferably more than 20%, 30%, 40% and more preferably more than 50%, 60%, 70%, 80%, 90%, 95%, 98% or 100% of the cells in the cell population are endocrine (CHGA+) cells.

One embodiment provides a method for differentiating pluripotent stem cells in vitro to endocrine cells by removing the endocrine cells made during stage 4 PEC production thereby enriching for non-endocrine multipotent pancreatic progenitor (CHGA−) sub-population which is PDX1+ and NKX6.1+.

One embodiment provides a method for differentiating pluripotent stem cells in vitro to endocrine cells wherein stage 6 and stage 7 cells as defined in Table 17 are cultured in low levels of Matrigel from about 0.02% to 2%, preferably about 0.02% to 0.05%, preferably about 0.05% to 1%, preferably 0.05%.

One embodiment provides a method for improving cell adhesion of PEC and endocrine cells aggregates by treating cell cultures with Matrigel and a rho-kinase or ROCK inhibitor. In one aspect the rho-kinase or ROCK inhibitor is Y-27632.

In one embodiment, PEC cultures enriched for the non-endocrine multipotent progenitor sub-population (CHGA−) are made by not adding a Noggin family member at stage 3 and/or stage 4. In one embodiment, PEC cultures which are relatively replete of cells committed to the endocrine lineage (CHGA+) are made by not adding a Noggin family member at stage 3 and/or stage 4. In one aspect the Noggin family member is a compound selected from the group comprising Noggin, Chordin, Follistatin, Folistatin-like proteins, Cerberus, Coco, Dan, Gremlin, Sclerostin, PRDC (protein related to Dan and Cerberus).

One embodiment provides a method for maintaining endocrine cells in culture by culturing them in a media comprising exogenous high levels of glucose, wherein the exogenous glucose added is about 1 mM to 25 mM, about 1 mM to 20 mM, about 5 mM to 15 mM, about 5 mM to 10 mM, about 5 mM to 8 mM. In one aspect, the media is a DMEM, CMRL or RPMI based media.

One embodiment provides a method for differentiating pluripotent stem cells in vitro to endocrine cells with and without dissociating and re-associating the cell aggregates. In one aspect the non-dissociated or the dissociated and re-associated cell aggregates are cryopreserved or frozen at stage 6 and/or stage 7 without affecting the in vivo function of the endocrine cells. In one aspect, the cryopreserved endocrine cell cultures are thawed, cultured and, when transplanted, function in vivo.

Another embodiment provides a culture system for differentiating pluripotent stem cells to endocrine cells, the culture system comprising of at least an agent capable of suppressing or inhibiting endocrine gene expression during early stages of differentiation and an agent capable of inducing endocrine gene expression during later stages of differentiation. In one aspect, an agent capable of suppressing or inhibiting endocrine gene expression is added to the culture system consisting of pancreatic PDX1 negative foregut cells. In one aspect, an agent capable of inducing endocrine gene expression is added to the culture system consisting of PDX1-positive pancreatic endoderm progenitors or PEC. In one aspect, an agent capable of suppressing or inhibiting endocrine gene expression is an agent that activates a TGFbeta receptor family, preferably it is Activin, preferably, it is high levels of Activin, followed by low levels of Activin. In one aspect, an agent capable of inducing endocrine gene expression is a gamma secretase inhibitor selected from a group consisting of N—[N-(3,5-Difluorophenacetyl-L-alanyl)]-S-phenylglycine t-Butyl Ester (DAPT), RO44929097, DAPT (N—[N-(3,5-Difluorophenacetyl-L-alanyl)]-S-phenylglycine t-Butyl Ester), 1-(S)-endo-N-(1,3,3)-Trimethylbicyclo[2.2.1]hept-2-yl)-4-fluorophenyl Sulfonamide, WPE-III31C, S-3-[N'-(3,5-difluorophenyl-alpha-hydroxyacetyl)-L-alanilyl]amino-2,3-dih-ydro-1-methyl-5-phenyl-1H-1,4-benzodiazepin-2-one, (N)—[(S)-2-hydroxy-3-methyl-butyryl]-1-(L-alaninyl)-(S)-1-amino-3-methyl-4,5,6,7-tetrahydro-2H-3-benzazepin-2-one, BMS-708163 (Avagacestat), BMS-708163, Semagacestat (LY450139), Semagacestat (LY450139), MK-0752, MK-0752, YO-01027, YO-01027 (Dibenzazepine, DBZ), LY-411575, LY-411575, or LY2811376. In one aspect, high levels of Activin is meant levels greater than 40 ng/mL, 50 ng/mL, and 75 ng/mL. In one aspect, high levels of Activin are used during stage 3 or prior to production of pancreatic foregut endoderm cells. In one aspect, low levels of Activin means less than 30 ng/mL, 20 ng/mL, 10 ng/mL and 5 ng/mL. In one aspect, low levels of Activin are used during stage 4 or for production of PEC. In one aspect, the endocrine gene that is inhibited or induced is NGN3. In another aspect, Activin A and Wnt3A are used alone or in combination to inhibit endocrine expression, preferably to inhibit NGN3 expression prior to production of pancreatic foregut endoderm cells, or preferably during stage 3. In one aspect, a gamma secretase inhibitor, preferably RO44929097 or DAPT, is used in the culture system to induce expression of endocrine gene expression after production of PEC, or preferably during stages 5, 6 and/or 7.

An in vitro cell culture comprising endocrine cells wherein at least 5% of said human cells express an endocrine marker selected from the group consisting of, insulin (INS), NK6 homeobox 1(NKX6.1), pancreatic and duodenal homeobox 1 (PDX1), transcription factor related locus 2 (NKX2.2), paired box 4 (PAX4), neurogenic differentiation 1 (NEUROD), forkhead box A1 (FOXA1), forkhead box A2 (FOXA2), snail family zinc finger 2 (SNAIL2), and musculoaponeurotic fibrosarcoma oncogene family A and B (MAFA and MAFB), and does not substantially express a marker selected from the group consisting of neurogenin 3 (NGN3), islet 1 (ISL1), hepatocyte nuclear factor 6 (HNF6), GATA binding protein 4 (GATA4), GATA binding protein 6 (GATA6), pancreas specific transcription factor 1a (PTF1A) and SRY (sex determining region Y)-9 (SOX9), wherein said endocrine cells are unipotent and can mature to pancreatic beta cells.

It is preferred that the endocrine cells are immature beta cells.

It is preferred that at least 10% of said human cells are immature beta cells.

It is preferred that at least 20% of said human cells are immature beta cells.

It is preferred that at least 50% of said human cells are immature beta cells.

It is preferred that the cells are non-recombinant.

It is preferred that the cells are derived from human pluripotent stem cells selected from a group consisting of human embryonic stem cell (hESC), induced pluripotent stem cells (iPSC), parthenote cells, embryonic carncinoma (EC) cells, mesendoderm cells, definitive endoderm cells, PDX1-1 negative pancreatic foregut endoderm cells, PDX1-positive pancreatic foregut endoderm cells, and pancreatic endoderm cells (PEC).

A method for producing an immature beta cell, said method comprising the steps of: a) contacting a PDX1-negative foregut endoderm cell population with a factor that activates a TGFβ receptor family member, thereby producing PDX1-positive pancreatic endoderm cell population; and b) contacting the PDX-positive pancreatic endoderm cell population with a gamma secretase inhibitor, thereby producing an immature beta cell that expresses INS and NKX6.1

It is preferred that the PDX1-negative foregut endoderm cell population is contacted with a Wnt and Heregulin family member.

It is preferred that the TGFbeta-receptor family member is selected from a group consisting of Activin A, Activin B, Nodal, GDF-8, GDF-10, GDF-11 and GDF15.

It is preferred that the TGFbeta-receptor family member is Actin A, GDF-8 and GDF-11.

It is preferred that the TGFbeta-receptor family member is Activin A.

It is preferred that the Wnt family member is selected from a group consisting of WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16 and WNT3A.

It is preferred that the Wnt family member is Wnt3a.

It is preferred that the Heregulin (HRG) family member is HRG1, HRG 2, HRG 3 and HRG4.

It is preferred that the HRG family member is HRG1 and HRG2.

A method for producing insulin in vivo, said method comprising the steps of: a) contacting a PDX1-negative foregut endoderm cell population with a factor that activates a TGFβ receptor family member, thereby producing PDX1-positive pancreatic endoderm cell population; and b) contacting the PDX-positive pancreatic endoderm cell population with a gamma secretase inhibitor, thereby producing an immature beta cells that express INS and NKX6.1; c) implanting the immature beta cells from step (b); and d) maturing the cells into mature beta cells that secrete insulin in vivo in response to glucose stimulation.

Preferred features and aspects of the invention are as follows.

At stage 7 agents can still modulate gene expression. It is preferred that a member of the FGF superfamily is added at stage 7. It is preferred that FGF2 is added at stage 7. FGF2 may increase SST expression and/or suppress INS, GCG or GHRL expression. It is preferred that BMP is added at stage 7. BMP may increase INS, PDX1 or IDI expression.

An immature beta cell population that gives rise to in vivo function. It is preferred that the immature beta population is CHGA+. It is preferred that the immature beta cell population are capable of functioning in vivo, i.e., when transplanted secrete insulin in response to blood glucose. It is preferred that the endocrine cell population, when transplanted, may develop and mature to functional pancreatic islet cells. It is preferred that the immature beta cell population is enriched for endocrine cells (or depleted of non-endocrine cells). In a preferred embodiment, greater than about 50% of the cells in the immature beta cell population are CHGA+. In a more preferred embodiment greater than about 60% or 70% or 80% or 90% or 95% or 98% or 100% of the cells in the immature beta cell population are CHGA+. In a preferred embodiment less than about 50% of the cells in the immature beta cell population are CHGA−. In a more preferred embodiment less than about 15% of the cells in the immature beta cell population are CHGA−. In a more preferred embodiment less than about 10% or 5% or 3% or 2% or 1% or 0.5% or 0% of the cells in the immature beta cell population are CHGA−. Further, expression of certain markers may be suppressed during production of the immature beta cells such as NGN3 expression during stage 3. It is preferred that the immature beta cell population is singly-hormonal (e.g. INS only). It is preferred that the immature beta cell population co-expresses other cell markers including NKX6.1 and PDX1. It is preferred that the immature beta cell population is both singly-hormonal and co-express other cell markers including NKX6.1 and PDX1. It is preferred that the immature beta cell population has more singly hormone expressing INS cells as a percentage of the total INS population. It is preferred that the immature beta cell population has at least 50% singly hormone expressing INS cells as a percentage of the total INS population. It is preferred that the immature beta cell population is CHGA+/INS+/NKX6.1+(triple positive). In a preferred embodiment greater than about 25% of the cells in the immature beta cell population are CHGA+/INS+/NKX6.1+(triple positive). In a preferred embodiment greater than about 30% or 40% or 50% or 60% or 70% or 80% or 90% or 95% 100% of the cells in the immature beta cell population are CHGA+/INS+/NKX6.1+(triple positive).

An enriched immature beta cell population made by dissociating and re-aggregating the cell aggregates. It is preferred that the enriched immature beta cell population is dissociated and re-aggregated at stage 7. It is preferred that the immature beta cell population is dissociated and re-aggregated at about day 25 day 26, or day 27 or day 28 or day 29 or day 30 or more.

Complex media is important for endocrine cell maintenance. It is preferred that the complex media is CMRL or RPMI. It is preferred that the complex media is used at stage 6 or stage 7 or both stages 6 and 7. CMRL increased endocrine marker expression. RPMI increased endocrine marker expression.

Cryopreservation does not reduce immature beta cell populations at stage 7. Cryopreservation does not reduce CHGA+ expression at stage 7.

Stage 7 cells are NKX6.1 positive. Stage 7 cells are C-peptide positive. Stage 7 cells are NKX6.1 and C-peptide co-positive. Stage 7 cells are singly hormonal. Stage 7 cells singly express INS and GCG.

Disassociation and re-aggregation of stage 7 cells does not affect in vivo function.

Cryopreservation of stage 7 cells does not affect in vivo function.

Stage 7 cells may be cryopreserved and retain their in vivo function.

Increasing glucose concentration increases INS, GCG or SST expression. It is preferred that glucose concentration is increased at stage 6 or stage 7 or both. It is preferred that GHRL expression decreases with increased glucose concentration.

An in vitro immature beta cell that is singly-hormonal (INS only).

An in vitro immature beta cell that co-expresses NKX6.1 and PDX1.

An in vitro immature beta cell that is singly-hormonal (INS only) and co-expresses NKX6.1 and PDX1.

An in vitro immature beta cell that is singly-hormonal (INS only), co-expresses NKX6.1 and PDX1 and can mature in vivo into a cell that can secrete insulin in response to blood glucose.

An in vitro immature beta cell that can mature in vivo into a cell that can secrete insulin in response to blood glucose.

An in vitro immature beta cell that is CHGA+, INS+ and NKX6.1+. It is preferred that greater than 10% of the total in vitro cell population comprises immature beta cells that are CHGA+, INS+ and NKX6.1+. It is immature beta that greater than 50% of the total in vitro cell population comprises immature beta cells that are CHGA+, INS+ and NKX6.1+. It is immature beta that greater than 80% of the total in vitro cell population comprises immature beta cells that are CHGA+, INS+ and NKX6.1+.

Purified immature beta cells. Purified immature beta cell precursors. It is preferred that immature beta cells or beta cell precursors are purified from stage 7 cell populations using a Zinc sensor. It is preferred that dim florescence due to the presence of Py 1 sensor bound to Zinc is enriched for beta cells. It is preferred that bright florescence due to the presence of Py 1 sensor bound to Zinc is enriched for alpha cells. A method for purifying beta cells using a Zinc sensor. A method for purifying alpha cells using a Zinc sensor. Purified alpha cells. Purified alpha cell precursors.

An enriched cell population that expresses markers of the beta cell lineage such as INS, IAPP, PDX1, NKX6.1, PAX4, PCSK1, G6PC2, GCK, or SLC30A8.

An enriched cell population that expresses markers of the alpha cell lineage such as GCG, ARX, or SLC30A8.

An enriched cell population, wherein greater than 50% of the cells are INS positive. It is preferred that the cell population has greater than 90% INS positive cells. In preferred embodiments 50%-99% of the cells are INS positive cells.

A method for producing insulin in vivo comprising: a) obtaining a population of CHGA+ cells in vitro; and b) transplanting the CHGA+ cells thereby producing insulin in vivo.

It is preferred that the CHGA+ cells are dissociated and re-aggregated at stage 7.

It is preferred that the CHGA+ cells express PDX1 and NKX6.1

It is preferred that the CHGA+ cells express INS and NKX6.1.

It is preferred that the CHGA+ cells are cultured in CMRL or RPMI.

It is preferred that the CHGA+ cells are cryopreserved and thawed prior to transplantation.

It is preferred that the CHGA+ cells are cultured in media containing high glucose.

An in vitro endocrine cell that can give rise to a physiologically functional insulin secreting cell in vivo.

An in vitro properly specified immature beta cell that can give rise to a physiologically functional insulin secreting cell in vivo.

It is preferred that the properly specified immature beta cells are dissociated and re-aggregated at stage 7.

It is preferred that the properly specified immature beta cells express PDX1 and NKX6.1

It is preferred that the properly specified immature beta cells express INS and NKX6.1.

It is preferred that the properly specified immature beta cells are cultured in CMRL or RPMI.

It is preferred that the properly specified immature beta cells are cryopreserved and thawed prior to transplantation.

It is preferred that the properly specified immature beta cells are cultured in media containing high glucose.

A method for producing an enriched immature beta cell population in vitro comprising: obtaining a population of CHGA+ cells and sorting. A method for producing an enriched cell population that expresses INS, IAPP, PDX1, NKX6.1 or PAX4 in vitro comprising: obtaining a population of CHGA+ cells and sorting.

A method for producing an enriched alpha cell population in vitro comprising: obtaining a population of CHGA+ cells and sorting.

A method for producing an enriched cell population that expresses GCG or ARX in vitro comprising: obtaining a population of CHGA+ cells and sorting.

It is preferred that enriched populations of alpha or beta cells are sorted using a Py 1 zinc sensor.

In embodiments, the immature beta cells express INS and NKX6.1 and do not express substantially NGN3. In embodiments, the immature beta cells express INS, NKX6.1 and MAFB and do not substantially express NGN3.

BRIEF DESCRIPTION OF THE DRAWINGS

FIGS. 3A-3D are photomicrographs of immunocytochemistry (ICC) of human iPS cell (E2021 using G4 hIPS cell line) cultures from Stage 4 differentiation (PDX1-positive pancreatic endoderm cells) using antibodies specific for (panel A) PDX-1; (panel B) NKX6.1; (panel C) PTF1A; and (panel D) Dapi. See Example 2.

FIGS. 4A-4D are pictures of immunocytochemistry (ICC) of iPS cell cultures (E2021 using G4 hIPS cell line) from Stage 5 differentiation using ligands specific for (panel A) Glucagon; (panel B) Insulin; (panel C) Somatostatin; and (panel D) Dapi. See Example 2.

FIGS. 5A-5B is an array location map and array key provided in the Proteome Profiler™ human phospho-RTK antibody arrays from R&D Systems. The location map in FIG. 5A shows the coordinates or location of the RTK antibodies. The identity or name of the RTK family and antibodies are described in the key, FIG. 5B. The positive signals observed on the developed film can therefore be identified by overlaying a transparency as in FIG. 5A and identifying the signals by referring to the coordinates on the overlay (FIG. 5A) with the name of the RTK in FIG. 5B. See Example 4.

FIGS. 6A-6D are an RTK array analyses of iPS cell-derived pancreatic endoderm cells (PEC) under four different conditions (panels A, B, C and D described in Example 5. Tyrosine phosphorylation of certain RTKs is observed by the identification of high to low-intensity signals. IGF1R/IR and ERBB (EGFR) family members are identified or boxed. See Example 5.

FIG. 7A: Treatment of PDX1-expressing cells with heregulin in vitro improves glucose-stimulated insulin secretion upon transplantation and maturation in vivo. FIG. 7B: Glucose-stimulated C-peptide levels at 23 weeks post-transplant, 3 weeks prior to STZ-induction of mouse diabetes model. Mice implanted with PEC were analyzed at the indicated post-engraftment times for serum levels of human C-peptide at fasting, and 30 min and 60 min after intraperitoneal glucose administration. In FIG. 7C, PEC was encapsulated with cell encapsulation devices (Encaptra® EN20, or EN20, ViaCyte, San Diego, Calif.) and in some instances the devices had micro-perforations (pEN20, ViaCyte, San Diego, Calif.). Such devices have been described in U.S. Pat. No. 8,278,106. See Example 7.

FIG. 8A: shows the blood glucose for each of the 13 mice (baseline with and without Heregulin). FIG. 8B shows the combined average measurements for each treatment (baseline with and without Heregulin). Measurements of random non-fasting blood glucose levels are shown for the 13 mice implanted with iPEC grafts up to 14 days before they were treated with STZ (day 0), and for the same mice after STZ treatment and after the grafts were explanted. STZ-treated animals were given STZ about 26 weeks post graft transplant (day 0). At 28 weeks post graft transplant, approximately 2 weeks after initiation of STZ-treatment, the iPEC grafts were explanted (removed). Nonfasting blood glucose measurements were collected over time for each of the animals. See Example 7.

FIGS. 11A-11G are a photographic images of aggregate suspension cultures at the end of stage 3 (day 8, top panel) and 4 (day 12, bottom panel) using 5 ng/mL (ACT5) or 10 ng/mL (ACT10) of Activin A at stage 3; or 5 ng/mL (ACT5) of Activin at stages 3 and 4. See Example 8.

FIGS. 12A-12J are photographic images of an aggregate suspension cultures during stage 4 (top panel) or at the end of stage 4 (bottom panel). The top panel shows 10 ng/mL of Activin A and 2 ng/mL Heregulin (ACT 10 HGN 2) or 20 ng/mL of Activin A and 2 ng/mL Heregulin (ACT 20 HGN 2), or 20 ng/mL of Activin A and 10 ng/mL Heregulin (ACT 20 HGN 10) or 10 ng/mL of Activin A, 2 ng/mL Heregulin and 50 ng/mL WNT (ACT 10 HGN 2 WNT 50) was added at stage 3. The bottom panel shows 25 ng/mL of Activin A (ACT 25), 50 ng/mL of Activin A (ACT 50), 75 ng/mL of Activin A (ACT 75) or 100 ng/mL of Activin A (ACT 100) was added at stage 3. All conditions received low Activin and Heregulin at stage 4. See Example 9.

FIG. 23A shows a field of cells stained for INS (cytoplasmic) and NKX6.1 (nuclear). FIG. 23B shows the same field of cells stained for INS (cytoplasmic) and PDX1 (nuclear). FIG. 23C shows the same field of cells stained with DAPI. See Example 12.

FIG. 25A is a control with no TT or BMP added, FIG. 25B shows the addition of TT at stage 7, FIG. 25C shows the addition of BMP at stage 7. FIGS. 25A-25C show staining for C-peptide (cytoplasmic) and PDX1 (nuclear).

FIG. 26A is treated with TT and BMP at stages 6 and 7, and FIG. 26B shows the addition of TT and BMP at stage 7. FIGS. 26A and 26B show staining for C-peptide (cytoplasmic) and PDX1 (nuclear).

FIG. 27A is a control with no TT or BMP added, FIG. 27B shows the addition of TT at stage 7, FIG. 27C shows the addition of BMP at stage 7. FIGS. 27A-27C show staining for C-peptide (cytoplasmic) and NKX6.1 (nuclear).

FIG. 28A is treated with TT and BMP at stages 6 and 7, and FIG. 28B shows the addition of TT and BMP at stage 7. FIGS. 28A and 28B show staining for C-peptide (cytoplasmic) and NKX6.1 (nuclear).

FIG. 36C is stained for NKX6.1 (nuclear) and C-peptide (cytoplasmic).

FIG. 37C is stained for NKX6.1 (nuclear) and C-peptide (cytoplasmic).

FIG. 40A shows staining for INS (cytoplasmic) and FIG. 40B for GCG (cytoplasmic).

DETAILED DESCRIPTION OF THE INVENTION

Figure 1:
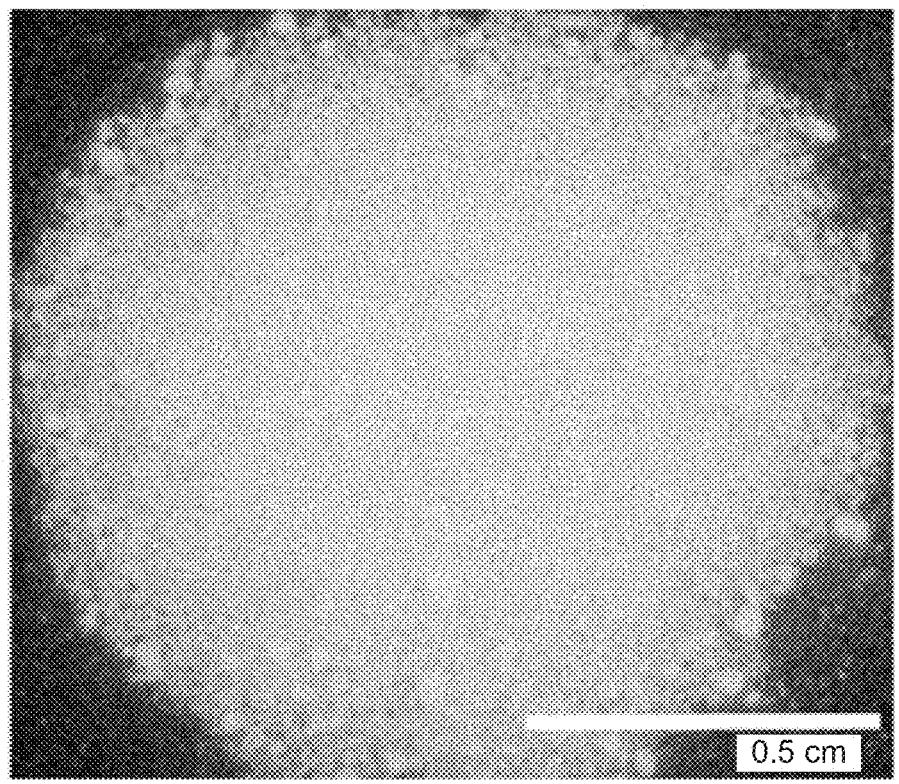
FIG. 1 is a photographic image of an aggregate suspension culture of dedifferentiated reprogrammed cells or, also referred to herein, as iPS cells. See Example 1.

The present invention may be understood more readily by reference to the following detailed description of the preferred embodiments of the invention and the Examples included herein. However, before the present compounds, compositions, and methods are disclosed and described, it is to be understood that this invention is not limited to specific cell types, specific feeder cell layers, specific conditions, or specific methods, etc., and, as such, may vary. Numerous modifications and variations therein will be apparent to those skilled in the art. It is also to be understood that the terminology used herein is for the purpose of describing specific embodiments only and is not intended to be limiting. All patent and non-patent publication references are incorporated herein by reference in their entireties.

Various cell compositions derived from pluripotent stem cells are described herein and can be found in Applicant's U.S. patent application Ser. No. 10/486,408, entitled METHODS FOR CULTURE OF HESC ON FEEDER CELLS, filed Aug. 6, 2002; Ser. No. 11/021,618, entitled DEFINITIVE ENDODERM, filed Dec. 23, 2004; Ser. No. 11/115,868, entitled PDX1 EXPRESSING ENDODERM, filed Apr. 26, 2005; Ser. No. 11/165,305, entitled METHODS FOR IDENTIFYING FACTORS FOR DIFFERENTIATING DEFINITIVE ENDODERM, filed Jun. 23, 2005; Ser. No. 11/573,662, entitled METHODS FOR INCREASING DEFINITIVE ENDODERM DIFFERENTIATION OF PLURIPOTENT HUMAN EMBRYONIC STEM CELLS WITH PI-3 KINASE INHIBITORS, filed Aug. 15, 2005; Ser. No. 12/729,084 entitled PDX1-EXPRESSING DORSAL AND VENTRAL FOREGUT ENDODERM, filed Oct. 27, 2005; Ser. No. 12/093,590, entitled MARKERS OF DEFINITIVE ENDODERM, filed Nov. 14, 2005; Ser. No. 11/993,399, entitled EMBRYONIC STEM CELL CULTURE COMPOSITIONS AND METHODS OF USE THEREOF, filed Jun. 20, 2006; Ser. No. 11/588,693, entitled PDX1-EXPRESSING DORSAL AND VENTRAL FOREGUT ENDODERM, filed Oct. 27, 2006; Ser. No. 11/681,687, entitled ENDOCRINE PROGENITOR/PRECURSOR CELLS, PANCREATIC HORMONE-EXPRESSING CELLS AND METHODS OF PRODUCTION, filed Mar. 2, 2007; Ser. No. 11/807,223, entitled METHODS FOR CULTURE AND PRODUCTION OF SINGLE CELL POPULATIONS OF HESC, filed May 24, 2007; Ser. No. 11/773,944, entitled METHODS OF PRODUCING PANCREATIC HORMONES, filed Jul. 5, 2007; Ser. No. 11/860,494, entitled METHODS FOR INCREASING DEFINITIVE ENDODERM PRODUCTION, filed Sep. 24, 2007; Ser. No. 12/099,759, entitled METHODS OF PRODUCING PANCREATIC HORMONES, filed Apr. 8, 2008; Ser. No. 12/107,020, entitled METHODS FOR PURIFYING ENDODERM AND PANCREATIC ENDODERM CELLS DERIVED FORM HUMAN EMBRYONIC STEM CELLS, filed Apr. 21, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. Nos. 12/765,714 and 13/761,078, both entitled CELL COMPOSITIONS FROM DEDIFFERENTIATED REPROGRAMMED CELLS, filed Apr. 22, 2010 and Feb. 6, 2013; Ser. No. 11/838,054, entitled COMPOSITIONS AND METHODS USEFUL FOR CULTURING DIFFERENTIABLE CELLS, filed Aug. 13, 2007; Ser. No. 12/264,760, entitled STEM CELL AGGREGATE SUSPENSION COMPOSITIONS AND METHODS OF DIFFERENTIATION THEREOF, filed Nov. 4, 2008; Ser. No. 13/259,15, entitled SMALL MOLECULES SUPPORTING PLURIPOTENT CELL GROWTH, filed Apr. 27, 2010; PCT/US11/25628, entitled LOADING SYSTEM FOR AN ENCAPSULATION DEVICE, filed Feb. 21, 2011; Ser. No. 13/992,931, entitled AGENTS AND METHODS FOR INHIBITING PLURIPOTENT STEM CELLS, filed Dec. 28, 2010; and U.S. Design application No. 29/408,366 filed Dec. 12, 2011; 29/408,368 filed Dec. 12, 2011; 29/423,365 filed May 31, 2012; and 29/447,944 filed Mar. 13, 2013; and U.S. Provisional Application No. 61/774,443, entitled SEMIPERMEABLE MACRO IMPLANTABLE CELLULAR ENCAPSULATION DEVICES, filed Mar. 7, 2013; 61/775,480, entitled CRYOPRESERVATION, HIBERNATION AND ROOM TEMPERATURE STORAGE OF ENCAPSULATED PANCREATIC ENDODERM CELL AGGREGATES, filed Mar. 8, 2013; and 61/781,005, entitled IN VITRO DIFFERENTIATION OF PLURIPOTENT STEM CELLS TO PANCREATIC ENDODERM CELLS (PEC) AND ENDOCRINE CELLS, filed Mar. 14, 2013.

Definitions

It will be appreciated that the numerical ranges expressed herein include the endpoints set forth and describe all integers between the endpoints of the stated numerical range.

Unless otherwise noted, the terms used herein are to be understood according to conventional usage by those of ordinary skill in the relevant art. Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The practice of embodiments described herein employs, unless otherwise indicated, conventional techniques of cell biology, molecular biology, genetics, chemistry, microbiology, recombinant DNA, and immunology.

The term "cell" as used herein also refers to individual cells, cell lines, or cultures derived from such cells. A "culture" refers to a composition comprising isolated cells of the same or a different type. "Culture," "population" or "cell population" as used herein can be and are used interchangeably and its meaning will be clear depending on the context. For example, the term "population" can be a cell culture of more than one cell having the same identifying characteristics or it can be a culture of more than one cell types having different identifying characteristics, e.g. a population in one context may be a sub-population in another context. The term "sub-population" refers to a subset of a cell culture or population when used to describe certain cell types within the cell culture or cell population.

As used herein, the phrase "totipotent stem cells" refer to cells having the ability to differentiate into all cells constituting an organism, such as cells that are produced from the fusion of an egg and sperm cell. Cells produced by the first few divisions of the fertilized egg can also be totipotent. These cells can differentiate into embryonic and extraembryonic cell types. Pluripotent stem cells, such as ES cells for example, can give rise to any fetal or adult cell type. However, alone they cannot develop into a fetal or adult animal because they lack the potential to develop extraembryonic tissue. Extraembryonic tissue is, in part, derived from extraembryonic endoderm and can be further classified into parietal endoderm (Reichert's membrane) and visceral endoderm (forms part of the yolk sac). Both parietal and visceral endoderm support developments of the embryo but do not themselves form embryonic structures. There also exist other extraembryonic tissue including extraembryonic mesoderm and extraembryonic ectoderm.

In some embodiments, a "pluripotent cell" is used as the starting material for differentiation to endoderm-lineage, or more particularly, to pancreatic endoderm type cells. As used herein, "pluripotency" or "pluripotent cells" or equivalents thereof refers to cells that are capable of both proliferation in cell culture and differentiation towards a variety of lineage-restricted cell populations that exhibit multipotent properties, for example, both pluripotent ES cells and induced pluripotent stem (iPS) cells can give rise to each of the three embryonic cell lineages. Pluripotent cells, however, are not capable of producing an entire organism. That is, pluripotent cells are not totipotent.

In certain embodiments, the pluripotent cells used as starting material are stem cells, including hES cells, hEG cells, iPS cells, even parthenogenic cells and the like. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. Still in another embodiment, pluripotent cells are not derived or are not immediately derived from embryos, for example, iPS cells are derived from a non-pluripotent cell, e.g., a multipotent cell or terminally differentiated cell. Human pluripotent stem cell lines used herein include hESC and iPSC, e.g., CyT49, CyT25, CyT203, CyT212, BG01, BG02, BG03, or any of those listed in Table 4 and 5, or any now known or publically available or later made.

Human pluripotent stem cells can also be defined or characterized by the presence of several transcription factors and cell surface proteins including transcription factors Oct-4, Nanog, and Sox-2, which form the core regulatory complex ensuring the suppression of genes that lead to differentiation and the maintenance of pluripotency; and cell surface antigens, such as the glycolipids SSEA3, SSEA4 and the keratin sulfate antigens, Tra-1-60 and Tra-1-81, and alkaline phosphatase.

As used herein, the phrase "induced pluripotent stem cells," or "iPS cells" or "iPSCs", refer to a type of pluripotent stem cell artificially prepared from a non-pluripotent cell, typically an adult somatic cell, or terminally differentiated cell, such as a fibroblast, a hematopoietic cell, a myocyte, a neuron, an epidermal cell, or the like, by inserting certain genes or gene products, referred to as reprogramming factors. See Takahashi et al., Cell 131:861-872 (2007); Wernig et al., Nature 448:318-324 (2007); Park et al., Nature 451:141-146 (2008). These and later known methods for making iPSC are well known and how iPSC are derived or produced is not limiting to the invention herein. Induced pluripotent stem cells are substantially similar to natural human pluripotent stem cells, such as hES cells, in many respects including, the expression of certain stem cell genes and proteins, chromatin methylation patterns, doubling time, embryoid body formation, teratoma formation, viable chimera formation, and potency and differentiability. Human iPS cells provide a source of pluripotent stem cells without the associated use of embryos.

As used herein, the term "reprogramming", "reprogrammed" or equivalents thereof, refers to a process that confers on a cell a measurably increased capacity to form progeny of at least one new cell type, either in culture or in vivo, than it would have under the same conditions without reprogramming. In certain embodiments described herein, somatic cells are "reprogrammed" to pluripotent cells. In certain aspects, somatic cells are reprogrammed when after sufficient proliferation, a measurable proportion of cells, either in vivo or in an in vitro cell culture, display phenotypic characteristics of the new pluripotent cell type. Without reprogramming, such somatic cells would not give rise to progeny displaying phenotypic characteristics of the new pluripotent cell type. If, even without reprogramming, somatic cells could give rise to progeny displaying phenotypic characteristics of the new pluripotent cell type, the proportion of progeny from these somatic cells displaying phenotypic characteristics of the new pluripotent cell type is measurably more than before reprogramming.

As used herein, the phrase "differentiation programming" refers to a process that changes a cell to form progeny of at least one new cell type with a new differentiation status, either in culture or in vivo, than it would have under the same conditions without differentiation reprogramming. This process includes differentiation, dedifferentiation and transdifferentiation. Hence, as used herein, the phrase "differentiation" refers to the process by which a less specialized cell becomes a more specialized cell type. In contrast, the phrase "dedifferentiation" refers to a cellular process in which a partially or terminally differentiated cell reverts to an earlier developmental stage, such as cell having pluripotency or multipotency. In further contrast, the phrase "transdifferentiation" refers to a process of transforming one differentiated cell type into another differentiated cell type.

As used herein, "multipotency" or "multipotent cell" or equivalents thereof refers to a cell type that can give rise to a limited number of other particular cell types. That is, multipotent cells are committed to one or more embryonic cell fates, and thus, in contrast to pluripotent cells, cannot give rise to each of the three embryonic cell lineages as well as to extraembryonic cells. Multipotent somatic cells are more differentiated relative to pluripotent cells, but are not terminally differentiated. Pluripotent cells therefore have a higher potency than multipotent cells. Potency-determining factors that can reprogram somatic cells or used to generate iPS cells include, but are not limited to, factors such as Oct-4, Sox2, FoxD3, UTF1, Stella, Rex1, ZNF206, Sox15, Myb12, Lin28, Nanog, DPPA2, ESG1, Otx2 or combinations thereof.

As used herein, "unipotent" or "unipotentcy" or "unipotent cell" or equivalents thereof, refers to a cell type that can give rise to only one other lineage cell. For example, immature beta cells as described herein have the capacity to differentiate into only insulin beta cells and do not have the potential to differentiate into glucagon (alpha) cells, somatostatin (delta) cells and pancreatic polypeptide (gamma) cells for example. In contrast, endocrine precursor cells, PDX1-positive pancreatic endoderm cells, definitive endoderm cells, or mesendoderm cells, and hES cells are all multipotent or pluripotent (hESC) cells which can give rise to each of the pancreatic alpha, beta, delta and gamma islet cells. Similarly, pancreatic alpha, beta, delta and gamma islet cells are lineage cells of endocrine precursor cells, PDX1-positive pancreatic endoderm cells, definitive endoderm cells, or mesendoderm cells, and hES cells.

As used herein, "singly hormonal" and "polyhormonal" cells refers to cells that express only one hormone (e.g. immature beta cells and beta cells express only insulin protein, and not glucagon or somatostatin protein), or express more than one or multiple hormones (e.g. endocrine precursors or progenitor cells have subpopulations of cells that express 2, 3 or 4 or more hormones on the same cell). As used herein, "ERBB receptor tyrosine kinase activating agent" includes, but is not limited to, at least 16 different EGF family ligands that bind ERBB receptors: EGF (epidermal growth factor), AG or AREG (Amphiregulin), and TGF-Alpha (Transforming Growth Factor-Alpha), Btc (Betacellulin), HBEGF (Heparin-Binding EGF), and Ereg (Epiregulin), Neuregulins (or Heregulins) such as Neuregulin-1, -2, -3 and -4 (or Heregulin-1, -2, -3 and -4). However, the instant invention contemplates any ligand that is capable of binding to any one of the four ERBB receptors or a combination thereof to induce formation of homo- and heterodimer receptor complexes leading to activation of the intrinsic kinase domain and subsequent phosphorylation. See also Table 13.

The term "cell lineage" as used herein refers to all of the stages of the development of a cell type, from the earliest precursor cell to a completely mature cell (i.e. a specialized cell). For example, a "definitive endoderm lineage cell" or a "PDX1-negative endoderm lineage cell" or a "PDX1-positive pancreatic endoderm lineage cell" or an "endocrine precursor lineage cell" or an "endocrine lineage cell" or an "immature beta lineage cell" and the like refer to cells derived from or differentiated from a definitive endoderm cell, a PDX1-negative endoderm cell, a PDX1-positive pancreatic endoderm cell and the like. A definitive endoderm cell is a lineage of a mesendoderm cell, one of its precursors. A PDX-1 positive pancreatic endoderm cell is a lineage of a definitive endoderm cell, one of its precursors. An endocrine precursor in lineage of a PDX1-positive pancreatic cell, a definitive endoderm cell and a mesendoderm cell, all are its precursors. An immature beta cell in a lineage of an endocrine precursor cell, PDX1-positive pancreatic cell, a definitive endoderm cell and a mesendoderm cell, all are its precursors. A beta cell is the only lineage for example of an immature beta cell. Yet, all the endoderm lineage cells described herein are hES lineage cells.

A "precursor cell" or "progenitor cell" as used herein, in general, can be any cell in a cell differentiation pathway that is capable of differentiating into a more mature cell. As such, a precursor cell can be a pluripotent cell, or it can be a partially differentiated multipotent cell, or reversibly differentiated cell. The term "precursor cell population" refers to a group of cells capable of developing into a more mature or differentiated cell type. A precursor cell population can comprise cells that are pluripotent, cells that are stem cell lineage restricted (i.e. cells capable of developing into less than all ectodermal lineages, or into, for example, only cells of neuronal lineage), and cells that are reversibly stem cell lineage restricted. Therefore, the term "progenitor cell" or "precursor cell" may be a "pluripotent cell" or "multipotent cell."

An "endocrine progenitor/precursor cell" as used herein refers to a multipotent cell of the definitive endoderm lineage that expresses at least a marker from the list consisting of neurogenin 3 (NEUROG3), PDX1, PTF1A, SOX9, NKX6.1, HNF1b, GATA4, HNF6, FOXA1, FOXA2, GATA6, MYT1, ISLET1, NEUROD, SNAIL2, MNX1, IA1, RFX6, PAX4, PAX6, NKX2.2, MAFA and MAFB which can further differentiate into cells of the endocrine system including, but not limited to, pancreatic islet hormone-expressing cells. Endocrine progenitor/precursor cells cannot differentiate into as many different cell, tissue and/or organ types as compared to less specifically differentiated definitive endoderm lineage cells, such as PDX1-positive pancreatic endoderm cells or definitive endoderm cells or mesendoderm cells. Endocrine progenitor/precursor cells are described in detail in at least Applicant's U.S. Pat. No. 8,129,182.

As used herein, the terms "develop from pluripotent cells", "differentiate from pluripotent cells", "mature from pluripotent cells" or "produced from pluripotent cells", "derived from pluripotent cells", "differentiated from pluripotent cells" and equivalent expressions refer to the production of a differentiated cell type from pluripotent cells in vitro or in vivo, e.g., in the case of endocrine cells matured from transplanted PDX1 pancreatic endoderm cells in vivo as described in International Patent Application No. PCT/US2007/015536, entitled METHODS OF PRODUCING PANCREATIC HORMONES. All such terms refer to the progression of a cell from the stage of having the potential to differentiate into at least two different cellular lineages to becoming a specialized and terminally differentiated cell. Such terms can be used interchangeably for the purposes of the present application. Embodiments described herein contemplate culture conditions that permit such differentiation to be reversible, such that pluripotency or at least the ability to differentiate into more than one cellular lineage can be selectively regained.

The term "feeder cell" refers to a culture of cells that grows in vitro and secretes at least one factor into the culture medium, and that can be used to support the growth of another cell of interest in culture. As used herein, a "feeder cell layer" can be used interchangeably with the term "feeder cell." A feeder cell can comprise a monolayer, where the feeder cells cover the surface of the culture dish with a complete layer before growing on top of each other, or can comprise clusters of cells. In a preferred embodiment, the feeder cell comprises an adherent monolayer.

Similarly, embodiments in which pluripotent cell cultures or aggregate pluripotent suspension cultures are grown in defined conditions or culture systems without the use of feeder cells are "feeder-free". Feeder-free culture methods increase scalability and reproducibility of pluripotent cell culture and reduces the risk of contamination, for example, by infectious agents from the feeder cells or other animal-sourced culture components. Feeder-free methods are also described in U.S. Pat. No. 6,800,480 to Bodnar et al. (assigned to Geron Corporation, Menlo Park, Calif.). However, and in contrast to U.S. Pat. No. 6,800,480 patent, embodiments described herein, whether they be pluripotent, multipotent or differentiated cell cultures, are feeder-free and do not further contain an endogenous or exogenous extracellular-matrix; i.e. the cultures described herein are extracellular-matrix-free as well as being feeder free. For example, in the U.S. Pat. No. 6,800,480, extracellular matrix is prepared by culturing fibroblasts, lysing the fibroblasts in situ, and then washing what remains after lysis. Alternatively, in U.S. Pat. No. 6,800,480 extracellular matrix can also be prepared from an isolated matrix component or a combination of components selected from collagen, placental matrix, fibronectin, laminin, merosin, tenascin, heparin sulfate, chondroitin sulfate, dermatan sulfate, aggrecan, biglycan, thrombospondin, vitronectin, and decorin. Embodiments described herein neither produce an extracellular-matrix by growth of a feeder or fibroblast layer and lysing the cells to produce the extracellular-matrix; nor does it require first coating the tissue culture vessel with extracellular matrix component or a combination of extracellular-matrix components selected from collagen, placental matrix, fibronectin, laminin, merosin, tenascin, heparin sulfate, chondroitin sulfate, dermatan sulfate, aggrecan, biglycan, thrombospondin, vitronectin, and decorin. Hence, the aggregate suspension cultures described herein for pluripotent, multipotent and differentiated cells do not require a feeder layer, a lysed feeder or fibroblast cell to produce an extracellular matrix coating, an exogenously added extracellular matrix or matrix component; rather use of soluble human serum component as described in International Application PCT/US2008/080516, titled METHODS AND COMPOSITIONS FOR FEEDER-FREE PLURIPOTENT STEM CELL MEDIA CONTAINING HUMAN SERUM, overcomes the need for either a feeder-cell or feeder monolayer, as well as overcoming the need for an endogenous extracellular-matrix from a feeder or fibroblast cell or from exogenously added extracellular-matrix components.

As used herein, the terms "cluster" and "clump" or "aggregate" can be used interchangeably, and generally refer to a group of cells that have not been dissociated into single cells and then aggregated to form clusters or, have close cell-to-cell contact. The term "re-aggregated" as used herein refers to when clusters, clumps and/or aggregates are dissociated into smaller clusters, clumps and/or aggregates or single cells and then form new cell-to-cell contacts by re-aggregating into clusters, clumps and/or aggregates. This dissociation is typically manual in nature (such as using a Pasteur pipette), but other means of dissociation are contemplated. Aggregate suspension pluripotent or multipotent cell cultures are substantially as described in International Publications PCT/US2007/062755, titled COMPOSITIONS AND METHODS FOR CULTURING DIFFERENTIAL CELLS and PCT/US2008/082356, titled STEM CELL AGGREGATE SUSPENSION COMPOSITIONS AND METHODS OF DIFFERENTIATION THEREOF.

The term, "single cell suspension" or equivalents thereof refers to a pluripotent, multipotent or terminally differentiated single cell suspension, or a single cell suspension derived from a pluripotent or multipotent cell, by any mechanical or chemical means. Several methods exist for dissociating cell clusters to form single cell suspensions from primary tissues, attached cells in culture, and aggregates, e.g., physical forces (mechanical dissociation such as cell scraper, trituration through a narrow bore pipette, fine needle aspiration, vortex disaggregation and forced filtration through a fine nylon or stainless steel mesh), enzymes (enzymatic dissociation such as trypsin, collagenase, Accutase™ and the like), or a combination of both. Further, methods and culture media conditions capable of supporting single-cell dissociation of pluripotent, multipotent or differentiated cells are useful for expansion, cell sorting, and defined seeding for multi-well plate assays and enable automatization of culture procedures and clonal expansion.

In preferred embodiments, culturing methods or culturing systems are free of animal-sourced products. In another preferred embodiment, the culturing methods are xeno-free. In even more preferred embodiments, one or more conditions or requirements for the commercial manufacture of human cell therapeutics met or exceeded by the culturing methods described herein.

The population of pluripotent cells can be further cultured in the presence of certain supplemental growth factors to obtain a population of cells that are or will develop into different cellular lineages, or can be selectively reversed in order to be able to develop into different cellular lineages. The term "supplemental growth factor" is used in its broadest context and refers to a substance that is effective to promote the growth of a pluripotent cell, maintain the survival of a cell, stimulate the differentiation of a cell, and/or stimulate reversal of the differentiation of a cell. Further, a supplemental growth factor may be a substance that is secreted by a feeder cell into its media. Such substances include, but are not limited to, cytokines, chemokines, small molecules, neutralizing antibodies, and proteins. Growth factors may also include intercellular signaling polypeptides, which control the development and maintenance of cells as well as the form and function of tissues. In preferred embodiments, the supplemental growth factor is selected from the group comprising steel cell factor (SCF), oncostatin M (OSM), ciliary neurotrophic factor (CNTF), Interleukin-6 (IL-6) in combination with soluble Interleukin-6 Receptor (IL-6R), a fibroblast growth factor (FGF), a bone morphogenetic protein (BMP), tumor necrosis factor (TNF), and granulocyte macrophage colony stimulating factor (GM-CSF).

In certain processes for producing the cells as described herein, the growth factors are removed from the cell culture or cell population subsequent to their addition. For example, the growth factor, such as Activin A, Activin B, GDF-8, or GDF-11 can be added and removed within about one day, about two days, about three days, about four days, about five days, about six days, about seven days, about eight days, about nine days or about ten days after their addition. In some embodiments, the differentiation factors are not removed from the cell culture per se but their omission from the cell culture medium is a means of removal, e.g. change of a cell culture media that contained Activin to one that does not contain Activin.

Because the efficiency of the differentiation process can be adjusted by modifying certain parameters, which include but are not limited to, cell growth conditions, growth factor concentrations and the timing of culture steps, the differentiation procedures described herein can result in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or greater than about 95% conversion of pluripotent cells, which includes induced pluripotent cells, to multipotent or differentiated cells e.g., definitive endoderm. Moreover, conversion rate or efficiency rate can also refer to differentiation of one type of multipotent cell to a further differentiated multipotent cell, e.g., definitive endoderm to foregut endoderm, PDX1-positive foregut endoderm, PDX1-positive pancreatic endoderm or PDX1/NKX6.1 co-positive pancreatic endoderm, endocrine progenitor/precursor or NGN3/NKX2.2 co-positive endocrine progenitor/precursor, and hormone secreting endocrine cells or INS, GCG, GHRL, SST, PP singly-positive endocrine cells. In processes in which isolation of preprimitive streak or mesendoderm cells is employed, a substantially pure preprimitive streak or mesendoderm cell population can be recovered.

General methods for production of endoderm lineage cells derived from hES cells are described in related U.S. applications as indicated above, and D'Amour et al. 2005 *Nat Biotechnol.* 23:1534-41, published online Oct. 28, 2005; D'Amour et al. 2006 *Nat Biotechnol.* 24(11):1392-401, published online Oct. 19, 2006; Kroon et al. (2008) *Nat Biotechnol.* 26 (4):443-452, published online Feb. 20, 2008; Kelly et al. (2011) *Nat. Biotechnol.* 29(8):750-6, published online Jul. 31, 2011; and Schulz et al. (2012) PLosOne, 7(5): e37004, published online May 18, 2012. D'Amour et al. describe a 5 step differentiation protocol: stage 1 (results in mostly definitive endoderm production), stage 2 (results in mostly PDX1-negative foregut endoderm production), stage 3 (results in mostly PDX1-positive foregut endoderm production), stage 4 (results in mostly pancreatic endoderm or pancreatic endocrine progenitor production) and stage 5 (results in mostly hormone expressing endocrine cell production).

The term "trophectoderm" refers to a multipotent cell having the relative high expression of markers selected from the group comprising HAND1, Eomes, MASH2, ESXL1, HCG, KRT18, PSG3, SFXN5, DLX3, PSX1, ETS2, and ERBB genes as compared to the expression levels of HAND1, Eomes, MASH2, ESXL1, HCG, KRT18, PSG3, SFXN5, DLX3, PSX1, ETS2, and ERBB in non-trophectoderm cells or cell populations.

The term "extraembryonic endoderm" refers to a multipotent cell having relative high expression levels of markers selected from the group comprising SOX7, SOX17, THBD, SPARC, DAB1, or AFP genes as compared to the expression levels of SOX7, SOX17, THBD, SPARC, DAB1, or AFP in non-extraembryonic endoderm cells or cell populations.

The term "preprimitive streak cells" refers to a multipotent cell having relative high expression levels of the FGF8 and/or NODAL marker genes, as compared to BRACHURY low, FGF4 low, SNAI1 low, SOX17 low, FOXA2 low, SOX7 low and SOX1 low.

The term "mesendoderm cell" refers to a multipotent cell having relative high expression levels of brachyury, FGF4, SNAI1 MIXL1 and/or WNT3 marker genes, as compared to SOX17 low, CXCR4 low, FOXA2 low, SOX7 low and SOX1 low.

The term "definitive endoderm (DE)" refers to a multipotent endoderm lineage cell that can differentiate into cells of the gut tube or organs derived from the gut tube. In accordance with certain embodiments, the definitive endoderm cells are mammalian cells, and in a preferred embodiment, the definitive endoderm cells are human cells. In some embodiments of the present invention, definitive endoderm cells express or fail to significantly express certain markers. In some embodiments, one or more markers selected from SOX17, CXCR4, MIXL1, GATA4, HNF3β, GSC, FGF17, VWF, CALOR, FOXQ1, CMKOR1 and CRIP1 are expressed in definitive endoderm cells. In other embodiments, one or more markers selected from OCT4, alpha-fetoprotein (AFP), Thrombomodulin™, SPARC, SOX7 and HNF4alpha are not expressed or significantly expressed in definitive endoderm cells. Definitive endoderm cell populations and methods of production thereof are also described in U.S. application Ser. No. 11/021,618, entitled DEFINITIVE ENDODERM, filed Dec. 23, 2004.

The term "PDX1-negative foregut endoderm cells" or "foregut endoderm cells" or equivalents thereof are cells that express SOX17, HNF1β (HNF1B), HNF4alpha (HNF4A) and FOXA1 markers but do not substantially express PDX1, AFP, SOX7, or SOX1. PDX1-negative foregut endoderm cell populations and methods of production thereof are also described in U.S. application Ser. No. 11/588,693, entitled PDX1-expressing dorsal and ventral foregut endoderm, filed Oct. 27, 2006.

The term "PDX1-positive, dorsally-biased, foregut endoderm cells" (dorsal PDX1-positive foregut endoderm cells) or just "PDX1-positive endoderm" or equivalents thereof are cells that express one or more markers selected from Table 1 and/or one or more markers selected from Table 2, also described in related U.S. application Ser. No. 11/588,693 entitled PDX1 EXPRESSING DOSAL AND VENTRAL FOREGUT ENDODERM, filed Oct. 27, 2006, and also U.S. application Ser. No. 11/115,868, entitled PDX1-expressing endoderm, filed Apr. 26, 2005.

TABLE 1

Markers expressed in both dorsal and ventral PDX1-positive foregut endoderm

| Gene_Symbol | Unigene | LocusLink | OMIM | SeqDerivedFrom | Gene Descriptor |
|---|---|---|---|---|---|
| ANXA4 | Hs.422986 | 307 | 106491 | NM_001153 | annexin A4 |
| ASCL1 | Hs.524672 | 429 | 100790 | BC001638 | achaete-scute complex-like 1 (*Drosophila*) |
| BNC1 | Hs.459153 | 646 | 601930 | NM_001717 | basonuclin 1 |
| C10orf30 | Hs.498740 | 222389 | | AW195407 | Chromosome 10 open reading frame 30 |
| C2orf23 | Hs.368884 | 65055 | 609139 | BE535746 | chromosome 2 open reading frame 23 |
| C9orf150 | Hs.445356 | 286343 | | AI972386 | chromosome 9 open reading frame 150 |
| CDH6 | Hs.171054 | 1004 | 603007 | BC000019 | cadherin 6, type 2, K-cadherin (fetal kidney) |
| DACH1 | Hs.129452 | 1602 | 603803 | AI650353 | dachshund homolog 1 (*Drosophila*) |
| DUSP9 | Hs.144879 | 1852 | 300134 | NM_001395 | dual specificity phosphatase 9 |
| ELMOD1 | Hs.495779 | 55531 | | AL359601 | ELMO domain containing 1 |

TABLE 1-continued

Markers expressed in both dorsal and ventral PDX1-positive foregut endoderm

| Gene_Symbol | Unigene | LocusLink | OMIM | SeqDerivedFrom | Gene Descriptor |
|---|---|---|---|---|---|
| FLJ21462 fis | Hs.24321 | | | AW236803 | cDNA clone IMAGE: 5273964, partial cds |
| FLJ22761 | Hs.522988 | 80201 | | W81116 | hypothetical protein FLJ22761 |
| GABRA2 | Hs.116250 | 2555 | 137140 | NM_000807 | gamma-aminobutyric acid (GABA) A receptor, alpha 2 |
| GRIA3 | Hs.377070 | 2892 | 305915 | BC032004 | glutamate receptor, ionotrophic, AMPA 3 |
| HNF4G | Hs.241529 | 3174 | 605966 | AI916600 | hepatocyte nuclear factor 4, gamma |
| IDH2 | Hs.513141 | 3418 | 147650 | U52144 | isocitrate dehydrogenase 2 (NADP+), mitochondrial |
| IL6R | Hs.135087 | 3570 | 147880 | AV700030 | interleukin 6 receptor |
| KCNJ2 | Hs.1547 | 3759 | 170390 | AF153820 | potassium inwardly-rectifying channel, subfamily J, member 2 |
| KLF3 | Hs.298658 | 51274 | | AA130132 | Kruppel-like factor 3 (basic) |
| LGALS3 | Hs.531081 | 3958 | 153619 | AW085690 | Lectin, galactoside-binding, soluble, 3 (galectin 3) |
| LGALS3 /// GALIG | Hs.531081 | 3958/// | 153619 | BC001120 | lectin, galactoside-binding, soluble, 3 (galectin 3) /// galectin-3 internal gene |
| LIPC | Hs.188630 | 3990 | 151670 | NM_000236 | lipase, hepatic |
| MEIS1 | Hs.526754 | 4211 | 601739 | NM_002398 | Meis1, myeloid ecotropic viral integration site 1 homolog (mouse) |
| NR2F1 | Hs.519445 | 7025 | 132890 | AI951185 | Nuclear receptor subfamily 2, group F, member 1 |
| ONECUT2 | Hs.194725 | 9480 | 604894 | NM_004852 | one cut domain, family member 2 |
| PAPPA | Hs.494928 | 5069 | 176385 | AA148534 | pregnancy-associated plasma protein A, pappalysin 1 |
| PDE3B | Hs.445711 | 5140 | 602047 | NM_000753 | phosphodiesterase 3B, cGMP-inhibited |
| PGPEP1 | Hs.131776 | 54858 | | NM_017712 | pyroglutamyl-peptidase I |
| PMS2L1 | Hs.520575 | 5379 | 605038 | D38503 | postmeiotic segregation increased 2-like 1 |
| SERPINF2 | Hs.159509 | 5345 | 262850 | NM_000934 | serine (or cysteine) proteinase inhibitor, clade F (alpha-2 antiplasmin, pigment epithelium derived factor), member 2 |
| SLC27A2 | Hs.11729 | 11001 | 603247 | NM_003645 | solute carrier family 27 (fatty acid transporter), member 2 |
| SLN | Hs.334629 | 6588 | 602203 | NM_003063 | Sarcolipin |
| SOX9 | Hs.2316 | 6662 | 114290 | NM_000346 | SRY (sex determining region Y)-box 9 (campomelic dysplasia, autosomal sex-reversal) |
| SULT2A1 | Hs.515835 | 6822 | 125263 | U08024 | sulfotransferase family, cytosolic, 2A, dehydro- |

TABLE 1-continued

| Markers expressed in both dorsal and ventral PDX1-positive foregut endoderm | | | | | |
|---|---|---|---|---|---|
| Gene_Symbol | Unigene | LocusLink | OMIM | SeqDerivedFrom | Gene Descriptor |
| TFPI | Hs.516578 | 7035 | 152310 | BF511231 | epiandrosterone (DHEA)-preferring, member 1 Tissue factor pathway inhibitor (lipoprotein-associated coagulation inhibitor) |
| ZHX1 | Hs.521264 | 11244 | 604764 | AI123518 | zinc fingers and homeoboxes 1 |
| ZNF467 | Hs.112158 | 168544 | | BE549732 | zinc finger protein 467 |
| ZNF503 | Hs.195710 | 84858 | | AA603467 | zinc finger protein 503 |
| | Hs.142869 | | | AI935586 | Transcribed locus |

TABLE 2

| Markers expressed in dorsally-biased PDX1-positive foregut endoderm. | | | | | |
|---|---|---|---|---|---|
| Gene_Symbol | Unigene | LocusLink | OMIM | SeqDerived From | Gene Descriptor |
| ADORA2A | Hs.197029 | 135 | 102776 | NM_000675 | adenosine A2a receptor |
| AMSH-LP | Hs.16229 | 57559 | | AI638611 | associated molecule with the SH3 domain of STAM (AMSH) like protein |
| BAIAP2L1 | Hs.489237 | 55971 | | AA628400 | BAI1-associated protein 2-like 1 |
| CD47 | Hs.446414 | 961 | 601028 | BG230614 | CD47 antigen (Rh-related antigen, integrin-associated signal transducer) |
| CHN2 | Hs.203663 | 1124 | 602857 | AK026415 | Chimerin (chimaerin) 2 |
| CLDN3 | Hs.25640 | 1365 | 602910 | BE791251 | claudin 3 |
| CPVL | Hs.233389 | 54504 | | NM_031311 | carboxypeptidase, vitellogenic-like carboxypeptidase, vitellogenic-like |
| CREB3L1 | Hs.405961 | 90993 | | AF055009 | cAMP responsive element binding protein 3-like 1 |
| DACT1 | Hs.48950 | 51339 | 607861 | NM_016651 | dapper homolog 1, antagonist of β-catenin (*xenopus*) |
| DPP6 | Hs.490684 | 1804 | 126141 | AW071705 | Dipeptidylpeptidase 6 |
| ELF3 | Hs.67928 | 1999 | 602191 | AF017307 | E74-like factor 3 (ets domain transcription factor, epithelial-specific) |
| ENPP2 | Hs.190977 | 5168 | 601060 | L35594 | ectonucleotide pyrophosphatase/ phosphodiesterase 2 (autotaxin) |
| EPB41L1 | Hs.437422 | 2036 | 602879 | AA912711 | erythrocyte membrane protein band 4.1-like 1 |
| FAM46C | Hs.356216 | 54855 | | AL046017 | family with sequence similarity 46, member C |
| FAM49A | Hs.467769 | 81553 | | NM_030797 | family with sequence similarity 49, member A /// family with sequence similarity 49, member A |
| FLJ30596 | Hs.81907 | 133686 | | AI453203 | hypothetical protein FLJ30596 |
| HOXA1 | Hs.67397 | 3198 | 142955 | S79910 | homeo box A1 |
| HOXA3 | Hs.533357 | 3200 | 142954 | AW137982 | homeo box A3 |
| HOXB2 | Hs.514289 | 3212 | 142967 | NM_002145 | homeo box B2 |

TABLE 2-continued

Markers expressed in dorsally-biased PDX1-positive foregut endoderm.

| Gene_Symbol | Unigene | LocusLink | OMIM | SeqDerived From | Gene Descriptor |
|---|---|---|---|---|---|
| LAF4 | Hs.444414 | 3899 | 601464 | AW085505 | Lymphoid nuclear protein related to AF4 |
| LOC283658 | Hs.87194 | 283658 | | AA233912 | hypothetical protein LOC283658 |
| MAF | Hs.134859 | 4094 | 177075 | AF055376 | v-maf musculoaponeurotic fibrosarcoma oncogene homolog (avian) |
| MAG | Hs.515354 | 4099 | 159460 | X98405 | myelin associated glycoprotein |
| MYCPBP | Hs.513817 | 10260 | 600382 | BE268538 | c-myc promoter binding protein |
| NR4A2 | Hs.165258 | 4929 | 168600 / | NM_006186 | nuclear receptor subfamily 4, group A, member 2 |
| NRXN3 | Hs.368307 | 9369 | 600567 | AI129949 | neurexin 3 |
| NSE1 | Hs.260855 | 151354 | | AI601101 | NSE1 |
| PCGF5 | Hs.500512 | 84333 | | AL045882 | polycomb group ring finger 5 |
| PDE11A | Hs.130312 | 50940 | 604961 | AB038041 | phosphodiesterase 11A |
| PDE5A | Hs.370661 | 8654 | 603310 | BF221547 | Phosphodiesterase 5A, cGMP-specific |
| PGA3 | | 5220 | 169710 | AI570199 | pepsinogen 3, group I (pepsinogen A) |
| PLN | Hs.170839 | 5350 | 115200 | NM_002667 | Phospholamban |
| PTGIS | Hs.302085 | 5740 | 145500 | NM_000961 | prostaglandin I2 (prostacyclin) synthas /// prostaglandin I2 (prostacyclin) synthase |
| RARB | Hs.436538 | 5915 | 180220 | NM_000965 | retinoic acid receptor, β |
| RGN | Hs.77854 | 9104 | 300212 | D31815 | regucalcin (senescence marker protein-30) |
| RND1 | Hs.124940 | 27289 | 609038 | U69563 | Rho family GTPase 1 |
| SFRP5 | Hs.279565 | 6425 | 604158 | NM_003015 | secreted frizzled-related protein 5 |
| SGKL | Hs.380877 | 23678 | 607591 | AV690866 | serum/glucocorticoid regulated kinase-like |
| SLC16A10 | Hs.520321 | 117247 | 607550 | N30257 | solute carrier family 16 (monocarboxylic acid transporters), member 10 |
| SLC16A2 | Hs.75317 | 6567 | 300095 | NM_006517 | solute carrier family 16 (monocarboxylic acid transporters), member 2 |
| SLC1A3 | Hs.481918 | 6507 | 600111 | NM_004172 | solute carrier family 1 (glial high affinity glutamate transporter), member 3 |
| SLC30A4 | Hs.162989 | 7782 | 602095 | NM_013309 | solute carrier family 30 (zinc transporter), member 4 |
| SLICK | Hs.420016 | 343450 | | AI732637 | sodium- and chloride-activated ATP-sensitive potassium channel |
| SLITRK4 | Hs.272284 | 139065 | | AL080239 | SLIT and NTRK-like family, member 4 |
| ST8SIA3 | Hs.298923 | 51046 | | NM_015879 | ST8 alpha-N-acetyl-neuraminide alpha-2,8-sialyltransferase 3 |
| WNT5A | Hs.152213 | 7474 | 164975 | AI968085 | wingless-type MMTV integration site family, member 5A /// wingless-type MMTV integration site family, member 5A |
| XPR1 | Hs.227656 | 9213 | 605237 | AF089744 | xenotropic and polytropic retrovirus receptor |
| | Hs.535688 | | | AK001582 | CDNA FLJ10720 fis, clone NT2RP3001116 |

TABLE 2-continued

Markers expressed in dorsally-biased PDX1-positive foregut endoderm.

| Gene_Symbol | Unigene | LocusLink | OMIM | SeqDerived From | Gene Descriptor |
|---|---|---|---|---|---|
| | Hs.127009 | | | AI935541 | Transcribed locus |
| | Hs.4749 | | | AL137310 | CDNA FLJ31660 fis, clone NT2RI2004410 |

The term, "pancreatic endoderm," "pancreatic epithelial," "pancreatic epithelium" (all can be abbreviated "PE"), "pancreatic progenitor," "PDX-1 positive pancreatic endoderm" or equivalents thereof, such as "pancreatic endoderm cells" (PEC), are all precursor or progenitor pancreatic cells. PEC as described herein is a progenitor cell population after stage 4 differentiation (about day 12-14) and includes at least two major distinct populations: i) pancreatic progenitor cells that express PDX1 and NKX6.1 but do not express CHGA (or CHGA negative, CHGA−), or "non-endocrine multipotent progenitor sub-populations (CHGA−)", or "non-endocrine (CHGA−) sub-populations" or "non-endocrine (CHGA−) cells" or equivalents thereof; and ii) polyhormonal endocrine cells that express CHGA (CHGA positive, CHGA+), or "endocrine multipotent progenitor sub-populations (CHGA+)", or "endocrine (CHGA+) sub-populations" or "endocrine (CHGA+) cells" or equivalents thereof. The PEC pancreatic progenitor subpopulation that express PDX1 and NKX6.1 but not CHGA is also referred to as "non-endocrine multipotent pancreatic progenitor sub-population (CHGA−)" or "non-endocrine progenitor sub-population," "non-endocrine (CHGA−) sub-population," "non-endocrine (CHGA−) sub-population," "multipotent progenitor sub-population" and the like. The PEC polyhormonal endocrine cell subpopulation that expresses CHGA is also referred to as "cells committed to the endocrine lineage (CHGA+)," or endocrine cells" or "CHGA+ cells" and the like. Without being bound by theory, the cell population that expresses NKX6.1 but not CHGA is hypothesized to be the more active or therapeutic component of PEC, whereas the population of CHGA-positive polyhormonal endocrine cells is hypothesized to further differentiate and mature in vivo into glucagon-expressing islet cells. See Kelly et al. (2011) Cell-surface markers for the isolation of pancreatic cell types derived from human embryonic stem cells, *Nat Biotechnol.* 29(8):750-756, published online 31 Jul. 2011 and Schulz et al. (2012), A Scalable System for Production of Functional Pancreatic Progenitors from Human Embryonic Stem Cells, PLosOne 7(5): 1-17, e37004.

Still, sometimes, pancreatic endoderm cells are used without reference to PEC as described just above, but to refer to at least stages 3 and 4 type cells in general. The use and meaning will be clear from the context. Pancreatic endoderm derived from pluripotent stem cells, and at least hES and hIPS cells, in this manner are distinguished from other endodermal lineage cell types based on differential or high levels of expression of markers selected from PDX1, NKX6.1, PTF1A, CPA1, cMYC, NGN3, PAX4, ARX and NKX2.2 markers, but do not substantially express genes which are hallmark of pancreatic endocrine cells, for example, CHGA, INS, GCG, GHRL, SST, MAFA, PCSK1 and GLUT1. Additionally, some "endocrine progenitor cells" expressing NGN3 can differentiate into other non-pancreatic structures (e.g., duodenum). Pancreatic endoderm or endocrine progenitor cell populations and methods thereof are also described in U.S. patent application Ser. No. 11/773,944, entitled Methods of producing pancreatic hormones, filed Jul. 5, 2007, and U.S. patent application Ser. No. 12/107,020, entitled METHODS FOR PURIFYING ENDODERM AND PANCREATIC ENDODERM CELLS DERIVED FORM HUMAN EMBRYONIC STEM CELLS, filed Apr. 21, 2008.

The term, "endocrine cell" or "pancreatic islet hormone-expressing cell," "pancreatic endocrine cell," "pancreatic islet cell", "pancreatic islets" or equivalents thereof refer to a cell, which can be polyhormonal or singly-hormonal. The cells can therefore express one or more pancreatic hormones, which have at least some of the functions of a human pancreatic islet cell. Pancreatic islet hormone-expressing cells can be mature or immature and are further differentiated or are further developmentally committed than an endocrine progenitor/precursor type cell from which they are derived.

As used herein the phrase "properly specified endocrine cells" or "stage 7 cultures" or "immature endocrine cells" including "immature beta cells" refers to endocrine cell populations made in vitro which are capable of functioning in vivo, e.g., immature beta cells when transplanted secrete insulin in response to blood glucose. Properly specified endocrine cells or stage 7 cultures may have additional characteristics including the following: When transplanted, properly specified endocrine cells may develop and mature to functional pancreatic islet cells. Properly specified endocrine cells may be enriched for endocrine cells (or depleted of non-endocrine cells). In a preferred embodiment greater than about 50% of the cells in the properly specified endocrine cell population are CHGA+. In a more preferred embodiment greater than about 60% or 70% or 80% or 90% or 95% or 98% or 100% of the cells in the properly specified endocrine cell population are CHGA+. In a preferred embodiment less than about 50% of the cells in the properly specified endocrine cell population are CHGA−. In a more preferred embodiment less than about 15% of the cells in the properly specified endocrine cell population are CHGA−. In a more preferred embodiment less than about 10% or 5% or 3% or 2% or 1% or 0.5% or 0% of the cells in the properly specified endocrine cell population are CHGA−. Further, expression of certain markers may be suppressed in properly specified endocrine cells such as NGN3 expression during stage 3. Properly specified endocrine cells may have increased expression of NGN3 at stage 5. Properly specified endocrine cells may be singly-hormonal (e.g. INS only, GCG only or SST only). Properly specified endocrine cells may co-express other immature endocrine cell markers including NKX6.1 and PDX1. Properly specified endocrine cells may be both singly-hormonal and co-express other immature endocrine cell markers including NKX6.1 and PDX1. Properly specified endocrine cells may have more singly hormone expressing INS cells as a percentage of the total INS population. In a preferred embodiment properly specified endocrine cells have at least 50% singly hormone expressing INS cells as a percentage of the total INS population. Properly specified endocrine cells may be CHGA+/INS+/NKX6.1+ (triple positive). In a preferred embodiment greater than about 25% of the cells in the cell population are CHGA+/INS+/NKX6.1+(triple positive). In a preferred embodiment greater than about 30% or 40% or 50% or 60% or 70% or 80% or 90% or 95% 100% of the cells in the cell population are CHGA+/INS+/NKX6.1+ (triple positive).

The term "immature endocrine cell,", specifically an "immature beta-cell," or equivalents thereof refer to a cell derived from any other endocrine cell precursor including an endocrine progenitor/precursor cell, a pancreatic endoderm (PE) cell, a pancreatic foregut cell, a definitive endoderm cell, a mesendoderm cell or any earlier derived cell later described, that expresses at least a marker selected from the group consisting of INS, NKX6.1, PDX1, NEUROD, MNX1, NKX2.2, MAFA, PAX4, SNAIL2, FOXA1 or FOXA2. Preferably, an immature beta-cell described herein expresses, INS, NKX6.1 and PDX1, and more preferably it co-expresses INS and NKX6.1. The terms "immature endocrine cell," "immature pancreatic hormone-expressing cell," or "immature pancreatic islet" or equivalents thereof refer for example to at least a unipotent immature beta cell, or pre-beta cell as described in FIG. 45, and do not include other immature cells, for example, the terms do not include an immature alpha (glucagon) cell, or an immature delta (somatostatin) cell, or an immature epsilon (ghrelin) cell, or an immature pancreatic polypeptide (PP).

Many stem cell media culture or growth environments are envisioned in the embodiments described herein, including defined media, conditioned media, feeder-free media, serum-free media and the like. As used herein, the term "growth environment" or "milieu" or equivalents thereof is an environment in which undifferentiated or differentiated stem cells (e. g., primate embryonic stem cells) will proliferate in vitro. Features of the environment include the medium in which the cells are cultured, and a supporting structure (such as a substrate on a solid surface) if present. Methods for culturing or maintaining pluripotent cells and/or differentiating pluripotent cells are also described in PCT/US2007/062755 entitled COMPOSITIONS AND METHODS USEFUL FOR CULTURING DIFFERENTIABLE CELLS, filed Feb. 23, 2007; U.S. application Ser. No. 11/993,399, entitled EMBRYONIC STEM CELL CULTURE COMPOSITIONS AND METHODS OF USE THEREOF, filed Dec. 20, 2007; and U.S. application Ser. No. 11/875,057, entitled Methods and compositions for feeder-free pluripotent stem cell media containing human serum, filed Oct. 19, 2007.

The term "essentially" or "substantially" means mostly or a de minimus or a reduced amount of a component or cell present in any cell population or culture, e.g., immature beta cell cultures described herein are "essentially or substantially cells" or are "essentially or substantially immature beta cells expressing INS, NKX6.1 and PDX1 and not essentially or substantially expressing NGN3". Other examples include but not limited to "essentially or "essentially hES cells", "essentially or substantially definitive endoderm cells", "essentially or substantially foregut endoderm cells", "essentially or substantially PDX1-negative foregut endoderm cells", "essentially or substantially PDX1-positive pancreatic endoderm cells", "essentially or substantially pancreatic endocrine precursor cells", "essentially or substantially pancreatic endocrine cells" and the like.

With respect to cells in cell cultures or in cell populations, the term "substantially free of" means that the specified cell type of which the cell culture or cell population is free, is present in an amount of less than about 10%, less than about 9%, less than about 8%, less than about 7%, less than about 6%, less than about 5%, less than about 4%, less than about 3%, less than about 2% or less than about 1% of the total number of cells present in the cell culture or cell population.

The term "reduced serum" or "serum free" or equivalents thereof refers to cell cultures grown in medium containing reduced serum or substantially free of serum or no serum at all. Under certain culture conditions, serum concentrations can range from about 0% (v/v) to about 10% (v/v). For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v) or less than about 10% (v/v). In some processes, preprimitive streak cells are grown without serum or without serum replacement. In still other processes, preprimitive streak cells are grown in the presence of B27. In such processes, the concentration of B27 supplement can range from about 0.1% (v/v) to about 20% (v/v).

In still other processes, cell cultures are grown in the presence of B27. In such processes, the concentration of B27 supplement can range from about 0.1% (v/v) to about 20% (v/v) or in concentrations greater than about 20% (v/v). In certain processes, the concentration of B27 in the medium is about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). Alternatively, the concentration of the added B27 supplement can be measured in terms of multiples of the strength of a commercially available B27 stock solution. For example, B27 is available from Invitrogen (Carlsbad, Calif.) as a 50× stock solution. Addition of a sufficient amount of this stock solution to a sufficient volume of growth medium produces a medium supplemented with the desired amount of B27. For example, the addition of 10 ml of 50× B27 stock solution to 90 ml of growth medium would produce a growth medium supplemented with 5× B27. The concentration of B27 supplement in the medium can be about 0.1×, about 0.2×, about 0.3×, about 0.4×, about 0.5×, about 0.6×, about 0.7×, about 0.8×, about 0.9×, about 1×, about 1.1×, about 1.2×, about 1.3×, about 1.4×, about 1.5×, about 1.6×, about 1.7×, about 1.8×, about 1.9×, about 2×, about 2.5×, about 3×, about 3.5×, about 4×, about 4.5×, about 5×, about 6×, about 7×, about 8×, about 9×, about 10×, about 11×, about 12×, about 13×, about 14×, about 15×, about 16×, about 17×, about 18×, about 19×, about 20× and greater than about 20×.

In still another aspect, where insulin level requirements for differentiation are low, B27 is not employed because B27 contains high levels of insulin. For example, Applicant determined insulin levels in 100× B27 and ITS stocks and 1× working stock solutions of each in RPMI. Insulin levels were determined using a Mercodia Ultrasensitive Insulin ELISA kit according to the manufacturer's instructions. Assays were performed on unopened 100× and 50× B27 and ITS stocks, respectively, both purchased from Life Technologies (Carlsbad, Calif.). The results generated from the assay are shown below in Table 3.

| ITS Stock 100x | | | B27 Stock 50x | | |
|---|---|---|---|---|---|
| μg/L INSULIN | Ave (n = 4) | STDEV | μg/L INSULIN | Ave (n = 4) | STDEV |
| 1090 | 1030 μg/mL | 64 | 167.5 | 160 μg/mL | 7.6 |
| 962 | | | 161.3 | | |
| 1079 | | | 160.4 | | |
| 988 | | | 149.1 | | |

| ITS Stock RPMI | | | B27 1x in RPMI | | |
|---|---|---|---|---|---|
| μg/L INSULIN | Ave (n = 6) | STDEV | μg/L INSULIN | Ave (n = 4) | STDEV |
| 10.12 | 9.88 μg/mL | 0.31 | 2.73 | 2.66 μg/mL | 0.08 |
| 9.56 | | | 2.63 | | |
| 9.94 | | | 2.73 | | |
| 10.27 | | | 2.57 | | |
| 9.88 | | | | | |
| 9.49 | | | | | |

Table 3 shows that about 3 μg/mL and 10 μg/mL of insulin is present in 1×B27 and 1×ITS, respectively. Further, the insulin concentration in the 100× stock of ITS is consistent with the manufacturer's listed insulin concentration. Life Technologies does not provide the insulin concentration for 50× B27 so there is no comparison against the manufacturer's stated insulin levels, however, the above insulin concentration of about 160 μg/mL is accurate based on the accurate measurement of the 100× ITS stock which was performed at the same time and based on McLean et al. (2007) supra which showed that insulin and insulin like growth factor (IGF) both are well-established agonists of PI3-Kinase dependent signaling, suggesting that a PI3-Kinase inhibitor (e.g. LY 294002) would promote definitive endoderm formation by inhibiting effectors of insulin/IGF. See FIGS. 6A and B, specifically SOX17 expression is reduced by 4-fold with 1 μg/mL of insulin. Insulin and/or IGF are present at biologically active levels in various media supplements such as KSR, FCS (fetal calf serum), FBS (fetal bovine serum), B27 and StemPro34 and may inhibit definitive endoderm differentiation under such culture conditions, e.g. Jiang et al. (2007) supra.

As used herein, "exogenous" or "exogenously added," compounds such as agents, components, growth factors, differentiation factors, and the like, in the context of cultures or conditioned media, refers to that which is added to the cultures or media to supplement any compounds or growth factors that may or may not be already be present in the culture or media. For example, in some embodiments, cell cultures and/or cell populations do not include an exogenously-added retinoid.

As used herein, "retinoid" refers to retinol, retinal or retinoic acid as well as derivatives of any of these compounds. In a preferred embodiment, the retinoid is retinoic acid.

The term "FGF family growth factor," "a fibroblast growth factor" or "member of the fibroblast growth factor family" is meant an FGF selected from the group comprising FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23. In some embodiments, "FGF family growth factor," "a fibroblast growth factor" or "member of the fibroblast growth factor family" means any growth factor having homology and/or function similar to a known member of the fibroblast growth factor family.

The term "TGFβ superfamily growth factor" or "TGFβ superfamily ligand" or "TGFβ TGF-beta signaling pathway activator" or equivalents thereof is refers to over 30 structurally related proteins including subfamilies of TGF-beta1, TGF-beta2, TF-beta3, GDF-15, GDF-9, BMP-15, BMP-16, BMP-3, GDF-10, BMP-9, BMP-10, GDF-6, GDF-5, GDF-7, BMP-5, BMP-6, BMP-7, BMP-8, BMP-2, BMP-4, GDF-3, GDF-1, GDF 11, GDF8, Activins betaC, *betaE*, betaA and betaB, BMP-14, GDF-14, MIS, Inhibin alpha, Lefty1, Lefty2, GDNF, Neurteurin, Persephin and Artemin. See Chang et al. (2002) Endocrine Rev. 23(6):787-823. These ligands are typically synthesized as prepropeptides of approximately 400-500 amino acids (aa), and a "TGFβ superfamily growth factor" or "TGFβ superfamily ligand" or "TGFβ TGF-beta signaling pathway activator" or equivalents thereof can be the full-length protein or a proteolytic peptide thereof.

The term, "ERBB ligand" refers to a ligand that binds to any one of ErbB receptors, which in turn may dimerizes with another ErbB receptor, or may function as a monomer, thus activating the tyrosine kinase activity of the ErbB portion monomer or a dimer or a heterodimer receptor. Non-limiting examples of ErbB ligands include Neuregulin-1; splice variants and isoforms of Neuregulin-1, including but not limited to HRG-β, HRG-α, Neu Differentiation Factor (NDF), Acetylcholine Receptor-Inducing Activity (ARIA), Glial Growth Factor 2 (GGF2), and Sensory And Motor Neuron-Derived Factor (SMDF); Neuregulin-2; splice variants and isoforms of Neuregulin-2, including but not limited to NRG2-β; Epiregulin; and Biregulin.

The term, "expression" as used herein refers to the production of a material or substance as well as the level or amount of production of a material or substance. Thus, determining the expression of a specific marker refers to detecting either the relative or absolute amount of the marker that is expressed or simply detecting the presence or absence of the marker.

The term, "marker" as used herein refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule (for example, molecules having a molecular weight of less than 10,000 amu).

For most markers described herein, the official Human Genome Organization (HUGO) gene symbol is provided. Such symbols, which are developed by the HUGO Gene Nomenclature Committee, provide unique abbreviations for each of the named human genes and gene products. These gene symbols are readily recognized and can easily be associated with a corresponding unique human gene and/or protein sequence by those of ordinary skill in the art.

In accordance with the HUGO designations, the following gene symbols are defined as follows: GHRL—ghrelin; IAPP—islet amyloid polypeptide; INS—insulin; GCG—glucagon; ISL1—ISL1 transcription factor; PAX6—paired box gene 6; PAX4—paired box gene 4; NEUROG3—neurogenin 3 (NGN3); NKX2-2—NKX2 transcription factor related, locus 2 (NKX2.2); NKX6-1—NKX6 transcription factor related, locus 1 (NKX6.1); IPF1—insulin promoter factor 1 (PDX1); ONECUT1—one cut domain, family member 1 (HNF6); HLXB9—homeobox B9 (HB9); TCF2—transcription factor 2, hepatic (HNF1b); FOXA1—forkhead box A1; HGF—hepatocyte growth factor; IGF1—insulin-like growth factor 1; POU5F1—POU domain, class 5, transcription factor 1 (OCT4); NANOG—Nanog homeobox; SOX2—SRY (sex determining region Y)-box 2; CDH1—cadherin 1, type 1, E-cadherin (ECAD); T—brachyury homolog (BRACH); FGF4—fibroblast growth factor 4; WNT3—wingless-type MMTV integration site family, member 3; SOX17—SRY (sex determining region Y)-box 17; GSC—goosecoid; CER1—(cerberus 1, cysteine knot superfamily, homolog (CER); CXCR4—chemokine (C-X-C motif) receptor 4; FGF17—fibroblast growth factor 17; FOXA2—forkhead box A2; SOX7—SRY (sex determining region Y)-box 7; SOX1—SRY (sex determining region Y)-box 1; AFP—alpha-fetoprotein; SPARC—secreted protein, acidic, cysteine-rich (osteonectin); and THBD—thrombomodulin (TM), NCAM—neural cell adhesion molecule; SYP—synaptophysin; ZIC1—Zic family member 1; NEF3—neurofilament 3 (NFM); SST—somatostatin; MAFA—v-maf musculoaponeurotic fibrosarcoma oncogene homolog A; MAFB—v-maf musculoaponeurotic fibrosarcoma oncogene homolog B; SYP—synaptophysin; CHGA—chromogranin A (parathyroid secretory protein 1); NGN3—Neurogenin 3, NKX2.2—NK2 Homeobox 2; NKX6.1—NK6 Homeobox 1; ID1—Inhibitor Of DNA Binding 1, GHRL—Ghrelin/Obestatin Prepropeptide, GSK—Glycogen Synthase Kinase, G6PC2—glucose-6-phosphatase, UCN3—urocortin 3, PCSK1—proprotein convertase subtilisin/kexin type 1, SLC30A8—solute carrier family 30 (zinc transporter), member 8, and CADH1—E-Cadherin. The terms fibroblast growth factor 7 (FGF7) and keratinocyte growth factor (KGF) are synonymous.

The progression of pluripotent cells to various multipotent and/or differentiated cells can be monitored by determining the relative expression of genes, or gene markers, characteristic of a specific cell, as compared to the expression of a second or control gene, e.g., housekeeping genes. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest.

Additionally multiplexing assays and/or methodologies are available for analyzing many genes with high sensitivity and efficiency. For example, with at least the nCounter System provided by Nanostring (Seattle, Wash., USA), users can currently analyze the expression levels of up to 800 genes simultaneously, with sensitivity comparable to quantitative PCR systems and with less than 15 minutes of hands-on time per reaction. Hence, total RNA in any of the samples (e.g. stage 4 PEC and stage 7 endocrine progenitor/precursor and endocrine cell cultures, respectively) can be isolated (e.g. in triplicate) using the 6100 nucleic acid extractor (Applied Biosystems; Foster City, Calif., USA); and about 100 ng is required per reaction for quantitation of gene expression using the Nanostring nCounter System. And instead of analog detection, nCounter System uses digital detection whereby each gene transcript is detected by a probe bound to a segment of DNA that is attached to a unique string of colored fluorophores (the molecular barcode). Identification of that transcript therefore depends only on the order of fluors on the string, rather than intensities of the fluors. Secondly, the number of total transcripts in a sample is quantified by counting the total number of times a particular string of fluors (barcode) is detected. Father, this method does not require amplification of the target mRNA, so, the range is the biological range of expression, typically three orders of magnitude. Presently, the System can measure as little as 1.2-fold changes of a single transcript at 20 copies per cell (10 fM) with statistical significance ($p<0.05$). For genes expressed at levels between 0.5 and 20 copies per cell, 1.5-fold differences in expression levels is detectable with the same level of confidence.

In some processes, the higher expression of the following genes as compared to the lower expression of other genes is indicative of certain populations of cells, for example: SOX17, SOX7, AFP or THBD are indicative of extraembryonic endoderm; NODAL and/or FGF8 are indicative of preprimitive streak; brachyury, FGF4, SNAI1 and/or WNT3 are indicative of mesendoderm; CER, GSC, CXCR4, SOX17 and FOXA2 are indicative of definitive endoderm cells; SOX17, FOXA2, FOXA1, HNF1B and HNF4A are indicative of foregut endoderm (or PDX1-negative endoderm); PDX1, HNF6, SOX9 and PROX1 are indicative PDX1-positive endoderm; PDX1, NKX6.1, PTFA1, CPA and cMYC are indicative of pancreatic epithelium (PE or pancreatic progenitor); NGN3, PAX4, ARX and NKX2.2 are indicate of endocrine progenitor/precursor cells; and INS, GCG, GHRL, SST and PP are indicative of the various endocrine cells; relative high MAFA to MAFB gene expression is indicative of insulin secreting endocrine cell; and relative high expression of MAFB to MAFA gene expression is indicative of glucagon secreting endocrine cells. Still in certain figures and drawings only those "signature" or "key" markers typical of that particular cell type of a particular lineage are shown. It is well understood by one of skill in the art, that other markers or genes are expressed but are not shown or described, e.g. genes which are constitutively expressed or are expressed in every or most or the majority of cell types of a certain lineage or all lineages.

Methods for Production of Induced Pluripotent Stem (iPS) Cells

Embodiments described herein are not limited to any one type of iPS cell or any one method of producing the iPS cell. Embodiments are not limited to or dependent on levels of efficiency of production of the iPS cells, because various methods exist. Embodiments described herein apply to differentiation of iPS cells into endoderm-lineage cells and uses thereof.

Studies using certain nuclear reprogramming factors have allowed pluripotent stem cells or pluripotent-like stem cells to be derived from a patient's own somatic cells. These cells are also called induced pluripotent stem (iPS) cells. The present invention describes various iPS cell lines provided by Shinya Yamanaka, Kyoto University. However, other iPS cell lines, for example, those described by James Thomson et al. Al. are by the invention herein. See U.S. Publication 20090047263, International Publication WO2005/80598, U.S. Publication 20080233610 and International Publication WO2008/11882. Thus, as used herein, "induced pluripotent stem (iPS) cells" means cells having properties similar to other pluripotent stem cells, e.g., hES cells, hEG cells, pPS (primate pluripotent stem) cells, parthenogenic cells and the like.

Nuclear programming factors are described in U.S. Publication 20090047263, International Publication WO2005/80598, U.S. Publication 20080233610 and International Publication WO2008/11882 and were used to induce reprogramming of a differentiated cell without using eggs, embryos, or ES cells. Methods for preparing induced iPS cells from somatic cells by using the nuclear reprogramming factor similar to that used and described in the present invention are not particularly limited. In preferred embodiments, the nuclear reprogramming factor contacts the somatic cells under an environment in which the somatic cells and induced pluripotent stem cells can proliferate. An advantage of the certain embodiments described herein is that an induced pluripotent stem cell can be prepared by contacting a nuclear reprogramming factor with a somatic cell in the absence of eggs, embryos, or embryonic stem (ES) cells. By using a nuclear reprogramming factor, the nucleus of a somatic cell can be reprogrammed to obtain an iPS cell or an "ES-like cell."

Pluripotent stem cells described herein, whether it be hES cells or iPS cells, may express any number of pluripotent cell markers, including but not limited to: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; .β.III-tubulin; .alpha.-smooth muscle actin (.alpha.-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4 and the like. It is understood that the present invention is not limited to those markers listed herein, and encompasses markers such as cell surface markers, antigens, and other gene products including ESTs, RNA (including microRNAs and antisense RNA), DNA (including genes and cDNAs), and portions thereof.

In one embodiment, the iPS cell lines used herein contain the following nuclear reprogramming factor genes: an Oct family gene, a Klf family gene, and a Sox family gene. In one iPS cell line, each of the following three kinds of genes are provided: Oct3/4, Klf4, and Sox2. Other iPS cell lines gene products of each of the following three kinds of genes were employed: an Oct family gene, a Klf family gene, and a Myc family gene, e.g., Oct3/4, Klf4 and c-Myc. Accordingly, it is understood that the nuclear reprogramming factor can be with or without the Myc family gene.

The nuclear reprogramming factors described herein and also known in the art, can be used to generate iPS cells from differentiated adult somatic cells, and is not limited by the type of somatic cells to be reprogrammed, i.e., any kind of somatic cell may be reprogrammed or dedifferentiated. Because reprogramming a somatic does not require an egg and/or embryo, an iPS cell can be a mammalian cell, therefore, providing an opportunity to generate patient- or disease-specific pluripotent stem cells.

Viral, nonviral and nonintegrating viral methods for generating induced pluripotent stem cells (iPSCs) using adenovirus, plasmids or excision of reprogramming factors using Cre-loxP3, or piggy BAC transposition have been described. See Stadtfeld, M., et al., Science 322, 945-949 (2008); Okita, K. et al., Science 322, 949-953 (2008); Kaji, K. et al. Nature 458, 771-775 (2009); Soldner, F. et al. Cell 136, 964-977 (2009); and Woltjen, K. et al. Nature 458, 766-770 (2009). Also, see U.S. Patent Application number 20100003757 to Mack, A. et al. (published Jan. 7, 2010) and No.: PCT/US2009/037429 to Shi et al. These methods, however, have low reprogramming efficiencies (<0.003%), and may leave residual vector sequences despite excision, which limits their therapeutic applications. For example, viral integration in the host genome and over expression of the above transcription factors has been associated with tumorigenesis; and a residual transgene expression is potentially the feature which distinguishes ES cells and iPS cells. See Solder, F. et al., Cell 136:964-977 (2009); Foster et al., Oncogene 24:1491-1500 (2005); and Hochedlinger, K. et al., Cell 121:465-477 (2005).

In other embodiments of the invention, methods for generating iPSCs include episomal vectors derived from the Epstein-Barr virus. See Yu, J. et al. Science 324, 797-801 (2009) and U.S. Application 20100003757 to Mack, A. et al. published on Jan. 7, 2010. These methods require three separate plasmids carrying a combination of seven factors, including the oncogene SV40.

In another embodiment of the invention, methods for generating iPSCs include protein-based iPSCs from mouse and human fetal and neonatal cells. See Zhou, H. et al. Cell Stem Cell 4, 381-384 (2009); and Kim, D. et al. Cell Stem Cell 4, 472-476 (2009). These methodologies are accomplished using a chemical treatment (e.g. valproic acid in the case of Zhou et al. 2009 supra) or many rounds of treatment (Kim et al. 2009, supra).

In another embodiment of the invention, minicircle vectors or plasmids, which are supercoiled DNA molecules that lack a bacterial origin of replication and antibiotic resistance genes, can be used. See Chen, Z.-Y. et al., Mol. Ther. 8, 495-500 (2003); Chen, Z.-Y. et al., Hum. Gene Ther. 16, 126-131 (2005); and Jia, F. et al., Nature Methods Advance Publication Online 7 Feb. 2010. These methodologies generate iPSCs with abundant transfection efficiencies and longer ectopic expression because they have lower activation of exogenous silencing mechanisms.

Still in another embodiment of the invention, iPS cells can be generated from human patients with various diseases including, diabetic patients, ALS, spinal muscular dystrophy and Parkinson patients. See Maehr et al. PNAS USA 106 (37):15768-73 (2009); Dimos et al., Science, 321:1218-21 (2008); Ebert et al. Nature 457:277-80 (2009); Park et al. Cell 134:877-886 (2008); and Soldner et al., Cell 136:964-977. At least one advantage of producing hIPS cells from patients with specific diseases is that the cell derived would contain the genotype and cellular responses of the human disease. Also, see Table 4 listing at least some existing human iPS cell lines. This information was derived from the literature and publically available databases including for example the National Institutes of Health (NIH) Stem Cell Registry, the Human Embryonic Stem Cell Registry and the International Stem Cell Registry located at the University of Massachusetts Medical School, Worcester, Mass., USA. These databases are periodically updated as cell lines become available and registration obtained.

Embodiments of the compositions and methods described herein contemplate the use of various differentiable primate pluripotent stem cells including human pluripotent stem cells such as hESC, including but not limited to, CyT49, CyT212, CyT203, CyT25, (commercially available at least at the time of filing of this instant application from ViaCyte Inc. located at 3550 General Atomics Court, San Diego Calif. 92121) BGO1, BG02 and MEL1, and induced pluripotent stem (iPS) cells such as iPSC-482c7 and iPSC-603 (commercially available from Cellular Dynamics International, Inc., Madison, Wis.) and iPSC-G4 (hereinafter "G4")

and iPSC-B7 (hereinafter, "B7") (commercially available from Shinya Yamanaka, Center for iPS Cell Research, Kyoto University); studies using these and other human IPS cells are described in detail in U.S. patent application Ser. Nos. 12/765,714 and 13/761,078, both titled CELL COMPOSITIONS FROM DEDIFFERENTIATED REPROGRAMMED CELLS, filed Apr. 22, 2010 and Feb. 6, 2013, respectively. Certain of these human pluripotent stem cells are registered with national registries such as the National Institutes of Health (NIH) and listed in the NIH Human Stem Cell Registry (e.g., CyT49 Registration No. #0041). Information on CyT49, other available cell lines can also be found on the worldwide web at stemcells.nih.gov/research/registry. Still other cell lines, e.g., BG01 and BG01v, are commercially sold and distributed to third parties by WiCell®, an affiliate of the Wisconsin International Stem Cell (WISC) Bank (Catalog name, BG01) and ATCC (Catalog No. SCRC-2002), respectively. While other cell lines described herein may not be registered or distributed by a biological repository, such as WiCell® or ATCC, such cell lines are commercially available to the public directly or indirectly from the principle investigators, laboratories and/or institutions. Public requests for cell lines and reagents, for example, are customary for those skilled in the art in the life sciences. Typically, transfer of these cells or materials is by way of a standard material transfer agreement between the proprietor of the cell line or material and the recipient. These types of material transfers occur frequently in a research environment, particularly in the life sciences. In fact, Applicant has routinely transferred cells since the time they were derived and characterized, including CyT49 (2006), CyT203 (2005), Cyt212 (2009), CyT25 (2002), BG01 (2001), BG02 (2001), BG03 (2001) and BG01 v (2004), through such agreements with commercial and non-profit industry partners and collaborators. The year in parenthesis next to each cell line in the previous list indicates the year when the cell lines or materials became publically available and immortal (e.g. cell banks were made) and thus destruction of another embryo has not been performed or required since the establishment of these cell lines in order to make the compositions and practice the methods described herein.

Tables 4 and 5 are non-exhaustive lists of certain iPSC and hESCs, respectively, which are available worldwide for research and/or commercial purposes, and are suitable for use in the methods and compositions of the present invention. The information in Tables 3 and 4 were derived from the literature and publically available databases including, for example, the National Institutes of Health (NIH) Human Stem Cell Registry, the Human Embryonic Stem Cell Registry and the International Stem Cell Registry located at the University of Massachusetts Medical School, Worcester, Mass., USA. These databases are periodically updated as cell lines become available and registration obtained.

Human iPSC described herein (at least iPSC-603 and iPSC-482-c7) were provided by Cellular Dynamics International, Inc. (Madison, Wis., USA).

TABLE 4

Listing of Human Induced Pluripotent Stem (hIPS) Cell Lines

| Commercially Available From | Human Induced Pluripotent Stem (hIPS) Cell Lines |
|---|---|
| University of Wisconsin-Madison (USA) | 1. IPS(FORESKIN)-1 (Normal; 46XY; Yu, J., et al. [Thomas] Science. 2007 Induced pluripotent stem cell lines derived from human somatic cells 318(5858):1917-20.)<br>2. IPS(FORESKIN)-2 (Normal; 46XY; Yu, J., et al. [Thomas] Science. 2007 Induced pluripotent stem cell lines derived from human somatic cells 318(5858):1917-20.)<br>3. IPS(FORESKIN)-3 (Normal; 46XY; Yu, J., et al. [Thomas]Science. 2007 Induced pluripotent stem cell lines derived from human somatic cells 318(5858):1917-20.)<br>4. IPS(FORESKIN)-4 (Normal; 46XY; Yu, J., et al. [Thomas] Science. 2007 Induced pluripotent stem cell lines derived from human somatic cells 318(5858):1917-20.)<br>5. IPS(IMR90)-1 (Normal; 46XX; Yu, J., et al. [Thomas] Science. 2007 Induced pluripotent stem cell lines derived from human somatic cells 318(5858):1917-20.)<br>6. IPS(IMR90)-2 (Normal; 46XX; Yu, J., et al. [Thomas] Science. 2007 Induced pluripotent stem cell lines derived from human somatic cells 318(5858):1917-20.)<br>7. IPS(IMR90)-3 (Normal; 46XX; Yu, J., et al. [Thomas] Science. 2007 Induced pluripotent stem cell lines derived from human somatic cells 318(5858):1917-20.)<br>8. IPS(IMR90)-4 (Normal; 46XX; Yu, J., et al. [Thomas] Science. 2007 Induced pluripotent stem cell lines derived from human somatic cells 318(5858):1917-20.)<br>9. IPS-SMA-3.5 (Normal; 46XY; Type 1 Spinal Muscular Atrophy; Ebert, A. D., et al. 2009. Induced pluripotent stem cells from a spinal muscular atrophy patient Nature. 457:277-80)<br>10. IPS-SMA-3.6 (Normal; 46XY; Type 1 Spinal Muscular Atrophy; Ebert, A. D., et al. 2009. Induced pluripotent stem cells from a spinal muscular atrophy patient Nature. 457:277-80)<br>11. IPS-WT (Normal; 46XX; Type 1 Spinal Muscular Atrophy; Ebert, A. D., et al. 2009. Induced pluripotent stem cells from a spinal muscular atrophy patient Nature. 457:277-80) |
| University of California, Los Angeles (USA) | 1. IPS-1 (Karumbayaram, S. et al. 2009. Directed Differentiation of Human-Induced Pluripotent Stem Cells Generates Active Motor Neurons Stem Cells. 27:806-811; Lowry, W. E., et al. 2008. Generation of human induced pluripotent stem cells from dermal fibroblasts Proc Natl Acad Sci U S A. 105:2883-8) |

TABLE 4-continued

Listing of Human Induced Pluripotent Stem (hIPS) Cell Lines

| Commercially Available From | Human Induced Pluripotent Stem (hIPS) Cell Lines |
|---|---|
| | 2. IPS-2 (Karumbayaram, S. et al. 2009. Directed Differentiation of Human-Induced Pluripotent Stem Cells Generates Active Motor Neurons Stem Cells. 27:806-811; Lowry, W. E., et al. 2008. Generation of human induced pluripotent stem cells from dermal fibroblasts Proc Natl Acad Sci U S A. 105:2883-8)
3. IPS-5 (Lowry, W. E., et al. 2008. Generation of human induced pluripotent stem cells from dermal fibroblasts Proc Natl Acad Sci U S A. 105:2883-8)
4. IPS-7 (Lowry, W. E., et al. 2008. Generation of human induced pluripotent stem cells from dermal fibroblasts Proc Natl Acad Sci U S A. 105:2883-8)
5. IPS-18 (Karumbayaram, S. et al. 2009. Directed Differentiation of Human-Induced Pluripotent Stem Cells Generates Active Motor Neurons Stem Cells. 27:806-811; Lowry, W. E., et al. 2008. Generation of human induced pluripotent stem cells from dermal fibroblasts Proc Natl Acad Sci U S A. 105:2883-8)
6. IPS-24 (Lowry, W. E., et al. 2008. Generation of human induced pluripotent stem cells from dermal fibroblasts Proc Natl Acad Sci U S A. 105:2883-8)
7. IPS-29 (Lowry, W. E., et al. 2008. Generation of human induced pluripotent stem cells from dermal fibroblasts Proc Natl Acad Sci U S A. 105:2883-8) |
| Mt. Sinai Hospital (Samuel Lunenfeld Research Institute; USA) | 1. 60 (Woltjen, K. et al. 2009. Piggy Bac transposition reprograms fibroblasts to induced pluripotent stem cells Nature. 458(7239):766-70)
2. 61 (Woltjen, K. et al. 2009. PiggyBac transposition reprograms fibroblasts to induced pluripotent stem cells Nature. 458(7239):766-70)
3. 66 (Woltjen, K. et al. 2009. PiggyBac transposition reprograms fibroblasts to induced pluripotent stem cells Nature 458(7239):766-70)
4. 67 (Woltjen, K. et al. 2009. PiggyBac transposition reprograms fibroblasts to induced pluripotent stem cells Nature 458(7239):766-70)
5. HIPSC117 (Kaji K, et al. 2009 Virus-free induction of pluripotency and subsequent excision of reprogramming factors Nature 458(7239):771-5)
6. HIPSC121 (Kaji K, et al. 2009 Virus-free induction of pluripotency and subsequent excision of reprogramming factors Nature 458(7239):771-5)
7. HIPSC122 (Kaji K, et al. 2009 Virus-free induction of pluripotency and subsequent excision of reprogramming factors Nature 458(7239):771-5) |
| Children's Hospital-Boston (USA) | 1. 551-IPS8 (Park IH, et al. 2008. Reprogramming of human somatic cells to pluripotency with defined factors Nature 451:141-6).
2. ADA-IPS2 ((ADA-SCID) Adenosine Deaminase Deficiency-related Severe Combined Immunodeficiency (GGG > AGG, exon 7, ADA gene); Park, I. H. et al. 2008. Disease-Specific Induced Pluripotent Stem Cells Cell 134(5):877-86)
3. ADA-IPS3 ((ADA-SCID) Adenosine Deaminase Deficiency-related Severe Combined Immunodeficiency (GGG > AGG, exon 7, ADA gene); Park, I. H. et al. 2008. Disease-Specific Induced Pluripotent Stem Cells Cell 1134(5):877-86)
4. BJ1-IPS1 (Park, I. H. et al. 2008. Disease-Specific Induced Pluripotent Stem Cells Cell 134(5):877-86)
5. BMD-IPS1 (Male; (BMD) Becker Muscular Dystrophy (Unidentified mutation in dystrophin); Park, I. H. et al. 2008. Disease-Specific Induced Pluripotent Stem Cells Cell 134(5):877-86)
6. BMD-IPS4 (Normal; 46XY; (BMD) Becker Muscular Dystrophy (Unidentified mutation in dystrophin); Park, I. H. et al. 2008. Disease-Specific Induced Pluripotent Stem Cells Cell 134(5):877-86)
7. DH1CF16-IPS1 (Normal; 46XY; Park, I. H. et al. 2008. Disease-Specific Induced Pluripotent Stem Cells Cell 134(5):877-86)
8. DH1CF32-IPS2 (Male; Park, I. H. et al. 2008. Disease-Specific Induced Pluripotent Stem Cells Cell 134(5):877-86)
9. DH1F-IPS3-3(Normal; 46XY; Park, I. H. et al. 2008. Disease-Specific Induced Pluripotent Stem Cells Cell 134(5):877-86)
10. DMD-IPS1 ((Normal; 46XY; DMD) Duchenne Muscular Dystrophy (Deletion of exon 45-52, dystrophin gene; Park, I. H. et al. 2008. Disease-Specific Induced Pluripotent Stem Cells Cell 134(5):877-86)
11. DMD-IPS2 (Male; (DMD) Duchenne Muscular Dystrophy (Deletion of exon 45-52, dystrophin gene; Park, I. H. et al. 2008. Disease-Specific Induced Pluripotent Stem Cells Cell 134(5):877-86)
12. DS1-IPS4 (Male; Down syndrome (Trisomy 21); Park, I. H. et al. 2008. Disease-Specific Induced Pluripotent Stem Cells Cell 134(5):877-86)
13. DS2-IPS1 (Male; Down syndrome (Trisomy 21); Park, I. H. et al. 2008. Disease-Specific Induced Pluripotent Stem Cells Cell 134(5):877-86) |

TABLE 4-continued

Listing of Human Induced Pluripotent Stem (hIPS) Cell Lines

| Commercially Available From | Human Induced Pluripotent Stem (hIPS) Cell Lines |
|---|---|
| | 14. DS2-IPS10 (Male; Down syndrome (Trisomy 21); Park, I. H. et al. 2008. Disease-Specific Induced Pluripotent Stem Cells Cell 134(5): 877-86) |
| | 15. GD-IPS1(Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell 134(5):877-86) |
| | 16. GD-IPS3 (Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell 134(5):877-86) |
| | 17. HFIB2-IPS2 (Park, I. H., et al. 2008. Generation of human-induced pluripotent stem cells Nat Protoc. 3:1180-6 ; Park, I. H. et al. 2008. Reprogramming of human somatic cells to pluripotency with defined factors Nature 451:141-6) |
| | 18. HFIB2-IPS4 (Park, I. H., et al. 2008. Generation of human-induced pluripotent stem cells Nat Protoc. 3:1180-6 ; Park, I. H. et al. 2008. Reprogramming of human somatic cells to pluripotency with defined factors Nature 451:141-6) |
| | 19. HFIB2-IPS5 (Park, I. H., et al. 2008. Generation of human-induced pluripotent stem cells Nat Protoc. 3:1180-6 ; Park, I. H. et al. 2008. Reprogramming of human somatic cells to pluripotency with defined factors Nature 451:141-6) |
| | 20. JDM-IPS1 (Normal, 46XX; Juvenile diabetes mellitus (multifactorial); Park, I. H. et al. 2008. Disease-Specific Induced Pluripotent Stem Cells Cell 134(5):877-86) |
| | 21. JDM-IPS1 (Normal, 46XX; Juvenile diabetes mellitus (multifactorial); Park, I. H. et al. 2008. Disease-Specific Induced Pluripotent Stem Cells Cell 134(5):877-86) |
| | 22. JDM-IPS2 (Female; Juvenile diabetes mellitus (multifactorial); Park, I. H. et al. 2008. Disease-Specific Induced Pluripotent Stem Cells Cell 134(5):877-86) |
| | 23. JDM-IPS3 (Female; Juvenile diabetes mellitus (multifactorial); Park, I. H. et al. 2008. Disease-Specific Induced Pluripotent Stem Cells Cell 134(5):877-86) |
| | 24. LNSC-IPS2 (Female; Lesch-Nyhan syndrome (carrier, heterozygosity of HPRT1; Park, I. H. et al. 2008. Disease-Specific Induced Pluripotent Stem Cells Cell 134(5):877-86) |
| | 25. MRCS-IPS7 (Male; Park, I. H. et al. 2008. Disease-Specific Induced Pluripotent Stem Cells Cell134(5):877-86) |
| | 26. MRC5-IPS12 (Normal; 46XY; Park, I. H. et al. 2008. Disease-Specific Induced Pluripotent Stem Cells Cell 134(5):877-86) |
| | 27. MRC5-IPS1 (Male; Park, I. H. et al. 2008. Disease-Specific Induced Pluripotent Stem Cells Cell 134(5):877-86) |
| | 28. PD-IPS1 (Male; Parkinson disease (multifactorial); Park, I. H. et al. 2008. Disease-Specific Induced Pluripotent Stem Cells Cell 134(5): 877-86) |
| | 29. SBDS-IPS1 (Male; Swachman-Bodian-Diamond syndrome (IV2 + 2T > C and IV3 − 1G > A, SBDS gene; Park, I. H. et al. 2008. Disease-Specific Induced Pluripotent Stem Cells Cell 134(5):877-86) |
| | 30. SBDS-IPS2 |
| | 31. SBDS-IPS3 (Normal; 46XY; Swachman-Bodian-Diamond syndrome (IV2 + 2T > C and IV3 − 1G > A, SBDS gene; Park, I. H. et al. 2008. Disease-Specific Induced Pluripotent Stem Cells Cell 134(5):877-86) |
| Harvard University (USA) | 1. A29a (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321:1218-21) |
| | 2. A29b (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321:1218-21) |
| | 3. A29c (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science 321:1218-21) |

TABLE 4-continued

Listing of Human Induced Pluripotent Stem (hIPS) Cell Lines

| Commercially Available From | Human Induced Pluripotent Stem (hIPS) Cell Lines |
|---|---|
| Salk Institute (USA) | 1. HAIR-IPS1 (Aasen, T., et al [Belmonte, J. C.] 2008. Efficient and rapid generation of induced pluripotent stem cells from human keratinocytes Nat Biotechnol 26:1276-84)<br>2. HAIR-IPS2 (Aasen, T., et al [Belmonte, J. C.] 2008. Efficient and rapid generation of induced pluripotent stem cells from human keratinocytes Nat Biotechnol 26:1276-84) |
| Royan Institute (Iran) | 1. R.1.H.iPSC.1(OCT4, Sox2, KLF4, c-Myc; Human fibroblasts)<br>2. BOM.1.H.iPSC.1 (OCT4, Sox2, KLF4, c-Myc; Human fibroblasts)<br>3. FHC.1.H.iPSC.3 (OCT4, Sox2, KLF4, c-Myc; Human fibroblasts)<br>4. GSD.1.H.iPSC.7 (OCT4, Sox2, KLF4, c-Myc; Human fibroblasts)<br>5. TYR.1.H.iPSC.1 (OCT4, Sox2, KLF4, c-Myc; Human fibroblasts)<br>6. HER.1.H.iPSC.1 (OCT4, Sox2, KLF4, c-Myc; Human fibroblasts)<br>7. R.1.H.iPSC.4 (OCT4, Sox2, KLF4, c-Myc; Human fibroblasts)<br>8. R.1.H.iPSC.9 (OCT4, Sox2, KLF4, c-Myc; Human fibroblasts)<br>9. RP2.H.iPSC.3 (OCT4, Sox2, KLF4, c-Myc; iPS cells)<br>10. LCA.1.H.iPSC.1 (OCT4, Sox2, KLF4, c-Myc; iPS cells)<br>11. USH.1.H.iPSC.6 (OCT4, Sox2, KLF4, c-Myc; Human fibroblasts)<br>12. RP.1.H.iPSC.2 (OCT4, Sox2, KLF4, c-Myc; Human fibroblasts)<br>13. ARMD.1.H.iPSC.2 (OCT4, Sox2, KLF4, c-Myc; Human fibroblasts)<br>14. LHON.1.H.iPSC.5 (OCT4, Sox2, KLF4, c-Myc; iPS cells)<br>15. CNS.1.H.iPSC.10 (OCT4, Sox2, KLF4, c-Myc; iPS cells)<br>16. CNS.2.H.iPSC.7 (OCT4, Sox2, KLF4, c-Myc; iPS cells) |
| Centre of Regenerative Medicine in Barcelona (Spain) | 1. KiPS4F-1 (OCT4, Sox2, KLF4, c-Myc; human foreskin keratinocytes; 46XY)<br>2. KiPS3F-7 (OCT4, Sox2, KLF4); human foreskin keratinocytes)<br>3. KiPS4F-8 (OCT4, Sox2, KLF4, c-Myc human foreskin keratinocytes; 46XY)<br>4. cFA404-KiPS4F-1 (OCT4, Sox2, KLF4, c-Myc; Epidermal keratinocytes; 46XY)<br>5. cFA404-KiPS4F-3 (OCT4, Sox2, KLF4, c-Myc; Epidermal keratinocytes; 46XY) |
| Université Paris-Sud 11 (France) | 1. PB03 (Oct4, Sox2, Lin28, Nanog; Primary Amniocytes; 46XX; Lentivirus)<br>2. PB04 (Oct4, Sox2, Lin28, Nanog; Primary Amniocytes; B-Thalassemia affected; 46XY; Lentivirus)<br>3. PB05-1 (Oct4, Sox2, Lin28, Nanog; Primary Amniocytes; B-Thalassemia affected; 46XY; Lentivirus)<br>4. PB05 (Oct4, Sox2, Lin28, Nanog; Primary Amniocytes; B-Thalassemia affected; 46XY; Lentivirus)<br>5. PB06 (Oct4, Sox2, Lin28, Nanog; Primary Amniocytes; Down Syndrome; 47XY, +21; Lentivirus)<br>6. PB06-1 (Oct4, Sox2, Lin28, Nanog; Primary Amniocytes; Down Syndrome; 47XY, +21; Lentivirus)<br>7. PB07 (OCT4, Sox2, KLF4, c-Myc; Primary Amniocytes; 46XY; Retrotivirus)<br>8. PB08 (OCT4, Sox2, KLF4, c-Myc; Primary Amniocytes; 46XY; Retrotivirus)<br>9. PB09 (Oct4, Sox2, Lin28, Nanog; Primary Amniocytes; 46XY; Lentivirus)<br>10. PB10 (Oct4, Sox2; Primary Amniocytes46XY, Lentivirus) |
| Kyoto University (Japan) | 1. 201B1 (human fibroblast; 46XX)<br>2. 201B2 (human fibroblast; 46XX)<br>3. 201B3 (human fibroblast; 46XX)<br>4. 201B6 (human fibroblast; 46XX)<br>5. 201B7 (human fibroblast; 46XX)<br>6. 243H1 (human fibroblast)<br>7. 243H7 (human fibroblast)<br>8. 246B1 (Normal, 46XX)<br>9. 246B2 (Normal, 46XX)<br>10. 246B3 (Normal, 46XX)<br>11. 246B4 (Normal, 46XX)<br>12. 246B5 (Normal, 46XX)<br>13. 246B6 (Normal, 46XX)<br>14. 246G1 (human fibroblast; Takahashi, K., et al. 2007. Induction of pluripotent stem cells from adult human fibroblasts by defined factors Cell. 131:861-72)<br>15. 246G3 (human fibroblast; Takahashi, K., et al. 2007. Induction of pluripotent stem cells from adult human fibroblasts by defined factors Cell. 131:861-72) |

TABLE 4-continued

Listing of Human Induced Pluripotent Stem (hIPS) Cell Lines

| Commercially Available From | Human Induced Pluripotent Stem (hIPS) Cell Lines |
|---|---|
| | 16. 246G4 (human fibroblast; Takahashi, K., et al. 2007. Induction of pluripotent stem cells from adult human fibroblasts by defined factors Cell. 131:861-72) |
| | 17. 246G5 (human fibroblast; Takahashi, K., et al. 2007. Induction of pluripotent stem cells from adult human fibroblasts by defined factors Cell. 131:861-72) |
| | 18. 246G6 (human fibroblast; Takahashi, K., et al. 2007. Induction of pluripotent stem cells from adult human fibroblasts by defined factors Cell. 131:861-72) |
| | 19. 253F1 (Normal, 46XX; Takahashi, K., et al. 2007. Induction of pluripotent stem cells from adult human fibroblasts by defined factors Cell. 131:861-72) |
| | 20. 253F2 (Normal, 46XX; Takahashi, K., et al. 2007. Induction of pluripotent stem cells from adult human fibroblasts by defined factors Cell. 131:861-72) |
| | 21. 253F3 (Normal, 46XX; Takahashi, K., et al. 2007. Induction of pluripotent stem cells from adult human fibroblasts by defined factors Cell. 131:861-72) |
| | 22. 253F4 (Normal, 46XX; Takahashi, K., et al. 2007. Induction of pluripotent stem cells from adult human fibroblasts by defined factors Cell. 131:861-72) |
| | 23. 253F5 (Normal, 46XX; Takahashi, K., et al. 2007. Induction of pluripotent stem cells from adult human fibroblasts by defined factors Cell. 131:861-72) |
| Shanghai Institutes for Biological Sciences (China) | 24. HAFDC-IPS-6 (Li C., et al. 2009 Pluripotency can be rapidly and efficiently induced in human amniotic fluid-derived cells Hum Mol Genet. Nov.15, 2009;18(22):4340-9) |
| | 25. IPS-S (Liao, J., et al. 2008. Enhanced efficiency of generating induced pluripotent stem (iPS) cells from human somatic cells by a combination of six transcription factors Cell Res. 18:600-3) |

Another advantage of using hIPS cells is that such hIPS cells would be an immunologically matched autologous cell population; and patient-specific cells would allow for studying origin and progression of the disease. Thus, it is possible to understand the root causes of a disease, which can provide insights leading to development of prophylactic and therapeutic treatments for the disease.

Pluripotent Human Embryonic Stem (hES) Cells

Some embodiments are directed to methods for deriving definitive endoderm cells and ultimately any endoderm-lineage derived cell type, including but not limited to, foregut endoderm, pancreatic endoderm, endocrine progenitor/precursor cells and/or pancreatic islet hormone-expressing cells using human embryonic stem (hES) cells as the starting material. These hES cells can be cells that originate from the morula, embryonic inner cell mass or those obtained from embryonic gonadal ridges. Human embryonic stem cells can be maintained in culture in a pluripotent state without substantial differentiation using methods that are known in the art. Such methods are described, for example, in U.S. Pat. Nos. 5,453,357; 5,670,372; 5,690,926; 5,843,780; 6,200,806 and 6,251,671.

In some processes, pluripotent stem cells, e.g. hES cells, are maintained on a feeder layer. In such processes, any feeder layer which allows pluripotent cell to be maintained in a pluripotent state can be used. One commonly used feeder layer for the cultivation of human embryonic stem cells is a layer of mouse fibroblasts. More recently, human fibroblast feeder layers have been developed for use in the cultivation of pluripotent cell (see US Patent Application Publication No. 2002/0072117. Alternative processes permit the maintenance of pluripotent cells without the use of a feeder layer.

The pluripotent cells described herein can be maintained in culture either with or without serum, with or without extracellular matrix, with or without FGF. In some pluripotent cell maintenance procedures, serum replacement is used. These and other methods for culturing and differentiation pluripotent or multipotent cells, respectively, are described in PCT/US2007/062755, filed Feb. 23, 2007, and titled COMPOSITIONS AND METHODS FOR CULTURING DIFFERENTIAL CELLS and PCT/US2008/080516, filed Oct. 20, 2008, and titled METHODS AND COMPOSITIONS FOR FEEDER-FREE PLURIPOTENT STEM CELL MEDIA CONTAINING HUMAN SERUM.

The invention described herein is useful with all hES cell lines, and at least those listed in Table 5, which are commercially available from the identified company or for commercial purchase from WiCell on the world wide web at wicell.org/home/stem-cell-lines/order-stem-cell-lines/obtain-stem-cell-lines.cmsx. This information was derived from the literature and publically available databases including for example the National Institutes of Health (NIH) Stem Cell Registry, the Human Embryonic Stem Cell Registry and the International Stem Cell Registry located at the University of Massachusetts Medical School, Worcester, Mass., USA. These databases are periodically updated as cell lines become available and registration obtained. There are at least 254 iPSC commercially available lines listed with the International Stem Cell Registry and 1211 commercially available hESC lines. Table 5 below is not inclusive of all hESC and iPSC that are listed, but rather, are examples of the pluripotent stem cells potentially available.

TABLE 5

Listing of Human Embryonic Stem (hES) Cell Lines

| Commercially Available From | Human Embryonic Stem (hES) Cell Lines |
|---|---|
| U.S.A. | |
| ViaCyte, Inc. (formerly BresaGen, Inc.) Athens, Georgia (USA) | BG01, BG02, BG03; BG04; BG01v |
| Invitrogen (USA) | BG01v/hOG |
| ViaCyte, Inc. (formerly CyThera, Inc.) San Diego, California (USA) | CyT49, CyT203, CyT25 |
| Geron Corporation, Menlo Park, California (USA) | GE01, GE07, GE09, GE13, GE14, GE91, GE92 (H1, H7, H9, H13, H14, H9.1, H9.2) |
| University of California, San Francisco, California (USA) | UC01, UC06 (HSF-1, HSF-6); UCSFB1, UCSFB2, UCSFB3, UCSFB4, UCSFB5, UCSFB6, UCSFB7, UCSFB8, UCSFB9 & UCSFB10 |
| Wisconsin Alumni Research Foundation, Madison, Wisconsin (USA) | WA01, WA07, WA09, WA13, WA14 (H1, H7, H9, H13, H14) |
| Children's Hospital Corporation (USA) | CHB-1, CHB-2 CHB-3 CHB-4, CHB-5, CHB-6, CHB-8, CHB-9, CHB-10, CHB-11 & CHB-12 |
| The Rockefeller University (USA) | RUES1, RUES2 & RUES3 |
| Harvard University (USA) | HUES1, HUES2, HUES3, HUES4, HUES5, HUES6, HUES7, HUES8, HUES9, HUES10, HUES11, HUES12, HUES13, HUES14, HUES15, HUES16, HUES17, HUES18, HUES19, HUES20, HUES21, HUES22, HUES23, HUES24, HUES25, HUES26, HUES27; HUES28; HUES48; HUES49; HUES53; HUES55 & HUES 56 |
| Mt Sinai Hospital-amuel Lunenfeld Research Institute (USA) | CA1 & CA2 |
| Children's Memorial Hospital (USA) | CM-1, CM-2, CM-5, CM-6, CM-7, CM-8, CM-11, CM-12, CM-13, CM-14, CM-16 |
| The University of Texas Health Science Center at Houston (USA) | CR1 & CR2 |
| California Stem Cell, Inc. (USA) | CSC14 |
| University of Connecticut School of Medicine/Dentistry (USA) | CSC14, CT1, CT2, CT3, & CT4 |
| The Third Affiliated Hospital of Guangzhou Medical College (USA) | FY-3PN; FY-hES-1; FY-hES-3; FY-hES-5; FY-hES-7 & FY-hES-8 |
| Advanced Cell Technology, Inc. (USA) | MA 01; MA 09; MA 42; MA 50; MA135; NED 1; NED 2; NED 3 & NED 4 |
| Stanford University (USA) | MFS5 |
| New York University School of Medicine (USA) | NYUES1; NYUES2; NYUES3; NYUES4; NYUES5; NYUES6 & NYUES7 |
| Reprogenetics, LLC (USA) | RNJ7 |
| University of California, Los Angeles (USA) | UCLA1; UCLA2 & UCLA3 |
| Eastern Virginia Medical School (USA) | ES-76; ES-78-1; ES-78-2 |
| Reproductive Genetics Institute (USA) | RG-222; RG-230; RG-249; RG-308; RG-313; RG-148; DYSTROPHIA MYOTONICA 1 (DM1), affected, 46, XY; RG-153; DYSTROPHIA MYOTONICA 1 (DM1), affected, 46, XX; RG-170; MUSCULAR DYSTROPHY, BECKER TYPE (BMD), affected, 46, XY; RG-186; HUNTINGTON DISEASE (HD), affected, 46, XX; RG-194; HUNTINGTON DISEASE (HD), affected, 46, XY; RG-233; HEMOGLOBIN B LOCUS (HBB), affected (HbS/HbS - sickle cell anemia), 46, XX; RG-245; EMERY-DREIFUSS MUSCULAR DYSTROPHY, X-LINKED (EDMD), carrier, 47, XXY; RG-246; EMERY-DREIFUSS MUSCULAR DYSTROPHY, X-LINKED (EDMD), affected, 46, XY; RG-271; TORSION DYSTONIA 1 (DYT1), AUTOSOMAL DOMINANT, affected (N/GAG del), 46, XY; RG-283; MUSCULAR DYSTROPHY, DUCHENNE TYPE (DMD), affected, 46, XY; RG-288; CYSTIC FIBROSIS (CF), affected (deltaF508/deltaF508), 46, XY; RG-289; CYSTIC FIBROSIS (CF), affected (deltaF508/deltaF508), 46, XX; RG-301; MUSCULAR DYSTROPHY, DUCHENNE TYPE(DMD) affected, 46, XY; RG-302; MUSCULAR DYSTROPHY, DUCHENNE TYPE (DMD), carrier, 46, XX; |

TABLE 5-continued

Listing of Human Embryonic Stem (hES) Cell Lines

| Commercially Available From | Human Embryonic Stem (hES) Cell Lines |
|---|---|
| | RG-315; NEUROFIBROMATOSIS, TYPE I (NF1), affected (R19 47X/N), 46, XY; |
| | RG-316; TUBEROUS SCLEROSIS, TYPE 1(TSC1), TUBEROUS SCLEROSIS, TYPE 1(TSC1), affected (N/IVS7+1 G-A); |
| | RG-320; TUBEROUS affected (N/IVS7+1 G-A); RG-316; SCLEROSIS, TYPE 1(TSC1), affected (N/IVS7+1 G-A); |
| | RG-326; POPLITEAL PTERYGIUM SYNDROME (PPS), affected (R84H/N), 46, XY; |
| | RG-328; FACIOSCAPULOHUMERAL MUSCULAR DYSTROPHY 1A(FSHD), affected, 46, XY; |
| | RG-330; FACIOSCAPULOHUMERAL MUSCULAR DYSTROPHY 1A (FSHD), affected, 46, XY; |
| | RG-333; FACIOSCAPULOHUMERAL MUSCULAR DYSTROPHY 1A (FSHD), affected, 46, XX; |
| | RG-356; HEMOGLOBIN ALPHA LOCUS (HBA), affected (-alpha/--), 46, XX; |
| | RG-357; EMERY-DREIFUSS MUSCULAR DYSTROPHY, X-LINKED (EDMD), affected, 46, XY; |
| | RG-358; EMERY-DREIFUSS MUSCULAR DYSTROPHY, X-LINKED (EDMD), affected, 46, XY; |
| | RG-399; FACIOSCAPULOHUMERAL MUSCULAR DYSTROPHY 1A (FSHD), affected, 46, XX; |
| | RG-401; FACIOSCAPULOHUMERAL MUSCULAR DYSTROPHY 1A (FSHD), affected, 46, XX; |
| | RG-402; FACIOSCAPULOHUMERAL MUSCULAR DYSTROPHY 1A (FSHD), affected, 46, XX; |
| | RG-403; FACIOSCAPULOHUMERAL MUSCULAR DYSTROPHY 1A (FSHD), affected; |
| | RG-404; SPINAL MUSCULAR ATROPHY, TYPE I (SMA1), affected, 46, XY; |
| | RG-406; TORSION DYSTONIA 1, AUTOSOMAL DOMINANT (DYT1), affected (N/GAG del); |
| | RG-413; BREAST CANCER, FAMILIAL (BRCA2), affected (N/IVS7 GT del) & MULTIPLE ENDOCRINE NEOPLASIA, TYPE I (MEN1), affected (N/3036 4bp del); |
| | RG-414; MULTIPLE ENDOCRINE NEOPLASIA, TYPE I (MEN1), affected (N/3036 4bp del); |
| | RG-415; HUNTINGTON DISEASE (HD), affected; |
| | RG-416; CYSTIC FIBROSIS (CF), affected (deltaF508/1717-1 G-A); |
| | RG-417; CYSTIC FIBROSIS (CF), affected (deltaF508/1717-1 G-A); |
| | RG-418; HEMOGLOBIN B LOCUS (HBB), affected (cd8+G/619del); |
| | RG-420; HEMOGLOBIN B LOCUS (HBB), affected (cd8+G/619del); |
| | RG-422; CYSTIC FIBROSIS (CF), affected (N1303K/deltaF508); |
| | RG-423; CYSTIC FIBROSIS (CF), carrier (N/deltaF508); |
| | RG-424; MULTIPLE ENDOCRINE NEOPLASIA, TYPE 2 (MEN2B), affected (M918T/N); |
| | RG-426; PELIZAEUS-MERZBACHER DISEASE (PMLD), affected; |
| | RG-428; TUBEROUS SCLEROSIS, TYPE 1 (TSC1), affected (N/IVS7+1 G-A); |
| South American | |
| Instituto de Biociências, São Paulo (Brazil) | BR-1 |
| Middle East | |
| Technion-Israel Institute of Technology, Haifa (Israel) | TE03, TE04, TE06 (I 3, I 4, I 6) |

TABLE 5-continued

Listing of Human Embryonic Stem (hES) Cell Lines

| Commercially Available From | Human Embryonic Stem (hES) Cell Lines |
|---|---|
| Hadassah University Hospital (Israel) | HAD 1; HAD 2; HAD 3; HAD 4; HAD 5; HAD 6 |
| Hebrew University of Jerusalem | HEFX1 |
| Technion - Israel Institute of Technology | I3; I3.2; I3.3; 14; 16; 16.2; J3; J3.2 |
| Royan Institute (Iran) | ARMD.1.H.iPSC.2; BOM.1.H.iPSC.1; CNS.1.H.iPSC.10; CNS.2.H.iPSC.7; FHC.1.H.iPSC.3; GSD.1.H.iPSC.7; HER.1.H.iPSC.1; LCA.1.H.iPSC.1; LHON.1.H.iPSC.5; R.1.H.iPSC.1; R.1.H.iPSC.4; R.1.H.iPSC.9; Royan H1; Royan H10; Royan H2; Royan H3; Royan H4; Royan H5; Royan H6; Royan H7; Royan H8; Royan H9; RP.1.H.iPSC.2; RP2.H.iPSC.3; TYR.1.H.iPSC.1; USH.1.H.iPSC.6 |
| Europe | |
| Cellartis AB, Gotenberg (Sweden) | SA001, SA002 (Sahlgrenska 1, Sahlgrenska 2); SA002.2; SA003; AS034.1; AS034.1.1; AS034.2; AS038; AS046; FC018; ASo85; AS094; SA111; SA121; SA142; SA167; SA181; SA191; SA196; SA202; SA203; SA211; SA218; SA240; SA279; SA348; SA352; SA399; SA461; SA502; SA506; SA521; SA540; SA611 |
| Karolinska Institutet (Sweden) | HS181; HS207; HS235; HS237; HS293; HS306; HS346; HS351; HS356; HS360; HS361; HS362; HS363; HS364; HS366; HS368; HD380; HS382; HS400; HS401; HS402; HS415; HS420; HS422; HS426; HS429; HS429A; HS429B; HS429C; HS429D; HS475; HS480; HS481; HS539 |
| Göteborg University, Göteborg (Sweden) | SA04-SA19 (Sahlgrenska 4-Sahlgrenska 19) |
| Karolinska Institute, Stockholm (Sweden) | KA08, KA09, KA40, KA41, KA42, KA43 (hICM8, hICM9, hICM40, hICM41, hICM42, hICM43) |
| Geneva University (Switzerland) | CH-ES1 |
| University of Basel (Switzerland) | CH-ES3; CH-ES3; CH-ES5 |
| Roslin Cells Ltd (UK) | RC2; RC3; RC4; RC5 |
| University of Newcastle upon Tyne (UK) | NCL-1; NCL-2; NCL-3; NCL-4; NCL-5; NCL-6; NCL-7; NCL-8; NCL-9 |
| Roslin Institute (Edinburgh) & Geron Corporation (UK) | RH1; RH2; RH3; RH4; RH5; RH6; RH7; RH9; |
| University of Manchester (UK) | Man 2 |
| King's College London (UK) | KCL-001 (formerly WT3) |
| The University of Sheffield, Sheffield (UK) | SHEF-1; SHEF-2; SHEF-3; SHEF-4; SHEF-5; SHEF-6; SHEF-7; SHEF-8 |
| Universities of Edinburgh & Oxford; University of Cambridge (UK) | Edi-1; Edi-2; Edi-3; Edi-4 |
| Roslin Cells Ltd, Roslin Institute, Universities of Edinburgh & Manchester, Central Manchester & Manchester Children's University Hospitals NHS Trust (UK) | RCM-1; RC-1; RC-2; RC-3; RC-4; RC-5; RC-6; RC-7; RC-8; RC-9; RC-10 |
| King's College London & Guy's Hospital Trust/ Charitable Foundation of Guy's & St Thomas (UK) | KCL-003-CF1 (formerly CF1); KCL-005-HD1; KCL008-HD-2; KCL009-trans-1; KCL-001 (WT-3); KCL-001 (WT-4) |
| Stem Cell Sciences Ltd, Australia (SCS) & Australian Stem Cell Centre (AS CC) | MEL-1; MEL-2; MEL-3; MEL-4 |
| University of Edinburgh (UK) | CB660 |
| Axordia Ltd. (UK) | Shef-1; Shef-2; Shef-3; Shef-4; Shef-5; Shef-6; Shef-7 |
| University of Nottingham (UK) | Nott-1; Nott-2 |
| Centre of Regenerative Medicine in Barcelona (Spain) | ES-2; ES-3; ES-4; ES-5; ES-6; ES-7; ES-8; ES-9; ES-10; ES-11EM; cFA404-KiPS4F-1; cFA404-KiPS4F-3; KiPS3F-7; KiPS4F-1; KiPS4F-8 |
| Principe Felipe Centro de Investigacion (Spain) | VAL-3; VAL-4; VAL-5; VAL-6M; VAL-7; VAL-8; VAL-9; VAL-10B |
| Université Libre de Bruxelles (Belgium) | ERA-1; ERA2; ERA-3; ERAMUC-1; ERAMUC-1 |
| Vrije Universiteit Brussel (Belgium) | VUB01; VUB02; VUB06; VUB07; VUB03_DM1; VUB04_CF; VUB05_HD; VUB08_MFS; VUB09_FSHD; VUB1O_SCA7; VUB11_FXS; VUB13_FXS; VUB14; VUB19_DM1; VUB2O_CMT1A; VUB22_CF; VUB23_OI; VUB24_DM1; VUB26; VUB27; VUB28_HD_MFS |

TABLE 5-continued

Listing of Human Embryonic Stem (hES) Cell Lines

| Commercially Available From | Human Embryonic Stem (hES) Cell Lines |
|---|---|
| Central Manchester and Manchester Children's University Hospitals NHS (UK) | Man 1; Man 2 |
| Université Paris-Sud 11 (France) | CL01; CL02; CL03; PB04; PB05; PB05-1; PB06; PB06-1; PB07; PB08; PB09; PB10 |
| INSERM (France) | OSCAR; STR-I-155-HD; STR-I-171-GLA; STR-I-189-FRAXA; STR-I-203-CFTR; STR-I-209-MEN2a; STR-I-211-MEN2a; STR-I-221-Sca2; STR-I-229-MTMX; STR-I-231-MTMX; STR-I-233-FRAXA; STR-I-251-CFTR; STR-I-301-MFS; STR-I-305-APC; STR-I-315-CMT1a; STR-I-347-FRAXA; STR-I-355-APC; STR-I-359-APC |
| Masaryk University (Czech Republic) | CCTL 6; CCTL 8; CCTL 9; CCTL 10; CCTL 12; CCTL 13; CCRL 14 |
| Aalborg University (Denmark) | CLS1; CLS2; CLS3; CLS4 |
| University of Copenhagen (Denmark) | LRB001; LRB002; LRB003; LRB004; LRB005; LRB006; LRB007; LRB008; LRB009; LRB010; LRB011; LRB013; LRB014; LRB016; LRB017; LRB018; |
| University of Southern Denmark | KMEB1; KMEB2; KMEB3; KMEB4; KMEB |
| University of Helsinki (Finland) | FES21; FES22; FES29; FES30; FES61; FES75 |
| University of Tampere (Finland) | Regea 06/015; Regea 06/040; Regea 07/027; Regea 07/046; Regea 08/013; Regea 08/017; Regea 08/023; Regea 08/056 |
| Leiden University Medical Center (Netherlands) | HESC-NL1; HESC-NL2; HESC-NL3; HESC-NL4 |
| Russian Academy of Sciences (Russia) | ESM01; ESM02; ESM03; |
| Instanbul Memorial Hospital (Turkey) | MINE: NS-2; NS-3; NS-4; NS-5; NS-6; NS-7; NS-8; NS-9; NS-10; OZ-1; OZ-2; OZ-3; OZ-4; OZ-5; OZ-6; OZ-7; OZ-8 |
| Australia | |
| Monash University (Australia) | Envy |
| Prince of Wales Hospital, Sydney (Australia) | E1C1; E1C2; E1C3; E1C4; Endeavour 1; Endeavour 2; hES3.1; hES3.2; hES3.3 |
| Sydney IVF Limited (Australia) | SIVF01; SIVF03; SIVF05; SIVF06; SIVF07; SIVF08; SIVF09; SIVF10; SIVF11; SIVF12; SIVF13 |
| Asia | |
| Kyoto University (Japan) | 201B1; 201B2; 201B3; 201B6; 201B7; 243H1; 243H7; 246G1; 246G3; 246G4; 246G5; 246G6; khES-1; khES-2; khES-3; |
| Singapore Stem Cell Consortium | ESI-013; ESI-014; ESI-017; ESI-027; ESI-035; ESI-049; ESI-051; ESI-053 |
| ES Cell International Pte Ld (Singapore) | ES01, E502, E503, E504, E505, E506 (HES-1, HES-2, HES-3, HES-4, HES-5, HES-6 |
| Maria Biotech Co. Ltd. - Maria Infertility Hospital Medical Institute, Seoul (Korea) | MB01, MB02, MB03; MB04; MB05; MB06; MB07; MB08; MB09 |
| MizMedi Hospital-Seoul National University, Seoul (Korea) | MI01(Miz-hES1); Miz-hES2; Miz-hES3; Miz-hES4; Miz-hES5; Miz-hES6; Miz-hES7; Miz-hES8; Miz-hES9; Miz-hES10; Miz-hES11; Miz-hES12; Miz-hES13; Miz-hES14; Miz-hES15; |
| Pochon CHA University College of Medicine (Korea) | CHA-hES3; CHA-hES4 |
| Seoul National University (Korea) | SNUhES1; SNUhES2; SNUhES3; SNUhES4; SNUhES11; SNUhES16 |
| National Centre for Biological Sciences/Tata Institute of Fundamental Research, Bangalore (India) | NC01, NC02, NC03 (FCNCBS1, FCNCBS2, FCNCBS3); BJN-hem19; BJN-hem20 |
| Reliance Life Sciences, Mumbai (India) | RL05, RL07, RL10, RL13, RL15, RL20, RL21 (RLS ES 05, RLS ES 07, RLS ES 10, |
| National Institute for Research in Reproductive Health (India) | KIND-1; KIND-2 |
| Tata Institute of Fundamental Research (India) | FCNCBS1; FCNCBS2; FCNCBS3 |
| Kaohsiung Medical University (Taiwan) | T1; T2; T3; T4; T5 |
| Central South University (China) | chESC-3 (H3); chESC-8; chESC-20; chESC-22; EBNA1+H9 |

TABLE 5-continued

Listing of Human Embryonic Stem (hES) Cell Lines

| Commercially Available From | Human Embryonic Stem (hES) Cell Lines |
|---|---|
| Graduate University of Chinese Academy of Sciences (China) | hPES-1; hPES-2 |
| Huazhong University of Science and Technology (China) | hES-8; hES18 |
| Peking University Third Hospital (China) | B4; B7; PKU1; PKU2 |
| Shanghai Jiao Tong University School of Medicine (China) | SHhES1 |
| Shanghei Second Medical University (China) | SH1; SH2; SH4; SH7; SH28; SH35; SH35a; SH38; SH39; SH42 |
| Sun Yat-sen University (China) | CHES-1; SYSU-1; SYSU-2 |
| Sun Yat-sen University Second Affiliated Hospital (China) | CHE-1; CHE-2; CHE-3 |
| The Third Affiliated Hospital of Guangzhou Medical College (China) | FY-hES-5; FY-hES-9; FY-hES-10;; FY-hES-11 |

Alternative Methods for Deriving Pluripotent Stem Cells

Methods exist for deriving pluripotent stem cells, such as mammalian ES cells, without destruction of the embryo. Briefly, Advanced Cell Technology (Worcester, Mass., USA) published 3 scientific journal articles describing derivation of mouse and human ES cells from single blastomeres leaving the embryo intact and thus not causing its destruction. In late 2005, Chung et al. first described methods for making mouse ES cells from a single blastomere. See Chung et al. (2006) Nature 439: 216-219, published online Oct. 16, 2005. Chung et al. (2006) described taking biopsies from an embryo using micromanipulation techniques similar to techniques used for pre-implantation genetic diagnosis (PGD); see page 217. At the time, Chung et al. (2006) co-cultured the blastomere cell lines with other embryonic stem cells, but later developed methods where this was not required. See Chung et al. (2008) Human Embryonic Stem Cell Lines Generated without Embryo Destruction, Cell Stem Cell 2: 113-117.

Pre-implantation genetic diagnosis is used to analyze for genetic abnormalities in embryos prior to implantation. The method is performed on early stage normally developing embryos (e.g. eight-cell stage), when the genetic input of both parents can be studied, by making a hole in the zona pellucida and aspirating or extruding or dissection one or two blastomeres through the opening. Genetic analysis using fluorescent in situ hybridization (FISH) and polymerase chain reaction (PCR) are the commonly used in PGD to analyze for chromosomal abnormalities and monogenic disorders, respectively. Subsequently, if there are no genetic abnormalities, the remaining intact embryo is implanted into the female patient for the normal gestation period. Pre-implantation genetic diagnosis techniques were reported as early as 2004 by various groups including Staessen, C. et al. (2004), Comparison of blastocyst transfer with or without preimplantation genetic diagnosis for aneuploidy screening in couples with advanced maternal age: a prospective randomized controlled trial, Hum. Reprod. 19: 2849-2858 and Monni et al. (2004) Preimplantation genetic diagnosis for beta-thalassaemia: the Sardinian experience. Prenat Diagn 24: 949-954. So, Chung et al. (2006) merely described methods for which were available for extracting blastomeres from early stage embryos without destroying the embryo.

Further, in August of 2006, Klimanskaya et al., the $2^{nd}$ author in the Chung et al. (2006) publication and also from Advanced Cell Technology, described a procedure, which although was not efficient (only 2% of the blastomeres isolated generated an hES cell line), demonstrated that similar PGD techniques made possible derivation of human ES cell lines from a single blastomere; not significantly different from that first described by Chung et al. (2006) supra. See Klimanskanya et al. (2006) Human embryonic stem cell lines derived from single blastomeres, Nature 444, 481-485. Klimanskaya et al. co-cultured the newly derived hES cell lines with other ES cells, which Chung et al. (2006) stated may be critical. Chung et al. (2006) stated that "it is unclear whether the success of the ES co-culture system in [his] study is attributable to substances secreted by the ES cells or if cell-cell contact is required". See Chung et al. (2006) supra, p. 218, right column. But a later 2008 study by the same Chung. et al., supra, demonstrated that hES cell lines did not require co-culturing with ES cells at all because culturing the isolated blastomeres in medium with laminin enhanced their ability to give rise to hESCs. See Chung et al. (2008), Human Embryonic Stem Cell Lines Generated without Embryo Destruction, Cell Stem Cell (2):113-117, p. 116, published online Jan. 10, 2008. Further, that hES cells obtained in this manner had the same characteristics as other human pluripotent stem cells including hES cells including being capable of maintaining an undifferentiated state for over six (6) months, and showed normal karyotype and expression of markers of pluripotency, including Oct-4, SSEA-3, SSEA-4, TRA-1-60, TRA-1-81, Nanog and Alkaline Phosphatase; and can differentiate and form derivatives of all three (3) embryonic germ layers both in vitro and form in teratomas in vivo.

Therefore, if co-culturing of single blastomeres with other ES cells is not critical as first postulated by Chung et al. (2006), and that culturing them on just laminen, which is a common component of many extracellular matrices (commercially available and or made by lysing feeder cells for example) and was commonly used and known to grow mammalian cells, and such was known and available at the time of the first showing of the derivation of mouse ES cell lines from a single blastomere by Chung's 2006 publication. Thus, it is entirely possible that one of skill in the art was capable of taking the methodologies of Chung et al. (2006) supra and using the knowledge available as earlier described by Straessen et al. (2004) supra to derive a hES cell line from a single blastomere while preserving the embryo or preventing its destruction.

Aggregate Suspension of Pluripotent Stem Cells and Cells Derived from Pluripotent Stem Cells In contrast to previously known methods of tissue engineering which are based on seeding individual cells into polymer scaffolds, matrices and/or gels, embodiments described herein can use cell aggregate suspensions formed from pluripotent stem cell, single cell suspensions or differentiated single cell suspensions derived therefrom. Methods of processing and/or manufacturing of stem cell aggregate suspension and differentiation of cells thereof is described in PCT/US2007/062755, filed Feb. 23, 2007, and titled COMPOSITIONS AND METHODS FOR CULTURING DIFFERENTIAL CELLS, and now U.S. Pat. Nos. 8,211,699 and 8,415,158; and PCT/US2008/080516, filed Oct. 20, 2008, and titled METHODS AND COMPOSITIONS FOR FEEDER-FREE PLURIPOTENT STEM CELL MEDIA CONTAINING HUMAN SERUM, and now U.S. Pat. No. 8,334,138, and Schulz T. et al. (2012) supra.

Embodiments described herein relate to methods for generating a pluripotent cell aggregate in suspension from a pluripotent adherent culture, by culturing a pluripotent cell in an adherent growth culture condition which allows for expansion in an undifferentiated state; disassociating the adherent pluripotent cell culture into a single cell suspension culture; contacting the single cell suspension culture with a first differentiating culture condition which allows for formation of hES-derived cell aggregates in suspension by agitating the single cell suspension culture until such a period of time when the single cell suspension culture forms a pluripotent-derived cell aggregate in suspension, and thereby generating a pluripotent-derived cell aggregate in suspension. In preferred embodiments, agitation of the single cell suspension culture is performed by rotation at about 80 rpm to 160 rpm. In certain other embodiments described herein, a rho-kinase inhibitor is used to facilitate pluripotent stem cell aggregation, growth, proliferation, expansion and/or cell mass.

The phase "substantially uniform" or "substantially uniform in size and shape" or equivalents thereof, refers to the spread in uniformity of the aggregates and is not more than about 20%. In another embodiment, the spread in uniformity of the aggregates is not more than about 15%, 10% or 5%.

In yet another embodiment, hES cell aggregate suspensions were cultured in a media substantially free of serum and further in the absence of exogenously added fibroblast growth factor (FGF). This is distinguished from U.S. Pat. No. 7,005,252 to Thomson, J., which requires culturing hES cells in a media without serum but containing exogenously added growth factors, including FGF. In some embodiments, iPS cell aggregate suspensions are cultured in a media substantially free of serum and/or further in the absence of exogenously added fibroblast growth factor (FGF).

Although the exact number of cells per aggregate is not critical, it will be recognized by those skilled in the art that the size of each aggregate (and thus the number of cells per aggregate) is limited by the capacity of oxygen and nutrients to diffuse to the central cells, and that this number may also vary depending on cell type and the nutritive requirements of that cell type. Cell aggregates may comprise a minimal number of cells (e.g., two or three cells) per aggregate, or may comprise many hundreds or thousands of cells per aggregate. Typically, cell aggregates comprise hundreds to thousands of cells per aggregate. For purposes of the present invention, the cell aggregates are typically from about 50 microns to about 600 microns in size, although, depending on cell type, the size may be less or greater than this range. In one embodiment, the cell aggregates are from about 50 microns to about 250 microns in size, or about 75 to 200 microns in size, and preferably they are about 100 to 150 microns in size.

Still other methods describe making embryoid bodies (EBs). As used herein, the term "embryoid bodies", "aggregate bodies" or equivalents thereof, refer to aggregates of differentiated and undifferentiated cells that appear when ES cells overgrow in monolayer cultures, or are maintained in suspension cultures in undefined media or are differentiated via non-directed protocols towards multiple germ layer tissues. That is, EBs are not formed from a single cell suspension of pluripotent stem cells as described herein; nor are EBs formed from adherent cultures of pluripotent-derived multipotent cells. These features alone make the present invention clearly distinguished from an embryoid body.

In contrast to embryoid bodies, which are a mixture of differentiated and undifferentiated cells and typically consist of cells from several germ layers and go through random differentiation, the cell aggregates described herein are essentially or substantially homo-cellular, existing as aggregates of pluripotent, multipotent, bipotent, or unipotent type cells, e.g., embryonic cells, definitive endoderm, foregut endoderm, PDX1 positive pancreatic endoderm, pancreatic endocrine cells and the like.

The methods described herein in no way require first coating the culturing vessels with an extracellular matrix, e.g., as described in U.S. Pat. No. 6,800,480 to Bodnar et al. and assigned to Geron Corporation. In some embodiments described herein, iPS cells can be cultured in the same way that other pluripotent stem cells, e.g., hES and iPS cells, are cultured using soluble human serum as substantially described in Applicant's U.S. Pat. No. 8,334,138; and Schulz T. et al. (2012) supra.

The methods described herein in no way require exogenously added fibroblast growth factor (FGF) supplied from a source other than just a fibroblast feeder layer as described in U.S. Pat. No. 7,005,252 to Thomson, J. and assigned to the Wisconsin Alumni Research Foundation (WARF).

Multipotent and Differentiated Cell Compositions

Cell compositions produced by the methods described herein include cell cultures comprising pluripotent stem cells, preprimitive streak, mesendoderm, definitive endoderm, foregut endoderm, PDX1-positive foregut endoderm, PDX1-positive pancreatic endoderm or PDX1/NKX6.1 co-positive pancreatic endoderm, endocrine progenitor/precursor or NGN3/NKX2.2 co-positive endocrine progenitor/precursor, and hormone secreting endocrine cells or INS, GCG, GHRL, SST, PP singly-positive endocrine cells, wherein at least about 5-90% of the cells in culture are the preprimitive streak, mesendoderm, definitive endoderm, foregut endoderm, PDX1-positive foregut endoderm, PDX1-positive pancreatic endoderm or PDX1/NKX6.1 co-positive pancreatic endoderm, endocrine progenitor/precursor or NGN3/NKX2.2 co-positive endocrine progenitor/ precursor, and hormone secreting endocrine cells or INS, GCG, GHRL, SST, PP singly-positive endocrine cells produced.

Some embodiments described herein relate to compositions, such as cell populations and cell cultures that comprise both pluripotent cells, such as stem cells and iPS cells, and multipotent cells, such as preprimitive streak, mesendoderm or definitive endoderm, as well as more differentiated, but still potentially multipotent, cells, such as PDX1-positive foregut endoderm, PDX1-positive pancreatic endoderm or PDX1/NKX6.1 co-positive pancreatic endoderm, endocrine progenitor/precursor or NGN3/NKX2.2 co-positive endocrine progenitor/precursor, and hormone secreting endocrine cells or INS, GCG, GHRL, SST, PP singly-positive endocrine cells. For example, using the methods described herein, compositions comprising mixtures of pluripotent stem cells and other multipotent or differentiated cells can be produced. In some embodiments, compositions comprising at least about 5 multipotent or differentiated cells for about every 95 pluripotent cells are produced. In other embodiments, compositions comprising at least about 95 multipotent or differentiated cells for about every 5 pluripotent cells are produced. Additionally, compositions comprising other ratios of multipotent or differentiated cells to pluripotent cells are contemplated. For example, compositions comprising at least about 1 multipotent or differentiated cell for about every 1,000,000 pluripotent cells, at least about 1 multipotent or differentiated cell for about every 100,000 pluripotent cells, at least about 1 multipotent or differentiated cell for about every 10,000 pluripotent cells, at least about 1 multipotent or differentiated cell for about every 1000 pluripotent cells, at least about 1 multipotent or differentiated cell for about every 500 pluripotent cells, at least about 1 multipotent or differentiated cell for about every 100 pluripotent cells, at least about 1 multipotent or differentiated cell for about every 10 pluripotent cells, at least about 1 multipotent or differentiated cell for about every 5 pluripotent cells, and up to about every 1 pluripotent cell and at least about 1,000,000 multipotent or differentiated cell for about every 1 pluripotent cell are contemplated.

Some embodiments described herein relate to cell cultures or cell populations comprising from at least about 5% multipotent or differentiated cell to at least about 99% multipotent or differentiated cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 99% of the human cells are multipotent or differentiated cell. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or greater than 99% of the human cells are multipotent or differentiated cells. In embodiments where the cell cultures or cell populations comprise human feeder cells, the above percentages are calculated without respect to the human feeder cells in the cell cultures The compositions and methods described herein have several useful features. For example, the cell cultures and cell populations comprising, multipotent cells, e.g., preprimitive streak cells and/or mesendoderm cells as well as the methods for producing such cell cultures and cell populations, are useful for modeling the early stages of human development. Furthermore, the compositions and methods described herein can also serve for therapeutic intervention in disease states, such as diabetes mellitus. For example, since preprimitive streak cells and/or mesendoderm cells serve as the source for only a limited number of tissues, they can be used in the development of pure tissue or cell types. In some processes for producing preprimitive streak cells, the pluripotent cells used as starting material are pluripotent stem cells, e.g., hES, hEG or iPS cells.

Trophectoderm Cells

Using the methods described herein, compositions comprising trophectoderm cells substantially free of other cell types can be produced. In some embodiments described herein, the trophectoderm cell populations or cell cultures produced by the methods described herein substantially have high expression of markers selected from the group comprising HAND1, Eomes, MASH2, ESXL1, HCG, KRT18, PSG3, SFXN5, DLX3, PSX1, ETS2, and ERBB genes as compared to the expression levels of HAND1, Eomes, MASH2, ESXL1, HCG, KRT18, PSG3, SFXN5, DLX3, PSX1, ETS2, and ERBB in non-trophectoderm cells or cell populations.

Preprimitive Streak Cells

Using the methods described herein, compositions comprising preprimitive streak cells substantially free of other cell types can be produced. In some embodiments described herein, the preprimitive streak cell populations or cell cultures produced by the methods described herein are substantially express FGF8 and/or NODAL marker genes as compared to BRACHURYlow, FGF4 low, SNAI1 low, SOX17 low, FOXA2 low, SOX7 low and SOX1 low. Preprimitive streak cells and methods of producing preprimitive streak cells are described in detail in Applicant's U.S. Pat. No. 7,958,585, PREPRIMITIVE STREAK AND MESENDODERM CELLS, issued Jul. 26, 2011.

Extraembryonic Cells

Using the methods described herein, compositions comprising extraembryonic cells substantially free of other cell types can be produced. Primitive, visceral and parietal endoderm cells are extraembryonic cells. Primitive endoderm cells give rise to visceral and parietal endoderm cells. Visceral endoderm cells are endoderm cells that form part of the yolk sac. Visceral endoderm cells function in both nutrient uptake and transport. Parietal endoderm cells are contiguous with an extraembryonic tissue known as Reichert's membrane. One of the roles of parietal endoderm cells is to produce basement membrane components. Together, visceral endoderm cells and parietal endoderm cells form what is often referred to as extraembryonic endoderm. As the name suggests, extraembryonic endoderm cells do not give rise to embryonic structures formed during development. In contrast, definitive endoderm cells and other endoderm-lineage or pancreatic-lineage cells described herein are embryonic or derived from embryonic cells and give rise to tissues that are derived from the gut tube that forms during embryonic development. In some embodiments described herein, the extraembryonic cell populations or cell cultures produced by the methods described herein substantially have high expression of markers selected from the group comprising SOX7, SOX17, THBD, SPARC, DAB1, HNF4alpha or AFP genes as compared to the expression levels of at least SOX7, SOX17, THBD, SPARC, DAB1, or AFP, which is not expressed in other types of cells or cell populations, for example, definitive endoderm.

Mensendoderm Cells

Using the methods described herein, compositions comprising mesendoderm cells substantially free of other cell types can be produced. In some embodiments described herein, the mesendoderm cell populations or cell cultures produced by the methods described herein substantially have high expression of markers selected from the group comprising FGF4, SNAI1 MIXL1 and/or WNT3 marker genes, as compared to SOX17 low, CXCR4 low, FOXA2 low, SOX7 low and SOX1 low. Mesendoderm cells and methods of producing mesendoderm cells are described in detail in Applicant's U.S. Pat. No. 7,958,585, PREPRIMITIVE STREAK AND MESENDODERM CELLS, issued Jul. 26, 2011.

Screening Methods

In some embodiments, screening methods are employed to obtain certain cell populations comprising pluripotent, multipotent and/or differentiated cells, such as human pluripotent stem cells, induced pluripotent stem cells, preprimitive streak cells, mesendoderm cells, definitive endoderm cells, foregut endoderm or PDX1-negative foregut endoderm cells, PDX1-positive foregut endoderm or PDX1-positive pancreatic endoderm cells or pancreatic progenitor cells, endocrine progenitor/precursor cells, and/or endocrine cells. The cell population is then provided with a candidate differentiation factor. At a first time point, which is prior to or at approximately the same time as providing the candidate differentiation factor, expression of a marker is determined. Alternatively, expression of the marker can be determined after providing the candidate differentiation factor. At a second time point, which is subsequent to the first time point and subsequent to the step of providing the candidate differentiation factor to the cell population, expression of the same marker is again determined. Whether the candidate differentiation factor is capable of promoting the differentiation of the pancreatic precursor cells is determined by comparing expression of the marker at the first time point with the expression of the marker at the second time point. If expression of the marker at the second time point is increased or decreased as compared to expression of the marker at the first time point, then the candidate differentiation factor is capable of promoting the differentiation of pancreatic progenitor cells.

Some embodiments of the screening methods described herein utilize cell populations or cell cultures which comprise human definitive endoderm, PDX-1 negative foregut endoderm, PDX-1 positive foregut endoderm, PDX-1 positive pancreatic endoderm, or pancreatic progenitor or endocrine progenitor/precursor cells. For example, the cell population can be a substantially purified population of PDX-1-positive pancreatic endoderm or pancreatic progenitor cells. For example, the cell population can be an enriched population of human pancreatic progenitor cells, wherein at least about 50% to 97% of the human cells in the cell population are human pancreatic progenitor cells, the remainder comprising of endocrine progenitor/precursor or endocrine cells and other cell types. Enrichment of pancreatic progenitor populations is described in detail in Applicant's U.S. patent application Ser. No. 12/107,020, entitled METHOD FOR PURIFYING ENDODERM AND PANCREATIC ENDODERM CELLS DERIVED FROM HUMAN EMBRYONIC STEM CELLS, filed Apr. 21, 2008, now U.S. Pat. No. 8,338,170 and the corresponding publication Kelly et al. (2011) supra.

In embodiments of the screening methods described herein, the cell population is contacted or otherwise provided with a candidate (test) differentiation factor. The candidate differentiation factor can comprise any molecule that may have the potential to promote the differentiation of any of the above-mentioned cells, e.g. human pancreatic progenitor cells. In some embodiments described herein, the candidate differentiation factor comprises a molecule that is known to be a differentiation factor for one or more types of cells. In alternate embodiments, the candidate differentiation factor comprises a molecule that is not known to promote cell differentiation. In preferred embodiments, the candidate differentiation factor comprises a molecule that is not known to promote the differentiation of human pancreatic progenitor cells. Screening for factors which differentiate definitive endoderm for example is described in detail in Applicant's U.S. patent application Ser. No. 12/093,590, entitled MARKERS OF DEFINITIVE ENDODERM, filed Jul. 21, 2008.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor. In certain embodiments, marker expression is determined by Q-PCR. In other embodiments, marker expression is determined by immunocytochemistry.

In certain embodiments of the screening methods described herein, the marker having its expression determined at the first and second time points is a marker that is associated with the differentiation of pancreatic progenitor cells to cells which are the precursors of terminally differentiated cells which make up pancreatic islet tissues. Such cells can include immature pancreatic islet hormone-expressing cells.

In some embodiments of the screening methods described herein, sufficient time is allowed to pass between providing the cell population with the candidate differentiation factor and determining marker expression at the second time point. Sufficient time between providing the cell population with the candidate differentiation factor and determining expression of the marker at the second time point can be as little as from about 1 hour to as much as about 10 days. In some embodiments, the expression of at least one marker is determined multiple times subsequent to providing the cell population with the candidate differentiation factor. In some embodiments, sufficient time is at least about 1 hour, at least about 6 hours, at least about 12 hours, at least about 16 hours, at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 1 week, at least about 2 weeks, at least about 3 weeks, at least about 4 weeks, at least about 5 weeks, at least about 6 weeks, at least about 7 weeks, or at least about 8 weeks.

In some embodiments of the methods described herein, it is further determined whether the expression of the marker at the second time point has increased or decreased as compared to the expression of this marker at the first time point. An increase or decrease in the expression of the at least one marker indicates that the candidate differentiation factor is capable of promoting the differentiation of the endocrine progenitor/precursor cells. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

Monitoring the Production of Multipotent or Differentiated Cells

The progression of pluripotent cells to multipotent cells to further multipotent cells or differentiated cells, such as pancreatic progenitors or hormone endocrine secreting cells, can be monitored by determining the expression of markers characteristic of the specific cells, including genetic markers and phenotypic markers such as, the expression of islet hormones and the processing of proinsulin into insulin and C peptide in endocrine cells. In some processes, the expression of certain markers is determined by detecting the presence or absence of the marker. Alternatively, the expression of certain markers can be determined by measuring the level at which the marker is present in the cells of the cell culture or cell population. For example, in certain processes, the expression of markers characteristic of immature pancreatic islet hormone-expressing cells as well as the lack of significant expression of markers characteristic of pluripotent cells, definitive endoderm, foregut endoderm, PDX1-positive foregut endoderm, endocrine progenitor/precursor, extraembryonic endoderm, mesoderm, ectoderm, mature pancreatic islet hormone-expressing cells and/or other cell types is determined.

As described in connection with monitoring the production of other less differentiated cell types of the definitive endoderm lineage, qualitative or semi-quantitative techniques, such as blot transfer methods and immunocytochemistry, can be used to measure marker expression. Alternatively, marker expression can be accurately quantitated through the use of technique such as Q-PCR or nCounter by Nanostring or related high throughput multiplex technologies capable of analyzing and assaying hundreds or more markers simultaneously. Additionally, it will be appreciated that at the polypeptide level, many of the markers of pancreatic islet hormone-expressing cells are secreted proteins. As such, techniques for measuring extracellular marker content, such as ELISA, may be utilized.

In other embodiments, immunohistochemistry is used to detect the proteins expressed by the above-mentioned genes. In still other embodiments, Q-PCR can be used in conjunction with immunohistochemical techniques or flow cytometry techniques to effectively and accurately characterize and identify cell types and determine both the amount and relative proportions of such markers in a subject cell type. In one embodiment, Q-PCR can quantify levels of RNA expression in a cell culture containing a mixed population of cells. However, Q-PCR cannot provide or qualify whether the subject markers or proteins are co-expressed on the same cell. In another embodiment, Q-PCR is used in conjunction with flow cytometry methods to characterize and identify cell types. Thus, by using a combination of the methods described herein, and such as those described above, complete characterization and identification of various cell types, including endoderm lineage type cells, can be accomplished and demonstrated.

For example, in one preferred embodiment, pancreatic progenitors or pancreatic endoderm or PDX-1 positive pancreatic endoderm, expresses at least PDX1, Nkx6.1, PTF1A, CPA and/or cMYC as demonstrated by Q-PCR and/or ICC, but such a cell at least co-expresses PDX1 and Nkx6.1 as demonstrated by ICC and does not express other markers including SOX17 CXCR4, or CER, to be identified as a PDX1-positive expressing cell. Similarly, for proper identification of a mature hormone secreting pancreatic cell, in vitro or in vivo, for example, there is demonstrated that C-peptide (a product of proper processing of pro-insulin in a mature and functioning β cell) and insulin are co-expressed by ICC in the insulin secreting cell.

Still, other methods which are known in the art can also be used to quantitate marker gene expression. For example, the expression of a marker gene product can be detected by using antibodies specific for the marker gene product of interest (e.g., e.g. Western blot, flow cytometry analysis, and the like). In certain processes, the expression of marker genes characteristic of hES-derived cells as well as the lack of significant expression of marker genes characteristic of hES-derived cells. Still further methods for characterizing and identifying hES-derived cells types are described in related applications as indicated above.

Summary of the Production of PDX1-Positive Pancreatic Endoderm (Stages 1 to 4) and Insulin Production In Vivo The methods for production of certain endoderm-lineage and pancreatic endoderm-lineage cells are provided herein, and discussed elsewhere in related applications such as U.S. Pat. Nos. 7,534,608; 7,695,965; and 7,993,920, titled METHODS OF PRODUCING PANCREATIC HORMONES; and U.S. Pat. No. 8,129,182, titled ENDOCRINE PROGENITOR/PRECURSOR CELLS, PANCREATIC HORMONE-EXPRESSING CELLS AND METHODS OF PRODUCTION. See also Table 17 and FIGS. 42, 43 and 44.

Briefly, the directed differentiation methods herein for pluripotent stem cells, for example, hES and iPS cells, can be described into at least four or five or six or seven stages, depending on end-stage cell culture desired (PEC or endocrine cells). Stage 1 is the production of definitive endoderm from pluripotent stem cells and takes about 2 to 5 days, preferably 2 or 3 days. Pluripotent stem cells are suspended in media comprising RPMI, a TGFβ superfamily member growth factor, such as Activin A, Activin B, GDF-8 or GDF-11 (100 ng/mL), a Wnt family member or Wnt pathway activator, such as Wnt3a (25 ng/mL), and alternatively a rho-kinase or ROCK inhibitor, such as Y-27632 (10 µM) to enhance growth, and/or survival and/or proliferation, and/or cell-cell adhesion. After about 24 hours, the media is exchanged for media comprising RPMI with serum, such as 0.2% FBS, and a TGFβ superfamily member growth factor, such as Activin A, Activin B, GDF-8 or GDF-11 (100 ng/mL), and alternatively a rho-kinase or ROCK inhibitor for another 24 (day 1) to 48 hours (day 2). Alternatively, after about 24 hours in a medium comprising Activin/Wnt3a, the cells are cultured during the subsequent 24 hours in a medium comprising Activin alone (i.e., the medium does not include Wnt3a). Importantly, production of definitive endoderm requires cell culture conditions low in serum content and thereby low in insulin or insulin-like growth factor content. See McLean et al. (2007) Stem Cells 25: 29-38. McLean et al. also show that contacting hES cells with insulin in concentrations as little as 0.2 µg/mL at Stage 1 can be detrimental to the production of definitive endoderm. Still others skilled in the art have modified the Stage 1 differentiation of pluripotent cells to definitive endoderm substantially as described here and in D'Amour et al. (2005), for example, at least, Agarwal et al., Efficient Differentiation of Functional Hepatocytes from Human Embryonic Stem Cells, Stem Cells (2008) 26:1117-1127; Borowiak et al., Small Molecules Efficiently Direct Endodermal Differentiation of Mouse and Human Embryonic Stem Cells, (2009) Cell Stem Cell 4:348-358; and Brunner et al., Distinct DNA methylation patterns characterize differentiated human embryonic stem cells and developing human fetal liver, (2009) Genome Res. 19:1044-1056. Proper differentiation, specification, characterization and identification of definitive are necessary in order to derive other endoderm-lineage cells. Definitive endoderm cells at this stage co-express SOX17 and HNF3β (FOXA2) and do not appreciably express at least HNF4alpha, HNF6, PDX1, SOX6, PROX1, PTF1A, CPA, cMYC, NKX6.1, NGN3, PAX3, ARX, NKX2.2, INS, GSC, GHRL, SST, or PP. The absence of HNF4alpha expression in definitive endoderm is supported and described in detail in at least Duncan et al. (1994), Expression of transcription factor HNF-4 in the extraembryonic endoderm, gut, and nephrogenic tissue of the developing mouse embryo: HNF-4 is a marker for primary endoderm in the implanting blastocyst," Proc. Natl. Acad. Sci, 91:7598-7602 and Si-Tayeb et al. (2010), Highly Efficient Generation of Human Hepatocyte-Like cells from Induced Pluripotent Stem Cells," Hepatology 51:297-305.

Stage 2 takes the definitive endoderm cell culture from Stage 1 and produces foregut endoderm or PDX1-negative foregut endoderm by incubating the suspension cultures with RPMI with low serum levels, such as 0.2% FBS, in a 1:1000 dilution of ITS, 25 ng KGF (or FGF7), and alternatively a ROCK inhibitor for 24 hours (day 2 to day 3). After 24 hours (day 3 to day 4), the media is exchanged for the same media minus a TGFβ inhibitor, but alternatively still a ROCK inhibitor to enhance growth, survival and proliferation of the cells, for another 24 (day 4 to day 5) to 48 hours (day 6). A critical step for proper specification of foregut endoderm is removal of TGFβ family growth factors. Hence, a TGFβ inhibitor can be added to Stage 2 cell cultures, such as 2.5 µM TGFβ inhibitor no. 4 or 5 µM SB431542, a specific inhibitor of activin receptor-like kinase (ALK), which is a TGFβ type I receptor. Foregut endoderm or PDX1-negative foregut endoderm cells produced from Stage 2 co-express SOX17, HNF1β and HNF4alpha and do not appreciably co-express at least SOX17 and HNF3β (FOXA2), nor HNF6, PDX1, SOX6, PROX1, PTF1A, CPA, cMYC, NKX6.1, NGN3, PAX3, ARX, NKX2.2, INS, GSC, GHRL, SST, or PP, which are hallmark of definitive endoderm, PDX1-positive pancreatic endoderm or pancreatic progenitor cells or endocrine progenitor/precursors as well as typically poly hormonal type cells.

Stage 3 (days 5-8) for PEC production takes the foregut endoderm cell culture from Stage 2 and produces a PDX1-positive foregut endoderm cell by DMEM or RPMI in 1% B27, 0.25 µM KAAD cyclopamine, a retinoid, such as 0.2 µM retinoic acid (RA) or a retinoic acid analog such as 3 nM of TTNPB (or CTT3, which is the combination of KAAD cyclopamine and TTNPB), and 50 ng/mL of Noggin for about 24 (day 7) to 48 hours (day 8). Specifically, Applicants have used DMEM-high glucose since about 2003 and all patent and non-patent disclosures as of that time employed DMEM-high glucose, even if not mentioned as "DMEM-high glucose" and the like. This is, in part, because manufacturers such as Gibco did not name their DMEM as such, e.g. DMEM (Cat. No 11960) and Knockout DMEM (Cat. No 10829). It is noteworthy, that as of the filing date of this application, Gibco offers more DMEM products but still does not put "high glucose" in certain of their DMEM products that contain high glucose e.g. Knockout DMEM (Cat. No. 10829-018). Thus, it can be assumed that in each instance DMEM is described, it is meant DMEM with high glucose and this was apparent by others doing research and development in this field. More details describing use of exogenous high-glucose are described in Example 21. Again, a ROCK inhibitor or rho-kinase inhibitor such as Y-27632 can be used to enhance growth, survival, proliferation and promote cell-cell adhesion. PDX1-positive foregut cells produced from Stage 3 co-express PDX1 and HNF6 as well as SOX9 and PROX, and do not appreciably co-express markers indicative of definitive endoderm or foregut endoderm (PDX1-negative foregut endoderm) cells or PDX1-positive foregut endoderm cells as described above in Stages 1 and 2.

The above stage 3 method is one of four stages for the production of PEC. For the production of endocrine progenitor/precursor and endocrine cells as described in detail in Examples 9-24 below, in addition to Noggin, KAAD-cyclopamine and Retinoid; Activin, Wnt and Heregulin, alone and/or combined, are used to suppress NGN3 expression while maintaining good cell aggregate mass. See Examples 8, 9 and 10.

Stage 4 (days 8-14) PEC production takes the media from Stage 3 and exchanges it for media containing DMEM in 1% vol/vol B27 supplement, plus 50 ng/mL KGF and 50 ng/mL of EGF and sometimes also 50 ng/mL Noggin and a ROCK inhibitor and further includes Activin alone or combined with Heregulin. These new methods give rise to pancreatic progenitor cells co-expressing at least PDX1 and NKX6.1 as well as PTF1A. These cells do not appreciably express markers indicative of definitive endoderm or foregut endoderm (PDX1-negative foregut endoderm) cells as described above in Stages 1, 2 and 3. See FIG. 44.

Alternatively, the cells from Stage 4 can be further differentiated in Stage 5 to produce endocrine progenitor/precursor or progenitor type cells and/or singly and polyhormonal pancreatic endocrine type cells in a medium containing DMEM with 1% vol/vol B27 supplement for about 1 to 6 days (preferably about 2 days, i.e. days 13-15). Endocrine progenitor/precursors produced from Stage 5 co-express at least CHGA, NGN3 and Nkx2.2, and do not appreciably express markers indicative of definitive endoderm or foregut endoderm (PDX1-negative foregut endoderm) as described above in Stages 1, 2, 3 and 4 for PEC production. See FIG. 44.

For PEC production, PDX1-positive pancreatic endoderm produced from Stage 4 are loaded and wholly contained in a macro-encapsulation device and transplanted in a patient, and the PDX1-positive pancreatic endoderm cells mature into pancreatic hormone secreting cells, or pancreatic islets, e.g., insulin secreting beta cells, in vivo (also referred to as "in vivo function"). Encapsulation of the PDX1-positive pancreatic endoderm cells and production of insulin in vivo is described in detail in U.S. application Ser. No. 12/618,659 (the '659 Application), entitled ENCAPSULATION OF PANCREATIC LINEAGE CELLS DERIVED FROM HUMAN PLURIPOTENT STEM CELLS, filed Nov. 13, 2009. The '659 Application claims the benefit of priority to Provisional Patent Application No. 61/114,857, entitled ENCAPSULATION OF PANCREATIC PROGENITORS DERIVED FROM HES CELLS, filed Nov. 14, 2008; and U.S. Provisional Patent Application No. 61/121,084, entitled ENCAPSULATION OF PANCREATIC ENDODERM CELLS, filed Dec. 9, 2008; and now U.S. Pat. Nos. 8,278,106 and 8,424,928. The methods, compositions and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

For example, Activin A, a member of the TGFβ superfamily of growth factors or signaling proteins, is used to produce definitive endoderm from pluripotent cells, e.g., hES cells and iPS cells, however, other TGFβ super family members can be used, for example GDF-8 and GDF-11, to produce definitive endoderm such as those described in International Application PCT/US2008/065686, entitled GROWTH FACTORS FOR PRODUCTION OF DEFINITIVE ENDODERM, filed Jun. 3, 2008.

Still in a different context, Activin alone or in combination with Wnt and Heregulin are capable of suppressing and inhibiting the expression of NGN3 at high and low levels; at low levels alone or in combination with Heregulin, or alternatively at high levels in combination with WNT and Heregulin, cell mass and therefore yield can be maintained. See Examples 8, 9 and 10.

For PEC production, retinoic acid (RA) is used to differentiate PDX1-negative foregut endoderm cells in Stage 2 to PDX1-positive foregut cells in Stage 3. However, other retinoids or retinoic acid analogues such as 4-[(E)-2-(5, 6, 7, 8-tetrahydro-5,5,8,8-tetramethyl-2-napthalenyl)-1-propenyl]benzoic acid (or TTNPB) and similar analogs (e.g., 4-HBTTNPB) can be used. For endocrine and endocrine progenitor/precursor cell production, retinoic acid or any of its analog can also be added during stages 6 and/or 7 to induce hormone gene expression. See Examples 13 and 16.

Noggin is a protein for example that inactivates members of the TGFβ superfamily signaling proteins, such as bone morphogenetic protein-4 (BMP4). However, other BMP4 inhibitors such as Chordin and Twisted Gastrulation (Tsg) or anti-BMP neutralizing antibodies can prevent BMP binding to its cell surface receptors, thereby effectively inhibiting the BMP signaling. Alternatively, the gene for human Noggin has been cloned and sequenced. See U.S. Pat. No. 6,075,007. Analysis of the Noggin sequence shows a carboxy terminal region having homology to a Kunitz-type protease inhibitor, indicating that potentially other Kunitz-type protease inhibitors may have a similar effect on inhibiting BMP. Example 15 describes use of Noggin to increase production of non-endocrine (CHGA−) sub-populations.

Lastly, the macro-encapsulation devices described herein and in the '659 Application; U.S. Design application 29/447,944; 29/408,366; 29/408,368; 29/423,365; and 61/774,443, titled SEMIPERMEABLE MACRO IMPLANTABLE CELLULAR ENCAPSULATION DEVICES, filed Mar. 7, 2013, are again only exemplary and are not intended as limitations on the scope of the invention. Particularly, changes to the device design such as size of the device, plurality of chambers or subcompartments in the device, or plurality of ports, or even mechanisms for loading and extracting the device are all encompassed within the spirit of the invention. Hence, it will be apparent to one skilled in the art that varying substitutions and modifications not only to the described differentiation methods herein but to the encapsulation device as well may be made to the invention disclosed herein without departing from the scope and spirit of the invention. See Examples 10, 12 and 18.

With respect to some of the processes for the differentiation of pluripotent cells to definitive endoderm cells, the above-mentioned growth factors are provided to the cells so that the growth factors are present in the cultures at concentrations sufficient to promote differentiation of at least a portion of the pluripotent cells to definitive endoderm cells and pancreatic lineage cells. In some processes, the above-mentioned growth factors are present in the cell culture at a concentration of at least about 5 ng/mL, at least about 10 ng/mL, at least about 25 ng/mL, at least about 50 ng/mL, at least about 75 ng/mL, at least about 100 ng/mL, at least about 200 ng/mL, at least about 300 ng/mL, at least about 400 ng/mL, at least about 500 ng/mL, at least about 1000 ng/mL, at least about 2000 ng/mL, at least about 3000 ng/mL, at least about 4000 ng/mL, at least about 5000 ng/mL or more than about 5000 ng/mL. Still other agents or growth factors are present in cell cultures at a concentration of at least 0.1 mM or 10 mM or more.

In certain processes, pluripotent stem cell differentiation agents and/or growth factors are removed from the cell culture subsequent to their addition. For example, the growth factors can be removed within about one day, about two days, about three days, about four days, about five days, about six days, about seven days, about eight days, about nine days or about ten days after their addition. In a preferred process, the growth factors are removed about four days after their addition. Removal of the agent and/or growth factor can be accomplished by changing the media in the absence of the agent and/or growth factor, or using another agent which inhibits the function of that agent and/or growth factor.

In one preferred embodiment, stage 3 cell cultures include but are not limited to agents capable of repressing, suppressing, inhibiting and the like, cells committed to the endocrine lineage (CHGA+). Such agents also include Activin, heregulin and WNT and combinations of the three in amounts effective to promote differentiation and/or induce expression of markers which are indicative of non-endocrine multipotent pancreatic progenitor sub-population (CHGA−) and repress or minimize marker expression of cells committed to the endocrine lineage (CHGA+). Markers indicative of cells committed to the endocrine lineage (CHGA+) include but are not limited to NGN3, NKX2.2 and others.

In another preferred embodiment, stage 4 cell cultures include but are not limited to agents capable of repressing, suppressing, inhibiting and the like, cells committed to the endocrine lineage (CHGA+). Such agents also include Activin and heregulin and combinations of the two in amounts effective to promote differentiation and/or induce expression of markers which are indicative of non-endocrine multipotent pancreatic progenitor sub-population (CHGA−) and repress or minimize marker expression of cells committed to the endocrine lineage (CHGA+). Markers indicative of cells committed to the endocrine lineage (CHGA+) include but are not limited to NGN3, NKX2.2 and others. Means of suppressing at least NGN3 during stages 3 and 4 are described in detail in Examples 8-21 below.

In one embodiment, stage 4 cell cultures are further differentiated in stage 5 with at least Noggin, KGF, EGF, and a Notch signaling or pathway inhibitor. Markers indicative of endocrine differentiation include but are not limited to NGN3, NKX2.2 and others. In a preferred embodiment, agents are used in stages 1-7 which simulate or effectively mimic in vitro what is observed in in vivo developmental studies. For example, stages 3 and 4 herein and according to Table 17, use agents that are capable of delaying, repressing, suppressing and/or inhibiting endocrine differentiation or delaying, repressing, suppressing and/or inhibiting markers indicative of endocrine differentiation including but not limited to NGN3 and NKX2.2. During stages 5, 6, and/or 7, cell cultures are treated with agents that are capable of inducing, increasing and/or promoting endocrine differentiation, for example, by using a Notch pathway inhibitor such as a gamma secretase inhibitor. In short stages 3 and 4 cell culture conditions suppress endocrine phenotypes, whereas cell culture conditions from stages 5, 6, and/or 7 progressively induce endocrine phenotypes including but not limited to insulin (INS), glucagon (GCG), somatostatin (SST), pancreatic polypeptide (PP), ghrelin (GHRL), solute carrier family 30 member 8 (SLC30A8), Glucose-6-phosphatase 2 (G6PC2), prohormone convertase 1 (PCSK1) and glucose kinase (GCK).

In one embodiment, PDX1-positive pancreatic endoderm cells are differentiated to endocrine and endocrine progenitor/precursor cells by continuing the incubation of PDX1-positive pancreatic endoderm cells in the presence of a Notch signaling inhibitor, e.g., a gamma secretase inhibitor such as RO4929097, used alone or in combination with retinoids such as retinoic acid. The presence of a Notch signaling inhibitor induces the expression of NGN3 during stage 5. In other embodiments, the gamma secretase inhibitor is provided at the start of the differentiation process, for example, at the pluripotent stage, and remains in the cell culture throughout the differentiation to pancreatic islet hormone-expressing cells. In still other embodiments, the gamma secretase inhibitor is added subsequent to the initiation of differentiation but prior to differentiation to the PDX1-positive foregut endoderm stage. In preferred embodiments, the gamma secretase inhibitor is provided to the cell culture or cell population at about the same time as providing the differentiation factors which promote the conversion of definitive endoderm to PDX1-positive endoderm. In other preferred embodiments, the gamma secretase inhibitor is provided to the cell culture or cell population after a substantial portion of the cells in the cell culture or cell population have differentiated to PDX1-positive foregut endoderm cells.

In another embodiment, cell cultures from stage 5 are further differentiated in stage 6 and 7. During these stages agents are used that are capable of properly specifying endocrine progenitor/precursors or progenitor cells to differentiate to more developmentally advanced and/or mature endocrine cells in vivo. Such agents include but are not limited to a retinoid or retinoic acid, BMP, Nicotinamide, IGF, hedgehog proteins and the like. In a preferred embodiment, TTNPB (4-[(E)-2-(5,6,7,8-Tetrahydro-5,5,8,8-tetramethyl-2-naphthalenyl)-1-propenyl]benzoic acid or Arotinoid acid) is a selective and highly potent retinoic acid analog with affinity for retinoic acid receptors (RAR) α, β, and γ, which are nuclear transcription factors. TTNPB and other retinoic acid or retinoic acid analogs produce ligand-activated transcription of genes that possess retinoic acid responsive elements. Hence, other agents or ligands capable of activating retinoic acid responsive elements or binding to any of the RAR is potentially useful and amendable to this invention for promoting endocrine cell differentiation.

In another embodiment, cell cultures from stage 5 or stage 6 or stage 7 can be further treated with Matrigel alone or in combination with a rho-kinase inhibitor to improve cell adhesion. Alternatively, a rho-kinase inhibitor can be added at stages any of stages 5, 6, or 7 at concentrations sufficient to promote cell-survival, cell mass and yield. Alternatively, cell cultures can be disassociated and re-associated during or between stages 6 and 7 to remove or deplete unwanted cell types including but not limited to non-endocrine multipotent pancreatic progenitor sub-population (CHGA−). See Example 14.

In still another embodiment, any of stages 1-7 can be prolonged 1, 2, 3, 4, 5, 6, 7, 8, 9, 10 more days or shortened by 1, 2, 3, 4, 5, 6, 7 or more days. For example, in one preferred embodiment and according to Table 17, stage 6 occurs over about 6 days and stage 7 over about 9 days. However, both these stages can be shortened to accommodate production of an endocrine progenitor/precursor, for example, for lengthened and prolonged to 29, 30, 31, 32, 33, 34, 35, 36, 37, 38, 39, 40 or more days to produce a more developmentally advanced endocrine cell.

In another embodiment, there are provided methods to produce a more developmentally advanced PEC or pancreatic endocrine progenitor/precursor or pancreatic endocrine cell. In one aspect of the invention, there is provided a singly pancreatic hormone expressing endocrine cell that is co-positive with PDX1 and NKX6.1, e.g. an immature beta cell co-expressing INS, PDX1 and NKX6.1. In another aspect, a developmentally advanced cell can be a PEC culture that consists principally of non-endocrine pancreatic progenitor cells that express at least PDX and NKX6.1 but does not consist of or consists minimally of cells committed to the endocrine lineage (CHGA+) expressing at least CHGA+, NGN3 and/or NKX2.2. These PEC cultures are developmentally advanced because they are considered to be more akin to that which has been shown in vivo in developmental studies of pancreatic differentiation. See Jorgensen et al. (2007), An Illustrated Review of Early Pancreas Development in the Mouse, *Endocrine Reviews* 28(6):685-705 and Rukstalis and Habener (2009), Neurogenin3: A master regulator of pancreatic islet differentiation and regeneration, *Islets* 1(3): 177-184. Another example of a developmentally advanced cell or cell culture, is one which has been disassociated and re-aggregated or re-associated such that the re-aggregated cell culture consists of a more homogenous population of cells. This more homogenous population of cells in one aspect of the invention does not comprise earlier stage cell types, e.g. pancreatic endocrine progenitor/precursor or endocrine cells that are principally comprised of single hormone expressing cells that are co-positive for PDX1 and NKX6.1 but not comprising cells or sub-populations from stages 3 and 4 or PEC or PEC sub-populations including but not limited to non-endocrine multipotent pancreatic progenitor (CHGA−) cells, or residual/triple negatives cells (CHGA−/PDX1−/NKX6.1−) and the like, or multi-hormone expressing cells (i.e. cells expressing more than one hormone on any one cell type).

In another embodiment, the cell cultures provided herein are preferably properly specified which has a specific and certain meaning in the art of developmental biology. In the context of developmental biology, it is the mechanism by which cells obtain distinct fates or are specified or properly specified. Since cell culture differentiation in vitro lacks temporal organization and cues typical of in vivo developmental studies, use and reliance of cell markers (surface or internal markers such as transcription factors), in particular, signature or salient cell markers indicative of a specific cell type are essential. Thus, reference to properly specified cells, cell cultures, sub-populations and populations means that those cells have distinct fates and those fates are more certain and determined based on their marker expression, profile of markers which they express and, as important, markers which they do not express. Proper specification of cell cultures in vitro depends on in vivo developmental studies of similar cells, thus in one preferred embodiment, in vivo developmental studies are a guide to in vitro differentiation and characterizing properly specified cells.

In some embodiments of the invention described herein, exendin 4 is provided to the differentiating cell culture or cell population at about the same time as the gamma secretase inhibitor. In certain embodiments, exendin 4 is provided so as to be in present in the cell culture or cell population at a concentration of at least about 0.1 ng/mL, to 1000 ng/mL.

It will be appreciated that NGN3, NKX2.2 and/or PAX4 marker expression is induced over a range of different levels in endocrine progenitor/precursor cells depending on the differentiation conditions. As such, in some embodiments described herein, the expression of the NGN3, NKX2.2 and/or PAX4 marker in endocrine progenitor/precursor cells or cell populations is at least about 2-fold higher to at least about 10,000-fold higher than the expression of the NGN3, NKX2.2 and/or PAX4 marker in non-endocrine progenitor/precursor cells or cell populations, for example pluripotent stem cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells. In other embodiments, the expression of the NGN3, NKX2.2 and/or PAX4 marker in endocrine progenitor/precursor cells or cell populations is at least about 4-fold higher, at least about 6-fold higher to 10,000-fold higher than the expression of the NGN3, NKX2.2 and/or PAX4 marker in non-endocrine progenitor/precursor cells or cell populations, for example pluripotent stem cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells. In some embodiments, the expression of the NGN3, NKX2.2 and/or PAX4 marker in endocrine progenitor/precursor cells or cell populations is infinitely higher than the expression of the NGN3, NKX2.2 and/or PAX4 marker in non-endocrine progenitor/precursor cells or cell populations, for example pluripotent cells like iPS cells and hES cells, definitive endoderm cells, PDX1-positive foregut endoderm cells, immature pancreatic islet hormone-expressing cells, mature pancreatic islet hormone-expressing cells, extraembryonic endoderm cells, mesoderm cells and/or ectoderm cells.

Further embodiments of the present invention relate to compositions, such as cell cultures or cell populations, comprising human cells, including human endocrine progenitor/precursor cells, wherein the expression of the NGN3 marker is greater than the expression of the AFP, SOX7, SOX1, ZIC1, NFM, MAFA, SYP, CHGA, INS, GCG, SST, GHRL, and/or PAX6 marker in at least about 2% of the human cells. In other embodiments, the expression of the NGN3 marker is greater than the expression of the AFP, SOX7, SOX1, ZIC1, NFM, MAFA, SYP, CHGA, INS, GCG, SST, GHRL, and/or PAX6 marker in at least about 5% to 98% of the human cells. In some embodiments, the percentage of human cells in the cell cultures or populations, wherein the expression of NGN3 is greater than the expression of the AFP, SOX7, SOX1, ZIC1, NFM, MAFA, SYP, CHGA, INS, GCG, SST, GHRL, and/or PAX6 marker, is calculated without regard to feeder cells.

It will be appreciated that some embodiments of the present invention relate to compositions, such as cell cultures or cell populations, comprising human endocrine progenitor/precursor cells, wherein the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker in from at least about 2% to greater than at least about 98% of the human cells. In some embodiments, the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker in at least about 5% of the human cells to 98% of the human cells. In some embodiments, the percentage of human cells in the cell cultures or populations, wherein the expression of NKX2.2 and/or PAX4 is greater than the expression of the AFP, SOX7, SOX1, ZIC1, NFM, MAFA, SYP, CHGA, INS, GCG, SST, GHRL, and/or PAX6 marker, is calculated without regard to feeder cells.

Using the processes described herein, compositions comprising endocrine progenitor/precursor cells substantially free of other cell types can be produced. In some embodiments of the present invention, the endocrine progenitor/precursor cell populations or cell cultures produced by the methods described herein are substantially free of cells that significantly express the AFP, SOX7, SOX1, ZIC1 and/or NFM markers. In some embodiments, the endocrine progenitor/precursor cell populations of cell cultures produced by the methods described herein are substantially free of cells that significantly express the AFP, SOX7, SOX1, ZIC1, NFM, MAFA, SYP, CHGA, INS, GCG, SST, GHRL, and/or PAX6 markers.

In still other processes for the production of immature pancreatic islet hormone-expressing cells disclosed herein, HGF is provided to the cells so that it is present in the cell culture or cell population at concentrations sufficient to promote differentiation of at least a portion of the endocrine progenitor/precursor cells to immature pancreatic islet hormone-expressing cells. In some embodiments, HGF is present in the cell culture or cell population at a concentration of at least about 1 ng/mL at least about 5 ng/mL to 1000 ng/mL.

In yet other processes for the production of immature pancreatic islet hormone-expressing cells disclosed herein, IGF1 is provided to the cells so that it is present in the cell culture or cell population at concentrations sufficient to promote differentiation of at least a portion of the endocrine progenitor/precursor cells to immature pancreatic islet hormone-expressing cells. In some embodiments, IGF1 is present in the cell culture or cell population at a concentration of at least about 1 ng/mL to 1000 ng/mL.

In certain embodiments of the processes for producing immature pancreatic islet hormone-expressing cells as described herein, one or more of nicotinamide, exendin 4, HGF and IGF1 are provided after one or more previously provided differentiation factors have been removed from the cell cultures. In other embodiments, one or more of nicotinamide, exendin 4, HGF and IGF1 are provided to cell culture or cell population comprising one or more differentiation factors that were previously provided or provided at about the same time as one or more of nicotinamide, exendin 4, HGF and IGF1. In preferred embodiments, differentiation factors that were previously provided or provided at about the same time as one or more of nicotinamide, exendin 4, HGF and IGF1 include, but are not limited to, DAPT, FGF-10, KAAD-cyclopamine, activin A, activin B, BMP4 and/or RA.

Further embodiments of the present invention relate to compositions, such as cell cultures or cell populations, comprising human cells, including human immature pancreatic islet hormone-expressing cells, wherein the expression of the MAFB, SYP, CHGA, NKX2.2, ISL1, PAX6, NEUROD, PDX1, HB9, GHRL, IAPP, INS GCG, SST, PP, and/or C-peptide marker is greater than the expression of the NGN3, MAFA, MOX1, CER, POU5F1, AFP, SOX7, SOX1, ZIC1 and/or NFM marker in at least about 2% of the human cells. In other embodiments, the expression of the MAFB, SYP, CHGA, NKX2.2, ISL1, PAX6, NEUROD, PDX1, HB9, GHRL, IAPP INS GCG, SST, PP, and/or C-peptide marker is greater than the expression of the NGN3, MAFA, MOX1, CER, POU5F1, AFP, SOX7, SOX1, ZIC1 and/or NFM marker in at least about 5% of the human cells, in at least about 10% of the human cells to 95% of the human cells or in at least about 98% of the human cells.

In certain embodiments of the present invention, cell cultures and/or cell populations comprising immature pancreatic islet hormone-expressing cells also include a medium which comprises one or more secreted hormones selected from ghrelin, insulin, somatostatin and/or glucagon. In other embodiments, the medium comprises C-peptide. In a preferred embodiment, the concentration of one or more secreted hormones or C-peptide in the medium ranges from at least about 1 pmol of ghrelin, insulin, somatostatin, glucagon or C-peptide/µg of cellular DNA to at least about 1000 picomoles (pmol) of ghrelin, insulin, somatostatin, glucagon or C-peptide/µg of cellular DNA.

Method of Producing Insulin In Vivo

In some embodiments, in vitro-derived pancreatic progenitor cells or PDX-1-positive pancreatic endoderm type cells or equivalents thereof described-above are transplanted into a mammalian subject. These methods are described in detail in International Application PCT/US2007/015536, titled METHODS OF PRODUCING PANCREATIC HORMONES, and Kroon et al. (2008) supra. In a preferred embodiment, the mammalian subject is a human subject. Particularly preferred subjects are those that have been identified as having a condition which limits the ability of the subject to produce sufficient levels of insulin in response to physiologically high blood glucose concentrations. A range of blood glucose levels that constitutes a physiologically high blood glucose level for any particular mammalian species can be readily determined by those of ordinary skill in the art. Any persistent blood glucose level that results in a recognized disease or condition is considered to be a physiologically high blood glucose level.

Additional embodiments of the present invention relate to an in vivo insulin secreting cell that is derived from an in vitro pluripotent stem cell or progeny thereof, e.g., multipotent cells, such as PDX-1 positive foregut endoderm cell, a PDX-1 positive pancreatic endoderm or pancreatic progenitor cell, an endocrine progenitor/precursor, such as an NGN3 positive endocrine progenitor/precursor, or a functional differentiated hormone secreting cell, such as an insulin, glucagon, somatostatin, ghrelin, or pancreatic polypeptide secreting cell. Any of the above-described terminally differentiated or multipotent cells can be transplanted into the host, or mammal, and mature into physiologically functional hormone secreting cells, such as insulin secreting cells, in response to host blood glucose levels. In preferred embodiments the cell does not form a teratoma in vivo, and if so formed, remains localized to the area of transplant and can be easily excised or removed. In especially preferred embodiments, the cell does not contain any karyotypic abnormality during the in vitro differentiation process, or when transplanted into the mammal in vivo, or when maturing and developing into functional islets in vivo.

Further, although embodiments described herein relate to an engineered or genetically recombinant pluripotent cell, multipotent or differentiated cell derived from the pluripotent cell, such as a human iPS cell, based on the description provided herein, it is anticipated that because iPS cells demonstrate similar physiology and gene marker expression profiles to that of hES cells and hES-derived cells, they will have similar physiological characteristics in vivo.

Method of Encapsulating Pancreatic Progenitors

In some embodiments, the pluripotent, multipotent and differentiated cell composition described herein can be encapsulated in a biological and/or non-biological mechanical device, where the encapsulated device separates and/or isolates the cell compositions from the host.

Methods of encapsulation are described in detail in U.S. Application 61/114,857, filed Nov. 14, 2008, titled ENCAPSULATION OF PANCREATIC PROGENITORS DERIVED FROM HES CELLS, and U.S. Application No. 61/121,086 filed Dec. 12, 2008, titled ENCAPSULATION OF PANCREATIC ENDODERM CELLS.

In one embodiment, the encapsulation device contains the pluripotent derived cells, for example, PDX-1 positive foregut endoderm cell, a PDX-1 positive pancreatic endoderm or progenitor cell, an endocrine or endocrine progenitor/precursor, such as an NGN3 positive endocrine progenitor/precursor, or a functional differentiated hormone secreting cell, such as an insulin, glucagon, somatostatin, ghrelin, or pancreatic polypeptide secreting cell, in a semipermeable membrane that prevents passage of the transplanted cell population, retaining them in the device, while at the same time permitting passage of certain secreted polypeptides, e.g., insulin, glucagon, somatostatin, ghrelin, pancreatic polypeptide and the like. Alternatively, the device has a plurality of membranes, including a vascularizing membrane.

Use of Agents to Enhance and Promote Growth, Survival, Proliferation and Cell-Cell Adhesion of Human Pluripotent Stem Cells, e.g., hES Cells and iPS Cells Cellular regulation can be affected through the transduction of extracellular signals across the membrane that, in turn, modulates biochemical pathways within the cell. Protein phosphorylation represents one course by which intracellular signals are propagated from molecule to molecule resulting finally in a cellular response. These signal transduction cascades are highly regulated and often overlapping as evidenced by the existence of many protein kinases as well as phosphatases. It has been reported that in humans, protein tyrosine kinases are known to have a significant role in the development of many disease states including diabetes, cancer and have also been linked to a wide variety of congenital syndromes. Serine threonine kinases, e.g., Rho kinases, are a class of enzymes, which if inhibited can have relevance to the treatment of human disease, including diabetes, cancer, and a variety of inflammatory cardiovascular disorders and AIDS. The majority of inhibitors identified to date act at the ATP-binding site. Such ATP-competitive inhibitors have demonstrated selectivity by virtue of their ability to target the more poorly conserved areas of the ATP-binding site.

The Rho kinase family of small GTP binding proteins contains at least 10 members including Rho A-E and G, Rac 1 and 2, Cdc42, and TC10. The inhibitors are often referred to as ROK or ROCK inhibitors or Rho-kinase inhibitors, and they are used interchangeably herein. The effector domains of RhoA, RhoB, and RhoC have the same amino acid sequence and appear to have similar intracellular targets. Rho kinase operates as a primary downstream mediator of Rho and exists as two isoforms: α (ROCK2) and β (ROCK1). Rho kinase family proteins have a catalytic (kinase) domain in their N-terminal domain, a coiled-coil domain in its middle portion, and a putative pleckstrin-homology (PH) domain in their C-terminal region. The Rho-binding domain of ROCK is localized in the C-terminal portion of the coiled-coil domain and the binding of the GTP-bound form of Rho results in enhancement of kinase activity. The Rho/Rho-kinase-mediated pathway plays an important role in the signal transduction initiated by many agonists, including angiotensin II, serotonin, thrombin, endothelin-1, norepinephrine, platelet-derived growth factor, ATP/ADP and extracellular nucleotides, and urotensin II. Through the modulation of its target effectors/substrates Rho kinase plays an important role in various cellular functions including smooth muscle contraction, actin cytoskeleton organization, cell adhesion and motility and gene expression. By virtue of the role that Rho kinase proteins play in mediating a number of cellular functions perceived to be associated with the pathogenesis of arteriosclerosis, inhibitors of these kinases may also be useful for the treatment or prevention of various arteriosclerotic cardiovascular diseases and involved in endothelial contraction.

In some embodiments, agents which promote and/or support cell growth, survival, proliferation and cell-cell adhesion are added to various cell culture media conditions, including but not limited to, Rho-kinase inhibitors Y-27632, Fasudil (also referred to as HA1077), H-1152P and ITS (insulin/transferrin/selenium; Gibco), Wf-536, Y-30141 (described in U.S. Pat. No. 5,478,838) and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in the present invention (for example, refer to United State Patent Application Nos. 20050209261, 20050192304, 20040014755, 20040002508, 20040002507, 20030125344 and 20030087919, and International Patent Publication Nos. 2003/062227, 2003/059913, 2003/062225, 2002/076976 and 2004/039796).

In the present invention, a combination of one or two or more of the ROCK inhibitors can also be used. These agents function, in part, by promoting re-association of dissociated hES cell, iPS or differentiated cell cultures, e.g., definitive endoderm, foregut endoderm, pancreatic endoderm, pancreatic epithelium, pancreatic progenitor populations, endocrine progenitors and populations and the like. Likewise, the agents can function when cell dissociation is not performed. Increase in growth, survival, proliferation and cell-cell adhesion of the human pluripotent stem cells was achieved independent of whether the cells were produced from cell aggregates in suspension or from adherent plate cultures (with or with no extracellular matrix components, with or without serum, with or without fibroblast feeders, with or without FGF, with or without Activin). Increase in survival of these cell populations facilitates and improves purification systems using a cell-sorter and, therefore allows improved recovery of the cells. Use of Rho kinase inhibitors such as Y27632 may allow for expansion of differentiated cell types as well by promoting their survival during serial passaging dissociated single cells or from cryogenic preservation. Although, Rho kinase inhibitors such as Y27632 have been tested on human pluripotent stem cells (e.g., hES and iPS cells) and differentiated cells thereof, Rho kinase inhibitors can be applied to other cell types, for example, in general, epithelial cells including but not limited to intestinal, lung, thymus, kidney as well as neural cell types like pigmented retinal epithelium.

The concentration of the ROCK inhibitor in the cell culture medium is not limited to that described in the examples below so long as the concentration can achieve the desired effects such as enhancing, increasing, and/or promoting growth, survival, proliferation and cell-cell adhesion of cells is achieved. One skilled in the art will recognize that optimization of various ROCK inhibitors under various conditions may be necessary. For example, when employing Y-27632 a preferable concentration can range from about 0.01 to about 1000 μM, more preferably about 0.1 to about 100 μM, and even more preferably about 1.0 to about 50 μM, and most preferably about 5 to 20 μM. When Fasudil/HA1077 is used, it can be used at about two or three-fold the aforementioned Y-27632 concentration. When H-1152 is used, it can be used at about fraction, e.g., about $1/10^{th}$, $1/20^{th}$, $1/30^{th}$, $1/40^{th}$, $1/50^{th}$ or $1/60^{th}$ of the amount of the aforementioned Y-27632 concentration. The concentration of ROCK-inhibitor used will depend, in part, on the bioactivity and potency of the inhibitor and the conditions in which they are used.

The time and period for treating with the ROCK inhibitor may or may not be limited depending on the desired effects such as the enhancing, increasing, and/or promoting growth, survival, proliferation (cell mass) and cell-cell adhesion. However, addition of a ROCK inhibitor may also affect differentiation in surprising ways as better described in Example 7. The Examples below describe human pluripotent stem cell cultures and/or differentiated cell cultures treated for about 12 hours, 24 hours, 48 hours, or more.

The density of the human pluripotent stem cell cultures treated with the ROCK inhibitor is also not limited as far as it is a density at which the desired effects such as the enhancing, increasing, and/or promoting growth, survival, proliferation and cell-cell adhesion of cells is achieved. The cell density of the seeded cells may be adjusted depending on a variety of factors, including but not limited to the use of adherent or suspension cultures, the specific recipe of the cell culture media used, the growth conditions and the contemplated use of the cultured cells. Examples of cell culture densities include, but are not limited to, $0.01 \times 10^5$ cells/ml, $0.05 \times 10^5$ cells/ml, $0.1 \times 10^5$ cells/ml, $0.5 \times 10^5$ cells/ml, $1.0 \times 10^5$ cells/ml, $1.2 \times 10^5$ cells/ml, $1.4 \times 10^5$ cells/ml, $1.6 \times 10^5$ cells/ml, $1.8 \times^{105}$ cells/ml, $2.0 \times 10^5$ cells/ml, $3.0 \times 10^5$ cells/ml, $4.0 \times 10^5$ cells/ml, $5.0 \times 10^5$ cells/ml, $6.0 \times 10^5$ cells/ml, $7.0 \times 10^5$ cells/ml, $8.0 \times 10^5$ cells/ml, $9.0 \times 10^5$ cells/ml, or $10.0 \times 10^5$ cells/ml, or more, e.g., up to $5 \times 10^7$ cells/mL or more, or any value in between, have been cultured with good cell growth, survival, proliferation and cell-cell adhesion.

Use of Agents which Activate TGFβ Receptor Family Members

Still in another embodiment, agents that activate TGFβ receptor family member include members of the TGFβ super family of growth factors, are described herein. As used herein, "TGFβ superfamily member" or equivalents thereof refers to over 30 structurally related proteins including subfamilies including TGFβ1, TGFβ2, TF-β, GDF-15, GDF-9, BMP-15, BMP-16, BMP-3, GDF-10, BMP-9, BMP-10, GDF-6, GDF-5, GDF-7, BMP-5, BMP-6, BMP-7, BMP-8, BMP-2, BMP-4, GDF-3, GDF-1, GDF 11, GDF8, Activins βC, βE, βA and βB, BMP-14, GDF-14, MIS, Inhibin alpha, Lefty 1, Lefty2, GDNF, Neurteurin, Persephin and Artemin. See Chang et al. (2002) Endocrine Rev. 23(6):787-823.

A TGFβ family member can be replaced by, or used in conjunction with, a TGFβ signaling pathway activator, which is a compound that stimulates one or more of the polypeptides or interactions that participate in transducing or otherwise effectuating changes in the properties of a cell in response to a TGFβ family member. A TGFβ signaling pathway includes TGFβ family members themselves. TGFβ super family members transmit signals to the nucleus by signaling through type II and I serine-threonine kinase receptors and intracellular effectors known as Smads. These receptors fall into two subfamilies known as type I and type II receptors that act cooperatively to bind ligand and transduce signal (Attisano et al., Mol Cell Biol 16 (3), 1066-1073 (1996)). Ligands bind to type I and II receptors on the cell surface, promoting activation of the type I receptor via phosphorylation. This activated complex in turn activates intracellular Smads, which assemble multi-subunit complexes that regulate transcription. Members of the TGFbeta super family are divided into two signaling subgroups: those functionally related to TGFβ/Activin and those related to the BMP/GDF subfamily. Most TGFβ ligands are thought to bind first to a type II receptor and this ligand/type II receptor complex then recruits or phosphorylates a type I receptor (Mathews, L S, Endocr Rev 15:310-325 (1994); Massague, Nature Rev: Mol Cell Biol. 1, 169-178 (2000)). The type II receptor kinase by phosphorylating and activating the type I receptor kinase, which then phosphorylates and activates the Smad proteins. The TGFβ/Activin ligands bind to TGFβ and Activin type II receptors and can activate Smad-2 and -3. Nodal and Lefty signal through this Activin-type pathway. The BMP/GDF ligands bind to BMP type II receptors and can activate Smads 1, 5, and 8. See Derynck, R et al. Cell 95, 737-740 (1998)). Upon ligand stimulation, Smads move into the nucleus and function as components of transcription complexes.

TGFβ signaling is regulated positively and negatively though various mechanisms. Positive regulation amplifies signals to a level sufficient for biological activity. TGFβ superfamily ligands bind to a type II receptor, which recruits and phosphorylates a type I receptor. The type I receptor then phosphorylates receptor-regulated SMADs (R-SMADs e.g., SMAD1, SMAD2, SMAD3, SMAD5, and SMAD8) which can now bind common mediator Smad or co-SMAD. R-SMAD/coSMAD complexes accumulate in the nucleus where they act as transcription factors and participate in the regulation of target gene expression. For example, Growth differentiation factors include 1, 2, 3, 5, 6, 7, 8, 9, 10, 11, and 15. And in one preferred embodiment, GDF8 and GDF11, are TGFβ family members that are also TGFβ signaling pathway activators (positive regulation), and act by binding to the extracellular ligand binding domain portion of the ActRII receptor and then forming a complex with ActRI, leading to the inhibition of the Smad7 negative regulator and phosphorylation of the Smad2/Smad3 complex. The Smad2/Smad3 complex associates with Smad4 to regulate expression of certain genes.

As with the use of any agent, the concentration of any TGFβ super family member in the cell culture medium is not limited to that described in the examples below so long as the concentration can achieve the desired effects such as to activate a TGFβ receptor family member, for example. For example, when employing Activins, e.g., Activin A and/or B, or GDF8 and GDF-11, a preferable concentration can range from about 10 to about 300 nM, more preferably about 50 to about 200 nM, and even more preferably about 75 to about 150 nM, and most preferably about 100 to 125 nM. One of ordinary skill in the art can readily test any concentration and using standard techniques in the art can determine the efficacy of such concentration, e.g., evaluating differentiation by determining expression and non-expression of a panel of gene makers for any cell type.

Use of Agents to Produce Endocrine Cells

In one embodiment, the present invention provides methods of making pancreatic endoderm-lineage type populations and/or sub-populations, specifically PEC and/or pancreatic endocrine-lineage cells, using a Notch pathway inhibitor, including but not limited to a gamma secretase inhibitor, in an amount effective to promote endocrine differentiation and/or induce expression of certain markers which are hallmark of endocrine cells and indicative of endocrine differentiation. Numerous gamma secretase inhibitors have been described. See, for example, U.S. Pat. Nos. 6,756,511; 6,890,956; 6,984,626; 7,049,296; 7,101,895; 7,138,400; 7,144,910; and 7,183,303. Gamma secretase inhibitors are readily available, for example, from Calbiochem (La Jolla, Calif.): gamma secretase inhibitor I, (GSI I), Z-Leu-Leu-Norleucine-CHO; gamma secretase inhibitor II; gamma secretase inhibitor III, (GSI III), N-Benzyloxycarbonyl-Leu-leucinal; gamma secretase inhibitor IV, (GSI IV), N-(2-Naphthoyl)-Val-phenylalaninal; gamma secretase inhibitor V, (GSI V), N-Benzyloxycarbonyl-Leu-phenylalaninal; gamma secretase inhibitor VI, (GSI VI), 1-(S)-endo-N-(1,3,3)-Trimethylbicyclo[2.2.1]hept-2-yl)-4-fluorophenyl Sulfonamide; gamma secretase inhibitor VII, (GSI VII), Menthyloxycarbonyl-LL-CHO; gamma secretase inhibitor IX, (GSI IX), (DAPT), N—[N-(3,5-Difluorophenacetyl-L-alanyl)]-S-phenylglycine t-Butyl Ester; gamma secretase inhibitor X, (GSI X), {1S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; gamma secretase inhibitor XI, (GSI XI), 7-Amino-4-chloro-3-methoxyisocoumarin; gamma secretase inhibitor XII, (GSI XII), Z-Ile-Leu-CHO; gamma secretase inhibitor XIII, (GSI XIII), Z-Tyr-Ile-Leu-CHO; gamma secretase inhibitor XIV, (GSI XIV), Z-Cys(t-Bu)-Ile-Leu-CHO; gamma secretase inhibitor XVI, (GSI XVI), N—[N-3,5-Difluorophenacetyl]-L-alanyl-S-phenylglycine Methyl Ester; gamma secretase inhibitor XVII, (GSI XVII), WPE-III-31C); gamma secretase inhibitor XIX, (GSI XIX), (2S,3R)-3-(3,4-Difluorophenyl)-2-(4-fluorophenyl)-4-hydroxy-N-((3S)-2-oxo-5-phenyl-2,3-dihydro-1H-benzo[e][1,4]diazepin-3-yl)-butyramide; gamma secretase inhibitor XX, (GSI XX), (Dibenzazepine (DBZ)), (S,S)-2-[2-(3,5-Difluorophenyl)acetylamino]-N-(5-methyl-6-oxo-6,7-dihydro-5H-dibenzo

[b,d]azepin-7-yl)propionamide, gamma secretase inhibitor XXI, (GSI XXI), (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide; gamma40 secretase inhibitor I, N-trans-3,5-Dimethoxycinnamoyl-Ile-leucinal; gamma40 secretase inhibitor II, N-tert-Butyloxycarbonyl-Gly-Val-Valinal; and Isovaleryl-V-V-Sta-A-Sta-OC$_3$.

In one aspect, the gamma secretase inhibitor is selected from the group consisting of one of more of: Z-Leu-Leu-Norleucine-CHO, N-Benzyloxycarbonyl-Leu-leucinal, N-(2-Naphthoyl)-Val-phenylalaninal, N-Benzyloxycarbonyl-Leu-phenylalaninal, 1-(S)-endo-N-(1,3,3) Trimethylbicyclo[2.2.1]hept-2-yl)-4-fluorophenyl Sulfonamide, Menthyloxycarbonyl-LL-CHO, N—[N-(3,5-Difluorophenacetyl-L-alanyl)]-S-phenylglycine t-Butyl Ester, {1S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester, 7-Amino-4-chloro-3-methoxyisocoumarin, Z-Ile-Leu-CHO, Z-Tyr-Ile-Leu-CHO, Z-Cys(t-Bu)-Ile-Leu-CHO, N—[N-3,5-Difluorophenacetyl]-L-alanyl-S-phenylglycine Methyl Ester, (2S,3R)-3-(3,4-Difluorophenyl)-2-(4-fluorophenyl)-4-hydroxy-N-((3S)-2-oxo-5-phenyl-2,3-dihydro-1H-benzo[e][1,4]diazepin-3-yl)-butyramide, (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide, N-trans-3,5-Dimethoxycinnamoyl-Ile-leucinal, N-tert-Butyloxycarbonyl-Gly-Val-Valinal, Isovaleryl-V-V-Sta-A-Sta-OCH$_3$, and wherein the renal disease is a glomerular renal disease or a tubular renal disease. In one aspect of this invention, about 0.5 to 10 mM, 0.5 to 5 mM, 0.5 to 3 mM, preferably 0.5 to 1 mM of gamma secretase inhibitor is used in any or all of stages 1-7 described herein and according to Table 8 and 17.

In one embodiment, Insulin Growth Factor (IGF) are part of a complex system that cells use to communicate with their physiologic environment and thus can be used to differentiate PSC to PEC and/or pancreatic endocrine-lineage cells. This complex system (often referred to as the IGF "axis") consists of two cell-surface receptors (IGF1R and IGF2R), two ligands (Insulin-like growth factor 1 (IGF-1) and Insulin-like growth factor 2 (IGF-2)), a family of six high-affinity IGF-binding proteins (IGFBP-1 to IGFBP-6), as well as associated IGFBP degrading enzymes, referred to collectively as proteases. IGF are known to bind the IGF1R, the insulin receptor, the IGF-2 receptor, the insulin-related receptor and possibly other receptors. Thus, in one aspect of the present invention, growth factors which bind to these receptors include but are not limited to IGF1 and IGF2, since any growth factor, agent or morphogen which bind to any or a combination of these receptors potentially has the same physiological effect as that described and anticipated herein. In one aspect of this invention, about 5 to 200 ng/mL, 10 to 100 ng/mL, 10 to 75 ng/mL, preferably 10 to 50 ng/mL, preferably 20 to 50 ng/mL of IGF is used in any or all of stages 1-7 described herein and according to Table 8 and 17.

In one embodiment, Platelet Derived Growth Factor (PDGF) is used to differentiate PSC to PEC and/or cells committed to the endocrine lineage (CHGA+). PDGF is a major protein growth factor that has been widely described as a potent mitogen of numerous kinds of cells. PDGF belongs to a family of dimeric isoforms of polypeptide chains, A, B, C and D that act through different tyrosine kinase receptors: PDGFR-α and PDGFR-β. In one aspect of the invention, the ligand is a PDGF or functional equivalent thereof including but not limited to PDGFaa, PDGFab or PDGFbb which bind to the two types of receptors. In one aspect of this invention, about 5 to 100 ng/mL, 10 to 75 ng/mL, 10 to 50 ng/mL, preferably 10 to 20 ng/mL of PDGF is used in any or all of stages 1-7 described herein and according to Table 8 and 17.

In one embodiment, Nicotinamide, also known as niacinamide and nicotinic acid amide, is the amide of nicotinic acid (vitamin B3/niacin), is used to differentiate PSC to PEC and/or pancreatic endocrine-lineage cells. Nicotinic acid, also known as niacin, is converted to nicotinamide in vivo, and, though the niacin and nicotinamide are identical in their vitamin functions, nicotinamide does not have the same pharmacological and toxic effects of niacin. Hence, other vitamin B or vitamin B derivatives which function similar to Nicotinamide in embodied in this invention. In one aspect of this invention, about 5 to 100 ng/mL, 10 to 75 ng/mL, 10 to 50 ng/mL, preferably 10 to 20 ng/mL of Nicotinamide is used in any or all of stages 1-7 described herein and according to Table 8 and 17.

In another embodiment, the Hedgehog family of proteins are used to differentiate PSC to PEC and/or pancreatic endocrine-lineage cells. The hedgehog family of vertebrate inter-cellular signaling molecules provided by the present invention consists of at least four members including but not limited to Desert hedgehog (Dhh), Sonic hedgehog (Shh), Indian hedgehog (Ihh) and Moonrat hedgehog (Mhh). In one aspect, about 5 to 200 ng/mL, 10 to 200 ng/mL, 10 to 150 ng/mL, preferably 10 to 100 ng/mL of a hedgehog protein is used in any or all of stages 1-7 described herein and according to Table 8 and 17.

Having generally described this invention, a further understanding can be obtained by reference to certain specific examples which are provided herein for purposes of illustration only, and are not intended to be limiting.

EXAMPLES

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

Example 1

Differentiation of Human iPS Cells to Pancreatic Progenitors and Endocrine Cells Via Definitive Endoderm and Endoderm Intermediates Human induced pluripotent stem (iPS) cells were differentiated in suspension aggregates using a four (4) stage procedure over the course of about 2 weeks (or 14 days) to generate a population of pancreatic cell types including pancreatic progenitors, endocrine progenitors and hormone expressing endocrine cells. Human iPS cell lines employed herein were provided by S. Yamanaka, Kyoto University, Japan and Cellular Dynamics International, Inc. (CDI).

The iPS cells described herein were first provided by Shinya Yamanaka and later by CDI. Undifferentiated iPS cells were grown on mitotically inactivated mouse embryo fibroblasts or preferably feeder-free (no fibroblast feeder cell layer) in DMEM/F12 containing 20% Knockout serum replacement. Differentiation was initiated by dissociating the undifferentiated iPS cells to single cells using Accutase, cell samples were taken for RNA isolation & analysis. The cells were resuspended at 1-2 million cells per milliliter in RPMI+0.2% vol/vol FBS containing 1:5000 dilution of insulin-transferrin-selenium (ITS), activin A (100 ng/mL), wnt3a (50 ng/mL), and rho-kinase or ROCK inhibitor, Y-27632, at 10 µM, placed into an ultra-low attachment 6-well plate, placed on a rotation platform and rotated at about 100 rpm. Cultures were rotated at 100 rpm for the remainder of the differentiation process with daily media exchange. Growth, passaging and proliferation of iPSC is substantially as described in U.S. Pat. Nos. 7,961,402 and 8,211,699.

The methods described herein for producing aggregate suspension cultures of pluripotent cells, e.g., hES or iPS cells, and cells derived from pluripotent cells, are as substantially described in PCT/US2007/062755, filed Feb. 23, 2007, and titled Compositions and methods for culturing differential cells and PCT/US2008/080516, filed Oct. 20, 2008, and titled Methods and compositions for feeder-free pluripotent stem cell media containing human serum.

The methods described herein can be facilitated by first coating the culturing vessels with an extracellular matrix, e.g., as described in U.S. Pat. No. 6,800,480 to Bodnar et al. and assigned to Geron Corporation. The methods as with other methods for culturing other pluripotent stem cells, e.g., hES and iPS cells, can be cultured using soluble human serum as substantially described in U.S. Application, PCT/US2008/080516, filed Oct. 20, 2008, and titled Methods and compositions for feeder-free pluripotent stem cell media containing human serum.

The methods described herein can be facilitated by exogenously added fibroblast growth factor (FGF) supplied from a source other than just a fibroblast feeder layer as described in U.S. Pat. No. 7,005,252 to Thomson, J. and assigned to the Wisconsin Alumni Research Foundation (WARF).

During about the first 24 hours of rotation, the single cells adhered to each other formed cell aggregates, and sufficient cell samples were taken for RNA isolation & analysis. The cell aggregates ranged from about 60 microns to 120 microns in diameter. About 1 day (or 24 hours) after the iPS cell samples were put on the rotation platform, the cultures were fed with RPMI+0.2% vol/vol FBS containing 1:5000 dilution of ITS, activin A (100-200 ng/mL), and Wnt3a (50-100 ng/mL), or about one day (time 0 to day 1) and an additional day or in the same media but without the Wnt3a (day 1 to day 2). Daily cell samples were taken for RNA isolation and analysis. After 2 days of differentiation, the cultures were fed RPMI+0.2% vol/vol FBS containing 1:1000 dilution of ITS, KGF (or FGF7, 25 ng/mL), and TGFβ inhibitor no. 4 (2.5 µM) for one day (or 24 hours, day 2 to day 3). For the next two days (day 3 to day 5) the iPS cell aggregate suspensions were fed with the same growth factor cocktail media, with the exception that the TGFβ inhibitor was removed from the culture media. Again, cell samples were taken for RNA isolation at the end of this stage (stage 2, or day 5). For stage 3 (day 5 to day 8), the cell culture media was changed to DMEM+1% vol/vol B27 supplement containing TTNPB [4-[E-2-(5,6,7,8-Tetrahydro-5,5,8,8-tetramethyl-2-naphthalenyl)-1-propenyl]benzoic acid] (3 nM), KAAD-cyclopamine (0.25 µM) and noggin (50 ng/mL). Again, cell samples were taken for RNA isolation & analysis at the end this stage (stage 3, day 8). For stage 4 (days 8 to day 14), the media was changed to DMEM+1% vol/vol B27 supplement containing Noggin (50 ng/mL), KGF (50 ng/mL) and EGF (50 ng/mL). Again, cell samples were taken for RNA isolation & analysis at the end of stage 4 (or day 14).

Real-time PCR was performed to measure the gene expression for various marker genes during the course of differentiation. Gene expression of the specific markers or genes was first normalized to the average expression levels of housekeeping genes, cyclophilin G and TATA Binding Protein (TBP) expression. Normalized relative gene expression was then displayed in the bar graphs relative to the expression level in the undifferentiated iPS cells and thus represents the fold up-regulation for the various differentiation markers. For OCT4, gene expression was normalized to set the lowest sample in the data set (day 14) and thus represents the fold down-regulation during the course of differentiation.

Figure 2A:
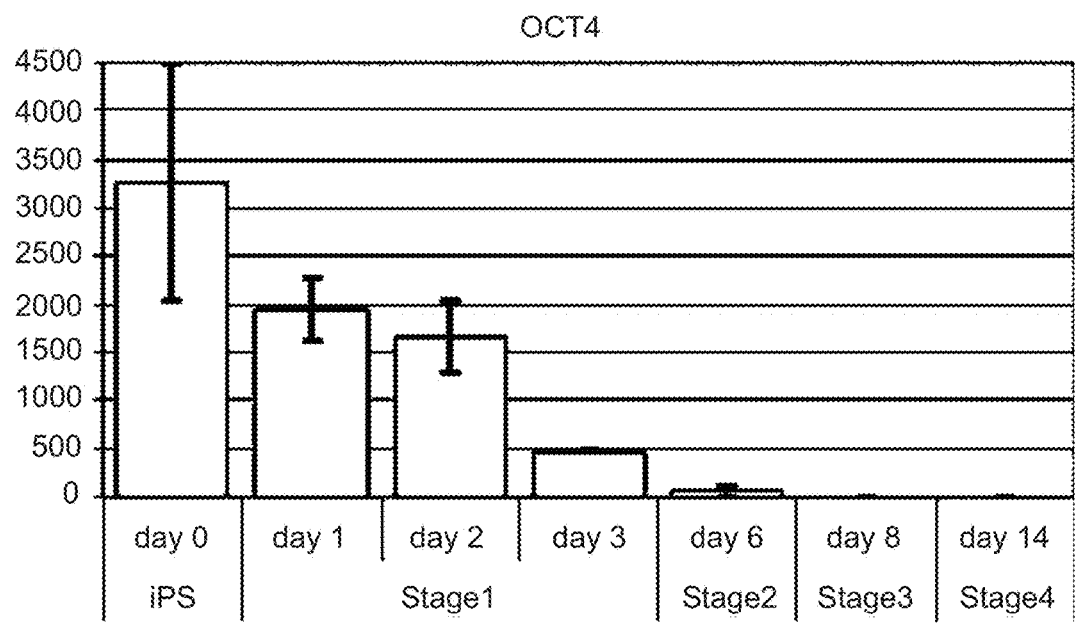
FIGS. 2A-2L are bar graphs showing the relative gene expression levels of OCT4 (FIG. 2A), BRACHYURY (FIG. 2B), CER1 (FIG. 2C), GSC (FIG. 2D), FOXA2 (FIG. 2E), FOXA1 (FIG. 2F), HNF6 (FIG. 2G), PDX1 (FIG. 2H), PTF1A (FIG. 2I), NKX6.1 (FIG. 2J), NGN3 (FIG. 2K) and INS (FIG. 2L). Expression levels are normalized to the average expression levels of housekeeping genes, cyclophilin G and TATA Binding Protein (TBP) expression. The graphs depict fold upregulation over the lowest data point in the data set. See Example 1.
Figure 2B:
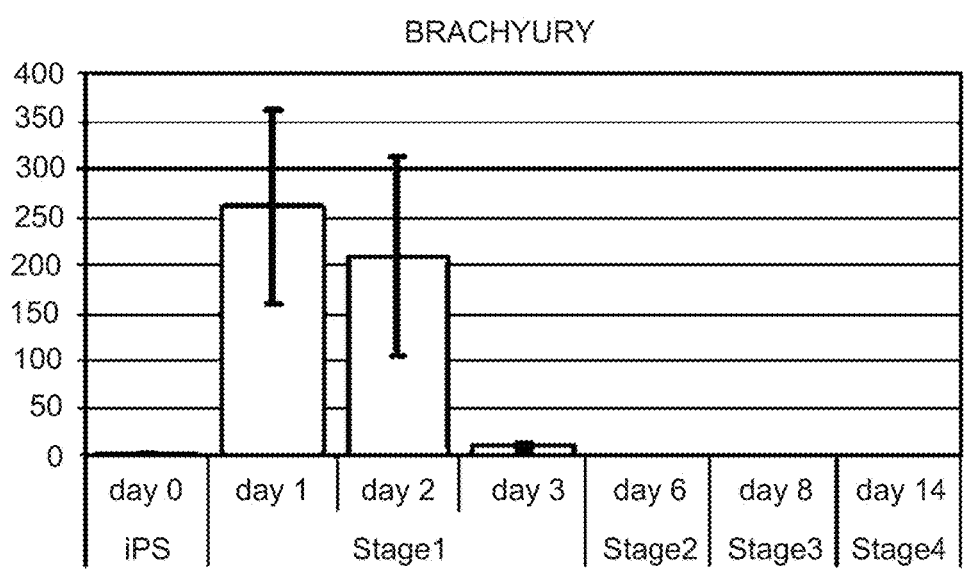

FIGS. 2A-L are bar graphs showing the relative gene expression of the identified gene (e.g., Oct4, Brachyury, Cer1, GSC, FOXA2, FOXA1, HNF6, PDX1, PTF1A, NKX6.1, NGN3 and INS) relative to the expression level of the same gene in the undifferentiated iPS cells. The expression level of the genes were normalized to a set of housekeeping genes (control) and comparing the gene expression level at the two different time points indicated whether there was up- or down-regulation for that gene or expression marker. For OCT4 (FIG. 2A), the gene expression was normalized and the lowest level expression sample was set at 1 (day 14). Hence, as indicated by FIG. 2A, the relative expression levels of OCT4 represent the fold down-regulation (Y axis) during the course of differentiation (X axis, stage 0 to 4, or day 0 to day 14).

Figure 2C:
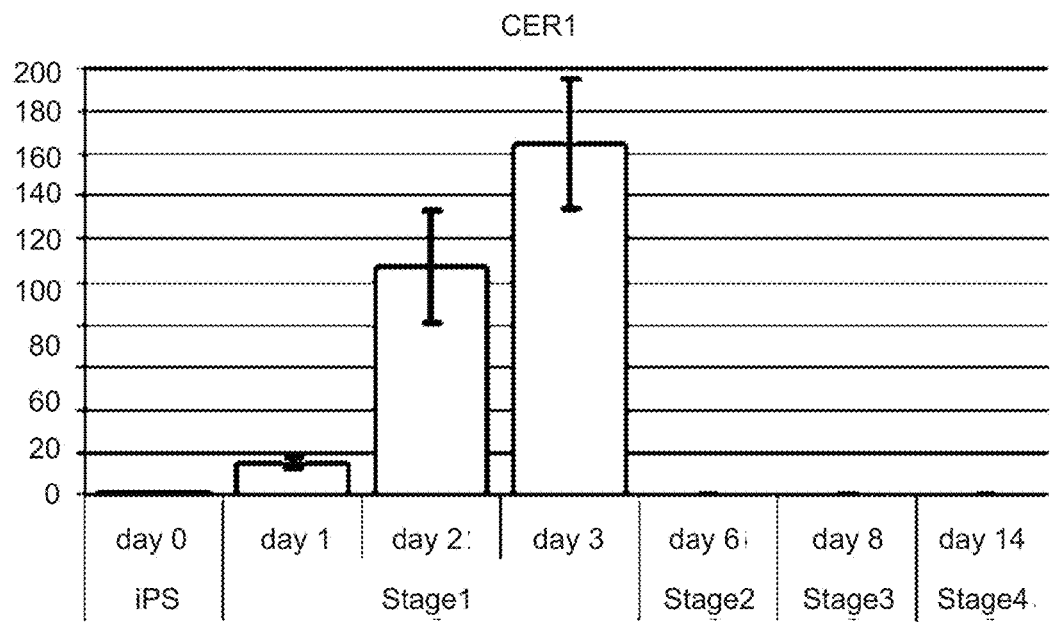
Figure 2D:
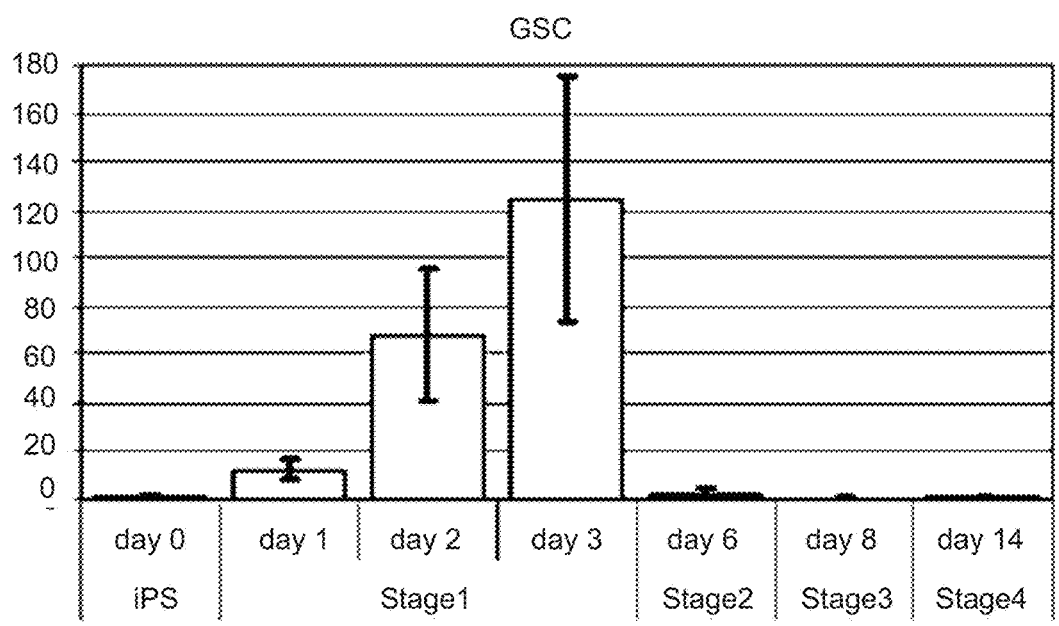
Figure 2E:
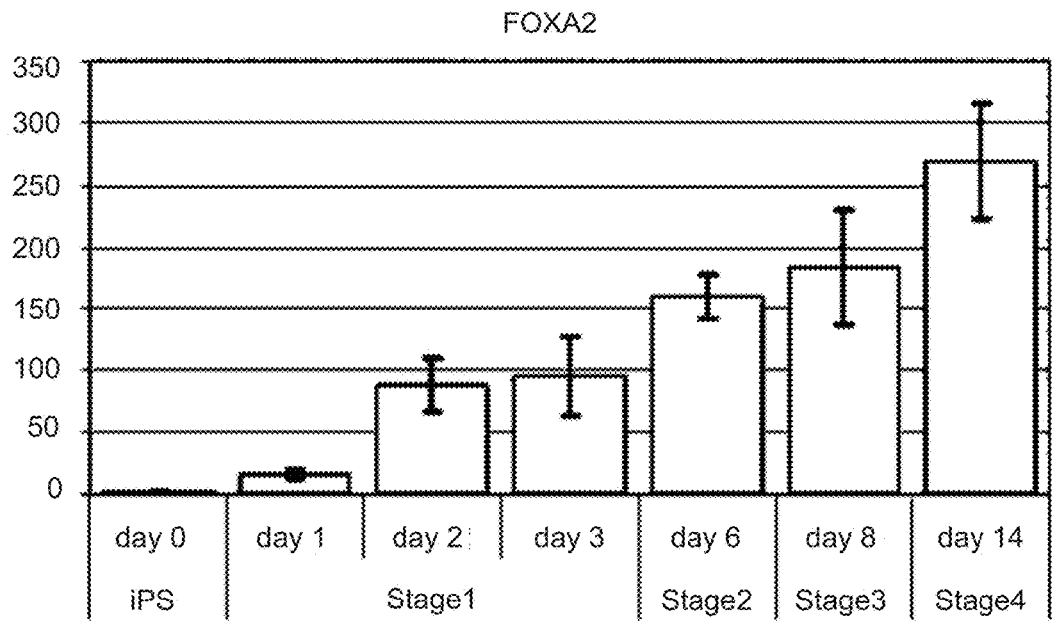
Figure 2F:
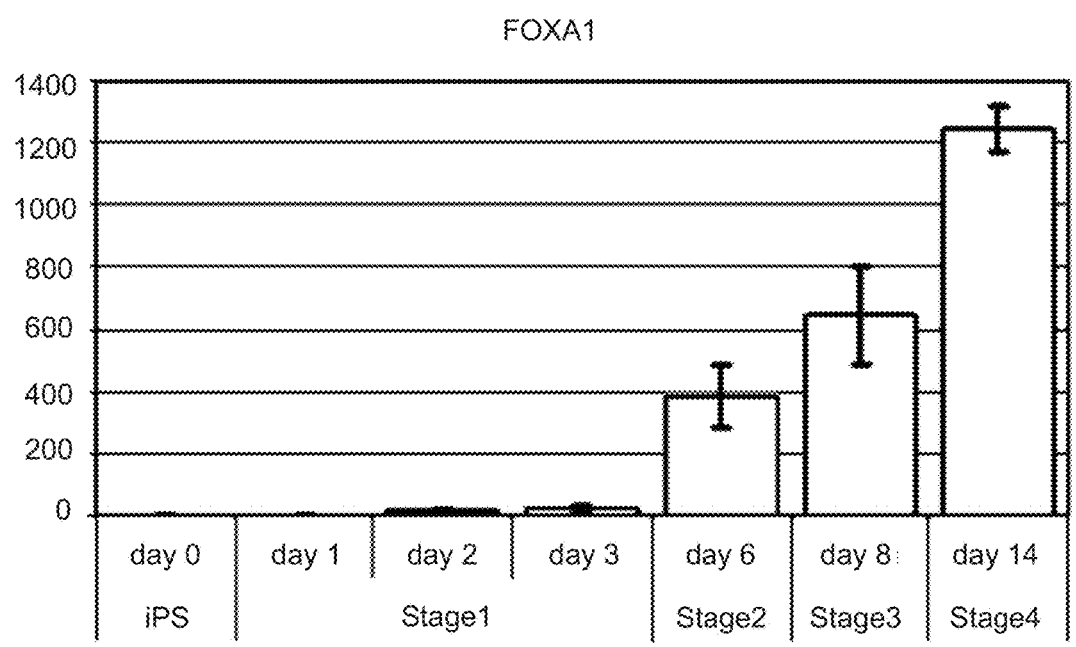
Figure 2G:
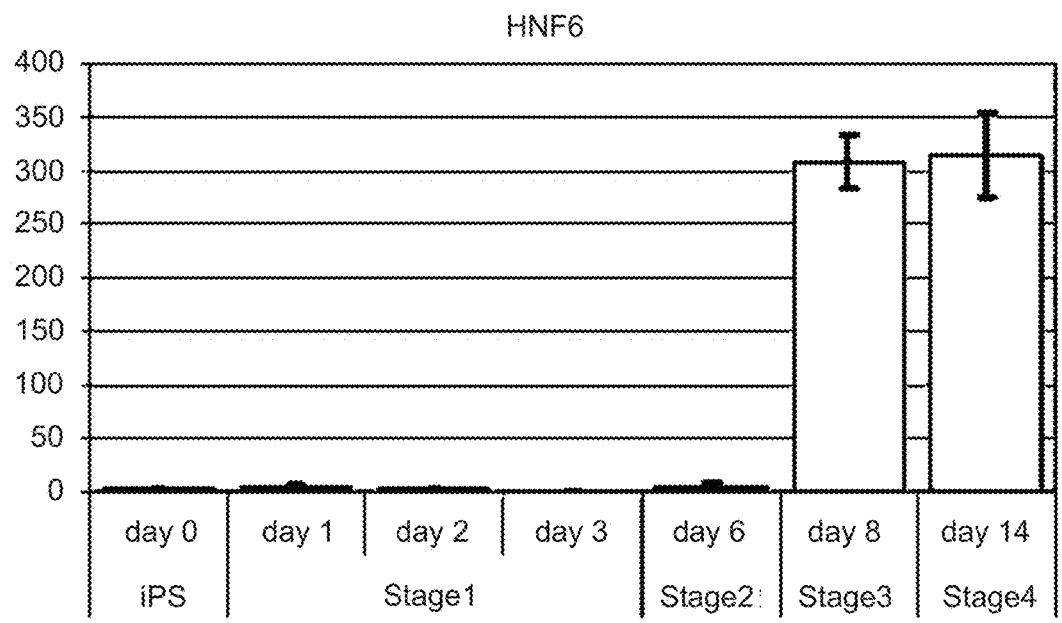
Figure 2H:
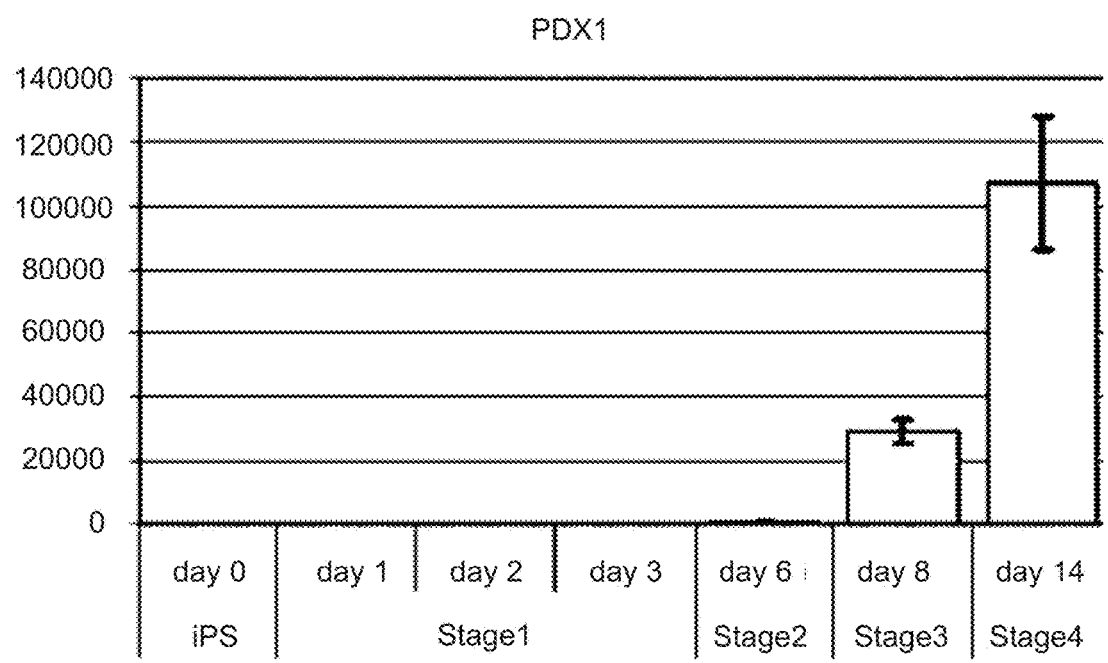
Figure 2I:
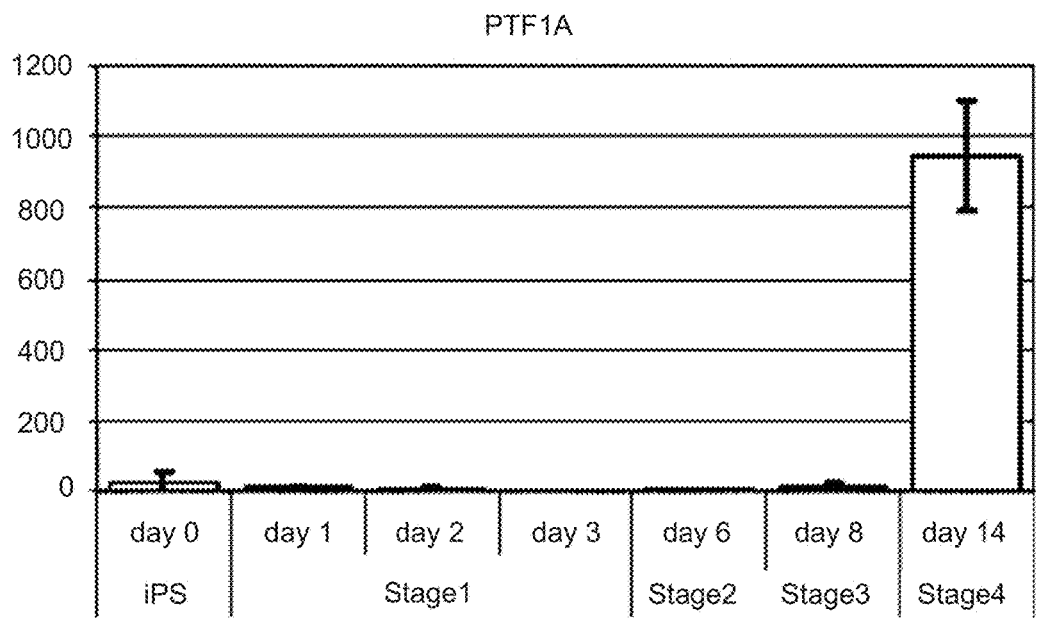
Figure 2J:
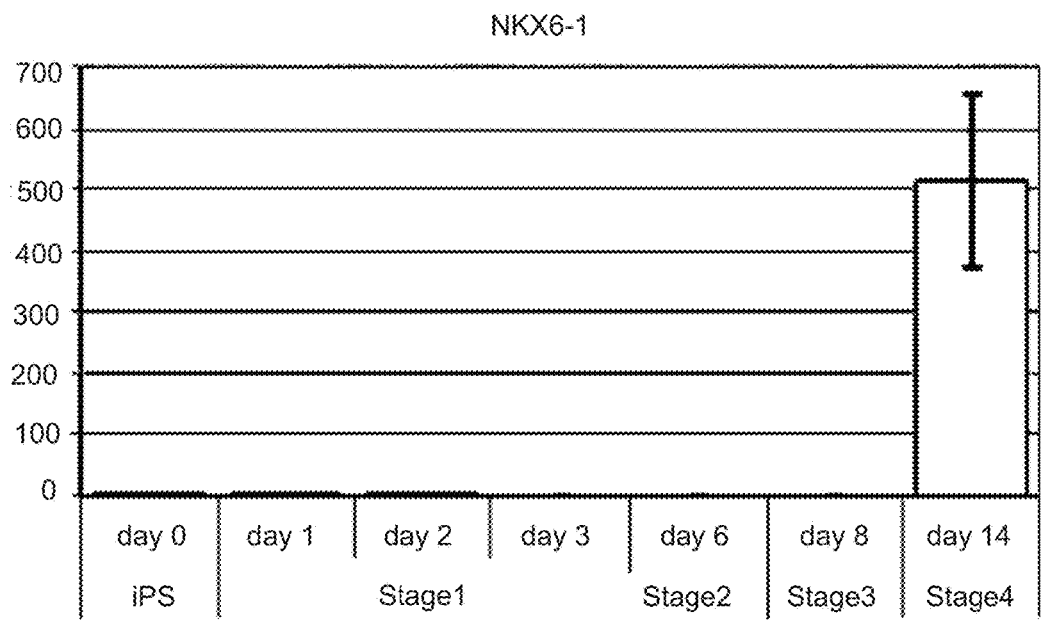
Figure 2K:
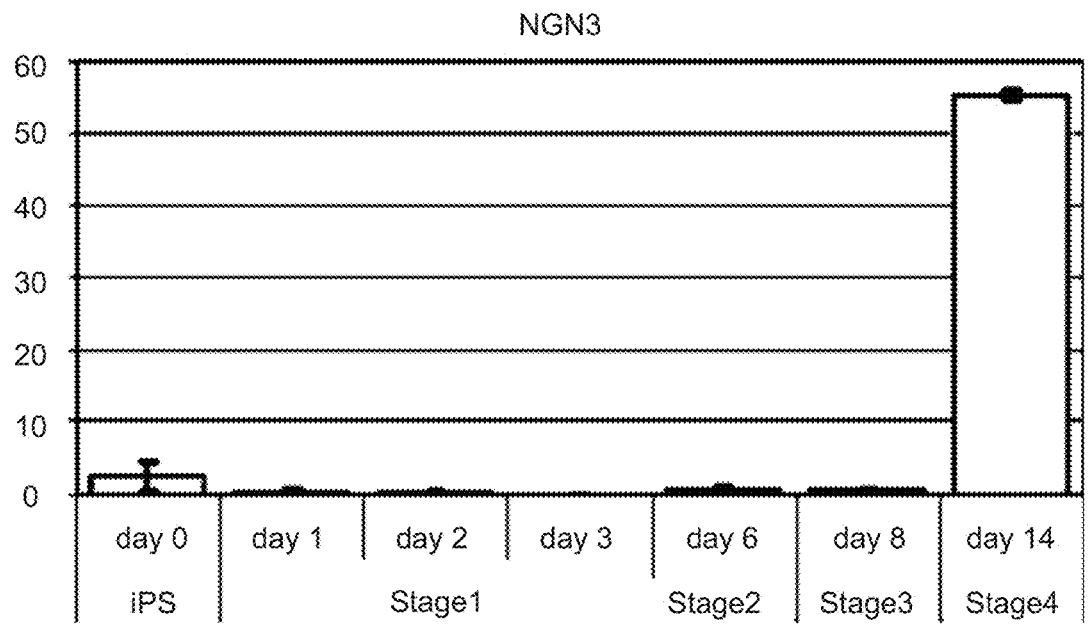
Figure 2L:
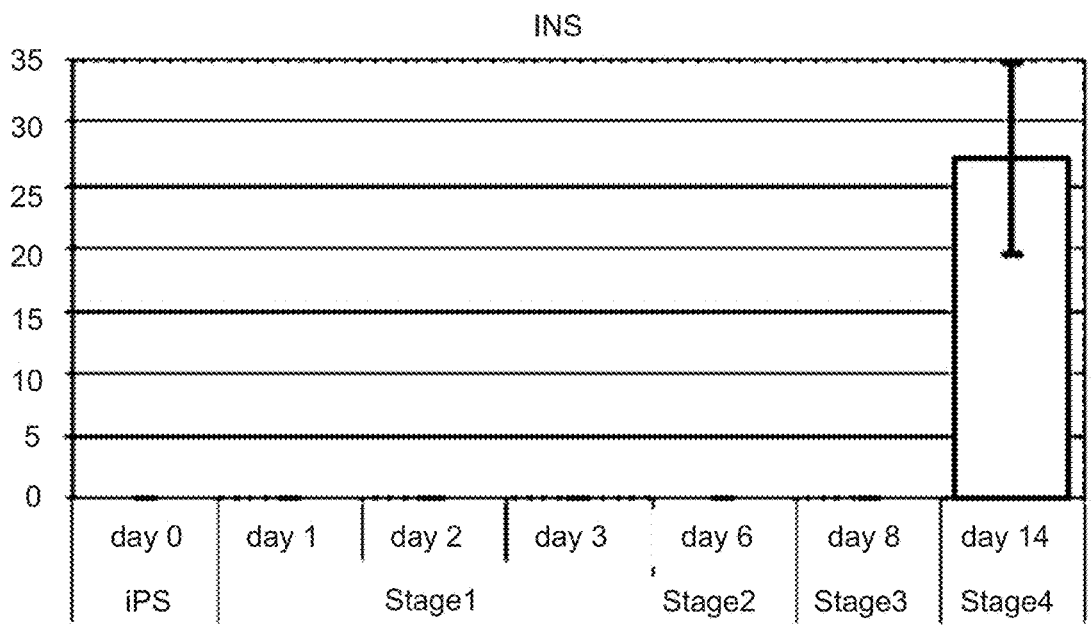

As shown in FIG. 2A, OCT4 (POU5F1) is expressed at high levels in the undifferentiated iPS cells and exhibits subsequent down regulation during the course of differentiation (day 0 to day 14). By day 14, the OCT4 expression levels were more than 3000-fold decreased from the expression levels observed in undifferentiated cells. In contrast, there was a transient up-regulation of brachyury gene (BRACHYURY, FIG. 2B) expression during the first 2 days (day 1 and day 2). Transient up-regulation of brachyury was a result of the directed differentiation of pluripotent/iPS cell into mesendoderm by the application of activin A and wnt3a. The mesendoderm was further differentiated into definitive endoderm during days 2 and 3 by continued exposure to activin A was indicated by the up-regulation of CER1, GSC and FOXA2 by the end of stage 1 at day 3 (FIG. 2C-E). During stage 2, the definitive endoderm was further directed to differentiate to gut tube endoderm as indicated by the up-regulation of FOXA1, maintenance of FOXA2 expression and down regulation of CER1 and GSC by day 6 of differentiation (FIG. 2C-F). During stage 3, upon exposure to retinoid, cyclopamine and noggin, the gut tube endoderm was further directed to differentiate to posterior foregut/PDX1-expressing endoderm as indicated by the up-regulation of HNF6 and PDX1 by day 8 (FIG. 2G-H). During stage 4, upon exposure to KGF and EGF, the posterior foregut/PDX1-expressing endoderm was further directed to differentiate to pancreatic progenitors, endocrine progenitors and hormone expressing endocrine cells as indicated by the up-regulation of PTF1A, NKX6-1, NGN3 and INS by day 14 (FIGS. 2I-L).

Example 2

Rho-Kinase Inhibitors Promote Growth, Survival, Proliferation and Cell-Cell Adhesion of iPS Cells Methods for differentiating various hES and iPS cell lines are substantially as described herein and in Example 1. In addition to the culture conditions as described for Stages 1, 2, 3, 4 and 5, apoptotic inhibitor and/or Rho-kinase or ROCK inhibitor was added to the culture media to enhance and promote growth, survival, proliferation and cell-cell adhesion during differentiation. Typically about 10 µM of a Rho-kinase inhibitor, for example, Y-27632 was added to the cell cultures at each of the stages. Alternatively, a Rho-kinase inhibitor was added to at least Stages 1 and 2 and stages 4 and 5, or any combination thereof. The morphology and gene marker expression profiles of the differentiated iPS suspension (aggregates) cell cultures are substantially similar to that of suspension cell cultures derived from hES cells.

FIGS. 3 and 4 show immunocytochemistry (ICC) of iPS cell cultures from Stages 4 & 5, respectively. FIG. 3 shows a cell aggregate from Stage 4 expressing typical gene markers characteristic of PDX1-positive pancreatic endoderm (also referred to as pancreatic epithelium or pancreatic progenitors) including PDX1/NKX6.1 co-positive cells. Although not shown in FIG. 3, Stage 4 cells do not express hormone secreting proteins or gene markers more typical of Stage 5 cells such as insulin (INS), glucagon (GCG), somatostatin (SST) and pancreatic polypeptide (PP). FIG. 4 shows cell aggregate of hormone expressing cells from Stage 5. These ICC results were further confirmed using QPCR. However, because QPCR is a total population study of the total level of RNA expressed in the sample or cell culture, it cannot definitively show that any one cell expresses multiple markers.

Example 3

Encapsulation of iPS-Derived Pancreatic Progenitors

To date, methods for production of IPS cells and sources for production of IPS cells have been reported. However, there is no sufficient description of differentiating any iPS cell to any functioning differentiated cell for potential use in a cell therapy to treat a particular disease, for example, diabetes.

To determine whether the Stage 4 PDX1-positive pancreatic endoderm or pancreatic progenitor cell cultures derived from human iPS cells were fully capable of developing and maturing in vivo to glucose sensitive insulin secreting cells, the pancreatic progenitor populations substantially as described in Examples 1 and 2 were loaded into macro-encapsulating devices substantially similar to that described in U.S. application Ser. No. 12/618,659, entitled ENCAPSULATION OF PANCREATIC LINEAGE CELLS DERIVED FROM HUMAN PLURIPOTENT STEM CELLS, filed Nov. 13, 2009; and U.S. Pat. Nos. 7,534,608 and 7,695,965 entitled METHODS OF PRODUCING PANCREATIC HORMONES. In brief, about 5-10-20 µL gravity settled cell suspension aggregates were loaded into each device, having substantially about $3 \times 10^6$ cells.

The encapsulated cells in the device were then prepared for implantation into a mammal, for example an immuno-compromised SCID/Bg mice, but can be implanted in larger animals including rats, pigs, monkey or human patient. Methods of implanting the encapsulated cells and device are substantially as that described U.S. patent application Ser. No. 12/618,659, U.S. Pat. Nos. 7,534,608 and 7,695,965, including pancreatic progenitor cells implanted on a GEL-FOAM matrix and implanted under the epididymal fat pad (EFP).

No immuno-suppression was necessary in these studies, however, immuno-suppression may be required for certain mammals for an initial interim period until the progenitors inside the device fully mature and are responsive to glucose. In some mammals immuno-suppression regimens may be for about 1, 2, 3, 4, 5, 6 or more weeks, and will depend on the mammal.

The transplanted cells were allowed to differentiate and further mature in vivo. To determine whether the transplanted cells had normal physiological function as a naturally occurring beta cell for example, levels of human insulin will be determined by testing levels of human C-peptide. Human C-peptide is cleaved or processed from human pro-insulin, hence, the detection of human C-peptide specifically, and not endogenous mouse C-peptide, indicates that insulin secretion is derived from the grafted (exogenous) cells. The animals with implants will be tested for levels of human C-peptide about every two, three or four weeks by injecting them with a bolus of arginine or glucose, preferably glucose. The then mature beta cells (derived from differentiated pluripotent iPS cells) should be physiologically functional and responsive to glucose not unlike naturally occurring or endogenous beta cells. Typically amounts of human C-peptide above 50 pM or the average basal (threshold) level, is an indicator of function of the now beta cells from the transplanted progenitors.

Similar to that described in Kroon et al. (2008) supra U.S. application Ser. No. 12/618,659, U.S. Pat. Nos. 7,534,608; 7,695,965 and 7,993,920, the encapsulated pancreatic progenitors derived from hIPS cells are expected to mature into functioning pancreatic islet clusters having endocrine, acinar and ductal cells not unlike that in naturally occurring islets. It is also anticipated that purified or enriched pancreatic progenitors derived from hIPS cells before transplantation will also mature and develop into functioning pancreatic islets and produce insulin in vivo. Certain embodiments for purifying and enriching various differentiated cell populations is described in more detail in U.S. application Ser. No. 12/107,020, entitled METHODS FOR PURIFYING ENDODERM AND PANCREATIC ENDODERM CELLS DERIVED FROM HES CELLS, filed Apr. 8, 2008, now U.S. Pat. No. 8,338,170. It is further anticipated that pancreatic progenitors derived from hIPS cells which have been cryopreserved can be thawed and adapted in culture before transplantation and mature and produce insulin in vivo accordingly. And that hypoglycemia can be ameliorated in diabetic induced animals having the transplanted pancreatic progenitors derived from hIPS cells.

In summary, wholly encapsulated pancreatic progenitor cells derived from hIPS cells in a macro-encapsulating device mature into physiologically functional pancreatic islets and are expected to produce insulin in response to glucose in vivo.

Example 4

Pancreatic Progenitor and Hormone Secreting Cell Compositions

Differentiated hIPS cell populations were analyzed using flow cytometry for their content of PDX1-positive pancreatic endoderm or pancreatic progenitor cells (at stage 4); and endocrine or endocrine progenitor/precursor cells (at stage 5) as shown in Tables 6a, 6b and 7, respectively. Table 6b is the same data set as that in Table 6a, but presented similar to that of Table 10 for comparison. Table 6a populations overlap each other, e.g. the total cell number is greater than 100% because the total PDX1+ and NKX6.1+ numbers overlap with that of the NKX6.1+/PDX1+/CHGA− cell population (5th column of Table 6a). Table 6b, includes the PDX1+ only and triple negative (residual) data, which is not shown in Table 6a. Certain of these iPEC grafts as well as others using substantially similar formulations did get implanted into animals to determine in vivo function, however, levels of human serum C-peptide was not sufficiently robust for any potential therapeutic purpose (data not shown). Values shown are the percentage of total cells which belong to a given population. The numbers of the pancreatic progenitors (NKX6.1(+)/PDX1(+)/ChromograninA(−)) and a very small population of NKX6.1+/PDX1-/CHGA− are in the suspension cell aggregates were consistent with that observed in pancreatic progenitor cell suspension aggregates derived from hES cells and aggregated at the ESC stage as described in U.S. application Ser. No. 12/264,760, entitled STEM CELL AGGREGATE SUSPENSIONCOMPOSITIONS AND METHODS OF DIFFERENTIATION THEREOF, filed Nov. 4, 2008. Levels of endocrine and/or endocrine progenitor/precursor cells were also substantially consistent with that obtained in hES-derived cell cultures in U.S. application Ser. No. 12/107,020, entitled METHODS FOR PURIFYING ENDODERM AND PANCREATIC ENDODERM CELLS DERIVED FROM HES CELLS, filed Apr. 8, 2008. Similar to hES-derived cell suspension aggregates, varying the concentrations of different growth factors in the culture medium at certain stages of differentiation (e.g., stage 4) should increase and/or decrease certain populations of pancreatic endoderm, endocrine, PDX1-positive endoderm or non-pancreatic cell types.

TABLE 6a

Stage 4 Pancreatic Progenitor Cell Compositions (Percent of Total Cells)

| Exp. # | iPS Cell line | PDX1+ | NKX6.1+ | Pancreatic Endoderm (NKX6.1(+)/ PDX1(+)/ ChromograninA(−)) | Endocrine (ChromograninA+) |
|---|---|---|---|---|---|
| 1 | G4 | 56.4 | 39.2 | 33.3 | 12.7 |
| 2 | B7 | 88.3 | 40.9 | 30.4 | 42.3 |
| 3 | B7 | 84.1 | 53.1 | 38.8 | 51.8 |
| 4 | B7 | 94.0 | 43.7 | 32.7 | 49.5 |

TABLE 6B

Stage 4 Pancreatic Progenitor Cell Compositions (Percent of Total Cells)

| | | PEC | | |
|---|---|---|---|---|
| Exp. # | Conditions | CHGA+ (Endocrine) | CHGA− NKX6.1+ PDX1 + or − (Pancreatic Progenitors, >96% PDX1+) | CHGA− NKX6.1− PDX1+ (PDX1+ only) | CHGA− NKX6.1− PDX1− (Triple negative; residual cells) |
| 1 | Baseline | 12.7 | 33.3 | 10.6 | 42.7 |
| 2 | Baseline | 42.3 | 30.4 | 18.5 | 7.9 |
| 3 | Baseline | 51.8 | 38.8 | 8.4 | 0.5 |
| 4 | Baseline | 49.5 | 32.7 | 16.3 | 1.2 |

TABLE 7

Stage 5 Endocrine Cell Compositions (Percent of Total Cells)

| Exp. # | iPS Cell Line | Insulin+ | Glucagon+ | Somatostatin+ |
|---|---|---|---|---|
| 5 | B7 | 15.9 | 15.0 | 12.1 |
| 6 | B7 | 17.4 | 15.9 | 10.5 |

Example 5

PEC Receptor Tyrosine Kinases

The above described methods are substantially similar to those described in Table 8 below, adapted from Schulz et al., (2012), supra. These and other methods described herein can be found in Applicant's many patent and non-patent publications including U.S. Pat. Nos. 7,964,402; 8,211,699; 8,334,138; 8,008,07; and 8,153,429.

TABLE 8

Standard Manufacturing Method For Making Pancreatic Endoderm Cells (PEC) Derived From hESC

| Time point (day) | Stage (1-4) | Media Condition | Roller Bottle Speed (rpm) | 6-well tray Speed (rpm) |
|---|---|---|---|---|
| d(−1) | hESC Agg. | XF HA; SP | 5-10 | 95 |
| d0 | 1 | r0.2FBS-ITS1:5000 A100 W50 | 5-10 | 95 |
| d1 | | r0.2FBS-ITS1:5000 A100 | 5-10 | 95 |
| d2 | 2 | r0.2FBS-ITS1:1000 K25 IV | 5-10 | 95 |
| d3 | | r0.2FBS-ITS1:1000 K25 | 5-10 | 95 |
| d4 | | r0.2FBS-ITS1:1000 K25 | 5-10 | 105 |
| d5 | 3 | db-CTT3 N50 | 5-10 | 105 |
| d6 | | db-CTT3 N50 | 5-10 | 105 |
| d7 | | db-CTT3 N50 | 5-10 | 105 |
| d8 | 4 | db-N50 K50 E50 | 5-10 | 105 |
| d9 | | db-N50 K50 E50 | 5-10 | 95 |
| d10 | | db-N50 K50 E50 (or no feed) | 5-10 | 95 |
| d11 | | db-N50 K50 E50 | 5-10 | 95 |
| d12 | | db-N50 K50 E50 | 5-10 | 95 | hESC Agg.: hESC aggregates;
XF HA: DMEM/F12 containing GlutaMAX, supplemented with 10% v/v of Xeno-free KnockOut Serum Replacement, 1% v/v non-essential amino acids, 0.1 mM 2-mercaptoethanol, 1% v/v penicillin/streptomycin (all from Life Technologies), 10 ng/mL heregulin-1β (Peprotech) and 10 ng/mL activin A (R&D Systems);
SP: StemPro ® hESC SFM (Life Technologies);
r0.2FBS: RPMI 1640 (Mediatech); 0.2% FBS (HyClone), 1 × GlutaMAX-1 (Life Technologies), 1% v/v penicillin/streptomycin;
ITS: Insulin-Transferrin-Selenium (Life Technologies) diluted 1:5000 or 1:1000;
A100: 100 ng/mL recombinant human Activin A (R&D Systems);
W50: 50 ng/mL recombinant mouse Wnt3A (R&D Systems);
K25: 25 ng/mL recombinant human KGF (R&D Systems);
IV: 2.5 μM TGF-β RI Kinase inhibitor IV (EMD Bioscience);
db: DMEM HI Glucose (HyClone) supplemented with 0.5 × B-27 Supplement (Life Technologies), 1 × GlutaMAX, and 1% v/v penicillin/streptomycin;
CTT3: 0.25 μM KAAD-Cyclopamine (Toronto Research Chemicals) and 3 nM TTNPB (Sigma-Aldrich);
N50: 50 ng/mL recombinant human Noggin (R&D Systems);
K50: 50 ng/mL recombinant human KGF (R&D Systems);
E50: 50 ng/mL recombinant human EGF (R&D Systems);
no feed: indicates that cells were not re-fed on the indicated day;
db, DMEM (high-Glucose).

When the above methods were applied to iPS cells and the pancreatic progenitors transplanted in animals, Applicant did not consistently obtain the same robust in vivo function as compared to when the same methods were applied to hESC and hES-derived pancreatic progenitors. This was surprising given iPS cells are human pluripotent stem cells that have the morphology and gene-expression pattern of hESCs and can form both embryoid bodies in vitro and teratomas in vivo, indicating that they can form cells from all three germ layers. See at least for example Yu et al.

(2007); U.S. Patent Application Publication No. 2009/0047263, International Patent Application Publication No. WO2005/80598; U.S. Patent Application Publication No. 2008/0233610; and International Patent Application Publication No. WO2008/11882, supra. These references describe that iPS cells meet the defining criteria for ESC. Hence, there is an expectation that iPS cells can substitute for ESCs in an in vitro differentiation protocol that yields hES-derived pancreatic progenitor cells that further mature and develop into fully functioning glucose responsive cells in vivo. However, given the inconsistent in vivo functioning data using the above methods, Applicants sought to explore a differentiation media formulation unique to pancreatic progenitors and/or pancreatic endoderm cells (PEC) i.e., stage 4 derived cells from hiPSC (or "iPEC") that are capable of providing substantially similar robust levels of in vivo function which has been consistently observed for PEC derived from hESC.

Applicants previously reported that endocrine (CHGA+ cells) cells present in PEC are polyhormonal endocrine cells and are not the sub-population of cells in PEC that give rise to islets having glucose-responsive insulin-secreting cells in vivo. See Kelly et. al. (2011) supra. Rather it is the non-endocrine cell population (CHGA− cells), especially those that co-express NKX6.1 and PDX-1, that are believed to be the PEC that actually give rise to the functioning islets in vivo. Thus, Applicant's explored whether modulating, changing or shifting the relative ratios of endocrine and non-endocrine sub-populations might affect later in vivo function.

Previous efforts to decipher receptor-ligand signaling in hESC successfully identified growth factors that promoted self-renewal and enabled the development of defined media culture conditions. See Wang et al (2007) supra. Wang et al. identified heregulin-1β as the ligand that bound to ERBB3 and induced dimerization with ERBB2 to affect self-renewal of hESC in that context. ERBB is a receptor tyrosine kinase (RTK) and RTK are widely expressed transmembrane proteins that act as receptors for growth factors and other extracellular signaling molecules. Upon ligand binding, they undergo tyrosine phosphorylation at specific residues in the cytoplasmic tail and setting off a signaling cascade for the binding of other protein substrates involved in RTK-mediated signal transduction. RTK function in several developmental processes, including regulating cell survival, proliferation, and motility and their role in cancer formation is well documented. ERBB tyrosine kinase receptors were also known to be expressed throughout the developing fetal human pancreas although specific roles of certain ERBB receptors and their ligands are unknown. See Mari-Anne Huotari et al. (2002) ERBB Signaling Regulates Lineage Determination of Developing Pancreatic Islet Cells in Embryonic Organ Culture, *Endocrinology* 143(11): 4437-4446.

Because of the role of ERBB RTK signaling in pluripotent stem cell self-renewal and their expression in fetal human pancreas as demonstrated by Wang et al. (2007) supra and ERBB RTK expression in the human fetal pancreas, Applicants then turned to investigate the potential activation of RTK in in vitro pancreatic endoderm cells (PEC) derived from hESC in an effort to identify receptors and ligands that might improve PEC specification during differentiation, or expansion via promotion of self-renewal, or some other unknown mechanism which promotes maturation to physiologically functioning islet hormone secreting cells in vivo.

PEC were generated in suspension in differentiating aggregates, substantially as described in Table 8, except with the following modifications.

Four PEC samples were generated for RTK blotting analysis. A "steady state" sample of PEC aggregates in db-N50 K50 E50 was collected at the end of stage 4 (or d13). A "starved" sample represented d12 PEC aggregates that were fed with db (DMEM high-glucose or DMEM high-glucose supplemented with 0.5× B-27 Supplement (Life Technologies)) media alone (no growth factors) and collected on d13. Two "pulsed" samples were fed and cultured in db media on d12, then on d13 fed with either db-K50 E50 media, or db media containing 2% FBS, for 15 minutes prior to harvesting. Such conditions were intended to detect RTKs that were active in stage 4 conditions, and what response could be elicited with a pulse of KGF, EGF and insulin (present in the B27 supplement), or serum. The serum pulse was intended as a broad-spectrum, growth factor stimuli, potentially identifying RTKs that are present on PEC and can be activated, but are not stimulated with the present stage 4 conditions.

RTK analysis was performed essentially as described previously in Wang et al, (2007) supra. Briefly, PROTEOME PROFILER™ human phospho-RTK antibody arrays (R&D Systems) were used according to the manufacturer's instructions. Protein lysates were prepared in 1% NP-40, 20 mM Tris-HCl (pH 8.0), 137 mM NaCl, 10% glycerol, 2.0 mM EDTA, 1.0 mM sodium orthovanadate, 10 μg/mL Aprotinin, and 10 μg/mL Leupeptin. 500 μg fresh protein lysates were incubated overnight with nitrocellulose membranes dotted with duplicate spots for 42 anti-RTK antibodies and 5 negative control antibodies, as well as 8 anti-phosphotyrosine positive control spots (FIG. 5A). The arrayed antibodies capture the extracellular domains of both phosphorylated and unphosphorylated RTKs, and bound phospho-RTKs are detected with a pan anti-phospho-tyrosine antibody conjugated to horseradish peroxidase (HRP) using chemiluminescence. See FIG. 5 for the RTK array layout as well as Table 9 below for the listing of RTK in the array.

TABLE 9

Listing of Receptor Tyrosine Kinase (RTK) for RTK Analysis of PEC

| Receptor Family | RTK | Receptor Family | RTK |
|---|---|---|---|
| EGF R | EGFR | ROR | ROR2 |
| EGF R | ERBB2 | Tie | Tie-1 |
| EGF R | ERBB3 | Tie | Tie-2 |
| EGF R | ERBB4 | NGF R | TrkA |
| FGF R | FGF R1 | NGF R | TrkB |
| FGF R | FGF R2A | NGF R | TrkC |
| FGF R | FGF R3 | VEGF R | VEGF R1 |
| FGF R | FGF R4 | VEGF R | VEGF R2 |
| Insulin R | Insulin R | VEGF R | VEGF R3 |
| Insulin R | IGF-1R | MuSK | MuSK |
| Axl | Axl | Eph R | EphA1 |
| Axl | Dtk | Eph R | EphA2 |
| Axl | Mer | Eph R | EphA3 |
| HGF R | HGF R | Eph R | EphA4 |
| HGF R | MSP R | Eph R | EphA6 |
| PDGF R | PDGF Ra | Eph R | EphA7 |
| PDGF R | PDGF Rb | Eph R | EphB1 |
| PDGF R | SCF R | Eph R | EphB2 |
| PDGF R | Flt-3 | Eph R | EphB3 |
| PDGF R | M-CSF R | Eph R | EphB4 |
| RET | c-Ret | Eph R | EphB6 |
| ROR | ROR1 | Insulin R | ALK |

Of the RTK blots (FIG. 6A) indicated that the insulin- and IGF1-Receptors (IR, IGF1R, respectively) were phosphorylated and activated in all conditions, similar to that observed previously with hESC. See Wang et al (2007) supra. The EGF receptor (EGFR, also known as ERBB1) was phosphorylated in steady state conditions, which was expected given the presence of EGF in the stage 4 medium. Indeed, low-level phosphorylation of ERBB2 was detected in both the steady state and starved conditions. Phosphorylation of both EGFR and ERBB2 was elevated in each of the pulsed conditions, confirming the capability of the assay to detect activation in response to a pulse of ligand. Phosphorylated VEGFR3 was also detected in all conditions and was elevated in the pulsed samples. This suggested that PEC produces an endogenous VEGFR3 ligand, possible candidates being VEGF-C and D. The serum pulse appeared to activate additional receptors, including low levels of ERBB3 phosphorylation. The detection of phosphorylated ERBB2/3 is suggestive that a heregulin-like EGF-family member could activate signaling in PEC. TIE-2 is one of two angiopoietin receptors and appeared to be phosphorylated at a low level in response to serum. Angiopoietin 1 and Angiopoietin 4 are known to be activating ligands of Tie-2, whereas Angiopoietin 2 and Angiopoietin 3 function as context dependent competitive antagonists. The HGF-receptor (HGFR) was also phosphorylated in response to the serum pulse, suggesting that hepatocyte growth factor could also elicit signaling in PEC. Finally, while low-level phosphorylation of the ephrin B2 RTK (EPHB2) was detected, ephrin/Eph signaling is a membrane bound cell-cell signaling system and not likely to be exploited easily in PEC differentiation. Interestingly, ERBB4 was not phosphorylated. RTK analysis therefore highlighted several receptors that are phosphorylated in PEC, or can become phosphorylated in response to different conditions, e.g. serum. These results suggest that several soluble ligands may elicit RTK signaling in PEC and potentially impact cell proliferation, differentiation and/or specification, and therefore, potentially affect later maturation into functioning pancreatic islets in vivo.

Example 6

Heregulin and Fgf2 Growth Factors Affect PEC Derived from HESC Compositions

In view of the RTK analyses, which demonstrated that certain RTK were activated (or phosphorylated) under certain conditions as described above in Example 5, and because it appeared that at least ERBB2 and ERBB3 were activated in PEC (after 13 days of differentiation from stages 1-4), Applicant sought to determine the effect of heregulin when applied to stage 3 and 4 cells.

Preliminary studies were performed using Heregulin and FGF. In certain of these studies, Rho-kinase inhibitor, Y-27632, was included. These preliminary studies showed that treatment of pluripotent stem cells for one day at stage 1 with 10 ng/mL Heregulin-1β (the same concentration and heregulin isomer as disclosed in Wang et al. (2007)) increased the cell aggregate size of the hES-derived cell aggregates in suspension culture as compared to the aggregate size of the hES-derived cell aggregates in suspension culture without Heregulin-1β (Hrg1β). An increase in cell aggregate size is advantageous in that it results in higher cell mass for later implantation and testing for function in animals. In addition, aggregate disk size increased when Hrg1β was increased from 10 ng/mL to 50 ng/mL at stage 3. This result was also observed when 50 ng/mL of another growth factor, FGF2, was used at stage 3 as compared to cultures in the absence of FGF2. An increase in cell aggregate size was also observed when the stage 3 cultures were exposed to additional days of FGF2 exposure, e.g. 3 days of 50 ng/mL FGF2 as compared to 2 days.

Table 10 provides a summary of the flow cytometry analysis of PEC cells treated with Hrg1β and FGF2 at stage 3. The endocrine cells are denoted as CHGA positive (or CHGA+) cells and the non-endocrine cells are denoted as CHGA negative (or CHGA−) cells. The endocrine (CHGA+) and non-endocrine cells (CHGA−) may stain positive for other markers, e.g., positive for PDX1 and/or NKX6.1. Cells which do not stain with any of the tested markers are denoted as triple negative cells or residual cells (CHGA−/NKX6.1−/PDX1).

TABLE 10

Flow Cytometry Analysis of PEC Derived From hESC and Treated With Heregulin and or FGF2

| | PEC | | |
|---|---|---|---|
| Treatment | CHGA+) (Endocrine | CHGA−, NKX6.1+, PDX1+ (Non-endocrine) | CHGA− NKX6.1− PDX1− (Triple Negative/ Residual Cells) |
| No Hrg & No FGF2 | 32.9 | 54.01 | 13.1 |
| Stg 3 Hrg10 | 30.3 | 61.2 | 8.55 |
| Stg 3Hrg50 | 28.9 | 64.2 | 6.9 |
| 2d Stg 3 FGF2-50 | 11.9 | 79 | 9.15 |
| 3d Stg 3 FGF2-50 | 0.33 | 76.9 | 22.7 |

Hg, Heregulin-β; FGF2, Fibroblast growth factor 2; Hrg10, 10 ng/mL Heregulin-1β; Hrg50, 50 ng/mL Heregulin-1β; 2d FGF-50, 50 ng/mL of FGF2 for 2 days at stage 3; 3d FGF2-50, 50 ng/mL of FGF2 for 3 days at stage 3

To determine whether the increase in cell aggregate size affected the PEC sub-populations, the composition of the PEC populations was analyzed by flow cytometry. As compared to the control cultures, whereby no Hrg1β and FGF2 were used to differentiate the cells, the PEC non-endocrine sub-population (CHGA−) increased from 54.01% to 61.2% with the addition of 10 ng/mL Hrg1β at stage 3, and increased from 54.01% to 64.2% with the addition of 50 ng/mL Hrg1β at stage 3. The endocrine sub-population (CHGA+) was not significantly affected with the treatment of 10 ng/mL Hrg1β but more so with 50 ng/mL. Meanwhile, the relative levels of residual cells did decrease and more so with 50 ng/mL Hrg1β. So, the increase in cell aggregate size with Hrg1β treatment was mostly attributed to the increase in non-endocrine sub-populations relative to the endocrine and residual sub-populations.

The effect of FGF2 in the stage 3 cultures was similar but even more pronounced than that for Hrg1β. For example, the PEC non-endocrine sub-population (CHGA−) increased as it did for Hrg1β. The major effect of FGF2 in these cultures was the substantial decrease in the endocrine sub-population. In some instances, these cells were almost non-detectable with 3 days of treatment (32.9% to 0.33%). Hence, the increase in cell aggregate size for cultures treated with FGF2 was mostly attributed to the increase in non-endocrine, and in some instances, residual cell sub-populations (13.1% to 22.7% for 3 days at stage 3).

Thus, heregulin and/or FGF2 appear to play a role in the specification of cells in PEC populations. This is surprising given that Wang et al (2007) supra reported that heregulin alone played a role in cell renewal when used in the context with pluripotent stem cells.

Example 7

Methods for Improving In Vivo Graft Function of PEC by Treatment of iPS-Derived Cell Cultures with Heregulin Because the methods according to Table 8 when applied to iPSC to produce iPEC did not provide robust in vivo function in animals, Applicants explored other methods for iPEC production. Changes to the standard method as set forth in Table 8 include, but are not limited to: optimization of the number of times any iPSC is passaged; modulating levels of BMP signaling; modulating iPSC suspension aggregation parameters during expansion and differentiation (e.g. shear force, rotation speed and the like); optimization of the concentrations, time of use and duration of use of growth factors, such as Wnt, Activin and rho-kinase inhibitors; and treatment with other growth factors at various stages 1 through 4 of the differentiation protocol as candidates for improving cell mass, proliferation, differentiation, survival and the like (e.g. ERBB ligands). These many iterative experiments were tested alone, or in combination, to determine how differentiation methods for iPSC during stages 1-4 could be optimized. Such optimized differentiation methods produce iPEC populations that when grafted, resulted in robust glucose-responsive insulin-secreting cells in vivo similar to those observed and reported for hESC. Table 11 below describes the baseline conditions, with and without heregulin, that were demonstrated to differentiate iPSC to iPEC, which later matured to glucose-responsive islet cells in vivo. The baseline conditions were similar to those described in Examples 1, 2 and 5 as well as Table 8 herein, except that heregulin was added at stages 3 and 4. Although 30 ng/mL of Hrg1β was used, concentrations ranging from 10 ng/mL to 50 ng/mL, or even greater than 50 ng/mL are suitable. Also, addition of a rho-kinase inhibitor, Y-27632, was maintained in the differentiation cultures as described in Example 2.

TABLE 11

Comparison of Baseline and Heregulin Differentiation Media Formulations for Making Pancreatic Endoderm Cells (PEC) Derived from iPSC

| Baseline (No Heregulin) | Stage (1-4) | Baseline With Heregulin |
|---|---|---|
| 20% KSR-F10 A10 Y10 | iPSC Agg. | 20% KSR-F10 A10 Y10 |
| r0.2FBS-ITS1:5000 A100 W100 Y10 | 1 | r0.2FBS-ITS1:5000 A100 W100 Y10 |
| r0.2FBS-ITS1:5000 A100 Y10 |  | r0.2FBS-ITS1:5000 A100 Y10 |
| r0.2FBS-ITS1:1000 IV K25 Y10 | 2 | r0.2FBS-ITS1:1000 IV K25 Y10 |
| r0.2FBS-ITS1:1000 K25 Y10 |  | r0.2FBS-ITS1:1000 K25 Y10 |
| r0.2FBS-ITS1:1000 K25 |  | r0.2FBS-ITS1:1000 K25 |
| db-CTT3 N50 | 3 | db-CTT3 N50 H30 |
| db-CTT3 N50 |  | db-CTT3 N50 H30 |
| db-CTT3 N50 |  | db-CTT3 N50 H30 |
| db-N50 K50 E50 Y10 | 4 | db-N50 K50 E50 H30 Y10 |
| db-N50 K50 E50 Y10 |  | db-N50 K50 E50 H30 Y10 |
| db-N50 K50 E50 (or no feed) |  | db-N50 K50 E50 (or no feed) |
| db-N50 K50 E50 Y10 |  | db-N50 K50 E50 H30 Y10 |
| db-N50 K50 E50 Y10 |  | db-N50 K50 E50 H30 Y10 | iPSC Aggs: iPSC aggregates;
KSR: knock-out serum (Life Technologies);
F10: 10 ng/mL bFGF (R&D Systems);
A10: 10 ng/mL Activin A (R&D Systems);
A100: 100 ng/mL Activin A;
r0.2FBS: RPMI 1640 (Mediatech); 0.2% FBS (HyClone), 1 × GlutaMAX-1 (Life Technologies), 1% v/v penicillin/streptomycin;
ITS: Insulin-Transferrin-Selenium (Life Technologies) diluted 1:5000 or 1:1000;
A100: 100 ng/mL recombinant human Activin A (R&D Systems);
K25: 25 ng/mL recombinant human KGF (R&D Systems);
CTT3: 0.25 μM KAAD-Cyclopamine (Toronto Research Chemicals) and 3 nM TTNPB (Sigma-Aldrich);
N50: 50 ng/mL recombinant human Noggin (R&D Systems);
K50: 50 ng/mL recombinant human KGF (R&D Systems);
E50: 50 ng/mL recombinant human EGF (R&D Systems);
Y10: 10 μM Y-27632; stock 20 mM, 2000X;
H30: 30 ng/mL Heregulin (stock 100 ug/mL);
db, DMEM (high-Glucose)

To determine the effect of the addition of heregulin or heregulin and a rho-kinase inhibitor on stage 3 and 4 cell subpopulations, iPEC populations were analyzed by flow cytometry. Table 12 provides a summary of the flow cytometry analysis of various iPEC populations using the formulations set forth in Table 11, as well as such formulations having been modified by increasing the Activin concentration to 200 ng/mL. In addition, Table 12 shows the general conditions used for each set of experiments (baseline with or without heregulin) and the relative percentages of the types of cells in the iPEC population (endocrine, non-endocrine, PDX1 only and triple negative or residual cell sub-populations). Table 12 also discloses data regarding in vivo function of the cells produced in each experiment.

TABLE 12 iPEC Compositions from Heregulin Treated iPS-derived Cell Cultures

| | | PEC | | | | |
|---|---|---|---|---|---|---|
| Exp. No. | Conditions | CHGA+ (Endocrine) | CHGA–NKX6.1+PDX1+ (Non-endocrine) | CHGA–NKX6.1–PDX1+ (PDX1 only) | CHGA–NKX6.1–PDX1– (Triple negative/residual cells) | In vivo Function |
| E2314 | BL-hIPSC | 19.83 | 65.59 | 11.32 | 3.20 | FIG. 7A |
| | Hg30 St 3 + 4 | 9.00 | 64.21 | 16.83 | 9.88 | |
| E2344 | BL-hIPSC | 56.51 | 36.15 | 5.45 | 1.80 | Not |
| | Hg30 St 3 + 4 | 36.13 | 49.00 | 11.23 | 2.75 | transplanted |
| E2347 | BL-hIPSC | 49.78 | 37.16 | 10.97 | 2.11 | FIGS. 7B & |
| | Hg30 St 3 + 4 | 17.27 | 68.91 | 12.30 | 1.68 | 8A-B |
| E2380 | BL-hIPSC | 41.16 | 38.18 | 12.08 | 9.10 | FIG. 7A |
| | Hg30 St 3 + 4 | 45.91 | 29.72 | 17.24 | 7.03 | |
| E2354 | BL-hESC | 33.39 | 62.01 | 2.89 | 1.75 | FIG.7C |
| | Hg30 St3 + 4 hESC | 16.18 | 73.00 | 8.10 | 1.86 | |

BL, baseline conditions;
hIPSC, human induced pluripotent stem cells;
Hg30, 30 ng/mL heregulin-11 St 3 + 4, Stages 3 and 4;
hESC, human embryonic stem cells,
CHGA, chromogranin A Under certain conditions, the ratio of subpopulations of cells in the PEC (hESC, E2354) and iPEC (E2314, E2344, E2347) populations were altered. For example, sometimes, the percentage of endocrine (CHGA+) cells decreased and the percentage of non-endocrine cells (CHGA–/NKX6.1+/PDX1+) increased as compared to the baseline (no heregulin) conditions. Although it appeared that heregulin was responsible for changing the proportions of endocrine cells relative to non-endocrine cells in these PEC and iPEC populations, in experiment #2380 (E2380), the level of endocrine (CHGA+) cells increased rather than decreased with the addition of heregulin.

To determine whether the change in the composition of PEC and iPEC populations affected in vivo function, PEC and iPEC grafts from most of the experiments described in Table 12 were transplanted into mice substantially as previously described herein and in Applicant's other patent and non-patent publications, including Schulz et al. (2012) and Kroon et al (2008), supra and U.S. Pat. Nos. 7,534,608; 7,695,965; 7,993,920 and 8,278,106, supra. Briefly, PEC and iPEC populations were wholly encapsulated with a biodegradable semi-permeable cell encapsulation device, some of which included micro perforations. The devices were manufactured by Applicant and are described in detail in U.S. Pat. No. 8,278,106, entitled ENCAPSULATION OF PANCREATIC CELLS FROM HUMAN PLURIPOTENT STEM CELLS, filed Nov. 13, 2009. Glucose stimulated insulin secretion (GSIS) assays were performed starting from about 56 days post-implant. Blood was collected prior to (fasting) and at combinations of 30 and/or 60 minutes after glucose administration. Graft function was assessed by measuring human C-peptide concentrations in the serum in response to glucose administration.

The amount of human C-peptide released into the serum is indicative of the amount of insulin released. C-peptide is a short 31 amino acid peptide connecting or linking A and B-chains of proinsulin and preproinsulin, which is secreted by functioning beta or insulin secreting cells. As discussed previously by Kroon et al. (2008) supra and others, human C-peptide measurements are appropriate for assessing the release of de novo-generated insulin by the implanted cells. Hence, levels of human C-peptide in the serum of these animals is a measure of the in vivo function of the mature PEC and iPEC grafts. Human C-peptide was detected in the serum by at least 8 weeks post-implant. With additional weeks of implant and fasting, glucose-stimulated C-peptide levels increased with the peak levels of C-peptide shifting from 60 minutes to 30 minutes post-glucose administration, which is indicative of a more rapid response to glucose challenge as the insulin cells mature. There were a few mice that failed to exhibit function, or were sacrificed due to poor health; however, these mice were in cohorts that otherwise exhibited high-functioning animals, thus suggesting a failure of engraftment rather than an inability of the implanted cells to differentiate and function.

Figure 7A:
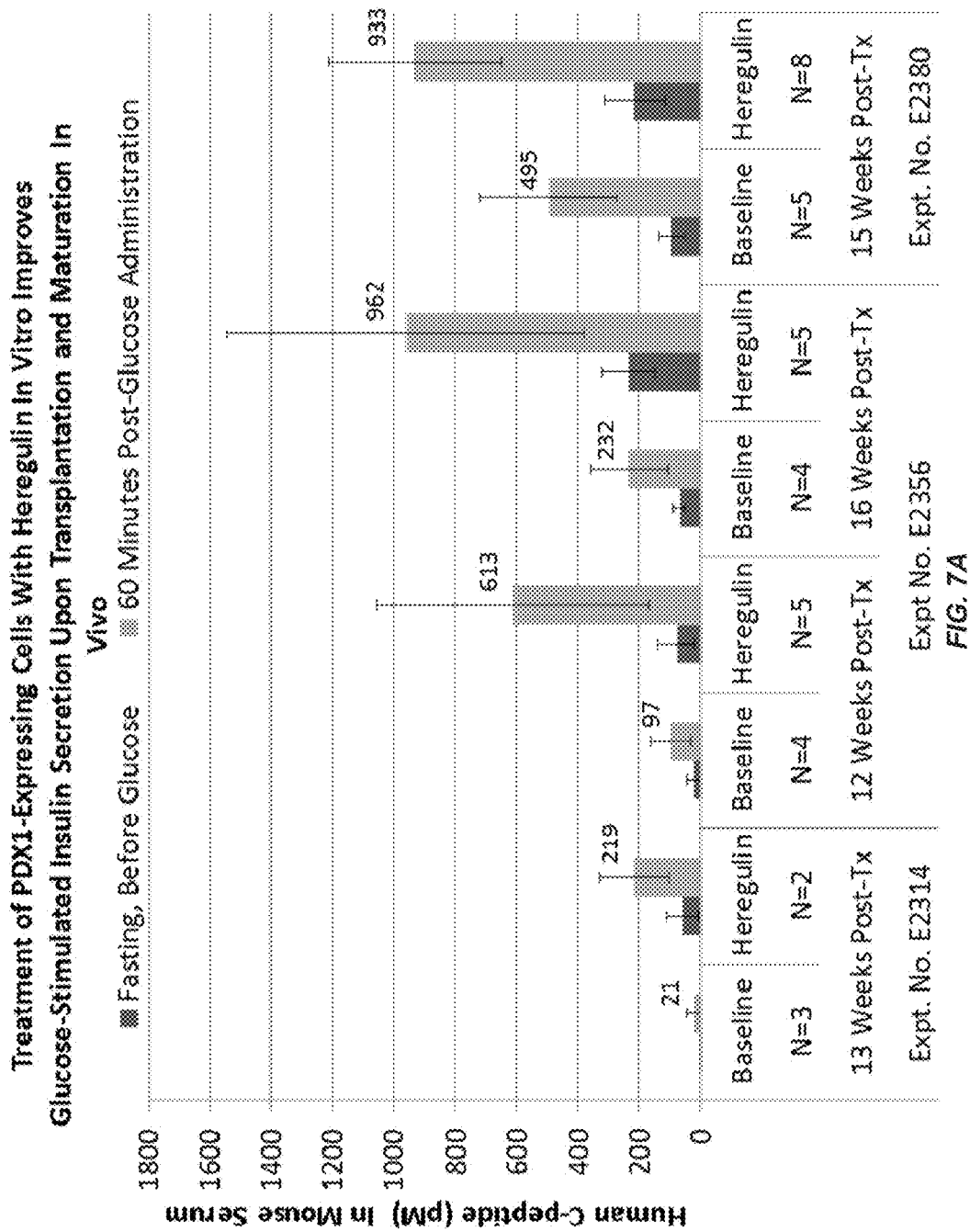
FIGS. 7A-7C are graphs showing the concentrations of human C-peptide and insulin in sera of implanted mice for experiments E2314, E2356 and E2380 (FIG. 7A), E2347 (FIG. 7B), and E2354 (FIG. 7C).
Figure 7B:
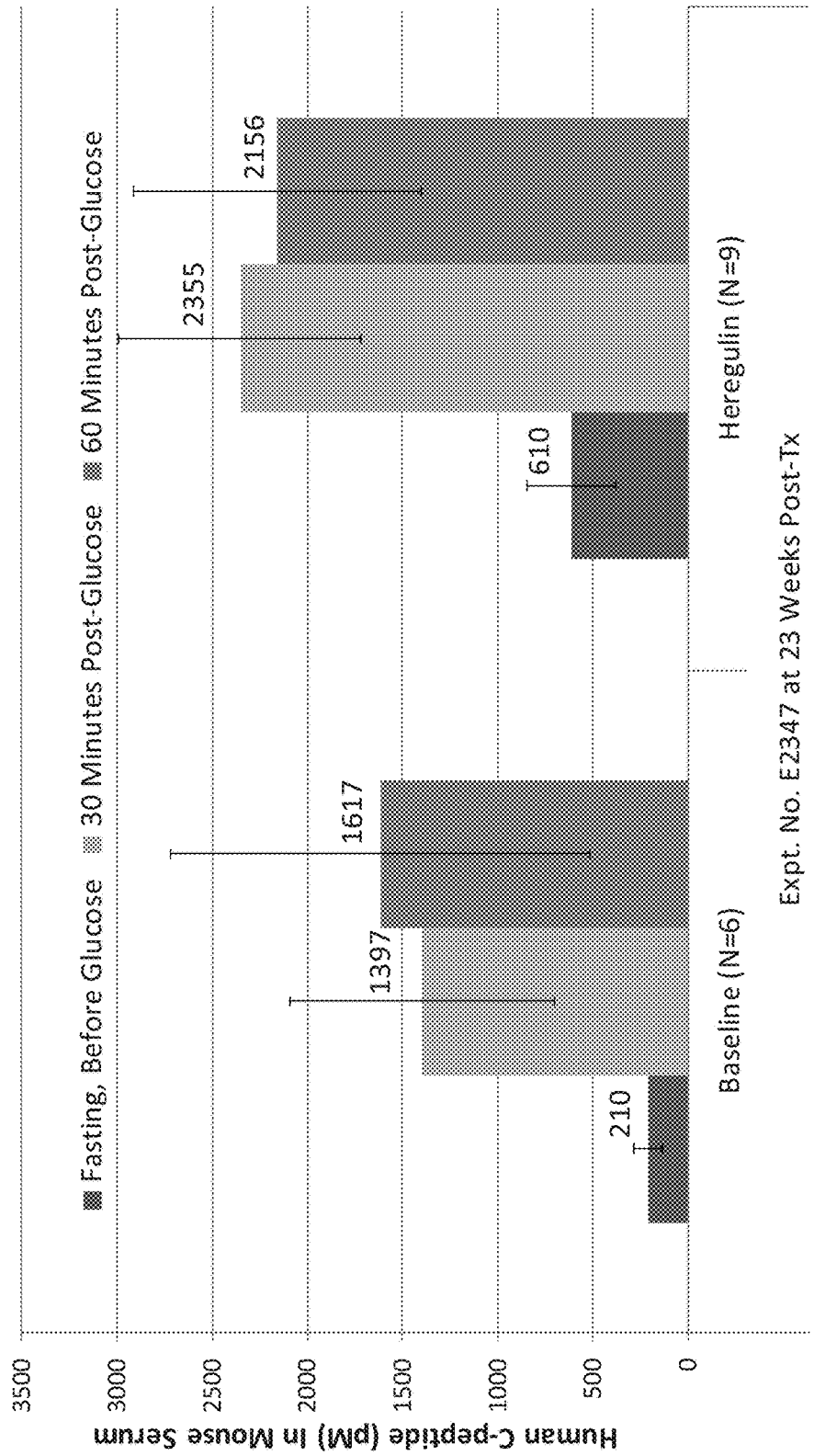
Figure 7C:
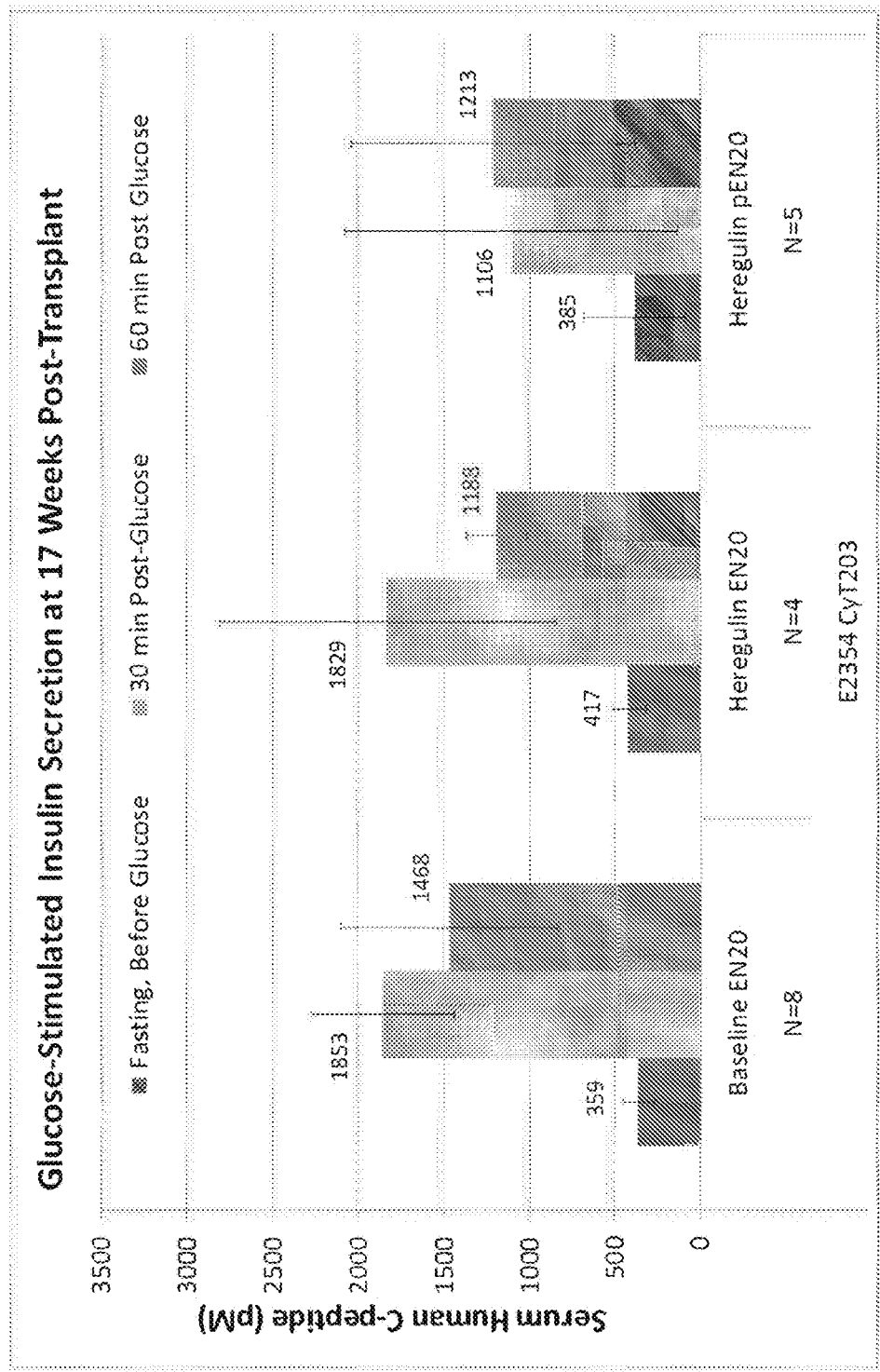

FIGS. 7A-C show human C-peptide levels in the serum post glucose administration for all of the experiments indicated in Table 12 except E2344. FIGS. 7A-C show that as compared to baseline controls, those grafts resulting from heregulin treatment, in general, had higher levels of serum human C-peptide. For example, in FIG. 7A, in experiment 2380, there is about a 5-fold increase (933 pM: 200 pM at 60 minutes post glucose administration) in the grafts resulting from the heregulin treatment as compared to those prepared without heregulin (baseline). Heregulin seem to have lesser effect on PEC produced from hESC, since experiment 2354 (FIG. 7C) does not show higher levels of serum C-peptide in those grafts resulting from heregulin treatment as compared to the baseline controls. Further, when comparing PEC derived from hESC (CyT203) and iPEC derived from iPSC, the iPEC grafts have comparable function in vivo to the PEC grafts (e.g. compare FIG. 7A and FIG. 7B (iPSC grafts) with FIG. 7C (CyT203 hESC). As such, the iPEC grafts are as robust as the PEC grafts. Also, the relative ratios of endocrine to non-endocrine cells, which appeared to affect some of the iPEC populations (e.g. E2314, E2347 and E2354), did not appear to affect in vivo function because iPEC from E2380, which did not have the same shift in endocrine and non-endocrine subpopulations, also showed good function (see FIG. 7A-C).

Figure 8A:
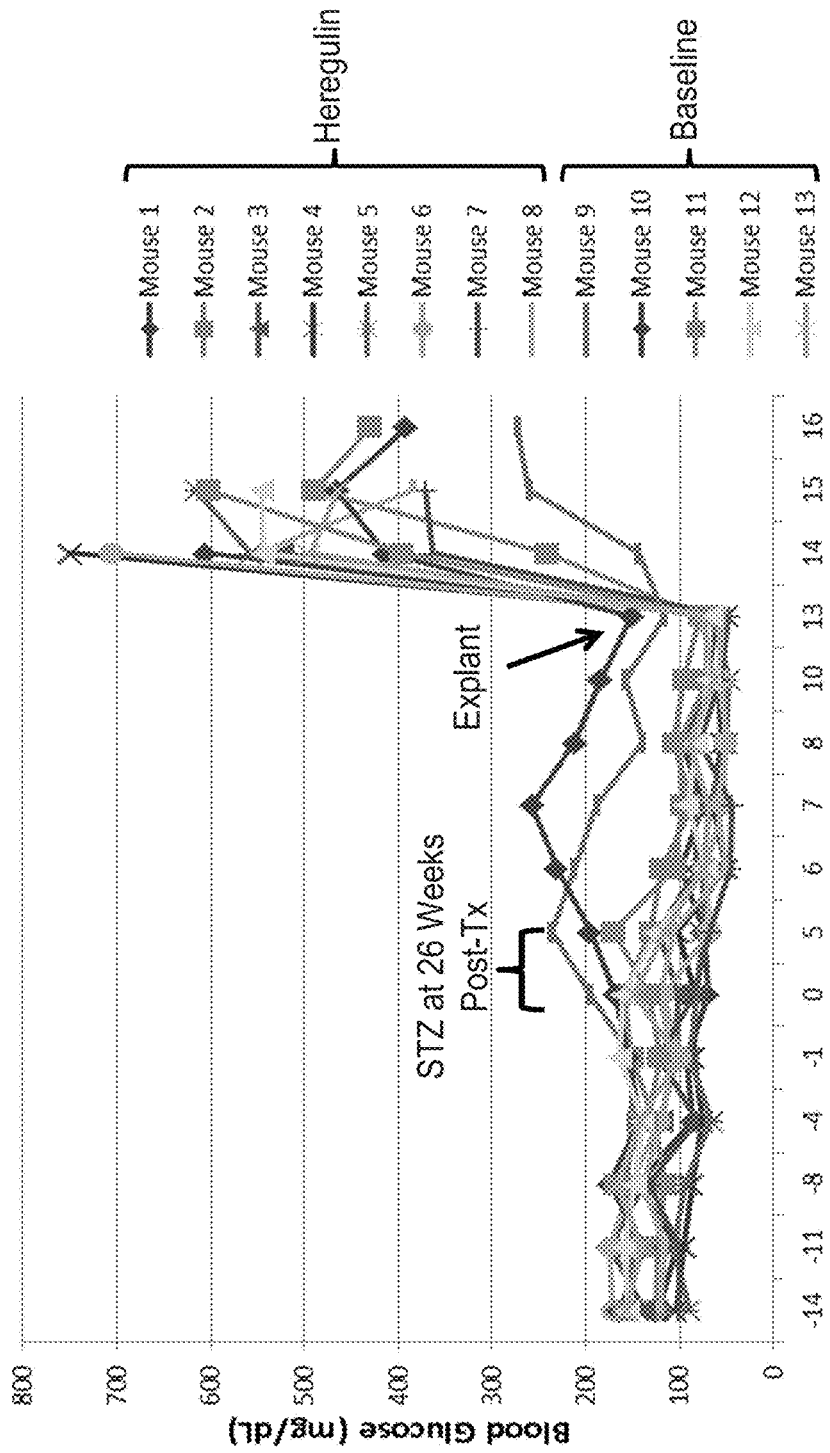
FIGS. 8A-8B are graphs showing the results of blood glucose analyses of STZ-treated mice for Experiment #2347. Glucose-responsive insulin-secreting beta cells derived from implanted iPEC control blood glucose in STZ-induced diabetes model are shown.
Figure 8B:
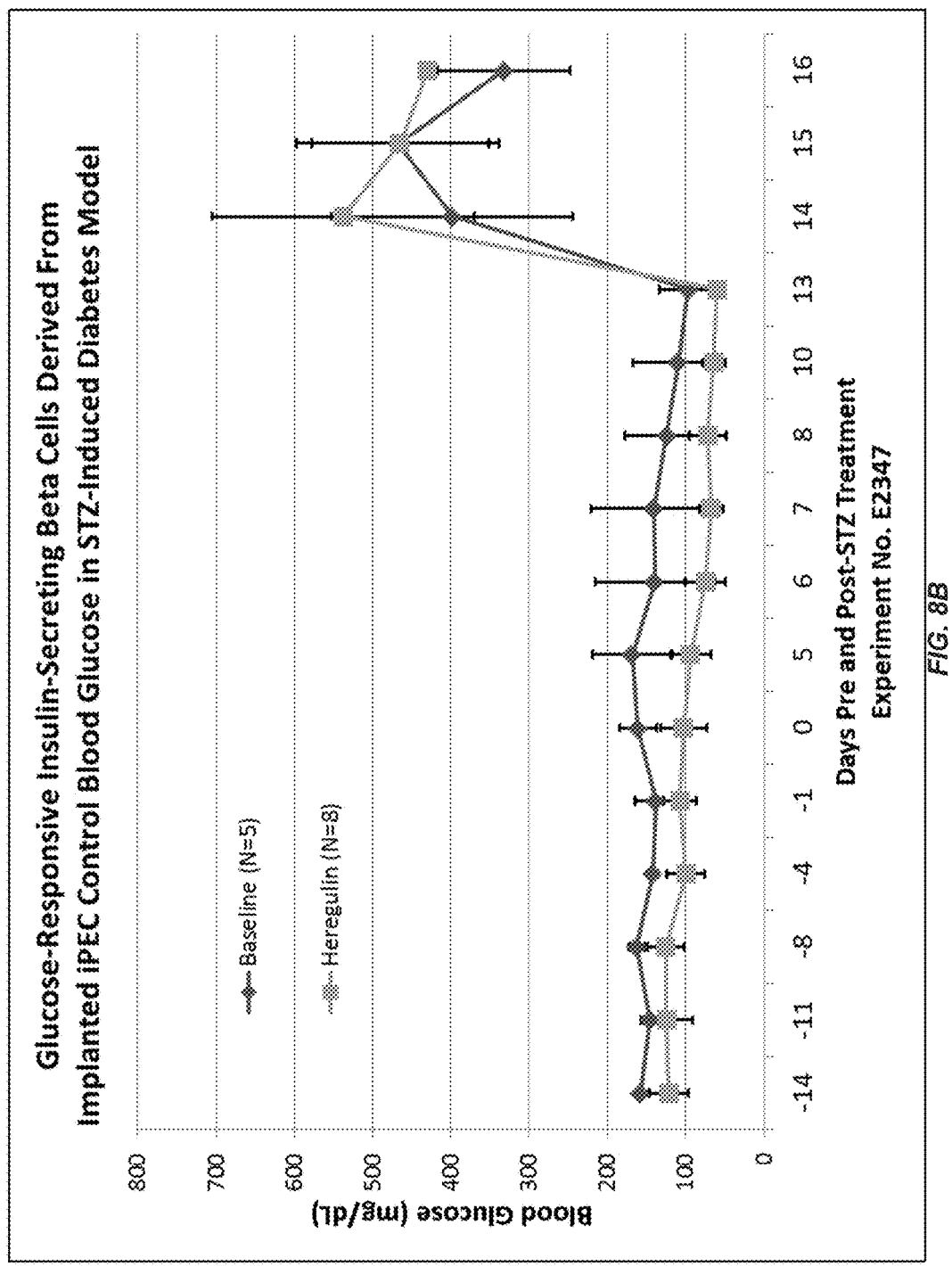
Figure 9A:
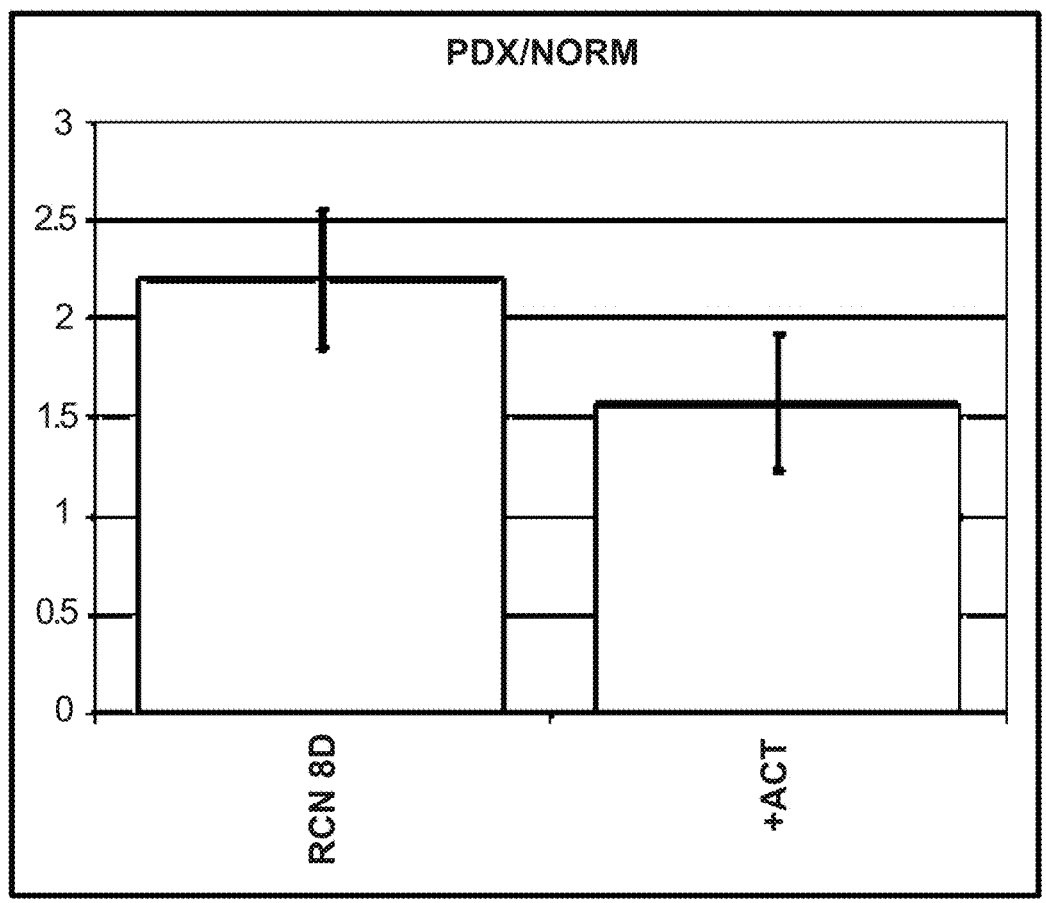
FIGS. 9A-9E are bar graphs showing the relative gene expression levels of PDX1 (FIG. 9A), NKX6.1 (FIG. 9B), PTF1A (FIG. 9C), NKX2.2 (FIG. 9D), and NGN3 (FIG. 9E). See Example 8.
Figure 9B:
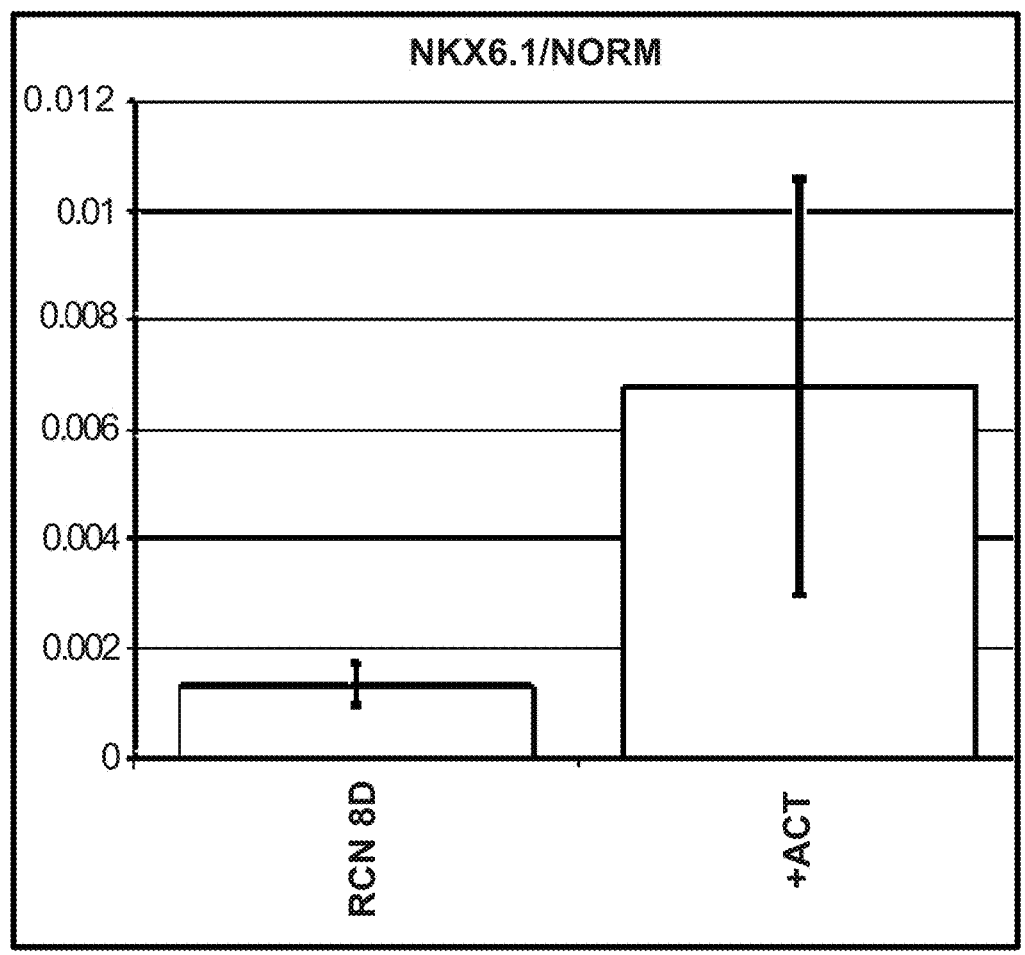
Figure 9C:
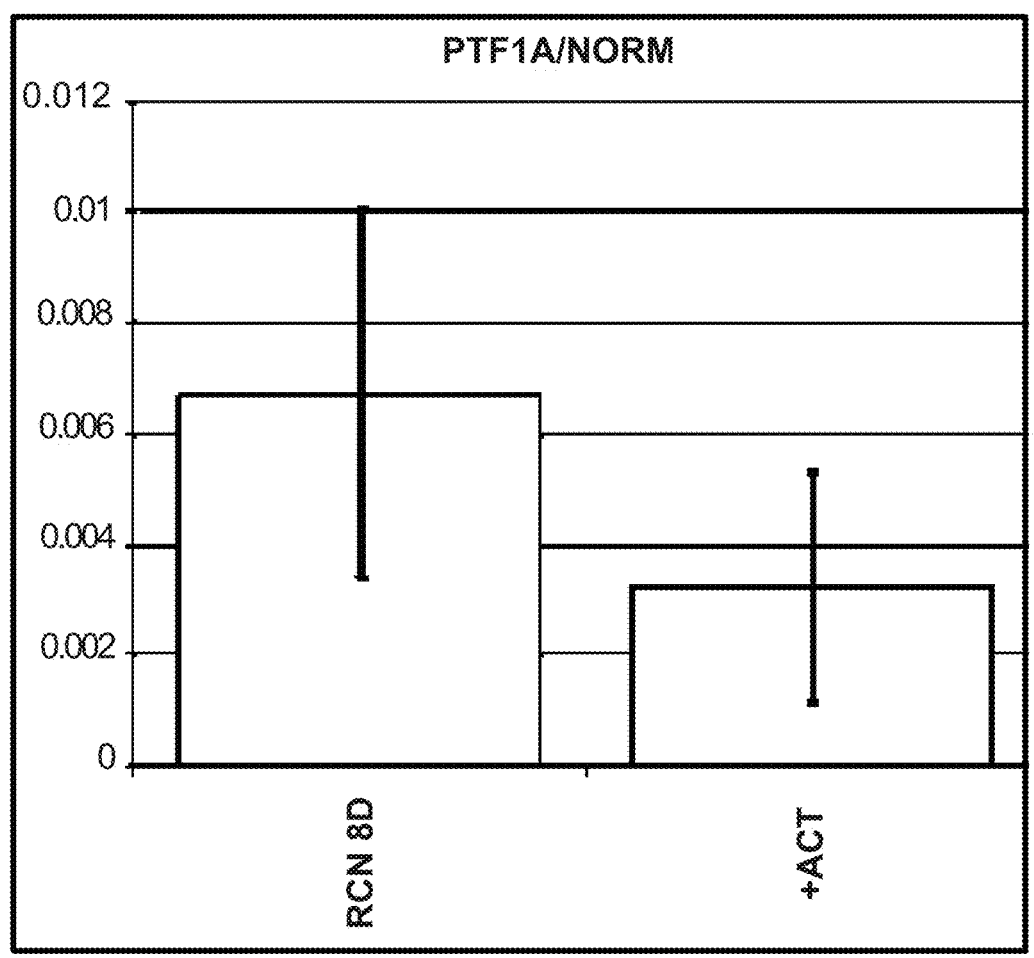
Figure 9D:
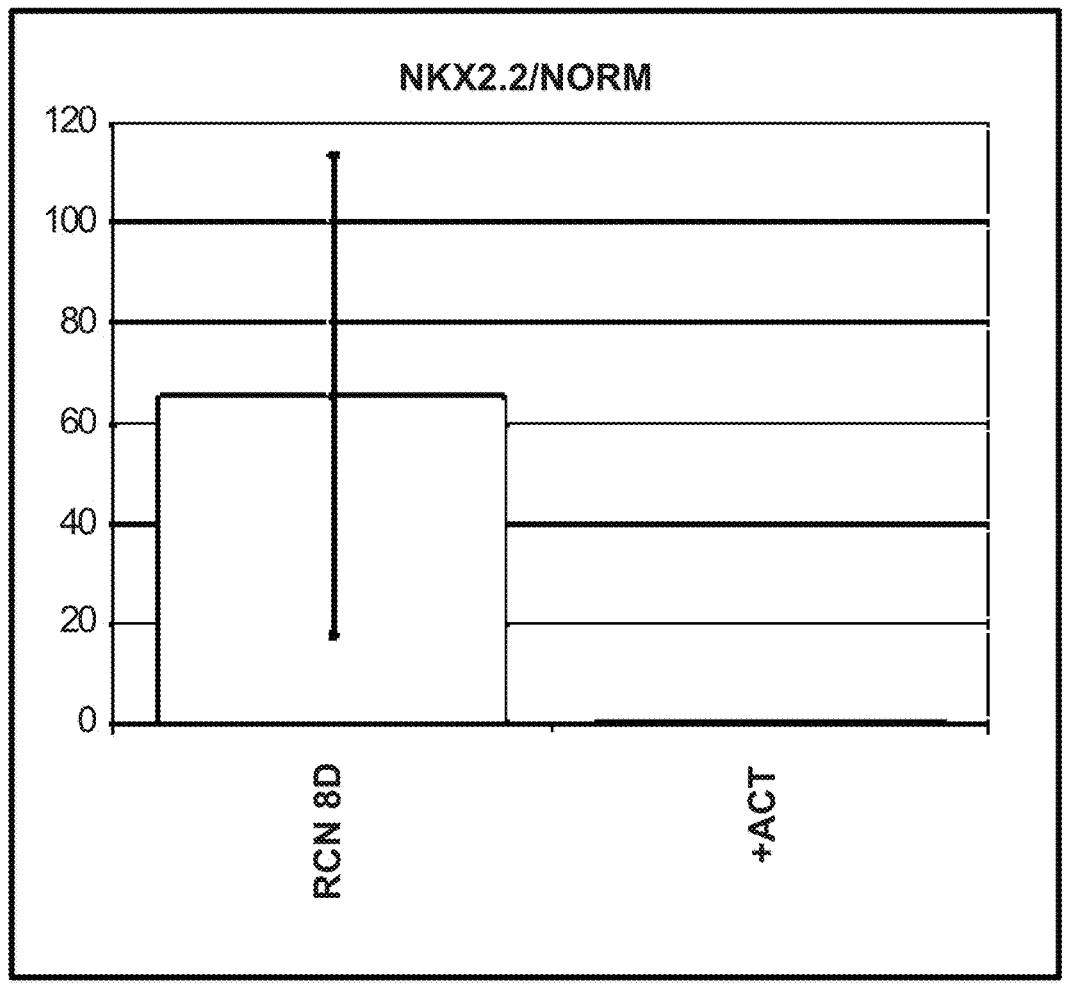
Figure 9E:
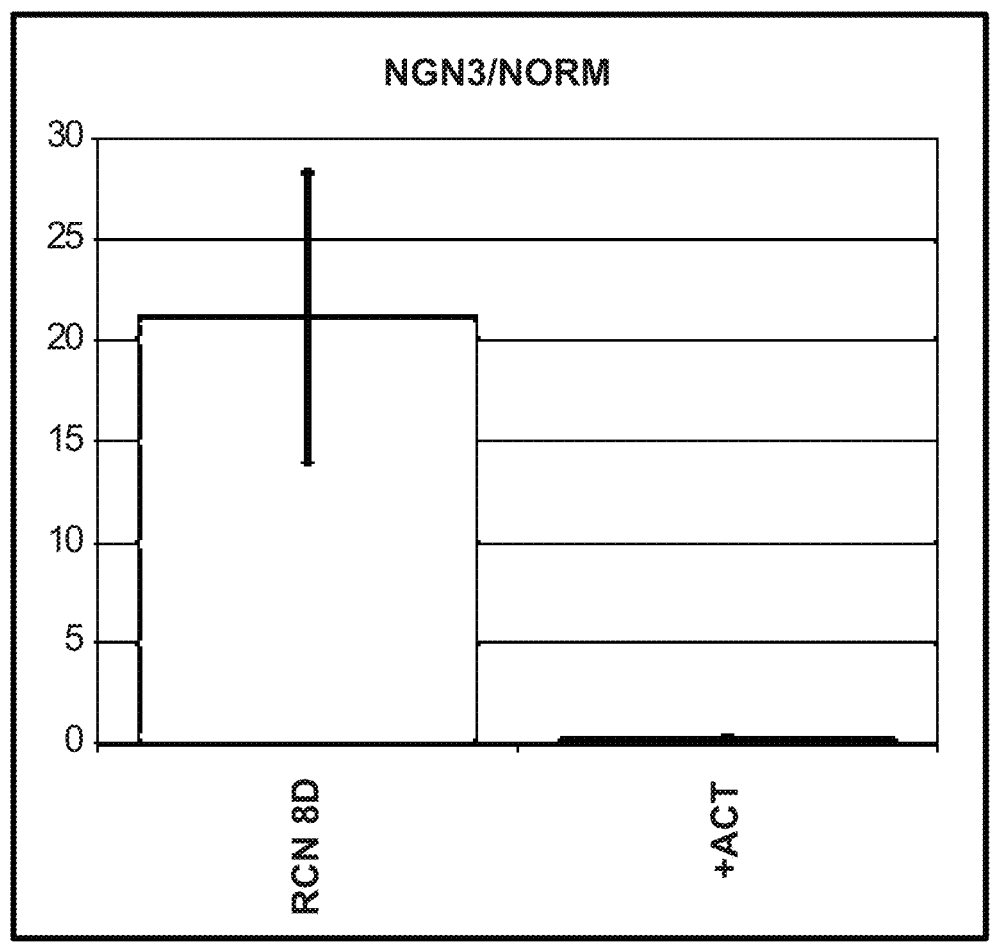

In addition to being tested for glucose-stimulated insulin secretion, the mature iPEC grafts were tested to determine whether they alone were able to maintain euglycemia, similar to euglycemia maintained by PEC derived from hESC, if the host animal's beta cells were destroyed. This involved destroying the beta cells of the implanted mouse using the beta cell toxin, streptozotocin (STZ), which exhibits greater cytotoxicity against murine beta cells as compared to human beta cells. Measurements of random non-fasting blood glucose were taken for each mouse before and after STZ-treatment. Upon explant of the iPEC graft on day 13 post-STZ treatment, hyperglycemia resumed (note the spike in blood glucose), which demonstrates the control of glycaemia by the iPEC graft rather than the endogenous mouse pancreas (see FIG. 8A and FIG. 8B).

In addition there appeared to be a synergistic effect when heregulin and a rho-kinase inhibitor were provided during stages 1-4 of differentiation (see Table 11). For example, iPSC treated with heregulin at stages 3 and 4 without a rho-kinase inhibitor resulted in visibly poor cell mass such that it made implantation impossible. Further support for synergy of heregulin and a rho-kinase inhibitor was evident in some of the experiments, e.g. E2356, E2380, whereby baseline conditions with a rho-kinase inhibitor alone did not function as robustly as a graft with rho-kinase inhibitor and heregulin (see FIGS. 7A and 7B). It appears that treatment with heregulin and a rho-kinase inhibitor were not additive because addition of heregulin alone provided insufficient cell mass for transplant and addition of a rho-kinase inhibitor alone (baseline conditions) had poor in vivo function. As such, the provision of heregulin alone or a rho-kinase inhibitor alone is not substantially similar to the sum effect of the two combined. That is, alone neither results in robust glucose responsiveness in vivo but combined they produce glucose responsiveness similar to that of hES-derived cells. Accordingly, it appeared that the provision of both heregulin and a rho-kinase inhibitor is synergistic since their combined effect is greater than the sum of the effect of each separately. That is, the rho-kinase inhibitor and heregulin treated iPEC matured in vivo exhibiting glucose-stimulated insulin secretion, and were able to maintain euglycemia in a diabetes mouse model (see FIG. 7A-7B and FIG. 8A-8B).

ERBB functionality requires ligand binding, receptor dimerization, and receptor trafficking. Variability in each process may produce differential regulation of the receptors and the downstream signals they control. For example, distinct ERBB ligands bind ERBB receptors with different affinities, thereby altering the patterns and dynamics of ERBB dimer formation. Table 13 shows the many possible different combinations of ligands and receptor binding complexes. Reviews relating to the complexity of this system are provided by Oda, et al. (2005) A comprehensive pathway map of epidermal growth factor receptor signaling, *Mol. Syst. Biol.*, 1 (2005) and Lazzara et al. (2009) Quantitative modeling perspectives on the ERBB system of cell regulatory processes, *Experimental Cell Research* 315(4):717-725.

TABLE 13

ERBB Receptor Tyrosine Kinases and Their Ligands

| Ligands | ErbB-1 | ErbB-2 | ErbB-3 | ErbB-4 |
|---|---|---|---|---|
| EGF | X | | | |
| TGFa | X | | | |
| HB-EGF | X | | | X |
| EPR | X | | | X |
| EPG | X | | | |
| b-Cell | X | | | X |
| AR | X | | | |
| Hrg1 | | | x | X |
| Hrg2 | | | x | X |
| Hrg3 | | | | X |
| Hrg4 | | | | X |

ERBB Receptor Tyrosine Kinases: ErbB1 (also named Her1, or epidermal growth factor receptor, EGFR); ErbB2 (also named human epidermal growth factor receptor, or Her2; or Neu); ErbB3 (also named, Her3), ErbB4 (also named Her4), ERBB Ligands: EGF, epidermal growth factor; TGFα, transforming growth factor α; HB-EGF, heparin-binding EGF-like growth factor; EPR, epiregulin; EPG, Epigen; AR, amphiregulin, Hrg1, heregulin-1 or neuregulin-1; Hrg2, heregulin-2 or neuregulin-2; Hrg3, heregulin-3 or neuregulin-3; Hrg4, heregulin-4 or neuregulin-4; heregulin is used interchangeably with neuregulin.

Huotari et al. suggested that neuregulin-4 may modulate the relative levels of the endocrine cell subpopulations by increasing the number of somatostatin (delta) cells at the expense of glucagon (alpha) cells, and that neuregulin-4 did not affect the ratio of exocrine (e.g., amylase) to endocrine (e.g., ß-insulin, α-glucagon, δ-somatostatin, PP-pancreatic polypeptide) cells. These studies, however, were performed by incubating neuregulin-4 on whole mount organ tissue cultures obtained from day E12.5 mice. These mouse explant cell populations were differentiated further than the stage 3 (e.g. PDX1 negative foregut endoderm) and/or stage 4 (PDX1 positive foregut endoderm) cell populations described herein. Neuregulin-4 only binds to ERBB4 RTK such that only the endocrine sub-population of the whole mount mouse culture can be modulated by neuregulin-4 in this context. Thus, treatment of the stage 3 (PDX1 negative foregut endoderm) and/or stage 4 (PDX1 positive foregut endoderm) cells as described herein with a different ERBB ligand, e.g. Hrg1, would not be expected to modulate the relative endocrine subpopulation as in Huotari because Hrg1 has already been shown to bind to ERBB3 and induce dimerization of ERBB2/3. However, due to the low-level expression of ERBB2 and 3 in PEC as shown in FIG. 6, it was unclear whether stages 3 and 4 type cells would express low or high levels of ERBB2 and 3 to bind to Hrg1.

Further, in a different context, Applicant had described that Hrg1 bound to ERBB 2/3 and promoted self-renewal of pluripotent stem cells (see Wang et al (2007). Although it is possible that Hrg1 may act in the same capacity in the context of stage 3 and 4, Applicant has previously described that most of the cell expansion for production of PEC occurs at the pluripotent stem cell stage (stage 0). During stage 0 the hESC are grown, passaged and expanded for about two (2) weeks. Thus, most of the cell expansion or self-renewal to produce the cell expansion does not occur during stages 1-4. See Schulz et al. (2012) supra. Also, assuming that ERBB2/3 is present during stages 3 and 4, one might expect heregulin to have the same effect as with pluripotent stem cells (self-renewal) as opposed to impacting directed differentiation. The difference in function appears then to depend on the context, that is, pluripotent stem cells versus an endoderm or pancreatic-lineage cell type.

In summary, providing heregulin or heregulin and a rho-kinase inhibitor in vitro to foregut endoderm (stage 3) and PDX1 expressing pancreatic endoderm cells (end of stage 3 and stage 4) produced PEC and iPEC populations, that when transplanted, mature and develop into glucose responsive insulin-secreting cells in vivo (see FIGS. 7 and 8). Such use of heregulin or heregulin and a rho-kinase inhibitor has been reported here for the first time. Such use and effect are not discernible from that previously described in the patent or non-patent literature.

Example 8

Activin Suppresses NGN3 Expression and Production of Cells Committed to the Endocrine Lineage in Pancreatic Endoderm Cell (PEC) Cultures Pancreatic endoderm cells, or "PEC", are a pancreatic population of cells comprised primarily of two distinct sub-populations: (i) a non-endocrine multipotent pancreatic progenitor sub-population (CHGA−) (hereinafter, "non-endocrine (CHGA−)"), which develops and matures to give rise to glucose-responsive insulin-secreting beta cells in vivo; and (ii) a sub-population of cells committed to the endocrine lineage (CHGA+) (hereinafter, "endocrine (CHGA+)"), that may give rise to other non-insulin secreting or islet support cells during in vivo maturation. The non-endocrine (CHGA−) sub-population is CHGA negative and predominantly PDX1 and NKX6.1 positive, whereas the sub-population of cells committed to the endocrine lineage is CHGA positive and mostly PDX1 and NKX6.1 negative. The non-endocrine (CHGA−) sub-population takes about 8 to 12 weeks or more to develop and mature to glucose-responsive insulin-secreting beta cells in quantities permitting systemic detection of insulin (as assayed by ELISA for C-peptide) responses in vivo. It takes, however, less than 8 weeks for glucose-responsive cells to develop and mature in vivo during normal embryonic development. Thus, it remains desirable to obtain (1) a PEC population with an increased non-endocrine (CHGA−) sub-population and/or (2) a true endocrine (CHGA+) cell population that is glucose-responsive in vitro and/or is a developmentally advanced population (e.g. properly specified and having certain signature markers consistent with that described for similar pancreatic populations in vivo) and/or (3) a progenitor cell population that is capable of shortening and/or reducing the time of the development and maturation period in vivo.

With regard to the first goal, it is desirable to obtain a PEC population whereby the non-endocrine (CHGA−) sub-population remains intact while at the same time differentiation to cells committed to the endocrine lineage (CHGA+) is repressed similar to that which occurs naturally in vivo. The Examples below describe methods for production of such a PEC population.

During normal in vivo development, it is believed that Neurogenin-3 (NGN3), a transcription factor, is the master regulator of endocrine cell development and that expression of NGN3 does not arise until after the up-regulation of PDX1 and NKX6.1 e.g. in pancreatic endoderm-lineage cells in vivo. See Rukstalis and Habener (2009), Neurogenin3: A master regulator of pancreatic islet differentiation and regeneration, Islets 1(3): 177-184. According to Table 8, at stage 3, retinoic acid (RA) or the retinoid analog, 4-[(E)-2-(5,6,7,8-Tetrahydro-5,5,8,8-tetramethyl-2-naphthalenyl)-1-propenyl]benzoic acid or "TTNPB" (or "TT3" in Table 8) is used to induce PDX1 expression. However, at the same time retinoic acid also prematurely induces NGN3 expression which initiates endocrine specification. Hence, suppression, repression or inhibition of NGN3 during stage 3 and/or stage 4 may provide one key to minimizing the cells committed to the endocrine lineage (CHGA+) sub-population in PEC and/or obtaining endocrine cells at later stages of development in vitro and/or in vivo. Importantly, any suppressor, repressor or inhibitor of NGN3 must at the same time not suppress, repress or inhibit the non-endocrine (CHGA−) and preferably increases this sub-population during PEC in vitro production.

Figure 10:
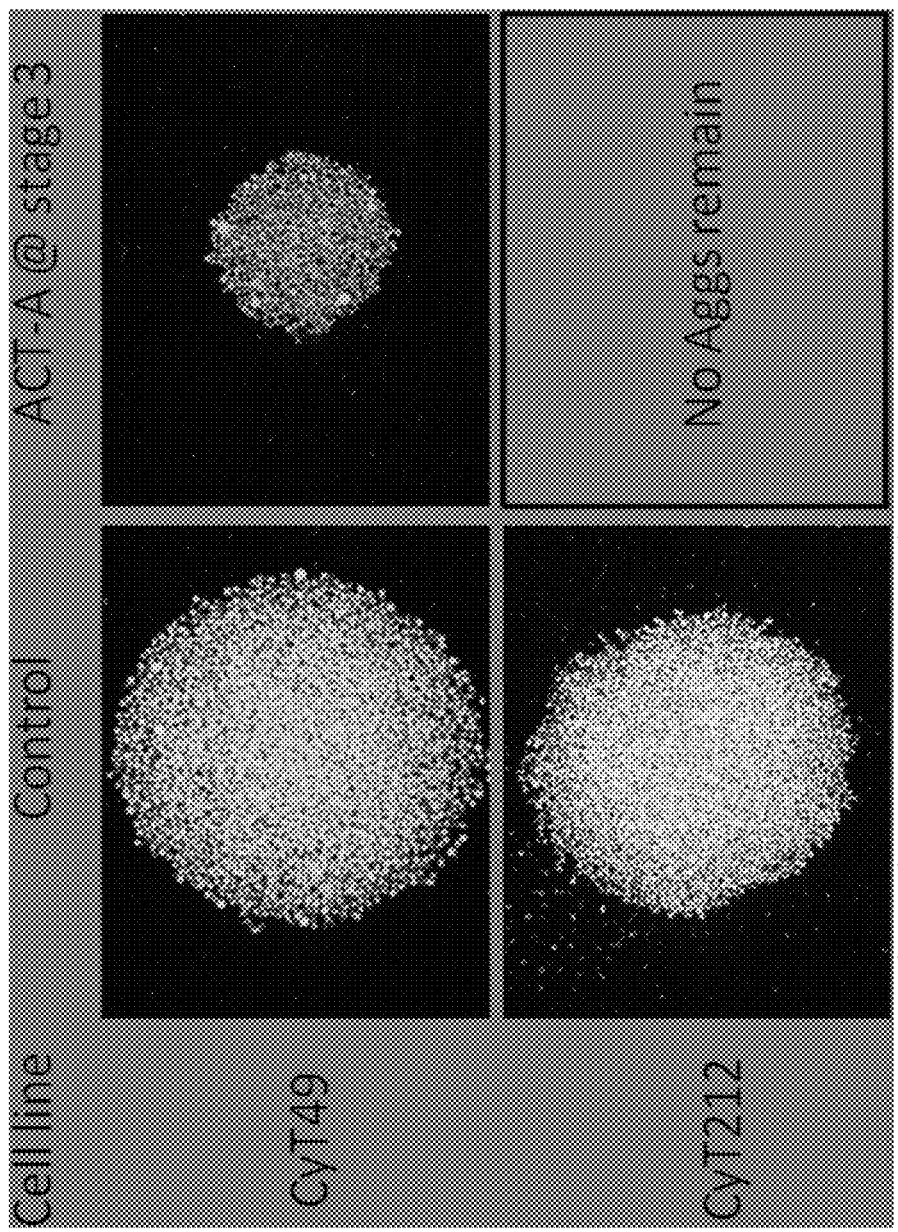
FIG. 10 is a photographic image of an aggregate suspension culture wherein PDX1-negative foregut endoderm cells (stage 2) were differentiated to PDX1-positive foregut endoderm (stage 3) with the addition of 50 ng/mL of Activin A. See Example 8.

Various growth factors were explored for their ability to suppress genes such as NGN3 during stages 3 and 4. One candidate growth factor was Activin which has diverse functions in stem cell expansion and differentiation. For example, at low levels (e.g. 10 ng/mL), Activin helps maintain pluripotent stem cell pluripotency and cell proliferation. At higher levels (e.g. 100 ng/mL) Activin acts as a differentiation growth factor responsible for definitive endoderm production at stage 1 (see e.g., Table 8). To test its effect on repressing cells committed to the endocrine lineage (CHGA+) during PEC formation, Applicant first tested Activin at a mid-level concentration of about 50 ng/mL with standard adherent differentiation. At this level Activin was capable of suppressing NGN3 expression without suppressing PDX1 and NKX6.1 gene expression in PEC (compare FIG. 9D-9E to FIG. 9A-9B). However, when the same level of Activin was used with a more scalable cell aggregate suspension culture during stage 3, the overall cell mass drastically decreased and in some instances cell aggregates were eradicated (compare the control vs. the Activin treated cell aggregates in FIG. 10). Similar decreases in cell aggregates were observed for Activin at 25 ng/mL as with 50 ng/mL (data not shown).

In view of these results, lower concentrations of Activin (e.g. 5 ng/mL and 10 ng/mL) were tested at stages 3 and 4. As shown in FIG. 11, at lower Activin concentrations, cell aggregates were capable of maintaining cell mass and yield as compared to the control (compare FIG. 11B-11C at day 8 and FIG. 11E-11G at day 12 to FIGS. 11A and 11D, control, for d8 and d12, respectively). So, Activin levels less than about 25 ng/mL are acceptable for maintaining cell mass and yield. Applicant then performed flow cytometry analysis on these cell cultures to determine whether Activin at low levels during stages 3 and 4 had any effect on cell aggregate composition; see Table 14. Table 14 shows that low levels of Activin does not decrease production of the non-endocrine (CHGA−) sub-population, and when the treatment is applied at both stages 3 and 4, it can in fact increase this sub-population (see Table 14 A5 Stg3&4 results). However, it appears that differentiation to cells committed to the endocrine lineage (CHGA+) is still being induced significantly given the very similar percentages of endocrine (CHGA+) cells seen with and without Activin (refer Table 13 endocrine column). So, although Activin can suppress or inhibit NGN3 and NKX2.2 expression as observed with QPCR, at lower levels (allowing cell mass to be maintained) it does not reduce the sub-population committed to the endocrine lineage (CHGA+) when analyzed at the end of stage 4. Advantageously, the PDX1 only and Triple Negative sub-populations are reduced as compared to the control, particularly when Activin is used in stages 3 and 4.

TABLE 14

Low Activin Levels Maintain PEC Non-Endocrine Sub-Populations

|  | CHGA+ (Endocrine) | CHGA−/ NKX6.1+/PDX1+ (Non-endocrine) | CHGA−/NKX6.1−/ PDX1+ (PDX ONLY) | CHGA−/NKX6.1−/ PDX1− (Residual or Triple Negative) |
|---|---|---|---|---|
| Control | 55.7 | 29.7 | 8.4 | 5.5 |
| A5 Stg3 | 54.7 | 31.7 | 6.7 | 5.4 |
| A10 Stg3 | 56.2 | 33.7 | 4.6 | 3.9 |
| A5 Stg3&4 | 54.9 | 38 | 4.1 | 2 |

Example 9

Activin, Heregulin and Wnt Suppress Production of Cells Committed to the Endocrine Lineage in PEC Cultures Example 8 showed that moderate levels of Activin (e.g., 50 ng/mL) during stages 3 and 4 were capable of suppressing or repressing NGN3 expression (FIG. 9) but these same levels did not maintain cell mass. Lower levels of Activin (e.g., 5 and 10 ng/mL) were capable of maintaining cell mass (FIG. 11) but were not sufficient to continue repressing endocrine differentiation during stage 4 since the percentage of endocrine lineage cells (CHGA+) remained substantially similar to the control (Table 14, CHGA+ column) and to that described in previous Examples. So, it appears that suppressing differentiation to cells committed to the endocrine lineage (CHGA+) principally during stage 3 at these low levels is not sufficient because continued suppression of differentiation of this sub-population through stage 4 is thought to be necessary still. See Rukstalis et al. (2009) supra. So, additional growth factors were explored that were capable of preventing cell loss and yield (i.e., counter the effect of moderate to high Activin levels) while simultaneously not affecting production of non-endocrine multipotent pancreatic progenitor sub-populations and suppressing differentiation of cells committed to the endocrine lineage (CHGA+).

In view of the above Examples describing Heregulin at 30 ng/mL during stages 3 and 4 often changing the relative levels of endocrine (CHGA+) and non-endocrine (CHGA−) sub-populations of PEC, Applicant's tested what effects reducing the concentrations of Heregulin might have when combined with Activin on PEC production.

Pluripotent stem cells were differentiated using the standard protocol according to Table 8, except during stage 3, Activin was included at 10 ng/mL or 20 ng/mL in combination with Heregulin at 2 ng/mL or 10 ng/mL; and during stage 4, Activin was reduced to 5 ng/mL with Heregulin at 1 ng/mL for two days then at 10 ng/mL thereafter. As shown in FIG. 12 (day 10 images; top panel), Activin at 10 ng/mL and Heregulin at 2 ng/mL showed some cell loss as compared to the control (compare FIGS. 12A and 12B, top panel). Increasing Activin to 20 ng/mL with Heregulin remaining the same at 2 ng/mL exacerbated the cell loss (compare FIGS. 12B and 12C, top panel). But prevention of higher cell loss at higher concentrations of Activin (20 ng/mL) was possible by increasing Heregulin to 10 ng/mL in the context of Activin at 20 ng/mL (compare FIGS. 12D and 12C, top panel). So, when Heregulin levels are too low, significant cell loss is observed, but when Heregulin levels are raised, e.g. at least 20 ng/mL, there is a change in the percentages of the non-endocrine cells (CHGA−) as compared to endocrine lineage (CHGA+) sub-populations.

Figure 13A:
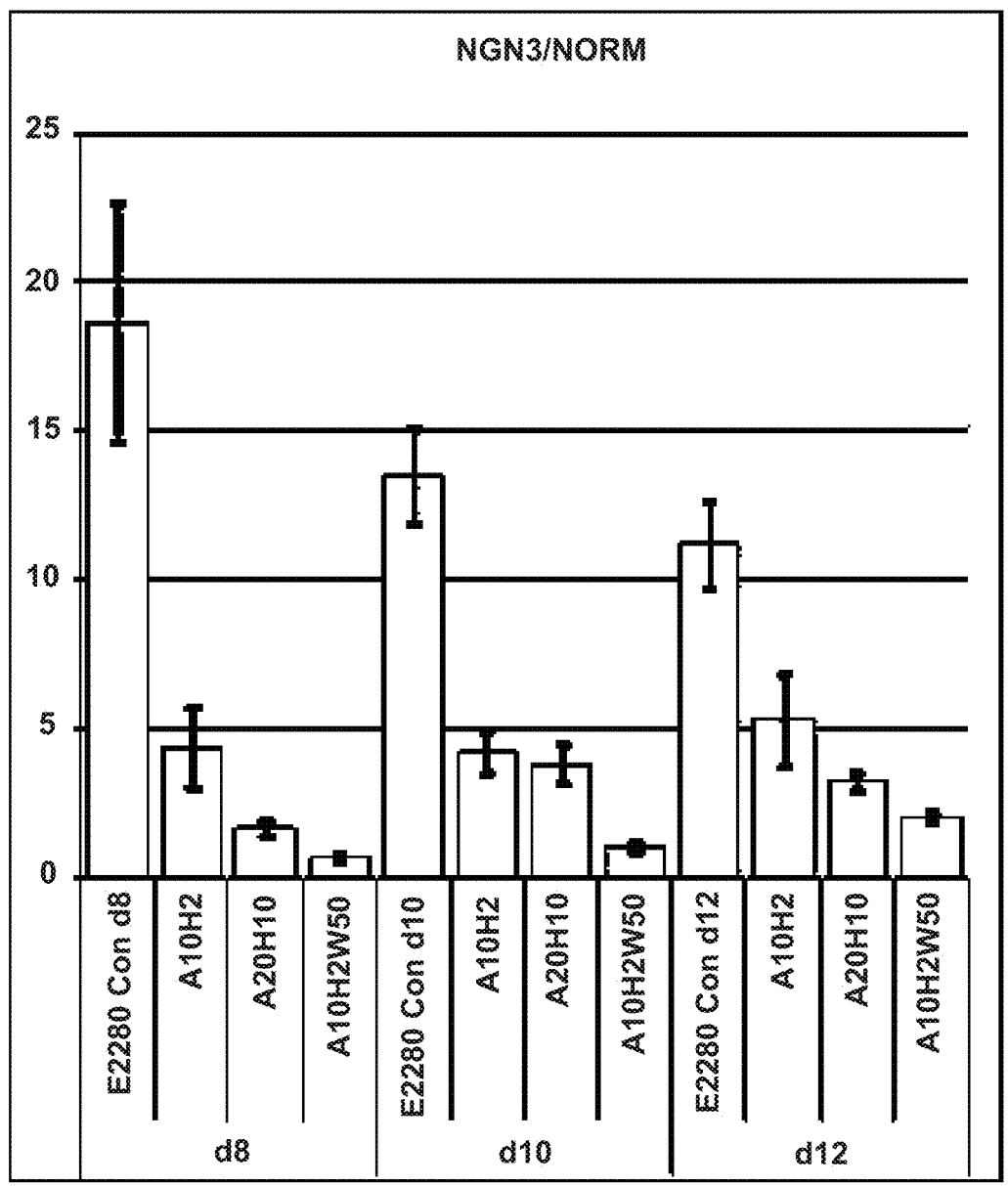
FIGS. 13A-13C are bar graphs showing the relative gene expression levels of NGN3 (FIG. 13A), NKX2.2 (FIG. 13B) and NKX6.1 (FIG. 13C) when Activin, Heregulin and WNT (AHW) are added at stage 3, and Activin and Heregulin (AH) were added at stage 4 as described in Example 9.
Figure 13B:
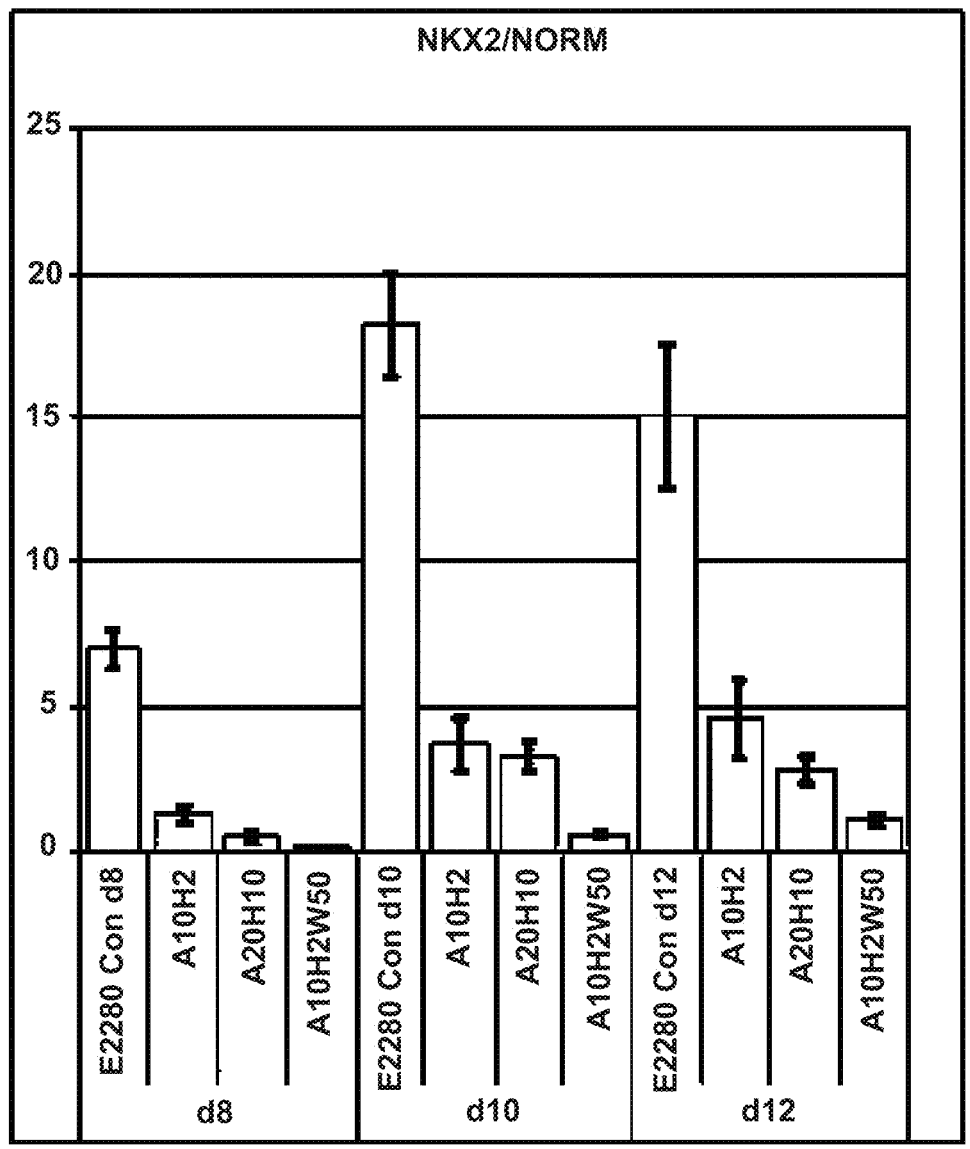

Quantitative PCR analysis was performed to determine the relative levels of gene expression at days 8, 10 and 12 of differentiation with the above combinations of Activin and Heregulin (FIG. 13). Similar to that shown in Example 8 (FIG. 9), Activin at 10 and 20 ng/mL was capable of repressing NGN3 and NKX2.2 (another endocrine differentiation marker) without diminishing NKX6.1 expression (compare FIGS. 13A and 13B to that of 13C). The fact that NKX6.1 expression remains high indicates that production of non-endocrine (CHGA−) sub-population remains unchanged or is not affected. Specifically, however, at 20 ng/mL of Activin and 10 ng/mL of Heregulin, or 10 ng/mL Activin and 2 ng/mL of Heregulin, the Activin-dependent cell loss which was previously observed when Activin was used at 25 ng/mL and 50 ng/mL (FIG. 10) was much reduced (FIGS. 12D & 12E, top panel). Thus, Heregulin appears to effectively counteract the cell loss originally observed by use of Activin at stage 3. And, although some NGN3 and NKX2.2 induction still occurs (i.e. it is not as highly repressed as observed when 50 ng/mL of Activin was used at stages 3 and 4 in adherent-based differentiation in Example 8, FIG. 9), it is significantly reduced as compared to the standard conditions (compare control conditions and A20H10 conditions of FIGS. 13A and 13B).

Although higher than 20 ng/mL of Activin would further repress markers NGN3 and NKX2.2, and therefore repress even more endocrine differentiation, higher levels of Heregulin would then be required to maintain cell mass to off-set the dose effect of Activin at high concentrations. Yet higher levels of Heregulin as observed in the above Examples can change the relative production of endocrine (CHGA+) and non-endocrine (CHGA−) sub-populations of PEC. Still, the effect of higher levels of Activin on repression of NGN3 expression was still desired. So, Applicants explored additional growth factors or morphogens that can effect anterior and posterior endoderm fates, and control other aspects of development including but not limited to WNT, FGF, PDGF, retinoic acid (RA or TTNPB), BMP, hedgehog, EGF, IGF and the like.

Figure 13C:
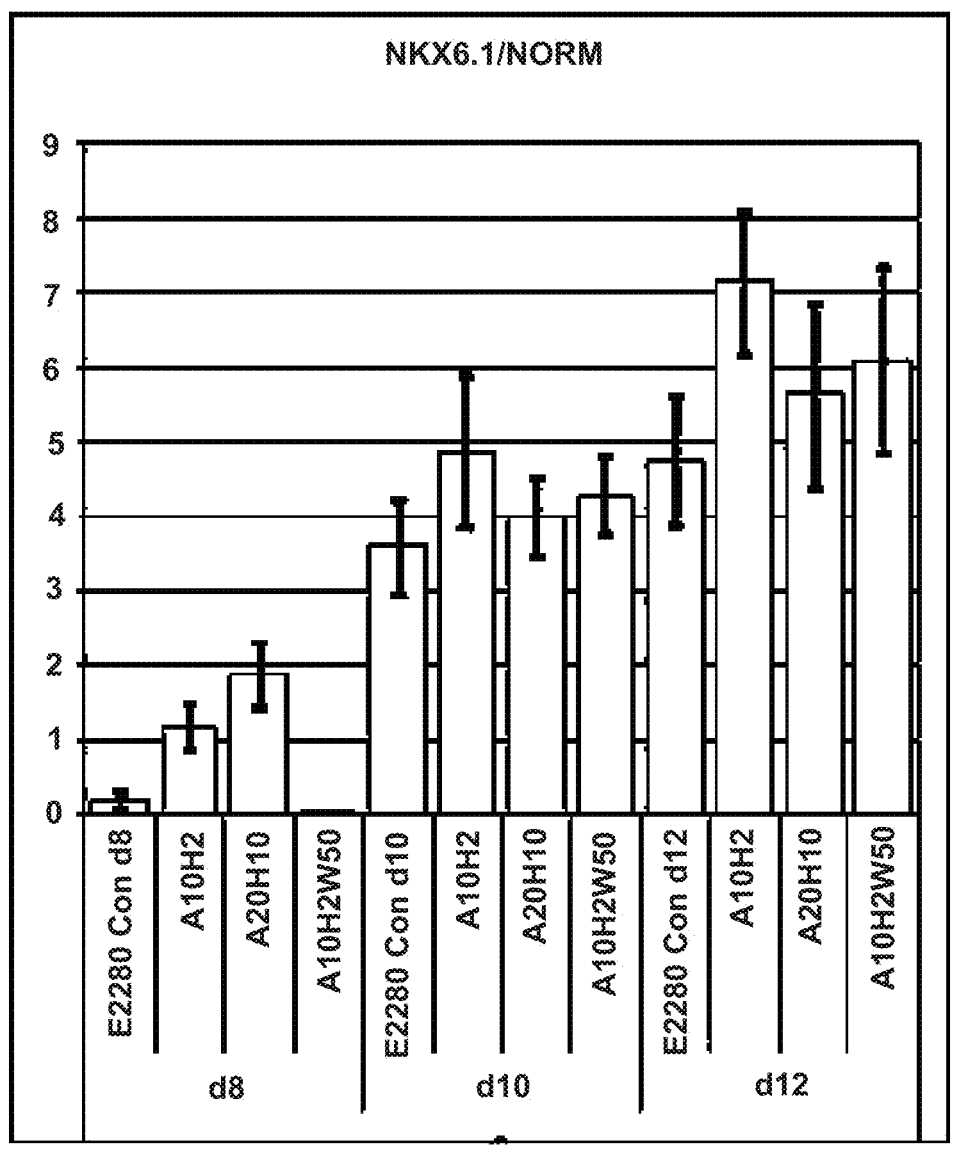

In particular, affecting canonical Wnt signaling pathways was explored by adding Wnt3A into the Activin and Heregulin differentiation media at stages 3 and/or 4. Again, any combination needs to suppress differentiation of cells committed to the endocrine lineage (CHGA+) as observed through repression of NGN3 and NKX2.2 expression and maintain good cell mass (i.e. limited cell mass loss), while at the same time not affecting the non-endocrine multipotent pancreatic progenitor sub-population. One such mixture tested was 50 ng/mL of Wnt along with 10 ng/mL of Activin and 2 ng/mL of Heregulin at stage 3; and as above, during stage 4, Activin at 5 ng/mL with Heregulin at 1 ng/mL for two (2) days then Activin at 5 ng/mL and Heregulin at 10 ng/mL thereafter. This resulted in greater cell (PEC) mass than Activin and Heregulin at the same concentrations alone (compare FIGS. 12D and 12E, top panel), and even greater cell mass than the control (compare FIGS. 12A and 12E, top panel). QPCR analysis of cell aggregates under these conditions (e.g., combination of Activin, Heregulin and Wnt at stage 3 and Activin and Heregulin at stage 4) showed that there was significant suppression of cells committed to the endocrine lineage (CHGA+) differentiation as observed by decreased NGN3 and NKX2.2 expression at stages 3 and 4, in particular days 8, 10 and 12 (FIGS. 13A and 13B). Yet, NKX6.1 expression while initially repressed at day 8, was significantly elevated by days 10 and 12 (stage 4) (FIG. 13C). Therefore, development of the non-endocrine (CHGA−) sub-population was not impaired with the addition of Wnt, and differentiation of cells committed to the endocrine lineage (CHGA+) appeared to be delayed or suppressed, and there was no apparent cell mass loss.

To determine the cell composition of the PEC population with the combination of Activin, Heregulin and Wnt during stage 3, flow cytometry was performed after stage 4 and the PEC cellular composition is shown in Table 14. As shown, the combined growth factors (Activin, Heregulin and Wnt, or "AHW") effectively reduced differentiation of cells committed to the endocrine lineage (CHGA+) as observed by the decreased percentage of this sub-population (15.6 vs. 58.8) while increasing the non-endocrine (CHGA−) sub-population (58.1 vs. 23.4) as compared to the control cell cultures under the standard protocol (Table 8). Data from flow cytometry supports and is consistent with data from QPCR that the combination of the three factors (AHW) in general delayed or suppressed differentiation of cells committed to the endocrine lineage (CHGA+) in PEC without affecting the production of the non-endocrine (CHGA−) sub-population. The delayed expression of these genes in vitro is consistent with their on-set (or delay) in in vivo mammalian pancreatic development, whereby NGN3 expression in endocrine differentiation occurs after the on-set of PDX1 and NKX6.1 expression in the non-endocrine (CHGA−) sub-population. Additionally, there was no compromise in the PEC mass and yield.

TABLE 15

Activin, Heregulin and Wnt (AHW) At Stage 3 Decreases Endocrine Sub-Populations And Increases Non-Endocrine (CHGA−) Sub-Populations

|  | CHGA+ (Endocrine) | CHGA−/ NKX6.1+/PDX1+/ (Non-endocrine) | CHGA−/ NKX6.1−/ PDX1+ (PDX ONLY) | CHGA−/ NKX6.1−/ PDX1− (Residual or Triple Negative) |
|---|---|---|---|---|
| Control | 58.8 | 23.4 | 14.5 | 2.76 |
| AHW | 15.6 | 58.1 | 16.1 | 7.28 |

In view of the results using the combination of Activin, Heregulin and Wnt, Activin levels were again titrated at stage 3 to establish a range of concentrations that Activin can be used. Tested Activin concentrations ranged from about 0, 25, 50, 75 and 100 ng/mL with Wnt at 50 ng/mL and Heregulin at 5 ng/mL during stage 3. Activin was reduced to 5 ng/mL, Heregulin to 5 ng/mL and Wnt was not included during stage 4. Cells were imaged at the end of stage 4 (day 13) and shown in FIG. 12 (bottom panel). Cell loss was again apparent at higher Activin concentrations, e.g. between 75 and 100 ng/mL (FIGS. 12I & 12J, bottom panel). Importantly, inclusion of WNT at stage 3 allowed use of a much higher concentration of Activin at stage 3, than would otherwise be possible due to cell loss.

To test the effect of continued Activin and Heregulin during stage 4, in the context of Activin, Heregulin and Wnt at stage 3, human ESC were differentiated using three conditions: (i) standard protocol (see Table 8; or Protocol No. 1 in Table 17); (ii) combination of Activin (75 ng/mL), Heregulin (5 ng/mL) and Wnt (50 ng/mL) at stage 3, followed by the standard stage 4 factors; and (iii) combination of Activin (75 ng/mL), Heregulin (5 ng/mL) and Wnt (50 ng/mL) at stage 3, followed by additional Activin (5 ng/mL) and Heregulin (5 ng/mL) during stage 4, see Table 17. Flow cytometry was performed after stage 4 for all three conditions and the PEC cellular composition is shown in Table 17. AHW at stage 3 decreases cells committed to the endocrine lineage and increases non-endocrine (CHGA−) sub-population content as compared to the control (21.8 vs. 42.2 for cells committed to the endocrine lineage sub-population; and 40.1 vs. 27.6 for non-endocrine (CHGA−) sub-population), and the additional treatment with AH at stage 4 further decreases cells committed to the endocrine lineage and further increases non-endocrine (CHGA−) sub-population content (6.46 vs. 21.8 for cells committed to the endocrine lineage; and 72.7 vs. 40.1 for non-endocrine (CHGA−) genitor sub-population).

TABLE 16

Activin, Heregulin and Wnt at Stages 3 And 4 Decreases Endocrine Sub-Populations and Increases Non-Endocrine (CHGA−) Sub-Populations

|  | CHGA+ (Endocrine) | CHGA−/ PDX1+/ NKX6.1+ (Non-endocrine) | CHGA−/ NKX6.1−/ PDX1+ (PDX ONLY) | CHGA−/ NKX6.1−/ PDX1− (Residual or Triple Negative) |
|---|---|---|---|---|
| Control | 42.2 | 27.6 | 27.1 | 2.98 |
| AHW 5tg3 | 21.8 | 40.1 | 33.7 | 2.88 |
| AHW 5tg3; AH Stg4 | 6.46 | 72.7 | 8.38 | 5.73 |

Example 10

PEC Grafts Produced Using the Activin, Heregulin and Wnt Combination have Improved Glucose Responsive Function In Vivo Example 9 showed that based on morphology (e.g. low-power microscopy images of differentiated cell aggregates), QPCR and flow cytometry data, it appears that the combination of Activin, Heregulin and Wnt ("AHW") can effectively repress cells committed to the endocrine lineage (CHGA+) differentiation as observed by the repression of NGN3 and NKX2.2 expression, maintain or increase non-endocrine (CHGA−) sub-populations while at the same time have no deleterious effect on, or improving, cell mass or yield. To determine whether these changes have an effect on the ultimate development and maturation of glucose-responsive, insulin-secreting cells, the AHW-derived PEC aggregates were implanted into animals, in conjunction with PEC made from the standard protocol according to Table 8 or Protocol No. 1 of Table 17.

Figures 14A, 14B:
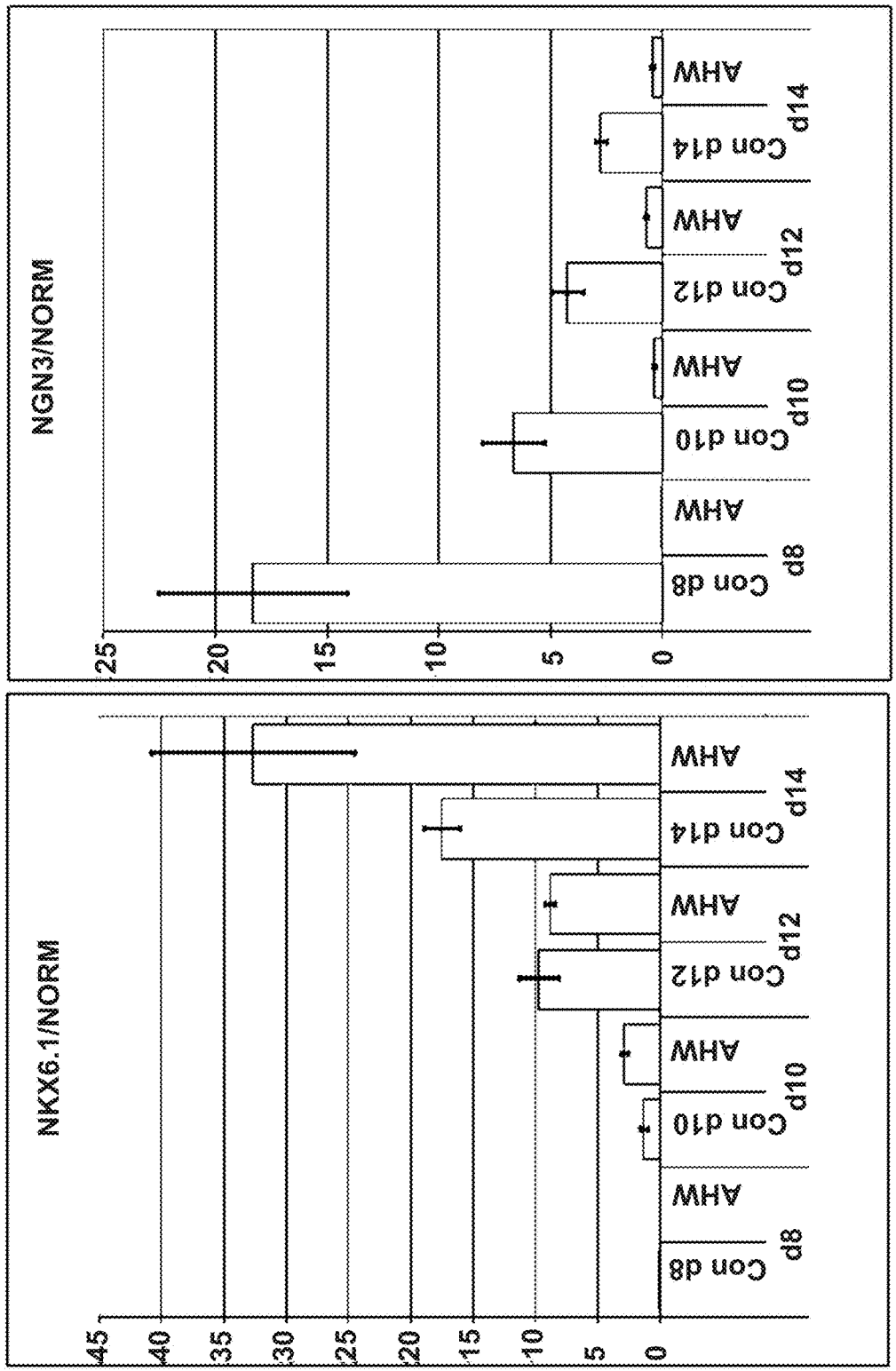
FIGS. 14A-14B are bar graphs showing the relative gene expression levels of NKX6.1 (FIG. 14A) and NGN3 (FIG. 14B) when Activin, Heregulin and WNT (AHW) are added at stage 3, and Activin and Heregulin (AH) were added at stage 4 as described in Example 10.

Specifically, human pluripotent stem cells were differentiated using the combination of the three factors (AHW) at stage 3 and then Activin and Heregulin alone at stage 4. Control PEC was made substantially as according to Table 8. Cell aggregates were analyzed by QPCR at days 8, 10, 12 and 14 as shown in FIG. 14. Both the control and modified AHW protocols produced PEC as observed by NKX6.1 expression (FIG. 14A), although there is more robust NKX6.1 expression using AHW at day 14 (after stage 4). At the same time, differentiation of cells committed to the endocrine lineage (CHGA+) was highly suppressed with the AHW protocol as observed by repression of NGN3 expression, especially at day 8 as compared to the control protocol (FIG. 14B).

Figure 15:
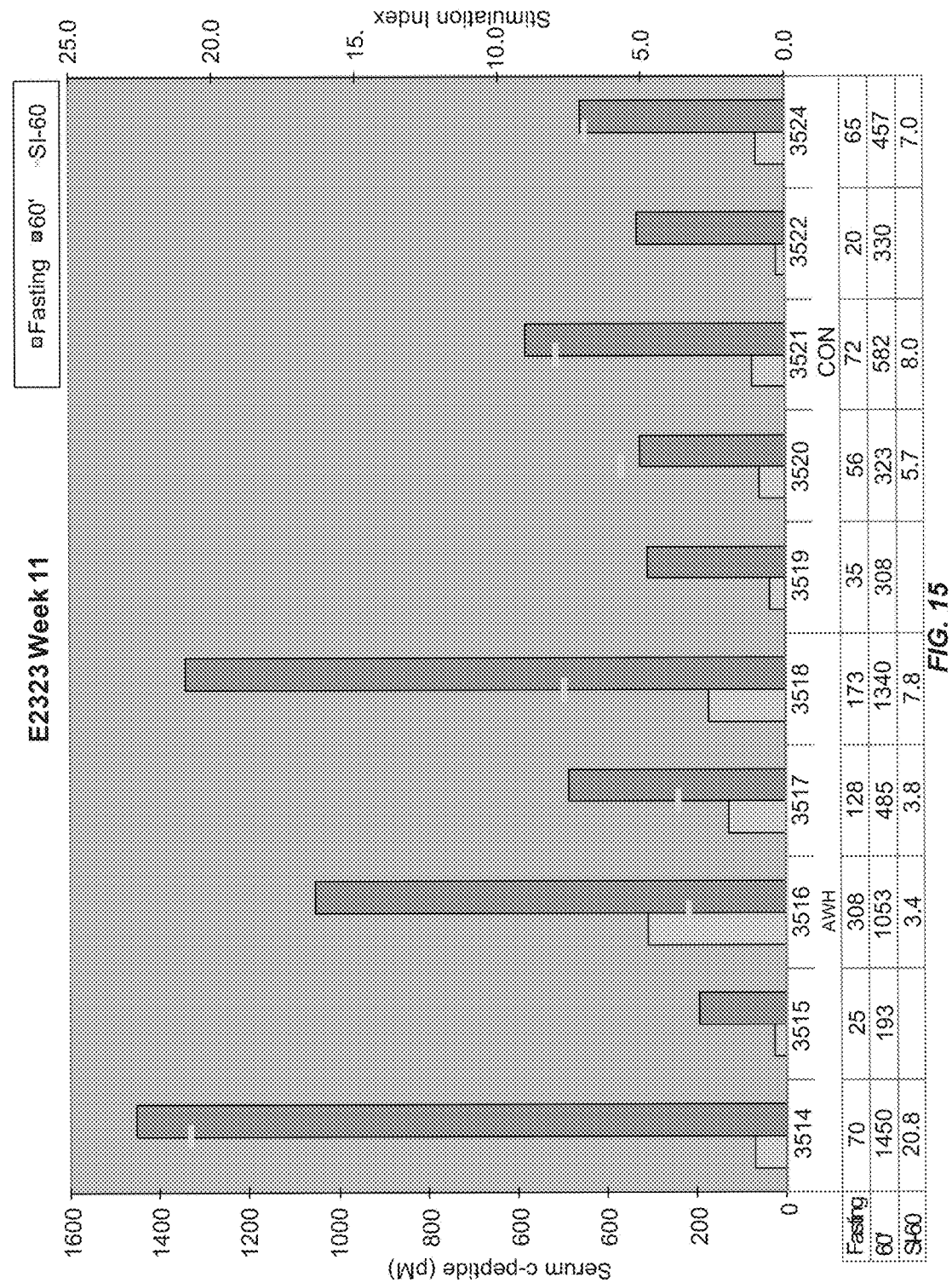
FIG. 15 is a graph showing the concentrations of human C-peptide in sera of mice implanted with encapsulated PEC (control) and encapsulated modified PEC (produced using Activin, Heregulin and WNT (AHW) at stage 3, and Activin and Heregulin (AH) at stage 4). Expression levels were analyzed 11 weeks post-engraftment at fasting, 30 min, and 60 min after intraperitoneal glucose administration. See Example 10.

PEC Aggregates from both methods were loaded in Applicant's proprietary implantable semi-permeable encapsulation devices at day 14 of differentiation and implanted into SCID-beige mice substantially as previously described (n=5 animals for each of AHW and control methods, n=10 total). At 11 weeks post-implant, the PEC produced using the AHW protocol averaged about 900 pM of C-peptide after one hour (60') following glucose challenge, while the control PEC averaged about 400 pM of C-peptide. See FIG. 15 comparing the AHW animals to that of the control. Specifically, at 11 weeks post-implant, 3 of the 5 mice with the AHW implants averaged over 1200 pM human C-peptide (FIG. 15, animal nos. 3514, 3516, and 3518), while the control animals' levels of C-peptide were significantly lower. Indeed, only 1 of the 5 control animals had levels close to 600 pM (FIG. 15, animal no. 3524). Thus, based on the C-peptide levels, at 11 weeks post-implant, the AHW protocol was able to produce a PEC population with at least a two-fold improvement in function in vivo, as measured by the level of human C-peptide following glucose stimulation. This potentially correlates to a faster maturation time.

Figure 16:
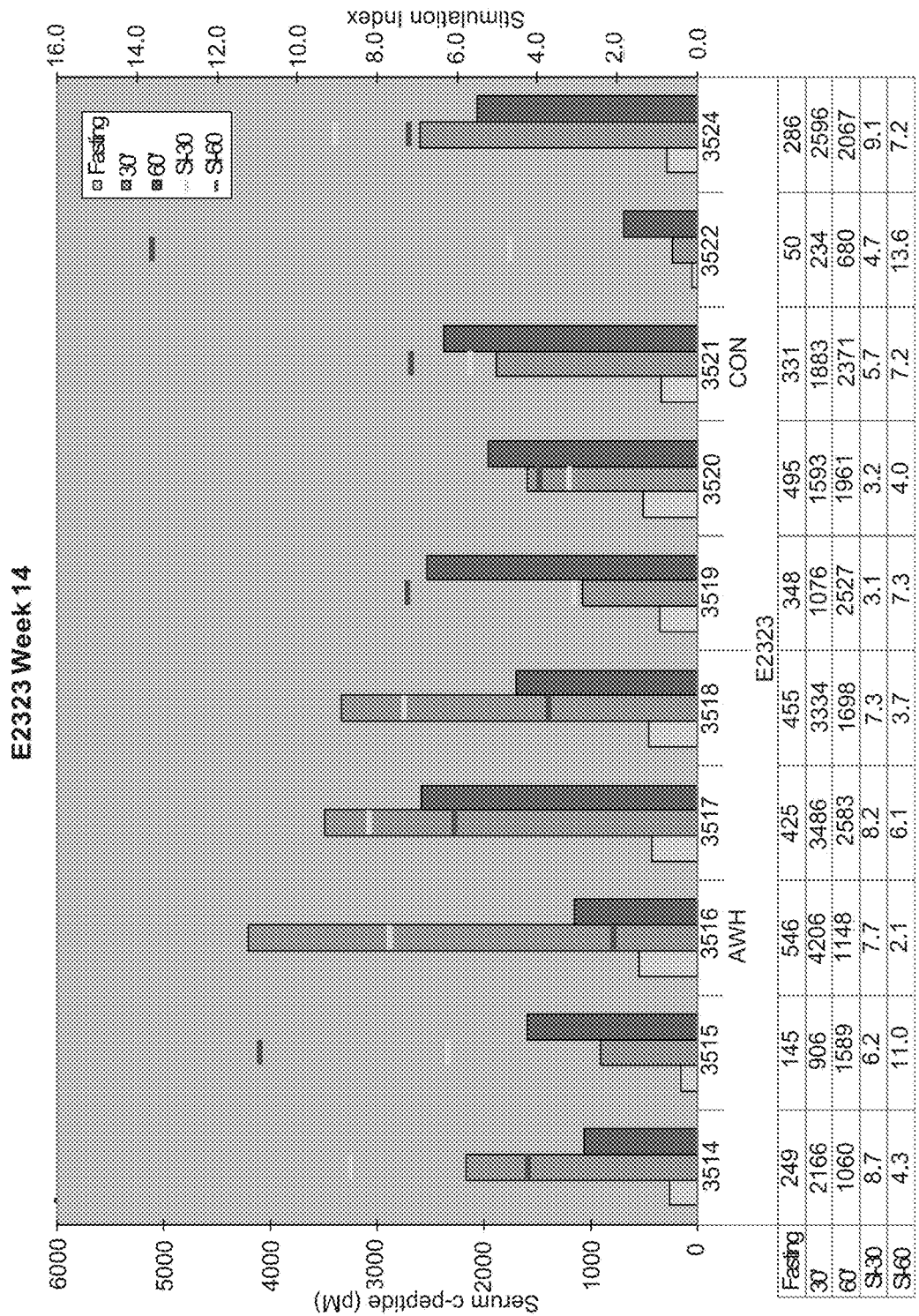
FIG. 16 is a graph showing the concentrations of human C-peptide in sera of mice implanted with encapsulated PEC (control) and encapsulated modified PEC (produced using Activin, Heregulin and WNT (AHW) at stage 3, and Activin and Heregulin (AH) were added at stage 4). Expression levels were analyzed 14 weeks post-engraftment at fasting, 30 min, and 60 min after intraperitoneal glucose administration. See Example 10.

At 14 weeks post implant, the AHW PEC implants continued to outperform the control graft implants, and with a faster insulin secretion response time because the C-peptide values 30 minutes post glucose challenge for AHW PEC implants were higher than the values 60 minutes post-challenge for control graft implants (FIG. 16). Specifically, 3 of the 4 animals with AHW PEC implants averaged over 3500 pM C-peptide 30 minutes after a glucose challenge, as compared to the top 3 control animals that averaged about 2300 pM but after 60 minutes post glucose challenge (FIG. 16). This data demonstrates that differentiation using the combination of the three growth factors (AHW) is capable of producing a PEC population that performs better (i.e. increased serum C-peptide levels 30 minutes post-glucose challenge which indicates faster glucose responsiveness from the implanted AHW-derived PEC grafts) or is potentially more potent than the standard PEC protocol at the time points studied. Without limiting this application to any one theory, it is believed that the increased potency in the AHW PEC implants is attributed to the fact that the combination of AHW (1) delayed or repressed differentiation of cells committed to the endocrine lineage (CHGA+) in PEC, (2) increased the non-endocrine multipotent pancreatic progenitor sub-population in PEC and (3) maintained good cell mass.

Example 11

Pancreatic Endocrine Cell Cultures In Vitro

Examples 9 and 10 describe deliberate delay, repression, suppression or inhibition of differentiation of cells committed to the endocrine lineage (CHGA+) at stages 3 and 4. In an effort to produce a developmentally advanced endocrine cell precursor or endocrine cell in vitro, Applicants tested various methods during stages 5, 6 and/or 7. For example, Applicant tested which growth factors, alone or in combination, were capable of stimulating or inducing endocrine differentiation, i.e. induce NGN3 expression.

Table 17 below summarizes various methods for endocrine production alongside the standard protocol to produce PEC (Protocol No. 1) and the protocol used to produce AHW PEC (Protocol No. 2). Table 17, Protocol No. 3, indicates a number of growth factors at specific days and stages, however, Applicants have tested and one of skill in the art will appreciate, that not all growth factors, alone or in combination, have to be used on the precise day/stage indicated. Hence, Table 17 represents the many iterations (e.g. growth factors, duration and the like) tested by Applicants.

TABLE 17

Methods for Producing PEC and Endocrine Cells In Vitro

| Days | Stage | Protocol #1: Standard PEC Production | Protocol #2: Production of PEC with Higher Non-Endocrine Sub-Populations | Days | Protocol #3: Production of Endocrine Cell Population (Composite) |
|---|---|---|---|---|---|
| −1 |   | XF HA; SP | XF HA; SP | −1 | XF HA; SP |
| 0 | 1 | r0.2FBS-ITS1:5000 A100 W50 | r0.2FBS-ITS1:5000 A100 W50 | 0 | r0.2FBS-ITS1:5000 A100 W50 |
| 1 |   | r0.2FBS-ITS1:5000 A100 | r0.2FBS-ITS1:5000 A100 | 1 | r0.2FBS-ITS1:5000 A100 |
| 2 | 2 | r0.2FBS-ITS1:1000 K25 IV | r0.2FBS-ITS1:1000 K25 IV | 2 | r0.2FBS-ITS1:1000 K25 IV |
| 3 |   | r0.2FBS-ITS1:1000 K25 | r0.2FBS-ITS1:1000 K25 | 3 | r0.2FBS-ITS1:1000 K25 |
| 4 |   | r0.2FBS-ITS1:1000 K25 | r0.2FBS-ITS1:1000 K25 | 4 | r0.2FBS-ITS1:1000 K25 |
| 5 | 3 | db-CTT3 N50 | db-CTT3 N50 A50 H5 W50 | 5 | db-CTT3 N50 A50 H5 W50 |
| 6 |   | db-CTT3 N50 | db-CTT3 N50 A50 H5 W50 | 6 | db-CTT3 N50 A50 H5 W50 |
| 7 |   | db-CTT3 N50 | db-CTT3 N50 A50 H5 W50 |   |   |
| 8 | 4 | db-N50 K50 E50 | db-N50 K50 E50 A5 H5 | 7 | db-N50 K50 E50 A5 H5 |
| 9 |   | db-N50 K50 E50 | db-N50 K50 E50 A5 H5 | 8 | db-N50 K50 E50 A5 H5 |
| 10 |   | db-N50 K50 E50 | db-N50 K50 E50 A5 H5 | 9 | db-N50 K50 E50 A5 H5 |
| 11 |   | db-N50 K50 E50 | db-N50 K50 E50 A5 H5 | 10 | db-N50 K50 E50 A5 H5 |
| 12 |   | db-N50 K50 E50 | db-N50 K50 E50 | 11 | db-N50 K50 E50 |
| 13 |   | db-N50 K50 E50 (optional) | db-N50 K50 E50 | 12 | db-N50 K50 E50 |
| 14 | 5 | Transplanted | Transplanted | 13 | db-N50 K50 E50 R0I NC10 |
| 14 |   |   |   | 14 | db-N50 K50 E50 R0I NC10 |
| 15 | 6 |   |   | 15 | db-Y10 MG0.05 SHH100 NC10 IGF50 BMP10 |
| 16 |   |   |   | 16 | db-Y10 MG0.05 SHH100 NC10 IGF50 BMP10 |
| 17 |   |   |   | 17 | db-Y10 MG0.05 SHH100 NC10 IGF50 BMP10 |

TABLE 17-continued

Methods for Producing PEC and Endocrine Cells In Vitro

| Days | Stage | Protocol #1: Standard PEC Production | Protocol #2: Production of PEC with Higher Non-Endocrine Sub-Populations | Days | Protocol #3: Production of Endocrine Cell Population (Composite) |
|---|---|---|---|---|---|
| 18 | | | | 18 | db-Y10 MG0.05 SHH100 NC10 IGF50 BMP10 |
| 19 | | | | 19 | db-Y10 MG0.05 SHH100 NC10 IGF50 BMP10 |
| 20 | 7 | | | 20 | db- MG0.05 SHH100 NCI?+0 IGF50 BMP10 |
| 21 | | | | 21 | db-FBS BMP10 TTNPB1 IGF50 |
| 22 | | | | 22 | db-Y10 MG0.05 BMP10 TTNPB1 IGF50 |
| 23 | | | | 23 | db-Y10 MG0.05 BMP10 TTNPB1 IGF50 |
| 24 | | | | 24 | db-Y10 MG0.05 BMP10 TTNPB1 IGF50 |
| 25 | | | | 25 | db-Y10 MG0.05 BMP10 TTNPB1 IGF250 |
| 26 | | | | 26 | db-Y10 MG0.05 BMP10 TTNPB1 IGF250 |
| 27 | | | | 27 | db-Y10 MG0.05 BMP10 TTNPB1 IGF250 |
| 28 | | | | 28 | db-Y10 MG0.05 BMP10 TTNPB1 IGF250 |
| 29 | | | | 29 | db-Y10 MG0.05 BMP10 TTNPB1 IGF250 |
| 30 | | | | 30 | db-Y10 MG0.05 BMP10 TTNPB1 IGF250 | hESC Agg.: hESC aggregates;
XF HA: DMEM/F12 containing GlutaMAX, supplemented with 10% v/v of Xeno-free KnockOut Serum Replacement, 1% v/v non-essential amino acids, 0.1 mM 2-mercaptoethanol, 1% v/v penicillin/streptomycin (all from Life Technologies), 10 ng/mL heregulin-1b (Peprotech) and 10 ng/mL Activin A (R&D Systems);
SP: StemPro ® hESC SFM (Life Technologies);
r0.2FBS: RPMI 1640 (Mediatech); 0.2% FBS (HyClone), 1 × GlutaMAX-1 (Life Technologies), 1% v/v penicillin/streptomycin;
cb: CMRL: CMRL 1066, 1 × Glutamax, 1% v/v penicillin/streptomycin, 2% B-27;
db: DMEM Hi Glucose (HyClone) supplemented with 0.5 × B-27 Supplement (Life Technologies), 1 × GlutaMAX, and 1% v/v penicillin/streptomycin;
A100, A50, A5: 100 ng/mL, 50 ng/mL, 5 ng/mL recombinant human Activin A (R&D Systems);
BMP20, BMP10: 20 ng/mL, 10 ng/mL BMP4 (Peprotech);
CTT3: 0.25 mM KAAD-Cyclopamine (Toronto Research Chemicals) and 3 nM TTNPB (Sigma-Aldrich);
E50: 50 ng/mL recombinant human EGF (R&D Systems);
H10, H5: 10 ng/mL, 5 ng/mL Heregulin1b;
IGF25: 25 ng/mL IGF2 (Peprotech);
ITS: Insulin-Transferrin-Selenium (Life Technologies) diluted 1:5000 or 1:1000;
IV: 2.5 mM TGF-b RI Kinase inhibitor IV (EMD Bioscience);
K50, K25: 50 ng/mL, 25 ng/mL recombinant human KGF (R&D Systems, or Peprotech);
MG0.05: 0.05% MATRIGEL (BD Biosciences);
N50: 50 ng/mL recombinant human Noggin (R&D Systems);
NC10: 10 mM Nicotinamide;
PDGF10: 10 ng/mL Platelet-derived growth factor (PDGF, R&D Systems);
RO1: gamma-secretase inhibitor, RO4929097, 1 mM;
SHH100: 100 ng/mL sonic hedgehog;
TTNPB1: 1nM TTNPB (Sigma-Aldrich);
W50: 50 ng/mL recombinant mouse Wnt3A (R&D Systems);
Y10: 10 mM Y-27632 (Tocris Bioscience).

Previously, Applicant's disclosed use of a gamma secretase inhibitor for production of endocrine progenitor/precursors in U.S. Pat. No. 8,129,182, ENDOCRINE PROGENITOR/PRECURSOR CELLS, PANCREATIC HORMONE EXPRESSING CELLS AND METHODS OF PRODUCTION, issued Mar. 6, 2012. As described and claimed in the '182 patent, to further induce PDX1 positive pancreatic endoderm cell differentiation towards the endocrine-lineage, growth factors or agents which inhibited Notch signaling were elucidated. This was achieved by the application of an inhibitor of gamma secretase (e.g. DAPT or N—[N-(3,5-difluorophenacetyl)-L-alanyl]-S-phenylglycine t-butyl ester and related analogs). Gamma-secretase inhibitors block the intramembrane cleavage of the Notch molecule, thereby precluding the release of the activated Notch intracellular domain. A 2 to 4 day application of the gamma secretase inhibitor DAPT, for example, either in the terminal days of retinoic acid addition or immediately following retinoic acid withdrawal was used to induce NGN3 expression. Here, another gamma-secretase inhibitor, RO44929097 was used during stage 5. See Table 17

As indicated in Table 17, to drive differentiation to, and/or maturation of, the endocrine lineage, during stages 6 and 7 a combination of growth factors was applied including but not limited to BMP4 ("BMP"), Sonic Hedgehog ("SHH"), Platelet-derived growth factor ("PDGF"), FGF2 ("FGF"), retinoic acid and/or retinoic acid analogs such as TTNPB ("TTNPB"), Insulin-like growth factor I (IGF-I or "IGF1") and -II (IGF-II or "IGF2"), a vitamin B3 derivative, Nicotinamide ("NC") or combinations of one or more of these growth factors. One such combination is described in Table 17 Protocol No. 3.

Figure 17:
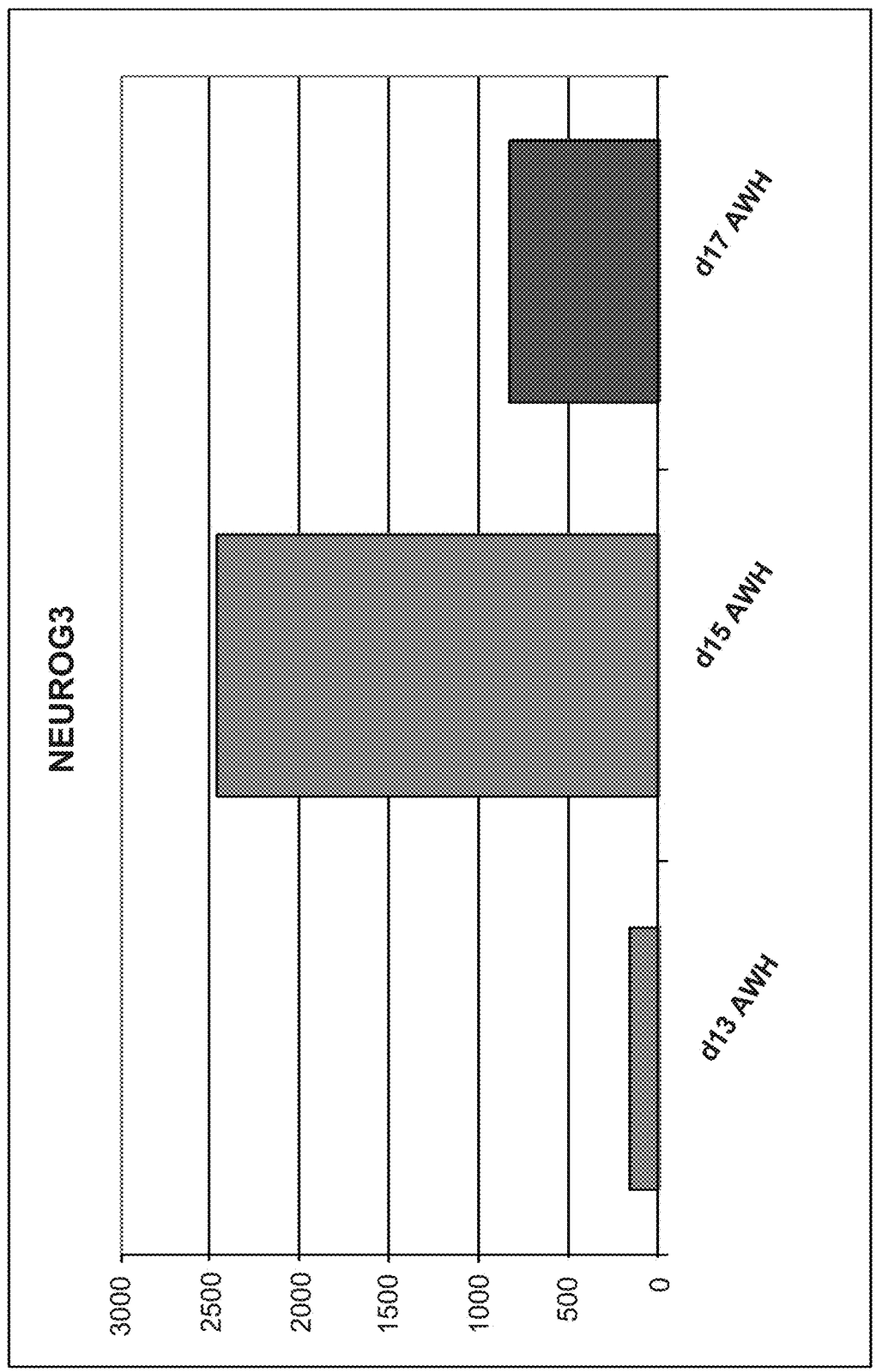
FIG. 17 is a bar graph showing the relative gene expression levels of Neurogenin 3 at day 13, 15 and 17 following treatment with a gamma-secretase inhibitor at stage 5 as described in Example 11.
Figure 18A:
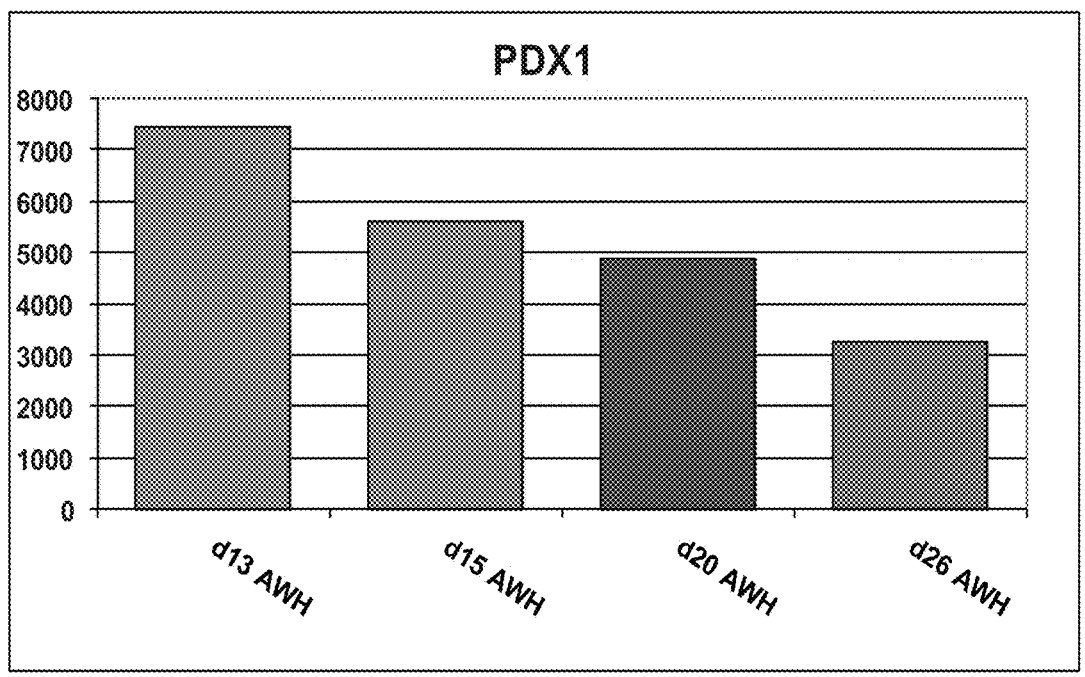
FIGS. 18A-18D are bar graphs showing the relative gene expression levels of PDX1 (FIG. 18A), NKX6.1 (FIG. 18B), SOX9 (FIG. 18C) and PTF1A (FIG. 18D) following differentiation according to Table 17 for stages 1-5, for stages 6 and 7, only FBS, Matrigel and a rho-kinase inhibitor was used in addition to the base DMEM media as described in Example 12.
Figure 18B:
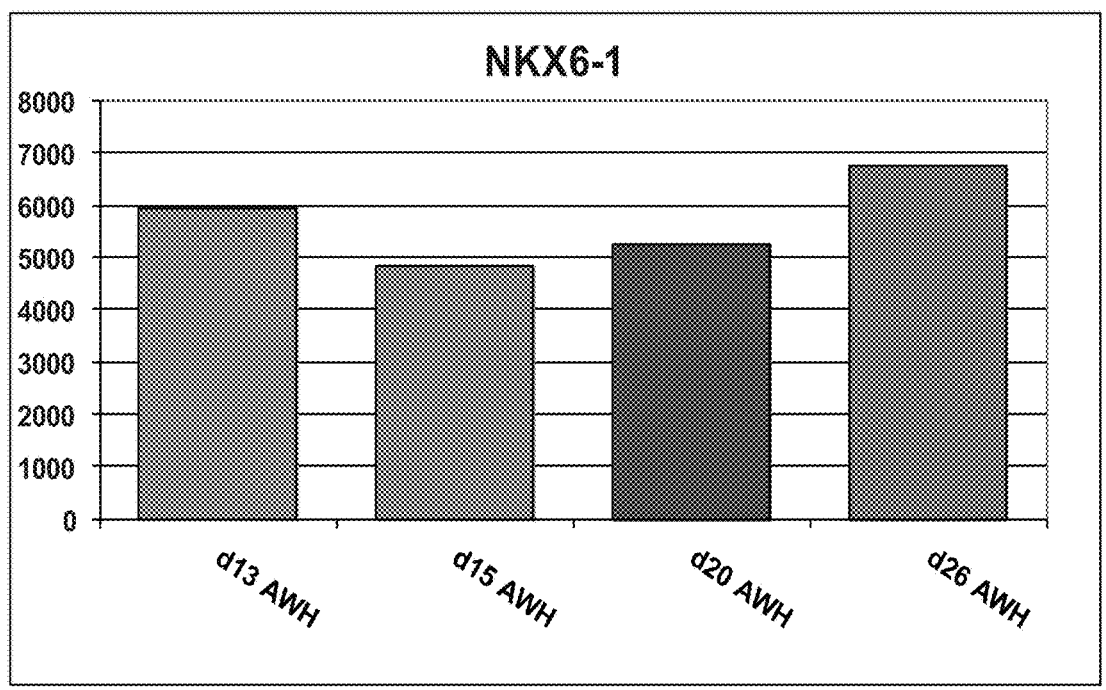
Figure 18C:
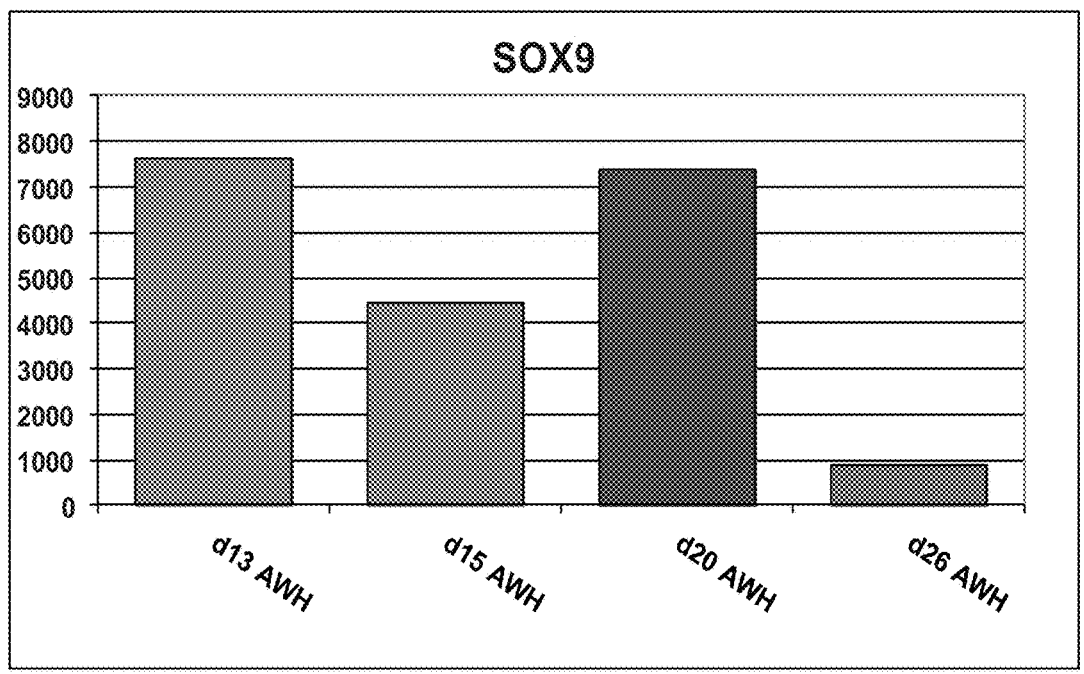
Figure 18D:
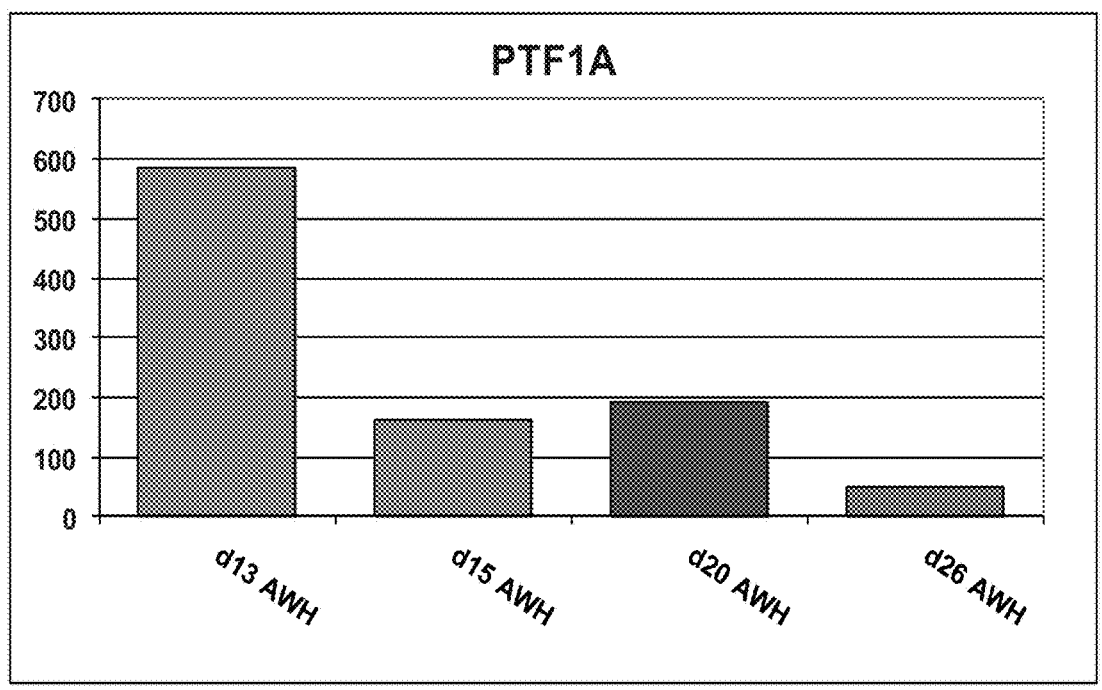
Figure 19A:
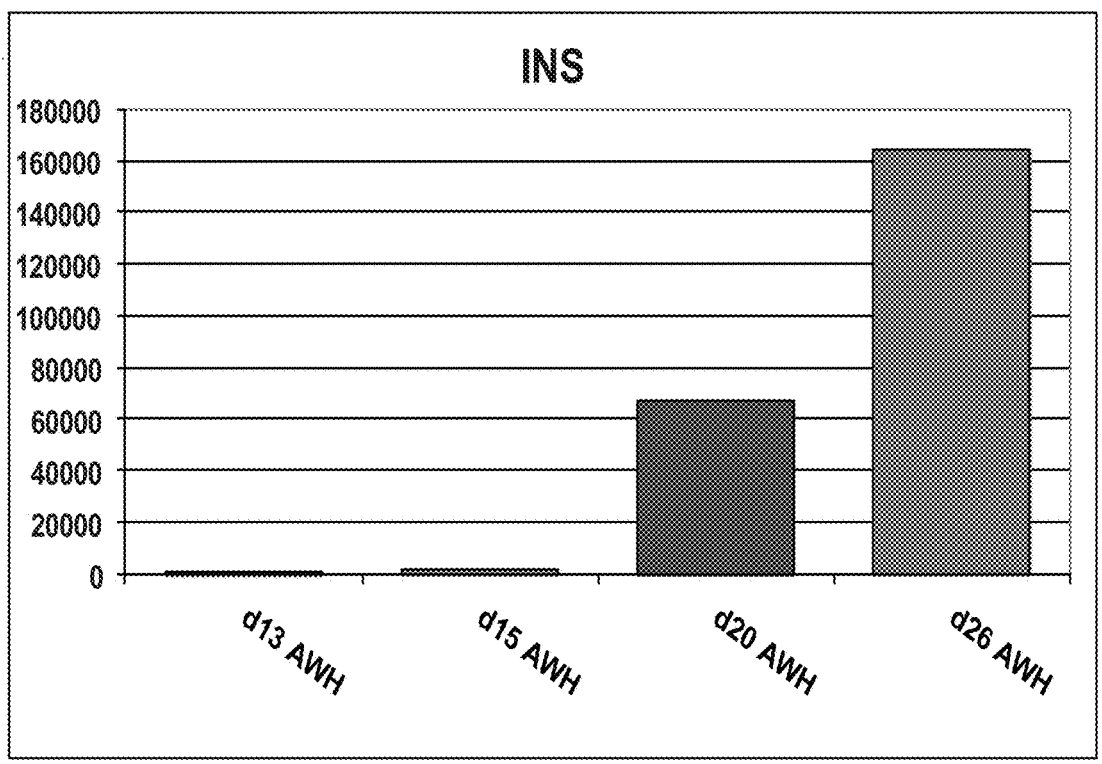
FIGS. 19A-19D are bar graphs showing the relative gene expression levels of INS (FIG. 19A), GCG (FIG. 19B), GHRL (FIG. 19C) and SST (FIG. 19D) under the same differentiation conditions as in FIG. 18 and as described in Example 12.
Figure 19B:
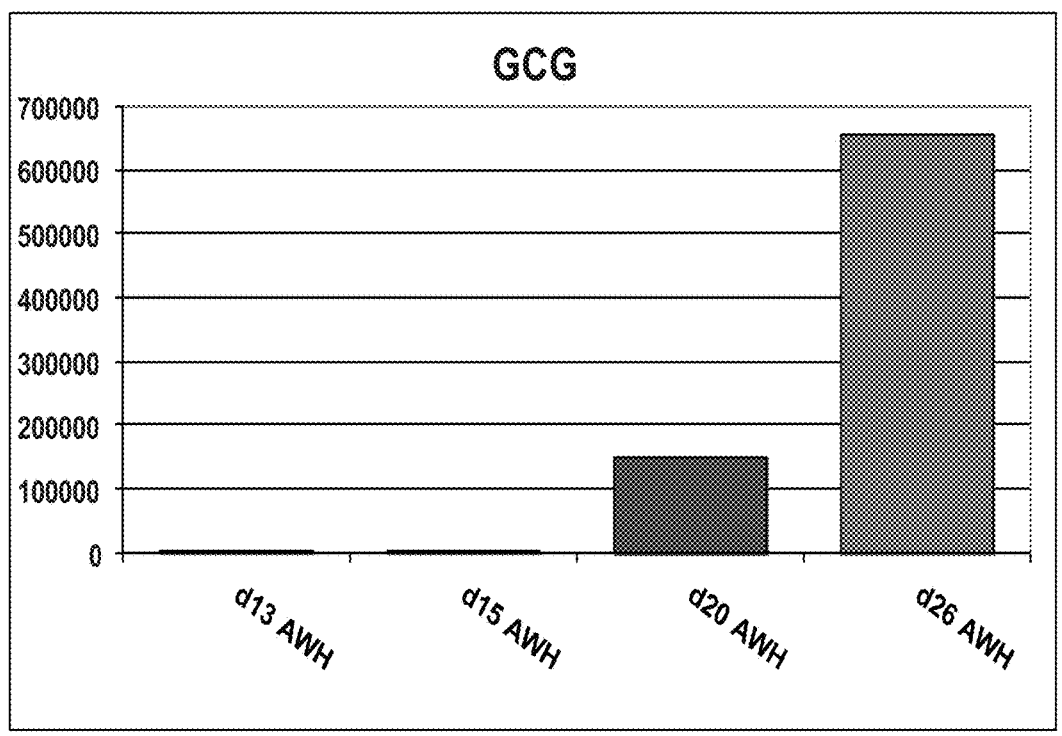
Figure 19C:
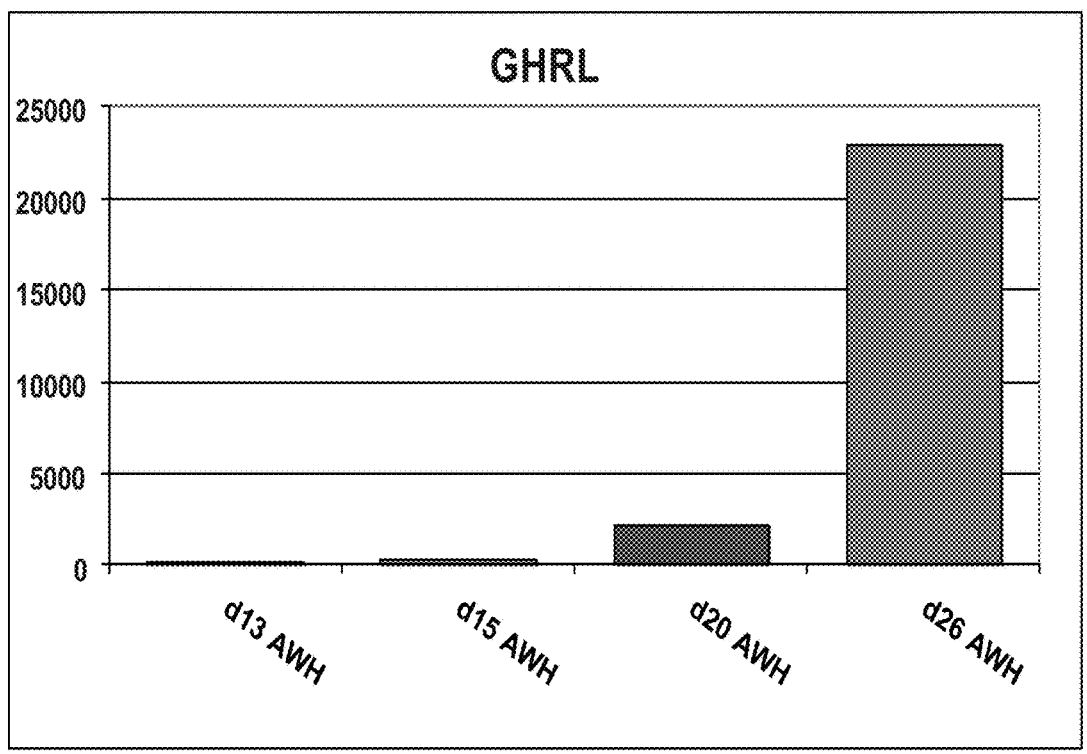
Figure 19D:
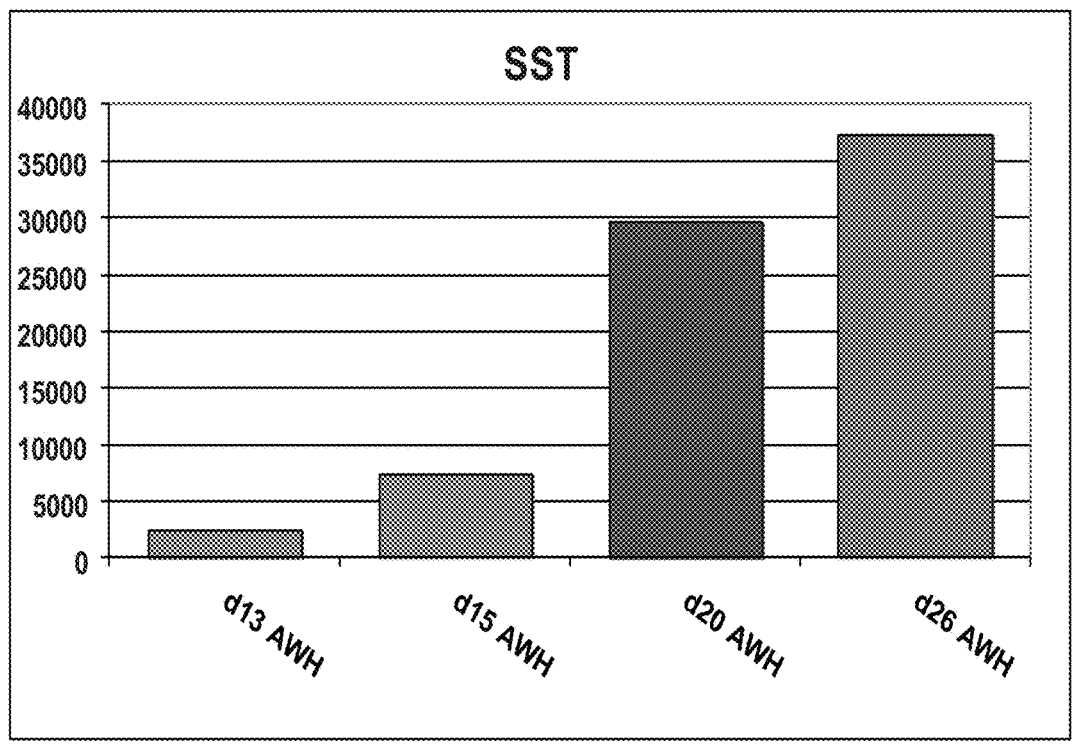

For example, PEC made from the AHW protocol substantially as described above in Example 10 was further treated at stage 5 (days 13 and 14) with the gamma-secretase inhibitor, RO4929097 ("RO1"), typically for 2 days at 1 μM, according to Table 17, Protocol No. 3. This stage 5 treatment results in induction of NGN3 expression and subsequently endocrine differentiation. Additionally, Nicotinamide was included during stages 5 and 6 to also induce NGN3 expression or endocrine differentiation. NGN3 gene expression was analyzed by Nanostring detection of mRNA after stage 4 (day 13 cultures), after stage 5 (day 15 cultures) and after 2 days of stage 6. As shown in FIG. 17, the gamma-secretase inhibitor strongly induced NGN3 expression after stage 5 at day 15 as compared to NGN3 low level expression at the end of stage 4 (day 13). After removal of the gamma-secretase inhibitor at day 15 (first day of stage 6), NGN3 expression decreases as observed at day 17 (FIG. 17). This transient increase in NGN3 expression during stage 5 is consistent with its transient expression observed during in vivo beta cell development. See Jorgensen et al. (2007) supra.

It is noted that the total number of days for any of the stages can vary and does vary, e.g. stage 5, 6 and/or 7 can be shortened or lengthened in the number of days. This applies to earlier stages 1, 2, 3 and 4 as well.

Additionally, a rho-kinase inhibitor can be added to the differentiation media continuously or intermittently during any of stages 1, 2, 3, 4, 5, 6 and 7 to promote cell-survival and cell mass and yield. A rho-kinase inhibitor at stages 1, 2 and 4, for example, appears to promote induced pluripotent stem cell differentiation by for example maintenance of cell mass and yield.

Also, at about day 20 (i.e. the juncture between stages 6 and 7 of Protocol #3 of Table 17), the cell aggregates can be dissociated and re-aggregated. This disassociation and re-aggregation removed certain cell sub-populations, thus leaving a predominantly endocrine and/or endocrine progenitor/precursor/progenitor (CHGA+) cell population. This physical manipulation also eases analysis of endocrine populations, and constitutes a purification step, if necessary. See Example 14 for more details.

Further, starting at stage 6 and through to stage 7, if necessary, a very low concentration, e.g. about 0.05%, of Matrigel can be used to help maintain the cell aggregates and/or prevent endocrine cells from migrating from the cell aggregates. Use of Matrigel or any other complex cell matrices may depend on the specific cellular aggregates themselves (e.g. PEC aggregates, endocrine progenitor/precursor cell aggregates as described below and the like) and potentially the PSC line from which the cellular aggregates were derived. It is possible that other complex matrices or defined matrices, e.g. serum, laminin, fibronectin, collagen and other extra-cellular matrix proteins, can be used to perform substantially similar functions. See Example 14 for more details.

Addition of insulin-like growth factor (IGF) 1 and/or 2 (IGF1 or IGF2) can be added at stage 6 or 7 or during stage 6, e.g. starting at day 16, 17 or 18. Pluripotent stem cells were differentiated substantially as described above according to Table 17, except IGF1 at 50 or 200 ng/mL or IGF2 at 25 or 100 ng/mL were added to the cell cultures during stage 6, specifically at day 17 for about 3 days. Cell aggregates were analyzed for mRNA using Nanostring after stage 6 (day 20). These preliminary studies showed that IGF2 was more capable of inducing INS expression than IGF1 (data not shown), however, longer treatment could produce a more robust effect from IGF2 alone or IGF1 or the combination of the two.

Table 17 describes use of various growth factors at certain concentrations, however, the invention is not limited to specific concentrations described herein since one skilled in the art will recognize that modification of growth factor concentration is standard in the art, and in fact, is described in the above Examples with at least changes in Activin and Heregulin levels and their effect on cell differentiation and composition. Modifications herein include but are not limited to 5, 10, 20, 50 to 100 ng/mL of Activin; 5, 25, 50 to 75 ng/mL of Wnt; 2, 5, 10, 30 ng/mL of Heregulin; 10 to 200 ng/mL of sonic hedge-hog (SHH); 10 to 100 ng/mL of PDGF; 10 to 20 ng/mL of BMP; 2 to 20 ng/mL of FGF2; and 25 to 200 ng/mL of IGF1 and/or IGF2. Additionally, any of the combinations of these factors can be used, and the stage or period when they are used can be varied, even significantly, without departure from the invention described.

Example 12

In Vivo Function of Pancreatic Endocrine Cells

To date, enriched populations of endocrine cells produced in vitro from PSC have not given rise to glucose-responsive insulin-secreting beta cells in vivo. Thus, Applicants tested whether the above methods according to Table 17 and described in Example 11 above could produce the first in vitro endocrine cell that is glucose responsive in vivo.

Human pluripotent stem cells were differentiated according to Protocol No. 3 of Table 17 for stages 1-5, however, at stages 6 and 7, only FBS, Matrigel and a rho-kinase inhibitor was used in addition to the base DMEM media with B-27 supplement. RNA expression was analyzed by Nanostring, with time points at the beginning of stages 5 (d13) and 6 (d15), and the end of stages 6 (d20) and 7 (d26). FIGS. 18A-18D and 19A-19D show relative mRNA expression levels for non-endocrine multipotent pancreatic progenitor sub-population markers including PDX1, NKX6.1, SOX9, and PTF1A, and endocrine cell markers including insulin (INS), glucagon (GCG), somatostatin (SST) and ghrelin (GHRL). At the end of stage 4 (day 13), PDX1, SOX9, NKX6.1 and PTF1A were all highly expressed. These markers are all reduced during stage 5 as endocrine differentiation or induction occurs (day 15). And, by the end of stage 6 (day 20) or start of stage 7, mRNA levels of PDX1, NKX6.1 and PTF1A have decreased while at the same time mRNA levels of INS, GCG, GHRL and SST were increasing (compare FIG. 18A-D and FIG. 19A-D at day 20). Specifically, the decrease of PDX1 and PFT1A expression and the dramatic concomitant increase in relative mRNA expression of INS, GCG, GHRL and SST through stages 5 and 6 is due to the combination of Activin, Heregulin and Wnt (AHW), and particularly to Activin, at stages 3 and 4. That is, inclusion of Activin in stages 3 and 4 repressed endocrine differentiation at stages 3 and 4, while the gamma-secretase at stage 5 induced endocrine differentiation in stages 5, 6 and 7. The similar levels of NKX6.1 expression at day 20 and 26 (stages 6 and 7) as compared with the earlier time points shown is consistent with this marker being expressed in pancreatic endocrine cells as well as non-endocrine multipotent pancreatic progenitor sub-populations. Thus, in later stages (e.g. stages 5, 6 and 7), the cells were directed towards endocrine differentiation while they were suppressed from doing the same in the earlier stages, stages 3 and 4.

Figure 20:
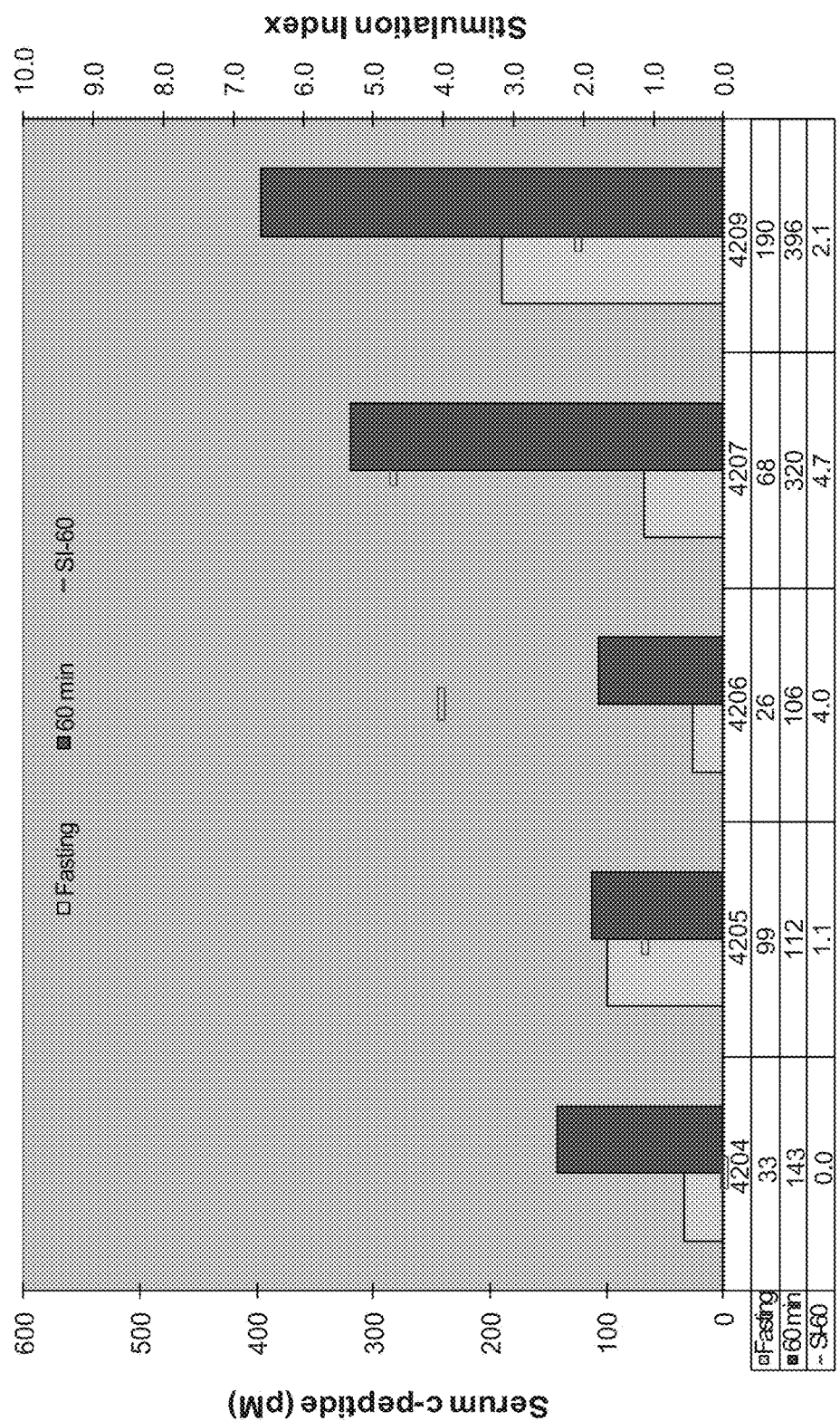
FIG. 20 is a graph showing the concentrations of human C-peptide in sera of mice implanted with encapsulated endocrine made as described in Example 12 (E2395, Rag 2, week 10 GSIS). Expression levels were analyzed 10 weeks post-engraftment at fasting and 60 min after intraperitoneal glucose administration. See Example 12.
Figure 21:
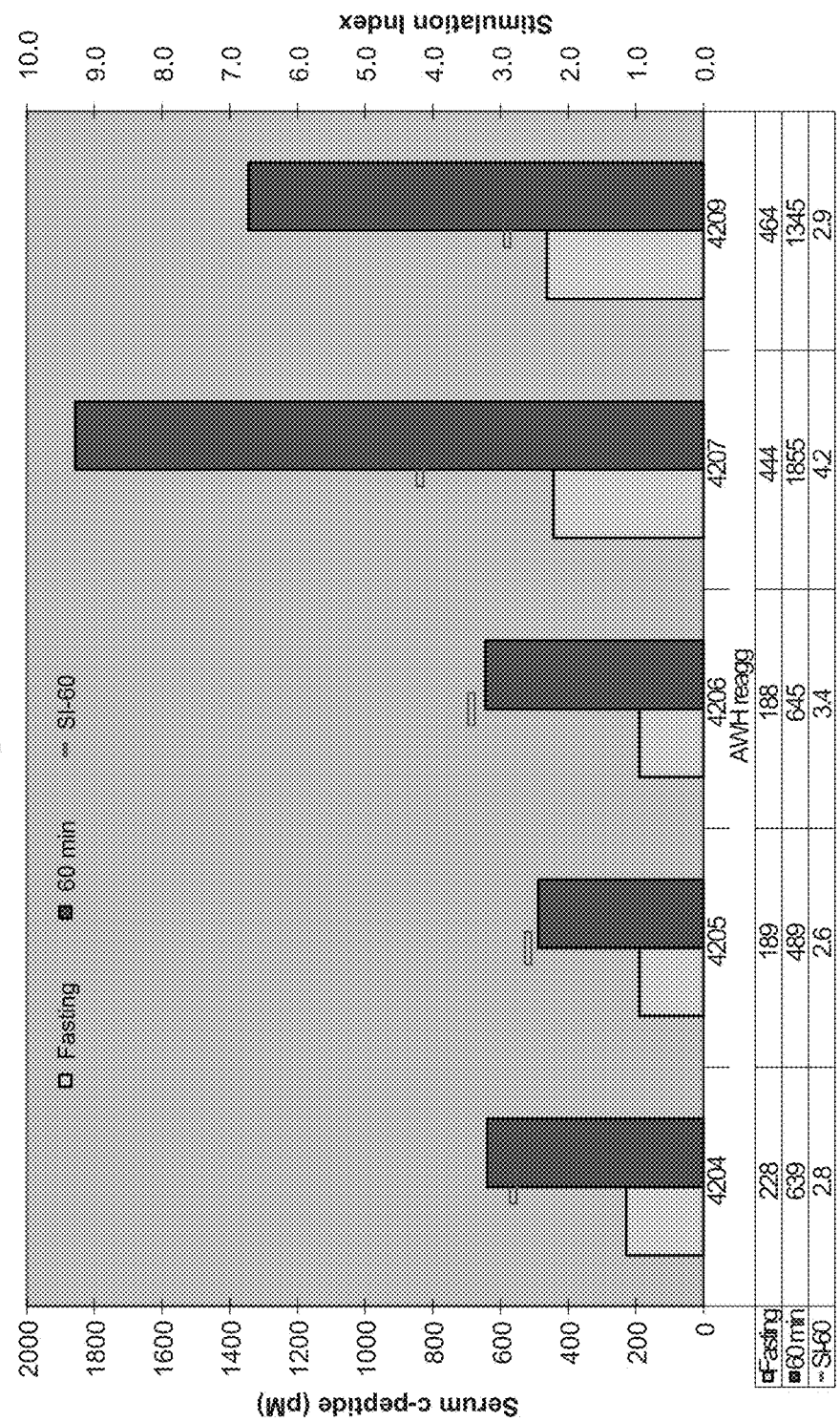
FIG. 21 is a graph showing the concentrations of human C-peptide in sera of mice implanted with encapsulated endocrine made as described in Example 12 (E2395, Rag 2, week 15 GSIS). Expression levels were analyzed 15 weeks post-engraftment at fasting and 60 min after intraperitoneal glucose administration. See Example 12.

After about stage 6, the cell aggregates were disassociated and re-aggregated (described in more detail below in Example 14), which removed some cell types made during stages 3 and 4 including certain PEC sub-populations, e.g. non-endocrine (CHGA−) cells. The removal of non-endocrine (CHGA−) sub-populations and/or exocrine and/or exocrine progenitor cells and/or duct and/or duct progenitor cells can be seen by the dramatic decrease in SOX9 and PTF1A following re-aggregation (FIG. 18, compare day 20 to day 26). After stage 7, the endocrine cells were loaded into devices on day 26 and transplanted into RAG2 mice on day 27 substantially as previously described for transplantation (or implantation) into SCID-Beige mice. FIG. 20 shows the serum human C-peptide levels after fasting and one hour (60') following glucose administration or challenge. At 10 weeks post-implant, all five animals were producing insulin as observed by human sera C-peptide. At 15 weeks post-implant (FIG. 21), all animals exhibited increased levels of insulin production as compared to 10 weeks post-implant levels, and 2 of the 5 animals averaged 1500 pM of C-peptide, which is evidence of robust glucose responsiveness in vivo.

Figure 22C:
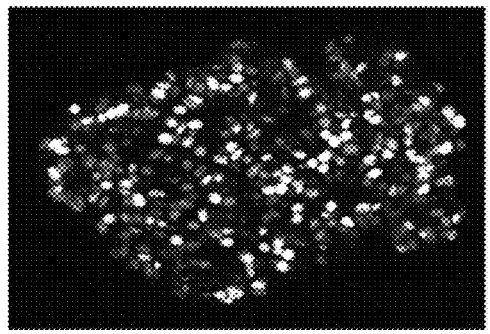
FIGS. 22A-22D are photo micrographs showing endocrine cell aggregates differentiated and matured in vivo as described in Example 12. Field of cells are stained with DAPI (FIG. 22A) or antibodies against NKX6.1 (FIGS. 22B & FIG. 22C, nuclear stain), and Chromogranin A (FIGS. 22B & FIG. 22D, cytoplasmic). The same field is shown in all images. See Example 12.
Figure 22D:
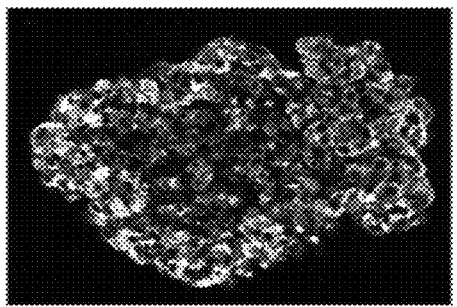
Figure 22B:
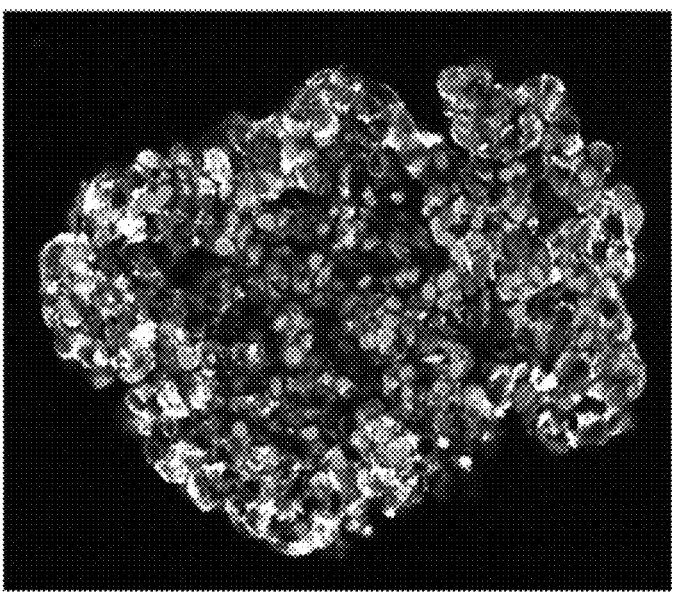
Figure 22A:
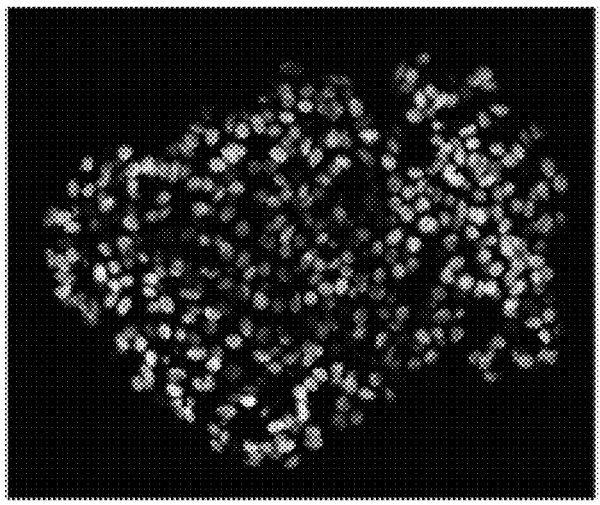

Prior to loading the endocrine cells into devices on day 26, samples were taken to verify that the functional beta cells developed, matured and arose from transplanted endocrine cells from stages 6 and 7 and not, for example, from any remaining non-endocrine multipotent pancreatic progenitor sub-population. Immunocytochemistry using both endocrine and non-endocrine markers was performed on the samples. Frozen sections of the day 26 samples were co-stained with antibodies using DAPI (FIG. 22A), NKX6.1 and Chromogranin A (FIG. 22B). It is clear that the vast majority of NKX6.1 positive (red) cells also stain positive for chromogranin (CHGA+), an endocrine marker. Thus, it appears that non-endocrine multipotent pancreatic progenitor cells, as shown by lack of CHGA−/NKX6.1+ cells, do not appear to be present in any significant number in these endocrine cell preparations.

Figure 23C:
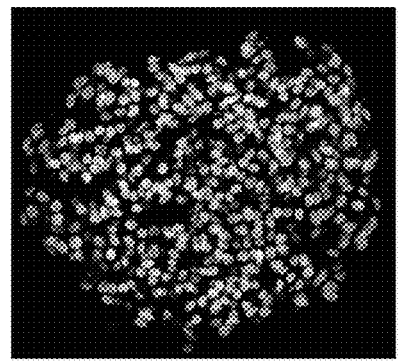
FIGS. 23A-23C are photo micrographs showing endocrine cell aggregates as described in Example 12.
Figure 23B:
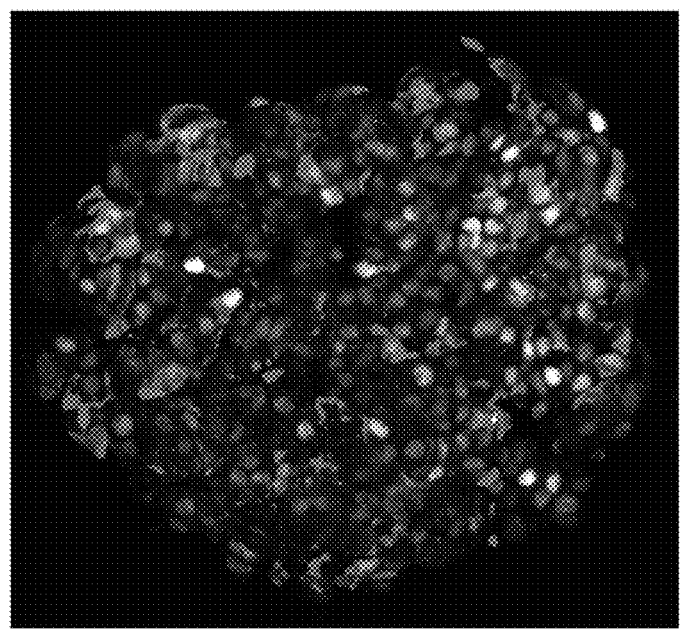
Figure 23A:
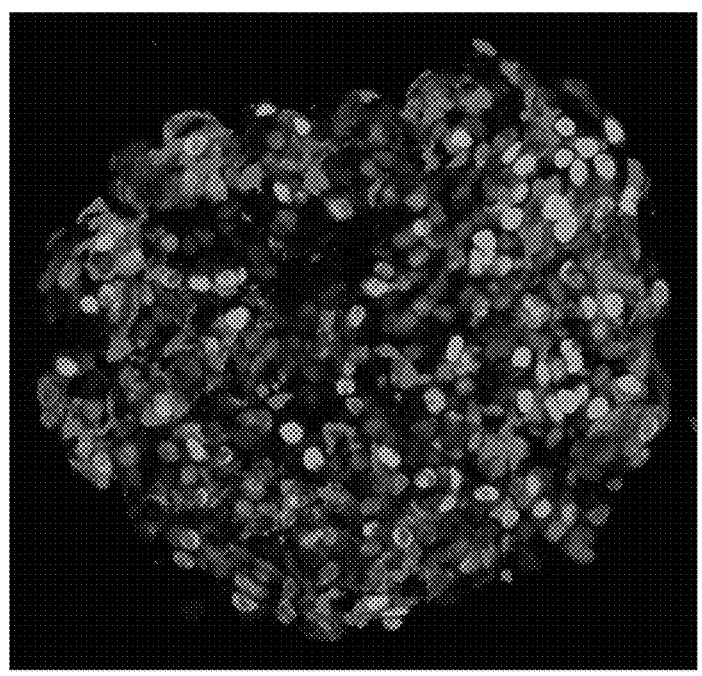

Samples of these same endocrine cell aggregates were also co-stained for INS, NKX6.1 and PDX1 (FIG. 23A-B). FIGS. 23A-B showed that most of the insulin-expressing cells also express NKX6.1 and PDX1. This is a surprising result given that previously published reports of in vitro-derived insulin expressing cells from PSC did not co-express NKX6.1 and/or PDX1. See U.S. Pat. No. 7,033,831 and related applications to Geron Corporation and Jiang et al. (2007), Generation of insulin-producing islet-like clusters from human embryonic stem cells, *Stem Cells* 2007 August; 25(8):1940-53. Epub 2007 May 17.

Taken together this data provide compelling evidence that, for the first time, an in vitro PSC-derived endocrine cell culture can (1) co-express INS, PDX1 and NKX6.1 in vitro and is likely glucose responsive in vitro; and (2) can give rise to glucose-responsive insulin-secreting cells in vivo.

Example 13

Figure 24A:
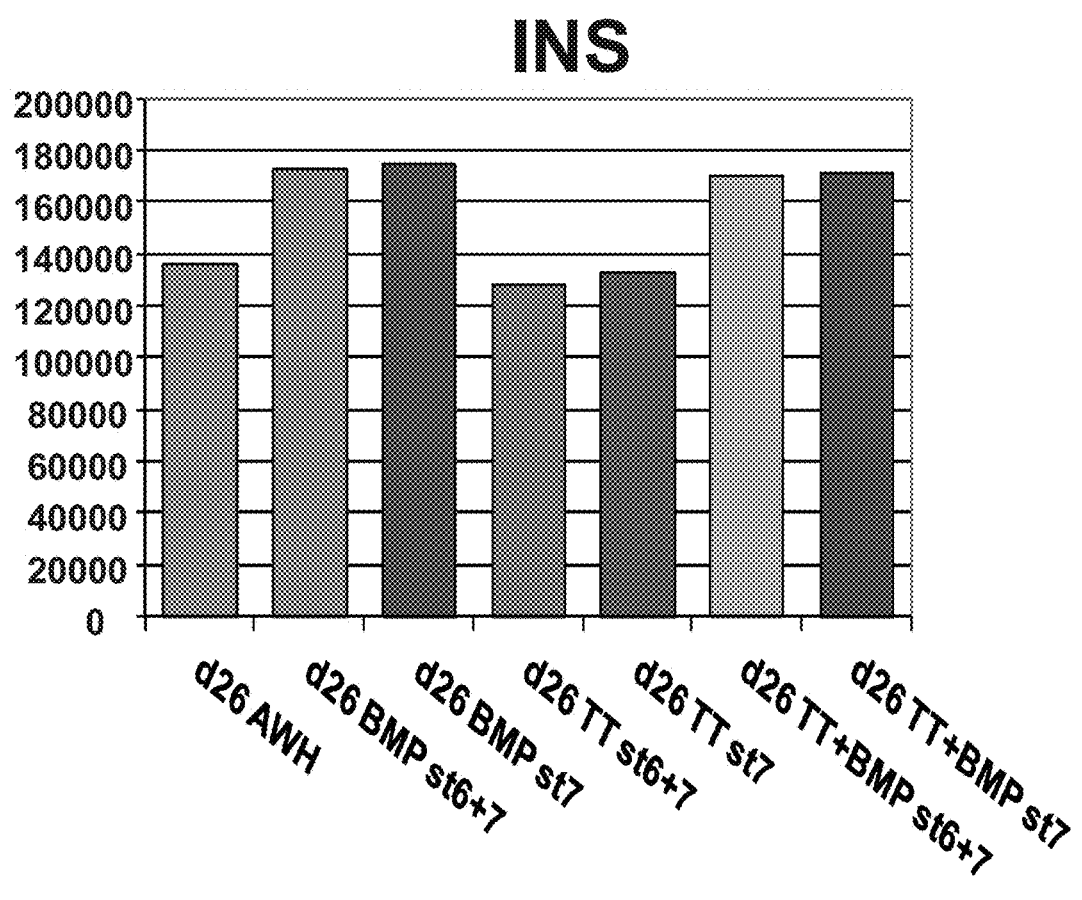
FIGS. 24A-24D are bar graphs showing Nanostring mRNA data of the relative gene expression levels of INS (FIG. 24A), NKX6.1 (FIG. 24B), PDX1 (FIG. 24C) and ID1 (FIG. 24D) under the differentiation conditions described in Example 13.
Figure 24B:
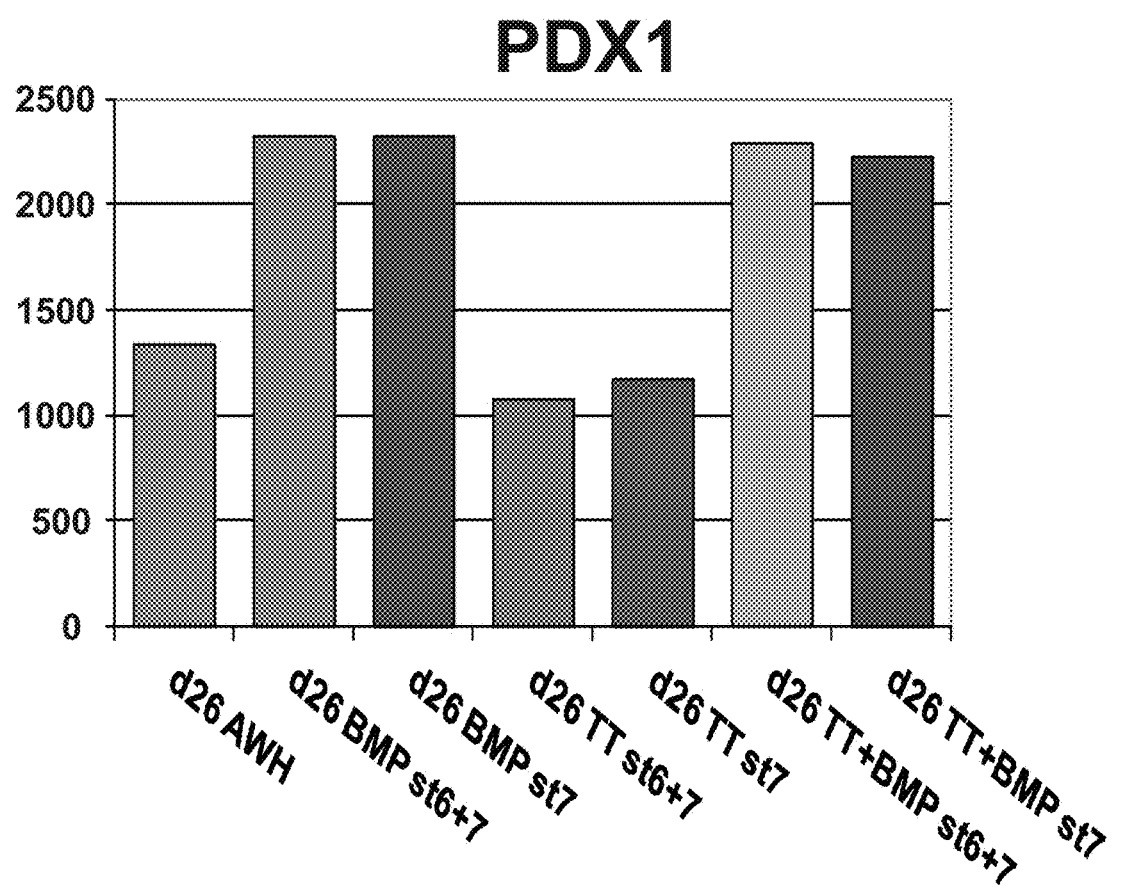
Figure 24C:
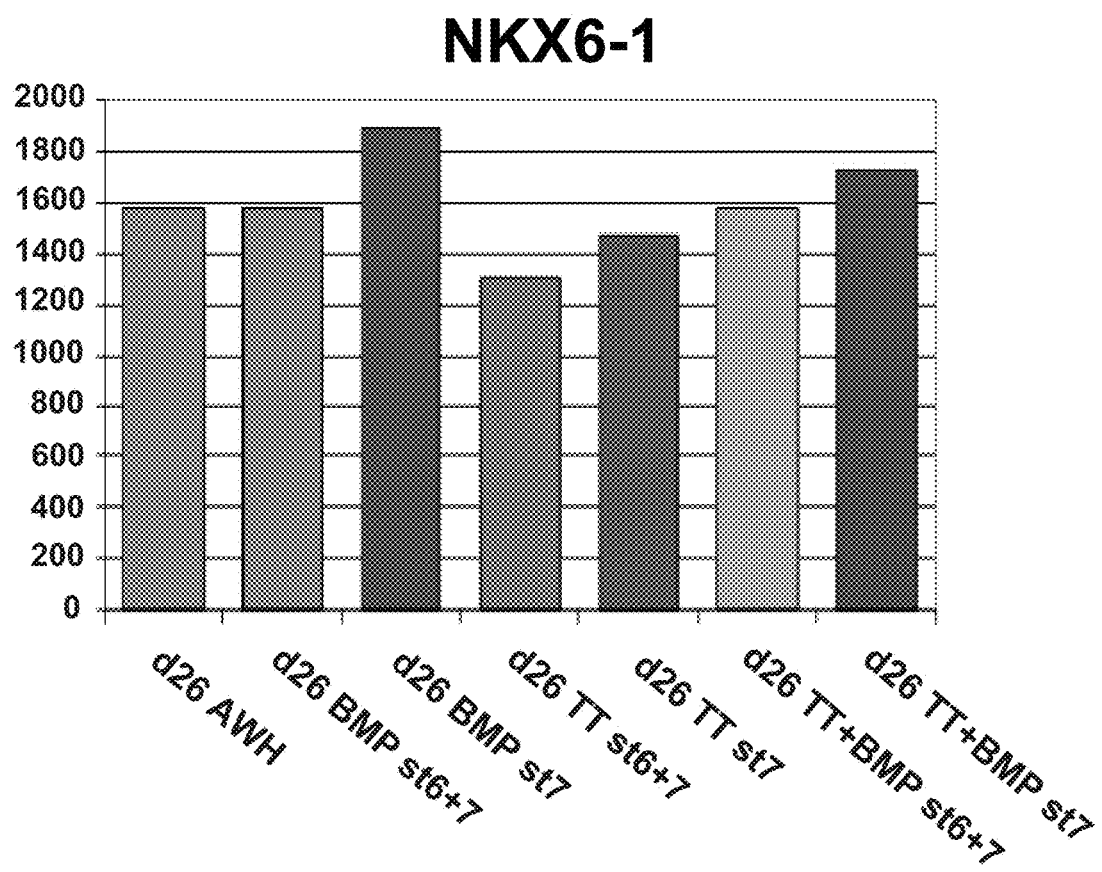
Figure 24D:
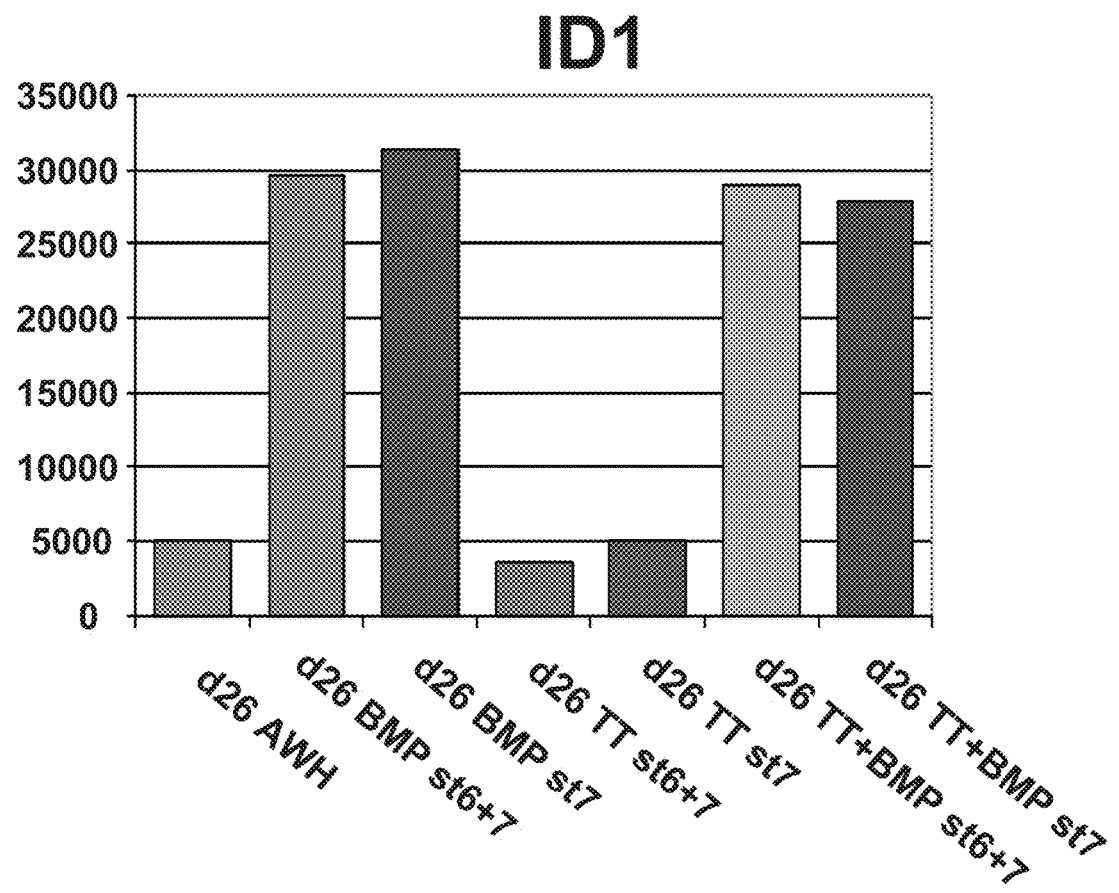

Retinoic Acid, Nicotinamide and BMP Increase PDX1 and NKX6.1 Expression in Endocrine Cells A hallmark of mature beta cells is that they up-regulate NKX6.1 and PDX1, at the individual cell level, relative to the levels seen in the non-endocrine (CHGA−) sub-populations of PEC. Examples 11 and 12 described endocrine cell production whereby the majority of the cells have NKX6.1 and PDX1 expression levels similar to that observed for the non-endocrine (CHGA−) sub-population of PEC. Hence, it is desirable to identify growth factors which specifically enhance the expression of at least these two markers in insulin positive endocrine cells Two candidate factors include TTNPB, a retinoic acid or retinoid analog, and BMP4, a member of the bone morphogenetic protein family which is part of the transforming growth factor-beta superfamily. TTNPB and BMP4 were tested in various combinations at stages 6 and 7 and at various concentrations, but typically at 0.5 nM and 10 ng/mL, respectively. As shown by Nanostring mRNA analysis in FIG. 24, BMP at stages 6 and 7, at stage 7 alone, or in combination with TTNPB, can simultaneously increase Insulin and PDX1 expression (FIGS. 24A & 24C). In contrast, TTNPB alone at these same stages (stages 6 & 7 and stage 7 alone) does not appear to increase PDX1 expression, and even appears to decrease PDX1 expression slightly as compared to BMP alone (compare FIG. 24C columns 4 & 5 with columns 2 & 3). The effects of BMP on NKX6.1 expression are less clear since under all conditions (BMP alone, TTNPB alone, BMP and TTNPB combined, treatment of each at stages 6 & 7, or stage 7 only), NKX6.1 expression is relatively stable. As a further indicator of BMP specificity, BMP was also observed to up-regulate inhibitor-of-differentiation (ID) gene expression (e.g., ID1), which is known to be regulated by members of the TGF-β superfamily, including BMP4 (FIG. 24D). Thus, without limiting this application to any one theory, it appears that BMP is the factor selectively inducing the up-regulation of PDX1, and ID1.

Figure 25A:
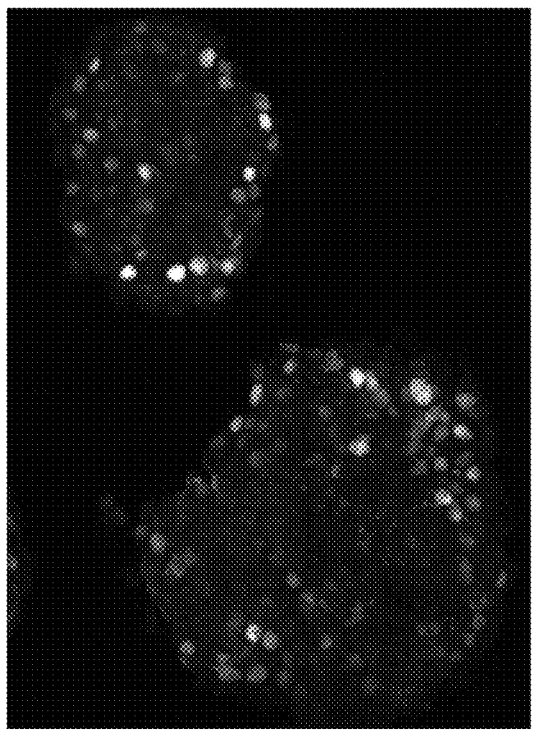
FIGS. 25A-25C are photo micrographs showing endocrine cell aggregates as described in Example 13.
Figure 25B:
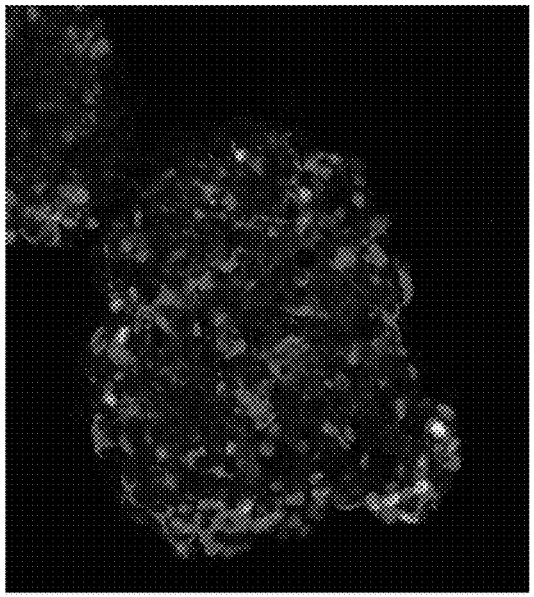
Figure 25C:
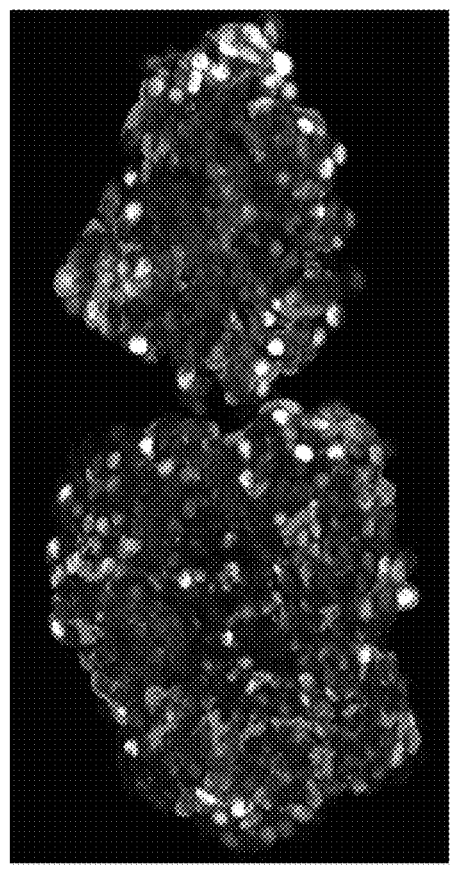
Figure 26B:
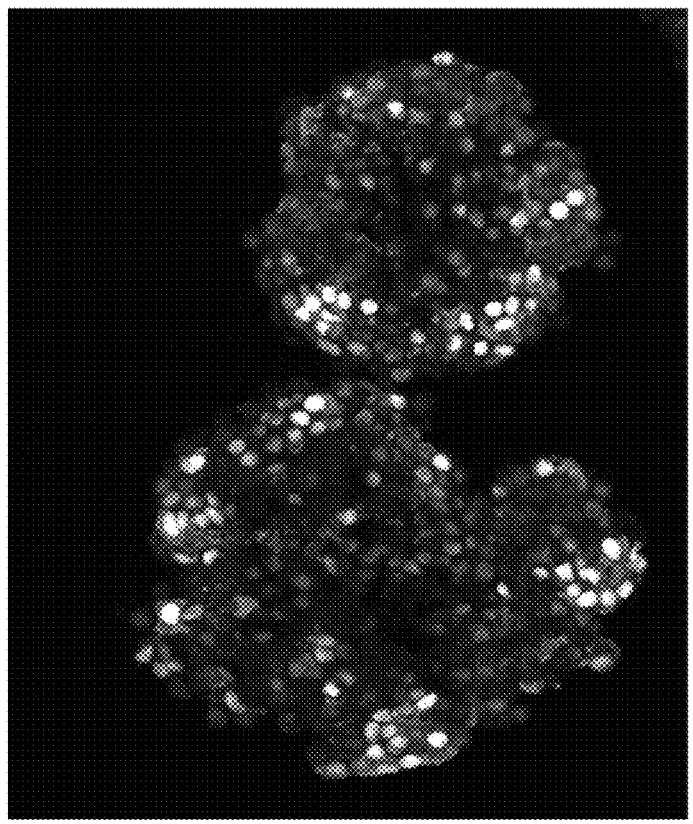
FIGS. 26A-26B are photo micrographs showing endocrine cell aggregates as described in Example 13.
Figure 26A:
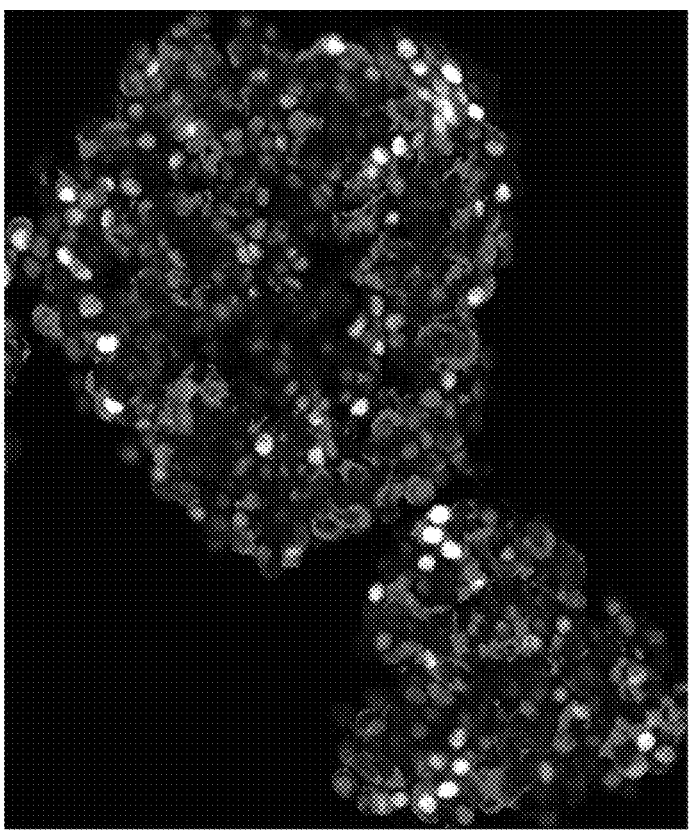

To determine whether certain of these markers were co-expressed in any one cell, the endocrine cell aggregates were fixed at day 27 (after stage 7) of differentiation and frozen sections were prepared and stained by immunocytochemistry (ICC) for C-peptide, NKX6.1 and PDX1. See FIGS. 25-28. Here, instead of staining with INS, cells were stained with an antibody against C-peptide, a central fragment of pro-insulin, and therefore this stain is also indicative of insulin expressing cells (FIG. 25). The ICC results were consistent with the Nanostring data above, i.e., that BMP alone, or combined with TTNPB, at stages 6 and 7 or at stage 7 only, was capable of inducing PDX1 expression in insulin (C-peptide) expressing cells (FIG. 25 and FIG. 26).

Figure 27B:
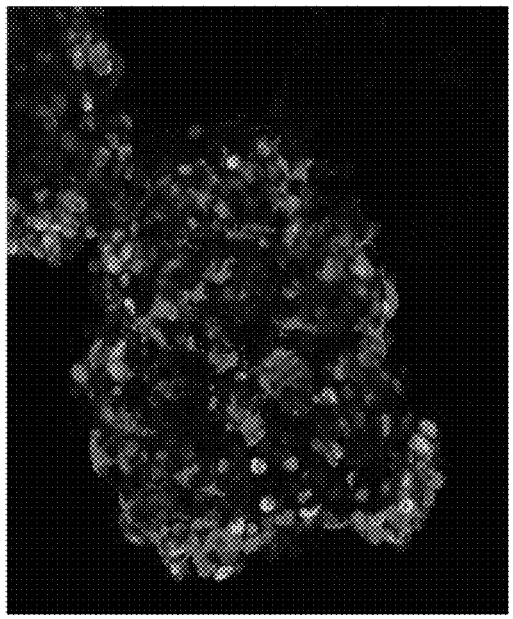
FIGS. 27A-27C are photo micrographs showing endocrine cell aggregates as described in Example 13 and depict the same fields as in FIG. 25.
Figure 27C:
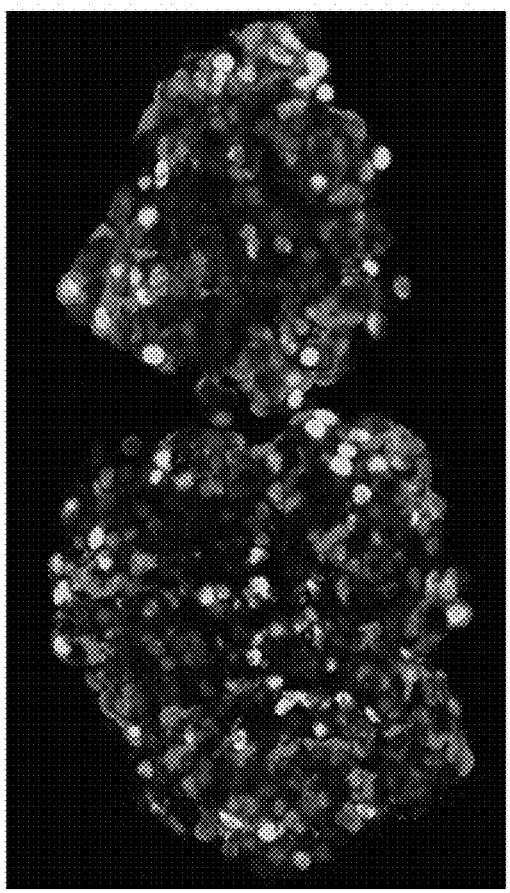
Figure 27A:
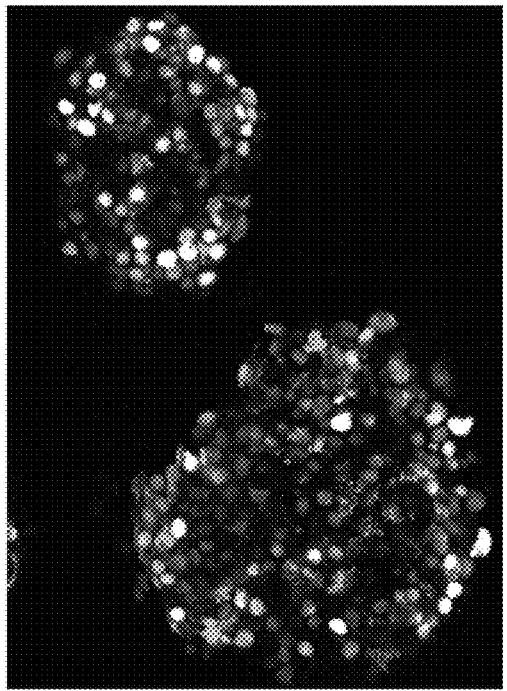
Figure 28B:
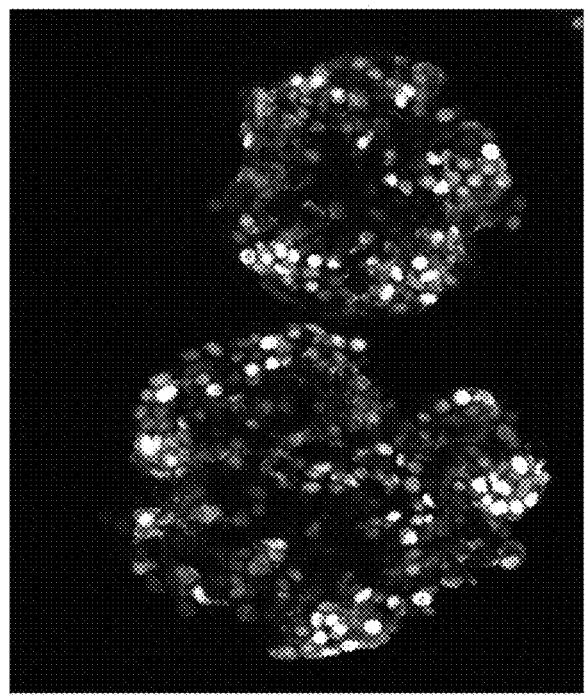
FIGS. 28A-28B are photo micrographs showing endocrine cell aggregates as described in Example 13 and depict the same fields as in FIG. 26.
Figure 28A:
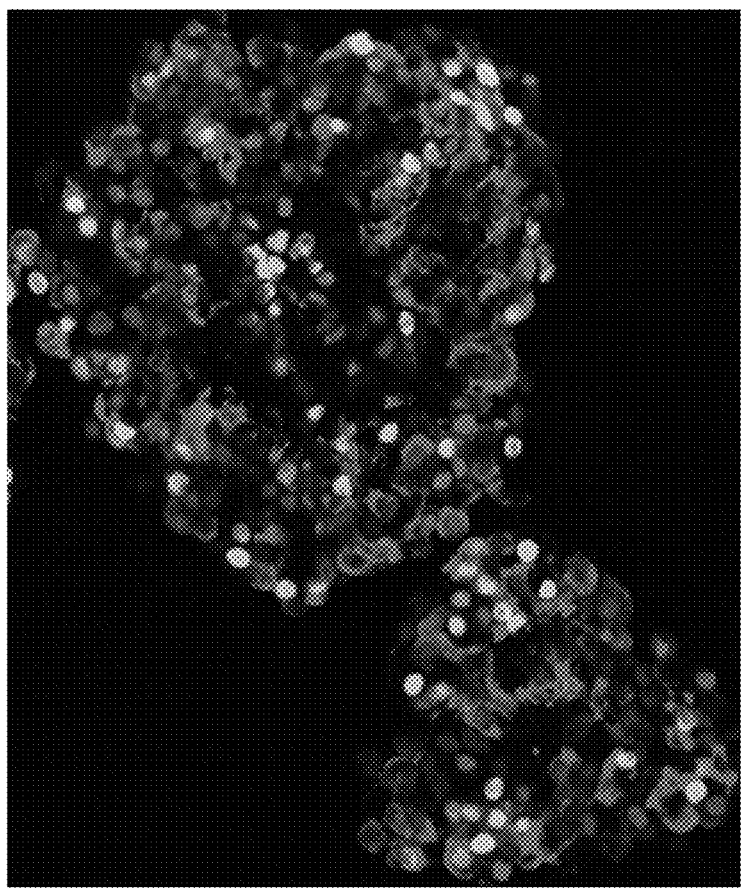
Figure 29A:
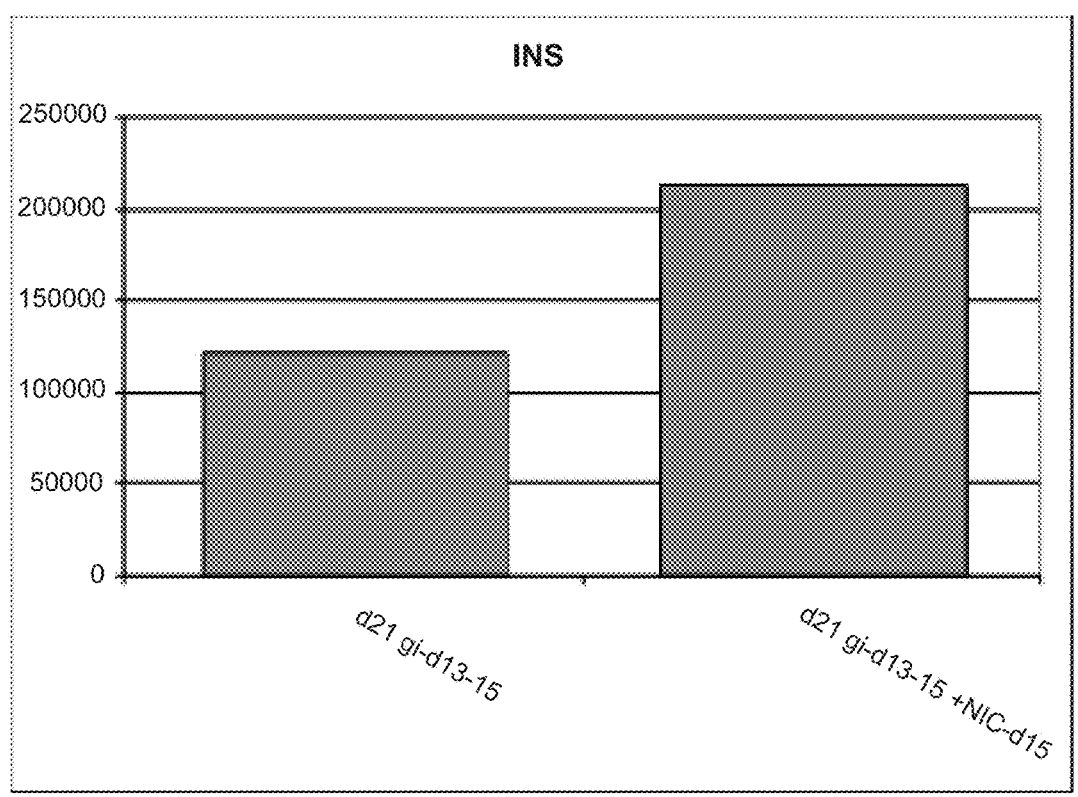
FIGS. 29A-29E are bar graphs showing the relative gene expression levels of endocrine aggregates treated with (right bar; d21 gi-d13-d15) or without (left bar; d21 gi-d13-d15+ NIC d15) nicotinamide at stage 6 and analyzed at day 21 as described in Example 13.
Figure 29B:
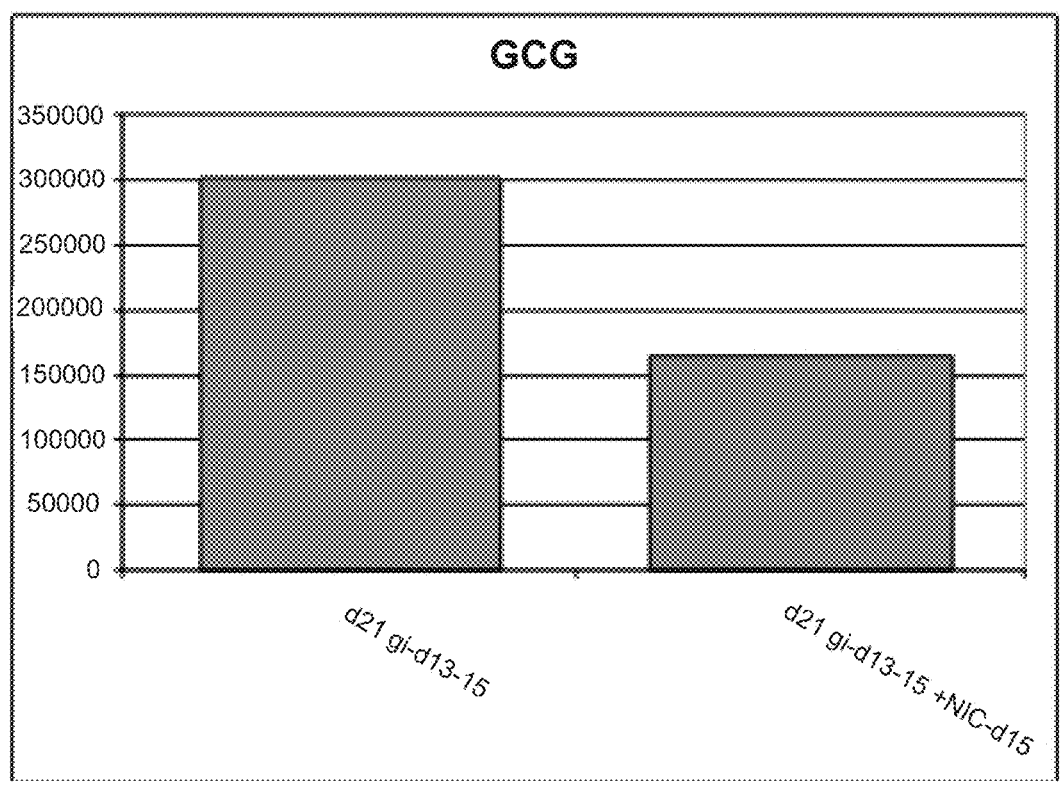
Figure 29C:
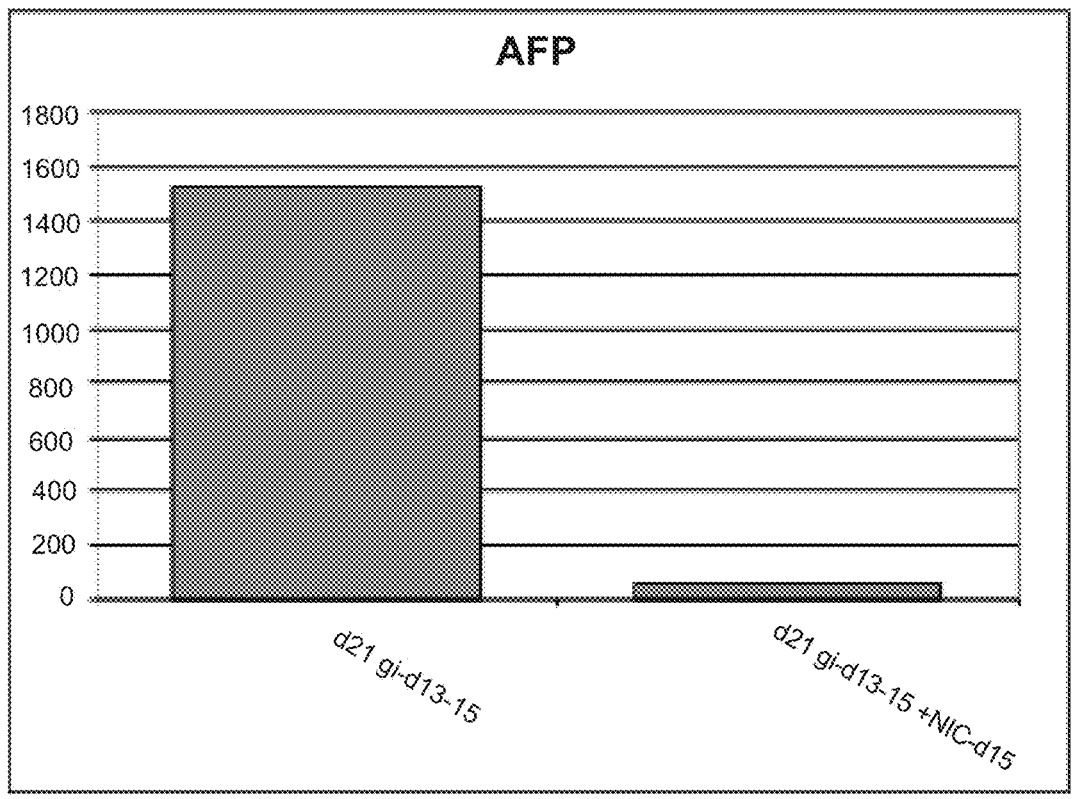
Figure 29D:
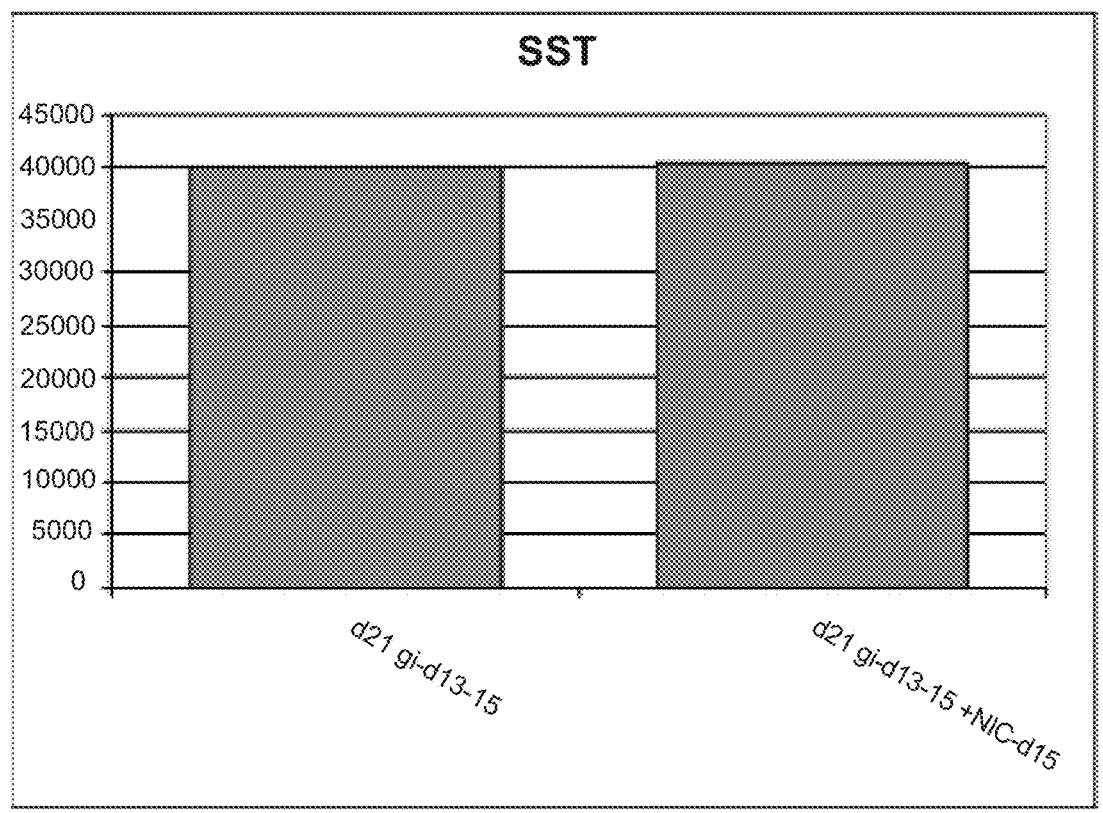
Figure 29E:
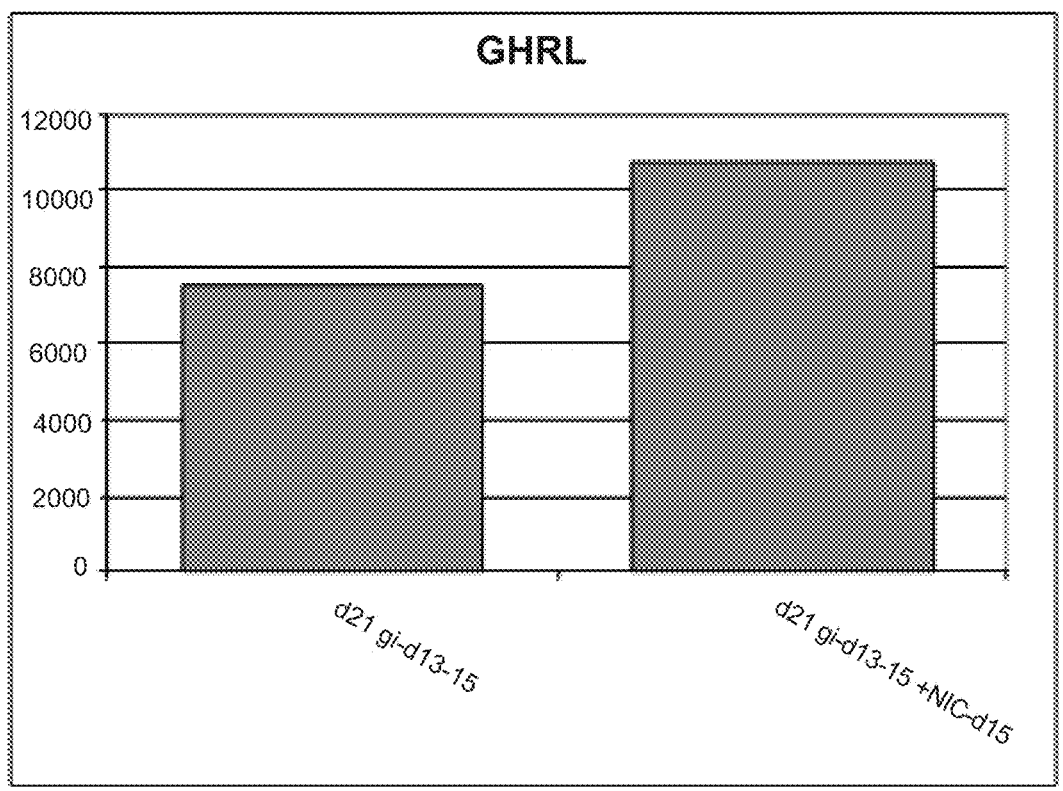

Despite the fact that the mRNA data suggested that BMP and TTNPB alone or in combination had little effect on NKX6.1 expression, the ICC studies showed that on a cellular level, the co-expression of NKX6.1 and C-peptide (or insulin) expressing cells is quite robust (FIGS. 27 and 28), i.e. the NKX6.1 staining is bright, and also often brighter than that observed in the non-endocrine multipotent pancreatic progenitor sub-population. Thus, NKX6.1 expression appears to be predominantly co-expressed with C-peptide (or insulin) expressing cells. The mRNA (Nanostring) and protein (ICC) data combined also demonstrate that in certain contexts there can be a limit to using just one methodology to initially characterize a cell type. Thus, the ICC data demonstrated that BMP alone or in combination with TTNPB at stages 6 and 7 or stage 7 alone was capable of increasing the levels of PDX1 and NKX6.1 in C-peptide (or insulin) expressing cells (FIG. 27 and FIG. 28). The strongest effect is observed when the two factors are used in combination, but BMP alone is also capable of the same. TTNPB may also be independently regulating PDX1 and NKX6.1. For example, TTNPB treatment for fewer days e.g. 2, 3, or 4 days during stage 7 was capable of inducing expression of NKX6.1 without BMP present (data not shown). Hence, use of these growth factors, in particular for TTNPB, may be time dependent.

Referring specifically to nicotinamide, FIG. 29 shows that nicotinamide in stage 6 culture conditions increases INS and decreases GCG expression, resulting in a 3 fold increase in the INS/GCG expression ratio. Function of nicotinamide is unclear but it has been reported that nicotinamide prevents beta cell loss in rodents resulting from streptozotocin treatment, by inhibition of PARP-1, poly (adenosine triphosphate [ADP]-ribose) polymerase-1, and by preventing NAD+ depletion. See Masiello, P. et al. (1998) Experimental NIDDM Development of a New Model in Adult Rats Administered Streptozotocin and Nicotinamide, *Diabetes*, 47(2):224-9. Nicotinamide can also increase endocrine differentiation and insulin content in human fetal islets. See Otonkoski T. et al. (1993), Nicotinamide is a potent inducer of endocrine differentiation in cultured human fetal pancreatic cells. *J Clin Invest* 92:1459-1466.

Again, mature beta cells in vivo express high levels of PDX1 and NKX6.1, and high levels of PDX1 and NKX6.1 are necessary for proper function. Therefore, BMP, and BMP in combination with TTNPB, by inducing high expression of both markers in insulin positive cells indicates that, for the first time, it is possible to make endocrine cells which are glucose-responsive not just in vivo but also potentially in vitro.

And as mentioned previously, the days for stages 6 and 7 are not rigid and may be shortened, or even lengthened, and one skilled in the art will recognize this since the 5 and 10 days for stage 6 and 7, respectively, can be easily manipulated; in particular, if substantially the same growth factors are used as described herein and according to Table 17.

Example 14

Matrigel Alone and in Combination with a Rho Kinase Inhibitor Improves Cell Adhesion of PEC and Endocrine Cell Aggregates In Example 11 above, the cell aggregates were dissociated and re-aggregated or re-associated between stage 6 and 7. Dissociation was performed using Accutase on or around day 20 and re-aggregated in rotation culture, substantially as described in Schulz et al. supra. The re-aggregation removes certain PEC sub-populations including any remaining non-endocrine (CHGA−) sub-populations as well as other non-endocrine cells as described in more detail in Kelly et al. (2011), supra. Endocrine cells have affinity for each other, however, this interaction in vitro is relatively weak, even the re-aggregated cells at stages 6/7 were only loosely associated. So, studies were performed to test various factors and agents for their ability to increase the cell-to-cell interactions within the endocrine cell aggregates.

It was discovered that the addition of a Y-27632, a rho-kinase inhibitor, and dilute Matrigel (0.05% v/v) were capable of promoting tighter cell associations of the re-aggregated endocrine cell aggregates. The combination of Y-27632 and Matrigel increased at least for example the cell-to-cell interaction of the cell aggregates over either component alone.

Figures 30A, 30B, 30C, 30D:
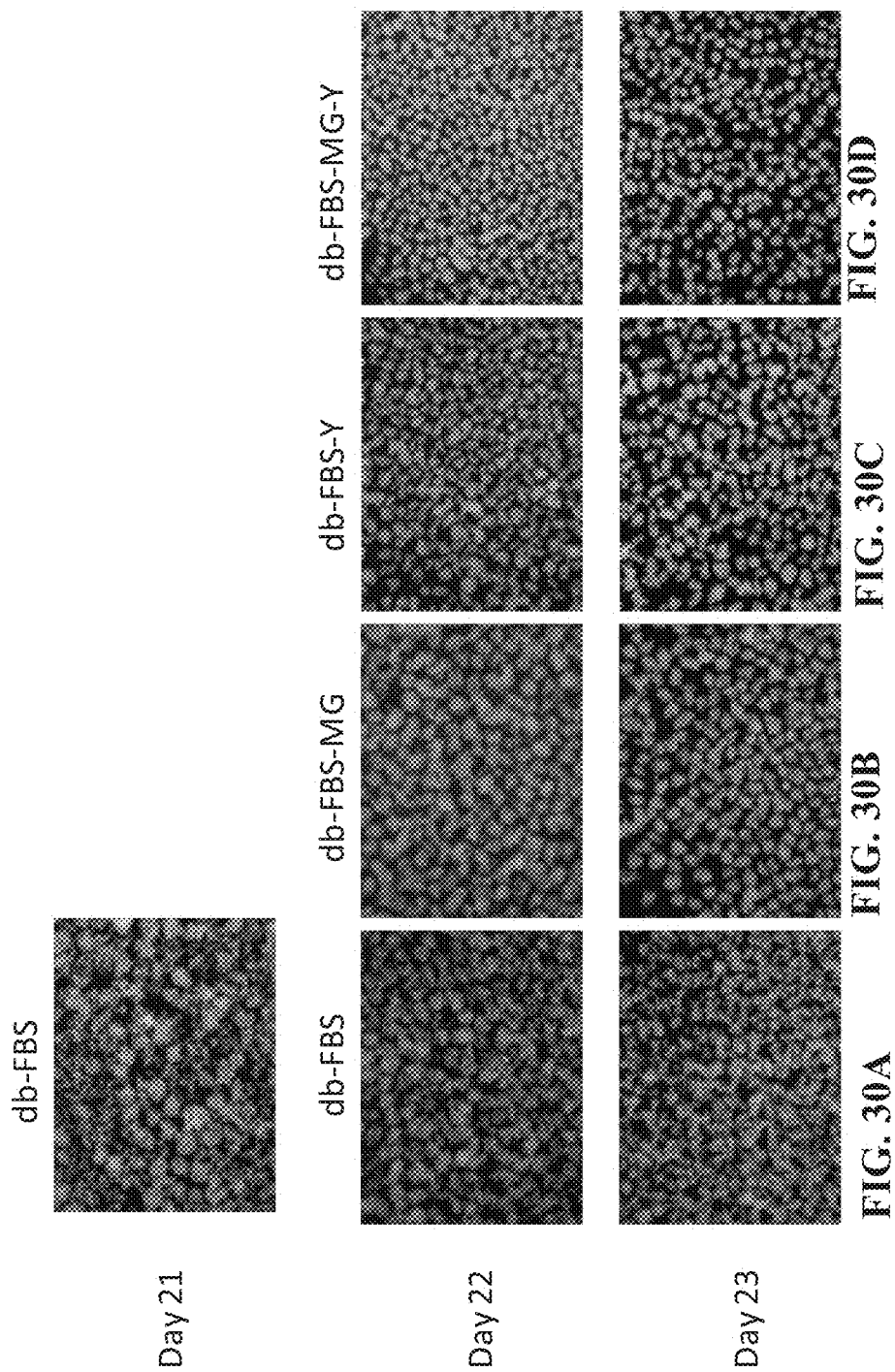
FIGS. 30A-30D shows photographic images (days 21, 22 and 23) of endocrine cell aggregate suspension cultures disassociated and re-aggregated at the beginning of stage 7, followed by the addition of FBS alone, both FBS (panel A) and 0.05% Matrigel (MG; panel B), both FBS and 10 µM Y-27632 (Y; panel C) or all three, FBS, 0.05% Matrigel (MG) and 10 µM Y-27632 (Y; panel D) as described in Example 14.

A differentiated culture produced substantially as described in Example 12, at day 20 was dissociated with Accutase and re-aggregated in db with 5% FBS (lower concentrations of FBS, i.e. 2% or 1% are also effective) and DNAse. Y-27632 was not included in the re-aggregation medium as doing so would result in incorporation of non-endocrine (CHGA−) sub-population as well as other non-endocrine cells into the newly formed aggregates. The following day, and each day thereafter, the cell aggregates were treated with Y-27632 or Matrigel or both components. Stereomicroscope images were taken 1, 2 and 3 days post-aggregation as shown in FIG. 30. FIG. 30 demonstrates that the combination of Matrigel, Y-27632 and db-FBS was the most effective. This combination was more effective than using db-FBS alone or db-FBS and Matrigel or db-FBS and Y-27632 (compare FIG. 30A-D). The cell aggregates using the combined agents appeared morphologically tighter than all the other samples (FIG. 30D). It is likely that the agents improve cell-to-cell contact and interactions between the cells and the matrix; although later experiments in the absence of FBS and just Matrigel and Y-27632 provided the same results. These tighter cell aggregates appear more morphologically like organ tissue. This is advantageous so that the cell aggregates can better withstand the stresses of rotation culture, loading into devices, handling for transplantation, have improved in vitro and in vivo development and maturation, and the like.

Example 15

No Noggin Produces PEC Enriched for the Non-Endocrine Multipotent Progenitor Sub-Population with Limited Endocrine Cell Content and without the Need for Fractionation or Purification of the PEC Population As discussed above, production of a PEC population (stage 4) that is highly enriched for the non-endocrine multipotent pancreatic progenitor sub-population (CHGA−) but relatively replete of cells committed to the endocrine lineage (CHGA+) is desirable. Such cell populations could, for example, be useful to screen for molecules or conditions that specifically induce their differentiation to endocrine lineage cells. Compounds with this activity may be useful for regenerative medicine applications to generate endocrine cells, including pancreatic beta cells either in vivo or ex vivo. Since fractionation and purification of specific cell populations from more complex cell mixtures are known to come with losses of efficiency, due to cell death and other reasons, it is beneficial to be able to make highly enriched cell populations for a desired phenotype through efficient directed differentiation alone, thus not requiring purification steps.

Undifferentiated human ESC were expanded and differentiated substantially as described above in Table 17 Protocol #1 for stages 1-4 and in Schulz et al. (2012) supra, except that during the three (3) days of stage 3, 4 different conditions were compared: (i) 0 noggin ("no noggin") for all 3 days; (ii) 1 day of Noggin at 50 ng/mL and 2 days with no additional Noggin; (iii) 2 days of Noggin at 50 ng/mL and 1 day with no additional noggin; and (iv) 3 days of Noggin at 50 ng/mL. After stage 3, each of these conditions (i) through (iv) then received the standard stage 4 differentiation media cocktail according to Table 8 and Table 17, but without additional Noggin. Flow cytometry analysis after stage 4 demonstrated that no Noggin produced a greater than 90% non-endocrine multipotent pancreatic progenitor sub-population with less than 5% cells committed to the endocrine lineage (CHGA+). See Table 17. Moreover, with each additional day of noggin treatment, fewer non-endocrine multipotent pancreatic progenitor sub-populations were produced (compare 90.6% with no noggin to 64.6% with 3 days of noggin treatment). Conversely, each additional day of noggin treatment increased levels of production of cells committed to the endocrine lineage (CHGA+).

TABLE 18

Increased Duration of Noggin Effects Endocrine to Non-Endocrine Cell Sub-Populations of PEC

|  | CHGA+ (Endocrine) | CHGA−/NKX6.1+ (Non-endocrine) |
| --- | --- | --- |
| No Noggin | 3.4 | 90.6 |
| N50-1day | 11.9 | 82 |
| N50-2day | 25.1 | 71.9 |
| N50-3d | 32.5 | 64.6 |

Figure 31A:
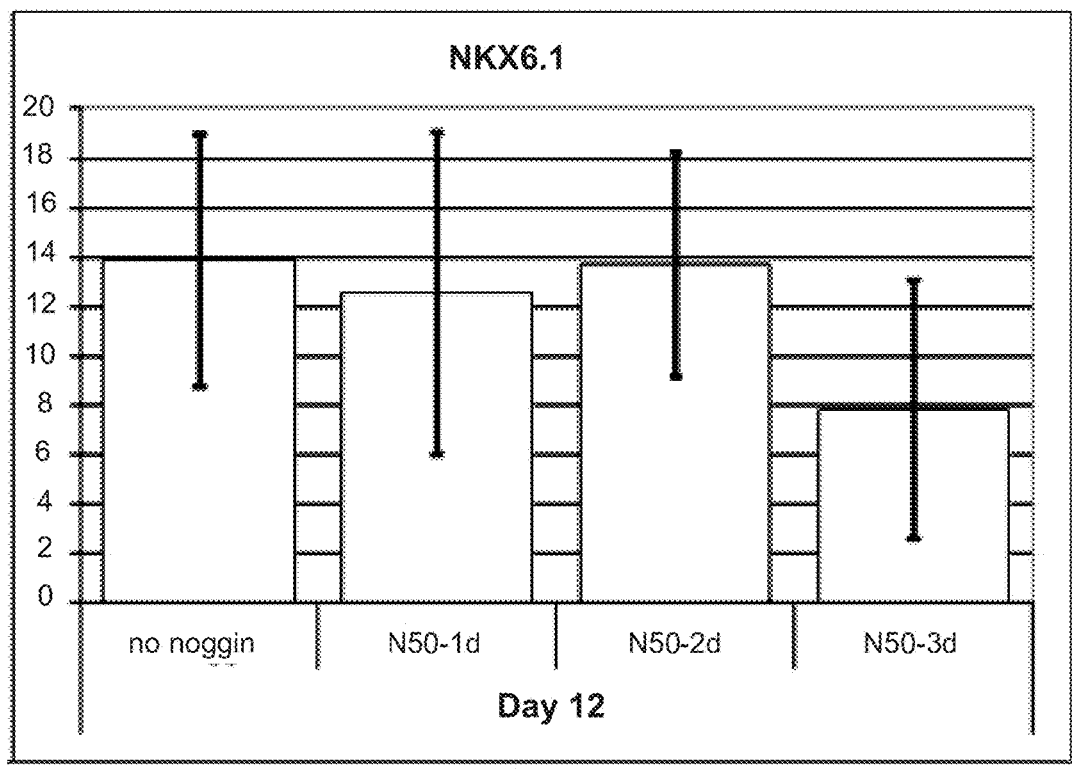
FIGS. 31A-31D are bar graphs showing the relative gene expression levels of NKX6.1 (FIG. 31A), NKX2.2 (FIG. 31B), PDX1 (FIG. 31C) and INS (FIG. 31D) comparing differentiation conditions with and without Noggin for 1, 2 and 3 days. See Example 15.
Figure 31B:
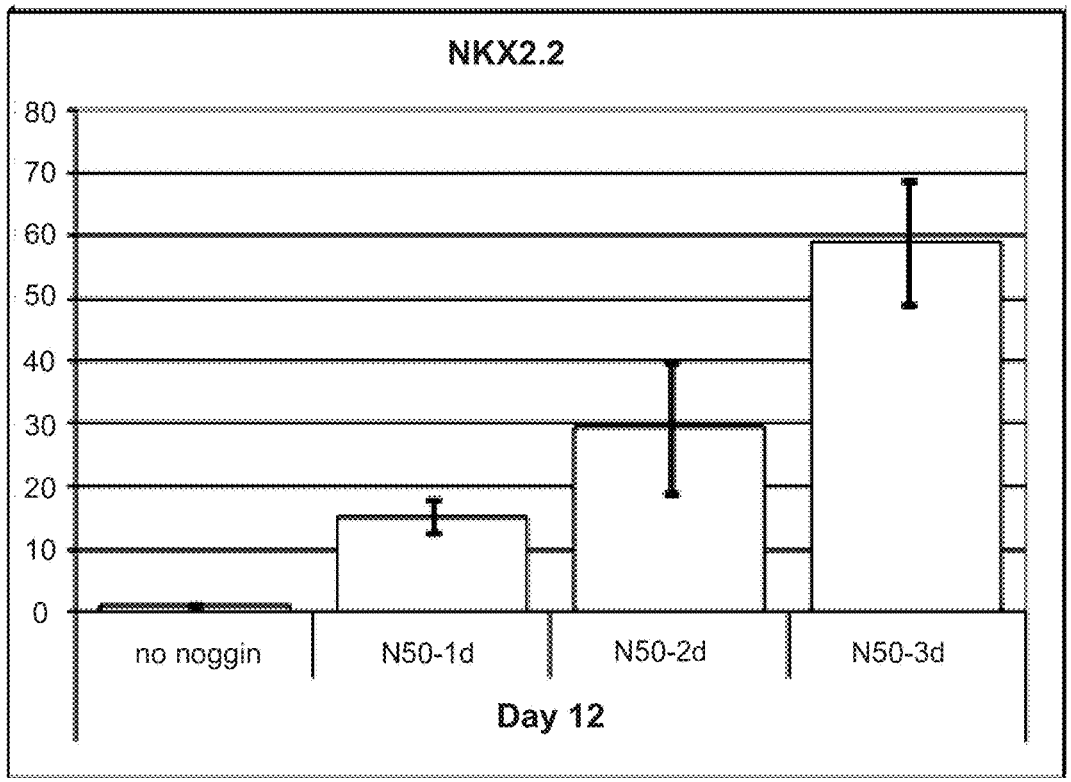
Figure 31C:
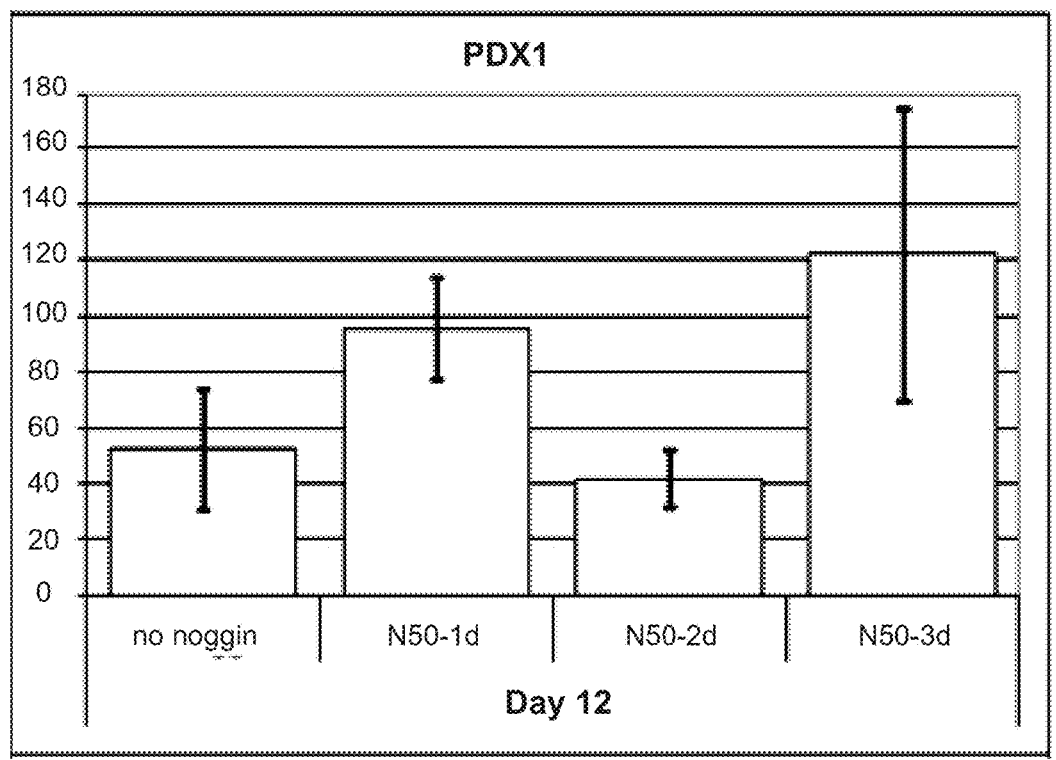
Figure 31D:
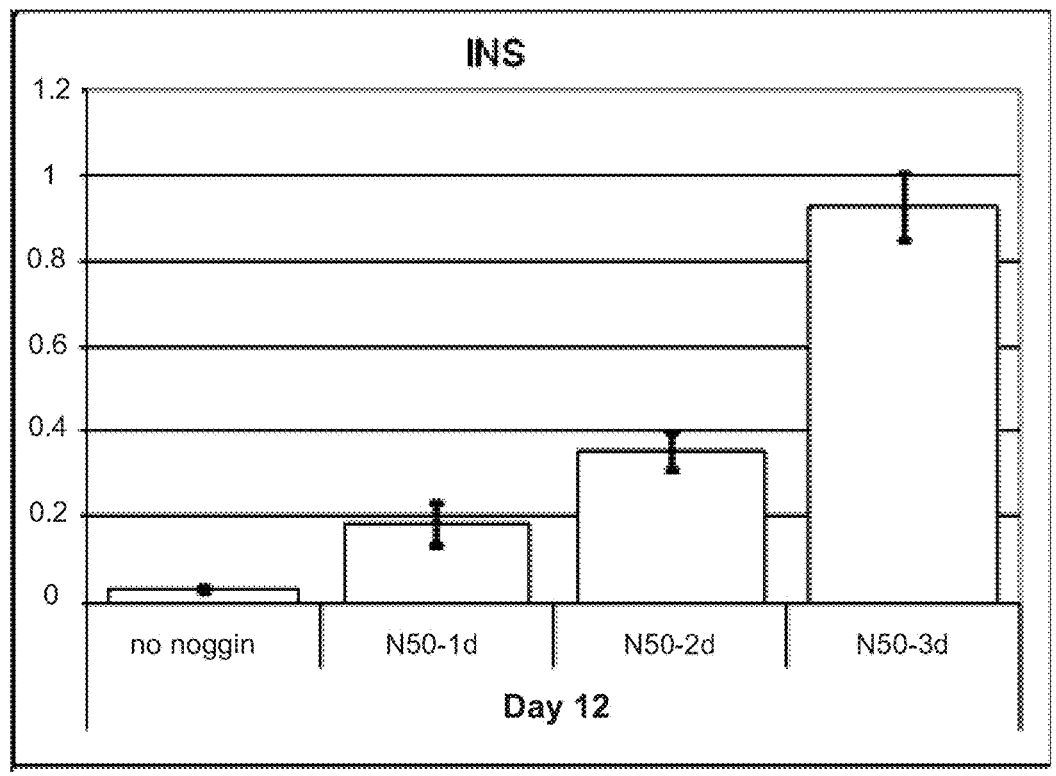

QPCR analysis of cell cultures after stage 4 (day 12) showed that with each additional day of noggin treatment, there was increased levels of endocrine lineage marker expression including NKX2.2 and INS (FIGS. 31B and D), which is consistent with the data from flow cytometry in Table 18. In contrast, the expression level of marker genes for non-endocrine multipotent pancreatic progenitor sub-population including NKX6.1 (and PDX1) were relatively abundant for any time period of noggin treatment.

Example 16

Agents Modulating Expression of Pancreatic Lineage Genes at Stage 7

Figure 32A:
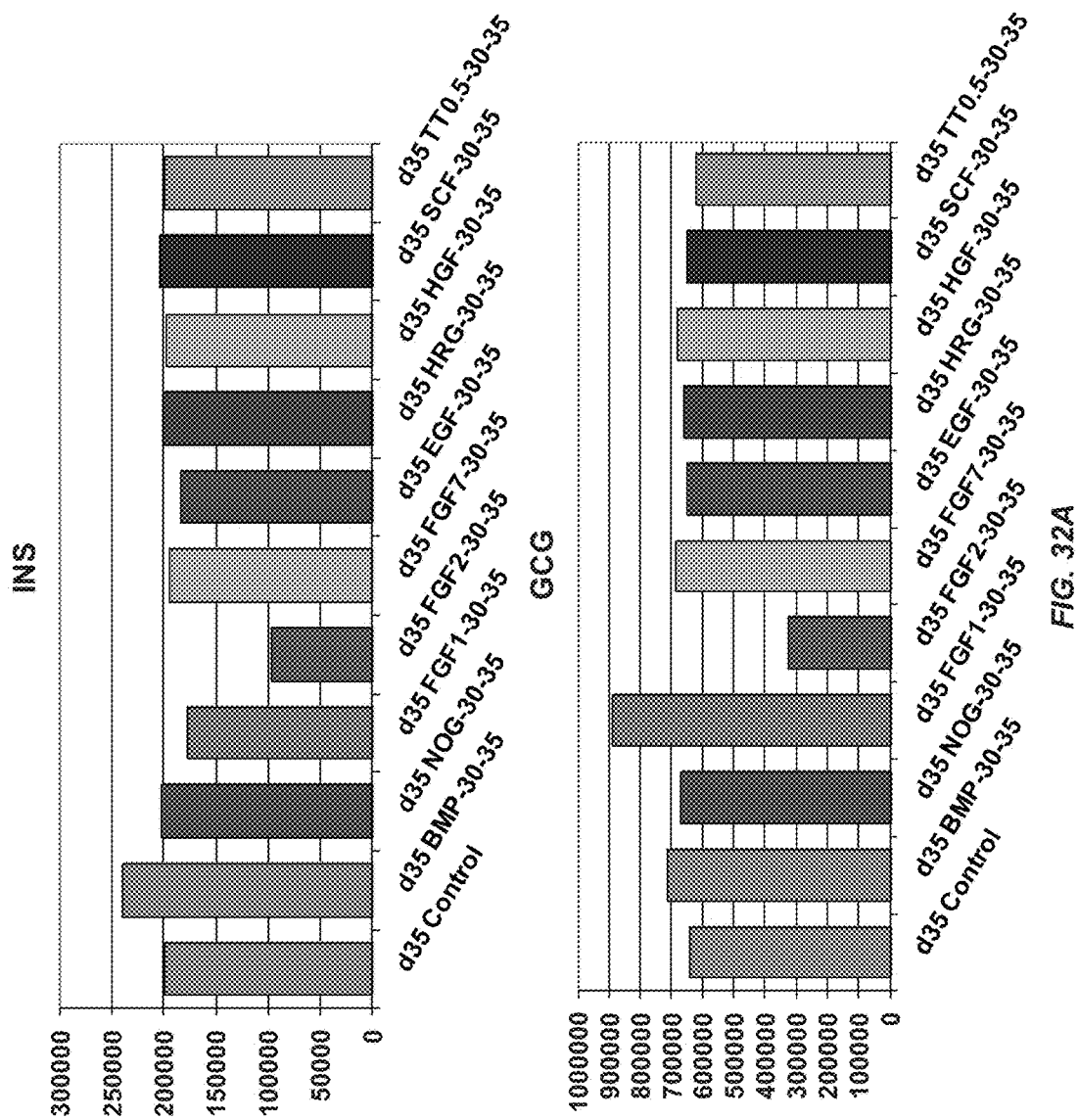
FIGS. 32A-32C are bar graphs showing Nanostring mRNA data of the relative gene expression levels of INS and GCG (FIG. 32A), GHRL and SST (FIG. 32B) and PDX1 and ID1 (FIG. 32C) describing the effect on gene expression by the indicated factors. See Example 16.
Figure 32B:
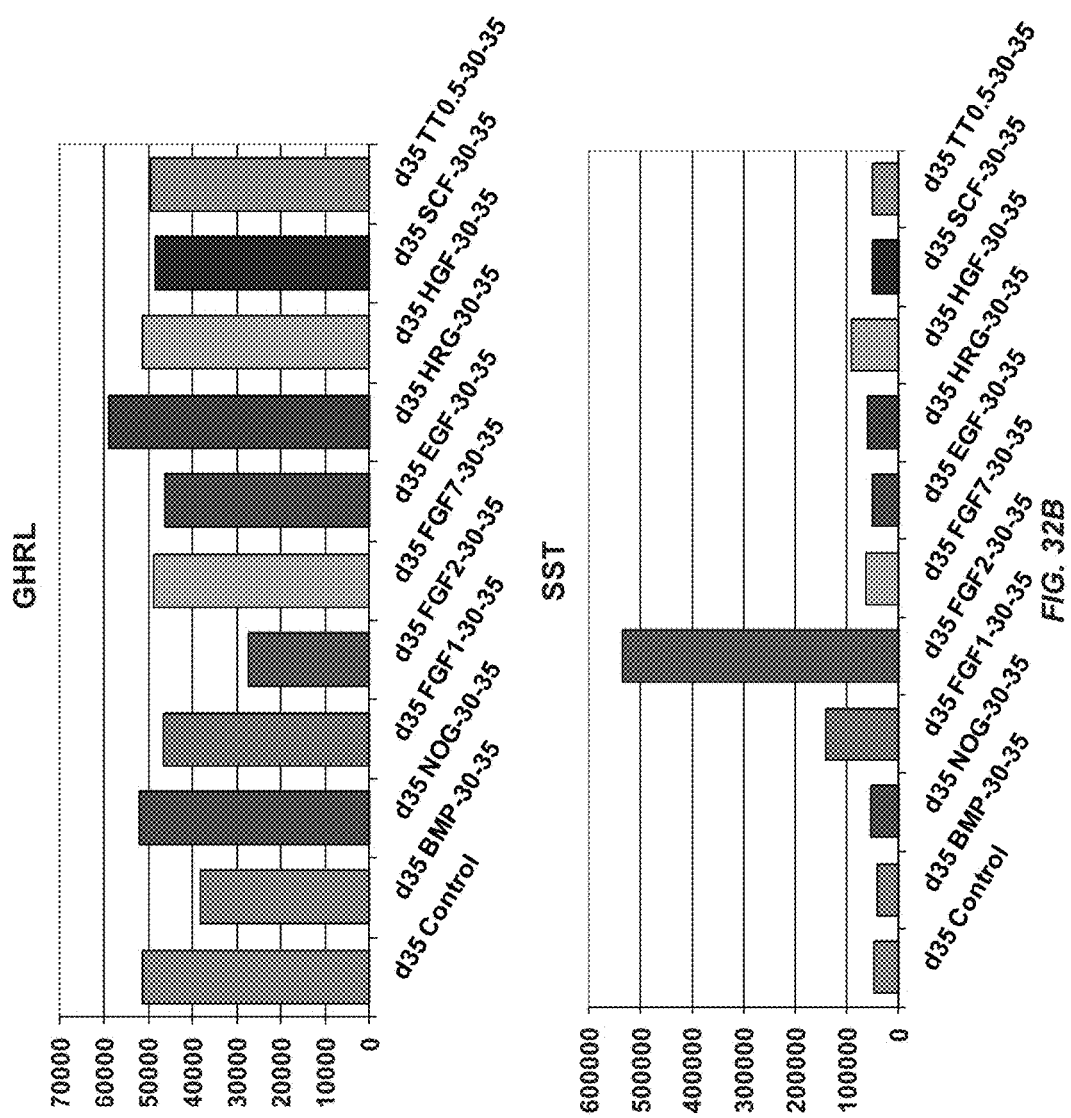
Figure 32C:
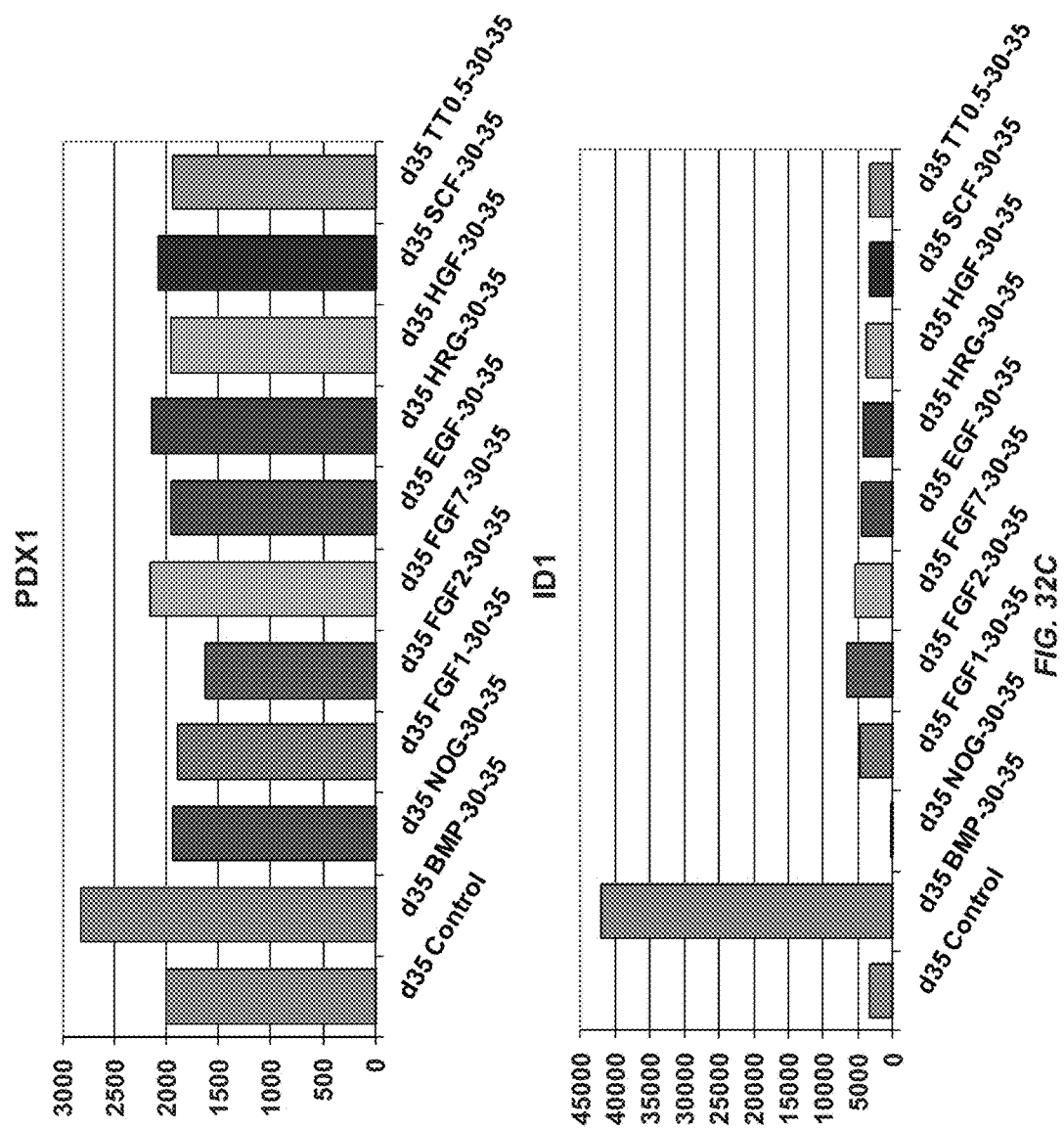

We next evaluated whether there were any additional modulators of pancreatic-lineage gene expression. Methods of differentiation substantially similar to that described in Examples 13 and 14 were performed (i.e. AHW at stage 3, AH at stage 4, gamma secretase and rho-kinase inhibitors at stage 5, Matrigel and rho-kinase inhibitor at stages 6 and 7). In addition, other agents were tested for their ability to modulate gene expression including BMP, Noggin, FGF1, FGF2, FGF7, EGF, Hrg, HGF, SCF, or TTNPB at days 30-35, during stage 7. RNA expression was analyzed by Nanostring at the end of an extended stage 7 (d35). FIGS. 32A-32C show that BMP increases expression of INS, PDX1 and IDI, consistent with data shown in FIG. 24 and described in detail in Example 13. BMP also decreased GHRL expression. FGF1 (acidic FGF) upregulated GCG and SST. Surprisingly, FGF2 at days 30-35 of stage 7 resulted in a significant increase in SST expression with the concomitant inhibition or suppression of the other hormone genes (e.g., INS, GCG, GHRL; FIG. 32B, SST panel).

These studies demonstrate that certain agents can still modulate and affect gene expression, and therefore cell culture differentiation and resulting cell type of these more differentiated/committed cells.

Example 17

Dissociating and Re-Aggregating Cell Cultures Reduces Non-Endocrine (CHGA−) and Increases Properly Specified Endocrine (CHGA+) Sub-Populations It was previously noted that dissociating and re-aggregating cell cultures may effectively deplete or reduce the presence of certain sub-populations of cells when re-aggregated and, as a consequence, re-aggregation can be used to enrich certain sub-populations of cells. Studies were designed to determine the effects, if any, of re-aggregated cell cultures with their enriched sub-populations, in this instance, endocrine (CHGA+) sub-populations. (see Example 14).

Figure 33A:
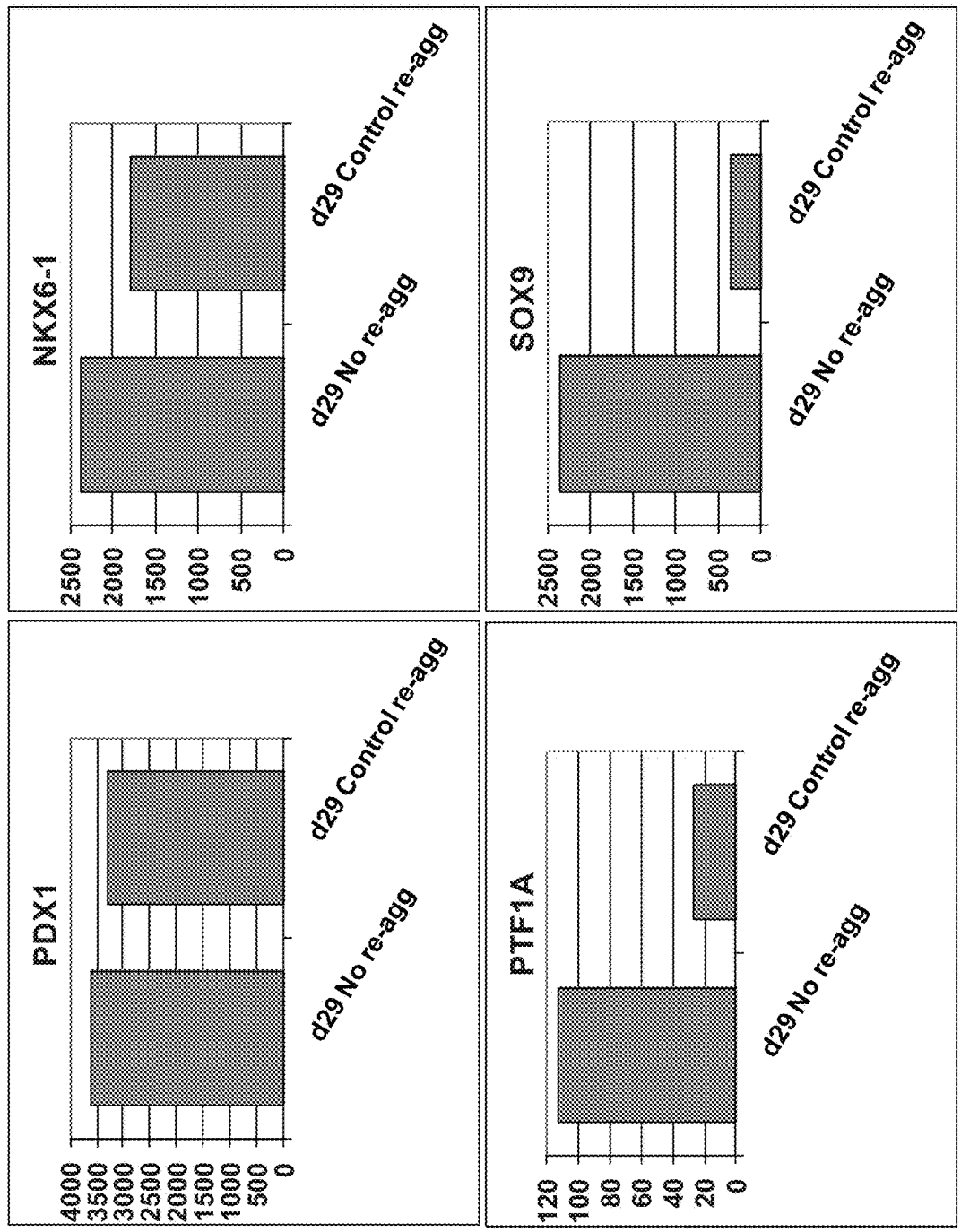
FIGS. 33A-33C are bar graphs showing Nanostring mRNA data of the relative gene expression levels of PDX1, NKX6.1, PTF1A, SOX9 (FIG. 33A); INS, GCG, PPY, GHRL (FIG. 33B) and PCSK1, GCK, SLC30A8, G6PC2 (FIG. 33C) describing endocrine (CHGA+) sub-populations and non-endocrine (CHGA−) sub-populations in re-aggregated as compared to non-reaggregated cultures. See Example 17.
Figure 33B:
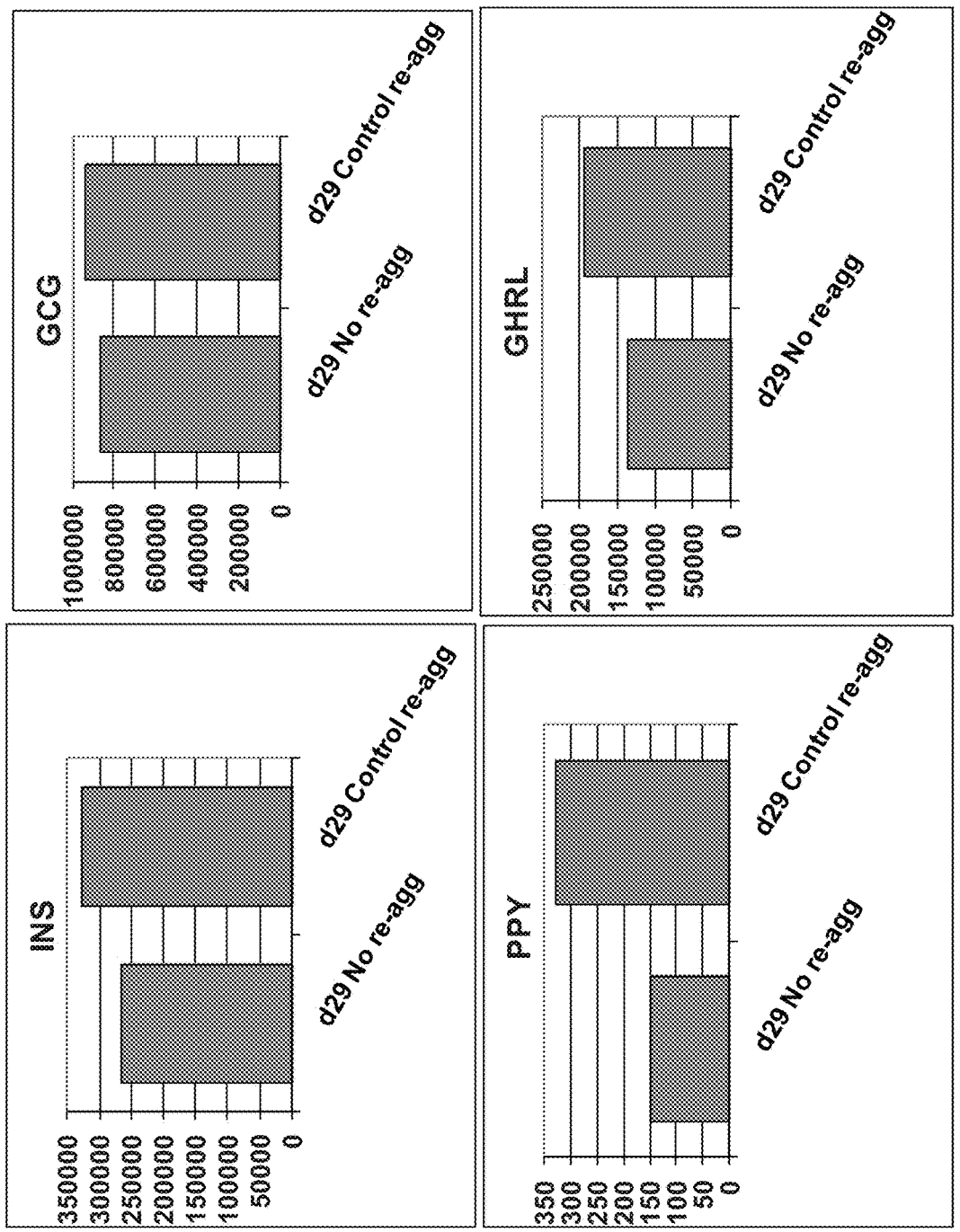
Figure 33C:
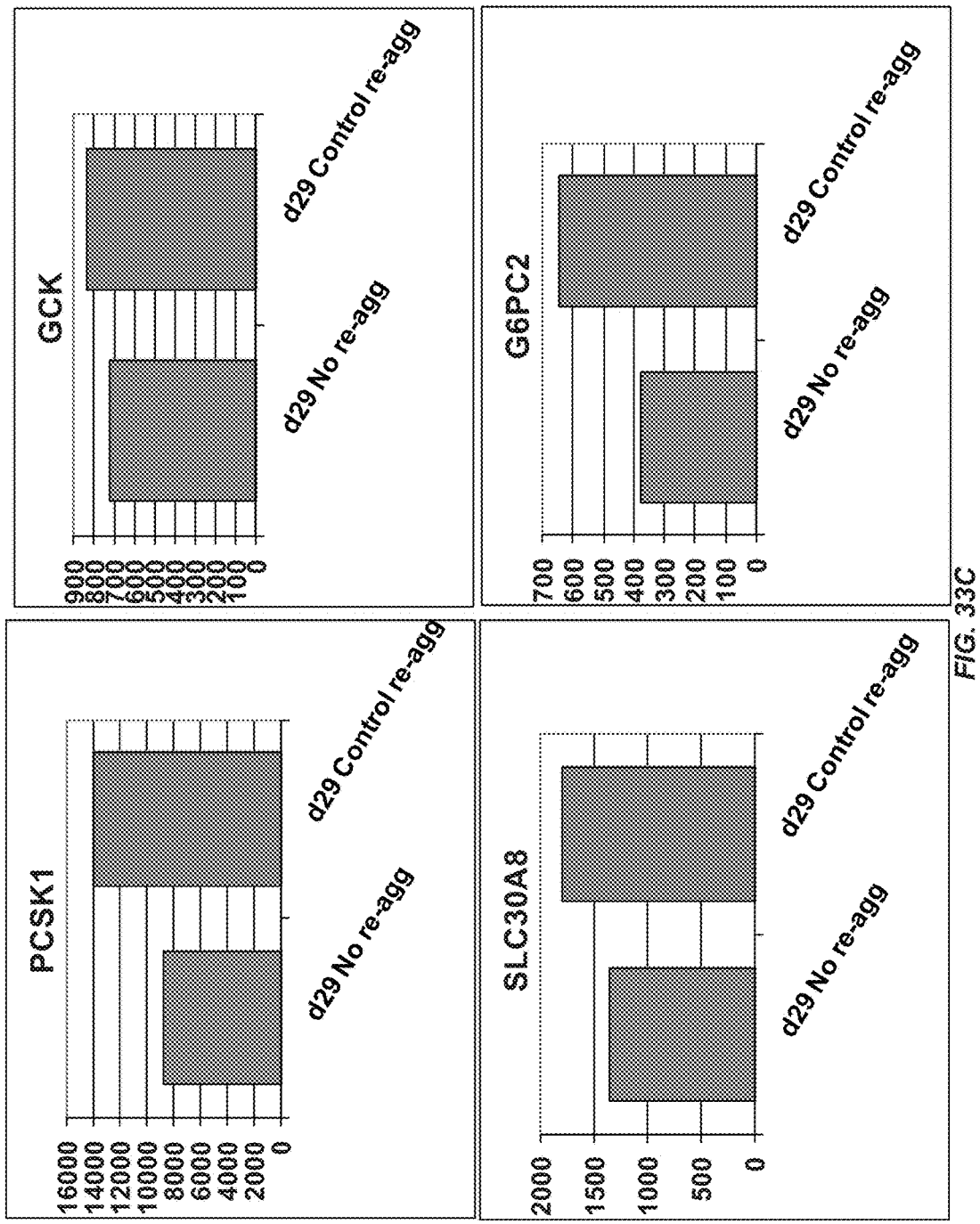

Methods of differentiation were substantially similar to that described in Example 14 including disassociation and re-aggregation of hES-derived cell aggregates prior to stage 7 (d20). FIGS. 33A-33C shows RNA analysis after stage 7 (about d29) demonstrating that non-endocrine (CHGA−) sub-populations were significantly diminished in re-aggregated cell cultures as demonstrated by Nanostring analysis using a combination of markers including PTF1A, SOX9, PDX1 and NKX6.1 (FIG. 33A). FIG. 33B also shows that re-aggregation resulted in an increase in endocrine and pancreatic islet cell markers including INS, GCG, pancreatic polypeptide (PPY), GHRL, solute carrier family 30 member 8 (SLC30A8), Glucose-6-phosphatase 2 (G6PC2), prohormone convertase 1 (PCSK1) and glucokinase (GCK).

Alone, these markers are observed in other cell types, for example, PTF1A is also expressed in exocrine cells, SOX9 in ductal cells, PDX1 and NKX6.1 in beta cells. So, Applicants obtained data from various PE, endocrine and islet markers as a reference to determine the significance of any one marker expression. And, although four PE and non-endocrine (CHGA−) markers were assayed (PTF1A, SOX9, PDX1 and NKX6.1), only PTF1A and SOX9 sub-populations were depleted from the re-aggregated cell cultures at the end of stage 7 (about d25, d26, d27, d28, d29, d30 and more). In contrast, PDX1 and NKX6.1 expression, which are also observed in beta cells and pancreatic endocrine, remained high after stage 7. See FIG. 33A.

Similarly, other endocrine (e.g. beta and alpha cells) markers including SLC30A8, G6PC2, PCSK1 and GCK were observed at higher expression levels in the d20 re-aggregated cell cultures as compared to those cultures which were not dissociated and re-aggregated (or "no-reagg"). See FIG. 33C. SLC30A8, for example, is a zinc transporter related to insulin secretion and certain alleles of SL30A8 may increase the risk for developing Type 2 diabetes; Glucose-6-phosphatase 2 (G6PC2) is an enzyme found in pancreatic islets; prohormone convertase 1 (PCSK1), along with PCSK2, processes proinsulin to insulin in pancreatic islets; and finally glucokinase (GCK) facilitates phosphorylation of glucose to glucose-6-phosphate and is expressed in cells in the liver, pancreas, gut, and brain where it regulates carbohydrate metabolism by acting as a glucose sensor, triggering shifts in metabolism or cell function in response to rising or falling levels of glucose, such as occur after a meal or when fasting. Mutations of GCK can cause unusual forms of diabetes or hypoglycemia. The increased expression of these markers at stage 7 indicates that disassociating and re-re-aggregating the cell cultures effectively depletes or reduces the non-endocrine (CHGA−) sub-populations, and increases the endocrine (CHGA+) sub-populations. Thus, Applicants have now further refined a method that produces properly specified endocrine cells in vitro for in vivo function.

Flow cytometry analysis of stages 1-7 cell cultures also confirms that disassociating and re-aggregating cell cultures as above increases the total endocrine sub-populations (enrichment of CHGA+ cells) with the concomitant decrease of the non-endocrine (CHGA−) sub-populations or PE sub-population of cells. See Table 19 below.

TABLE 19

Re-aggregated cell cultures increase total endocrine
(CHGA+) and decrease non-endocrine
(CHGA−) sub-populations after Stage 7

|  | Total Endocrine (CHGA+) | CHGA− NKX5.1+ PDX1+/− | CHGA− NKX6.1− PDX1+ |
|---|---|---|---|
| Stg7 No re-agg | 87.1 | 10.7 | 2.2 |
| Stg7 Re-agg | 98.2 | 1.45 | 0.63 |

To date, functional beta-cells can only be differentiated through an in vivo transplantation step, and a bona fide functional beta-cell fully in vitro has yet to be described. See Zhou, et al. (2008), *Nature* 455, 627-632. Thus, for the first time Applicants have demonstrated a greater than 50% in vitro cell population of endocrine cells (CHGA+) having less than 10% non-endocrine cells (CHIGA−) and are properly specified. And such cells are capable of developing and maturing into bona fide functional beta cells and islets in vivo; see Example 18 below.

Example 18

In Vivo Insulin Production from Endocrine (CHGA+) Sub-Populations

As a follow-on study to Example 17, studies were designed to determine the in vivo effects, if any, of re-aggregated cell cultures with their enriched endocrine (CHGA+) sub-populations.

Human pluripotent stem cell cultures were expanded and differentiated substantially similar to that described above in Examples 12-14 and 16 and in Schulz et al. (2012), supra, except that at about the start of stage 7 (about d20) cultures were pooled and separated into 2 samples: 1) cell aggregates were dis-associated and re-aggregated ("re-aggregated cell culture"); and 2) cell aggregates that were not disassociated and re-aggregated (the control). Further, both samples further included BMP, RA or an RA analog, TTNPB, and a rho-kinase inhibitor and 0.05% Matrigel during stage 7 (d20 to d28 cell cultures). Before samples were transplanted, samples were taken for Nanostring and flow cytometry analysis (Table 19 above). Table 19 shows that the re-aggregated cell culture at about d29 contained about 11% more endocrine (CHGA+) sub-populations than the control. Importantly, the re-aggregated sample contained 9.25% fewer non-endocrine (CHGA−) or PE type cells (only 1.45%) than the samples which were not re-aggregated.

The two samples were separately loaded into and encapsulated in Applicant's semi-permeable, biocompatible, ENCAPTRA® EN20™ drug delivery devices (an animal size research device) and transplanted subcutaneously substantially as described in Example 10 above into a total of 10 SCID-Beige mice (5 animals received re-aggregated cell culture; 5 animals received control cell cultures).

Figure 34:
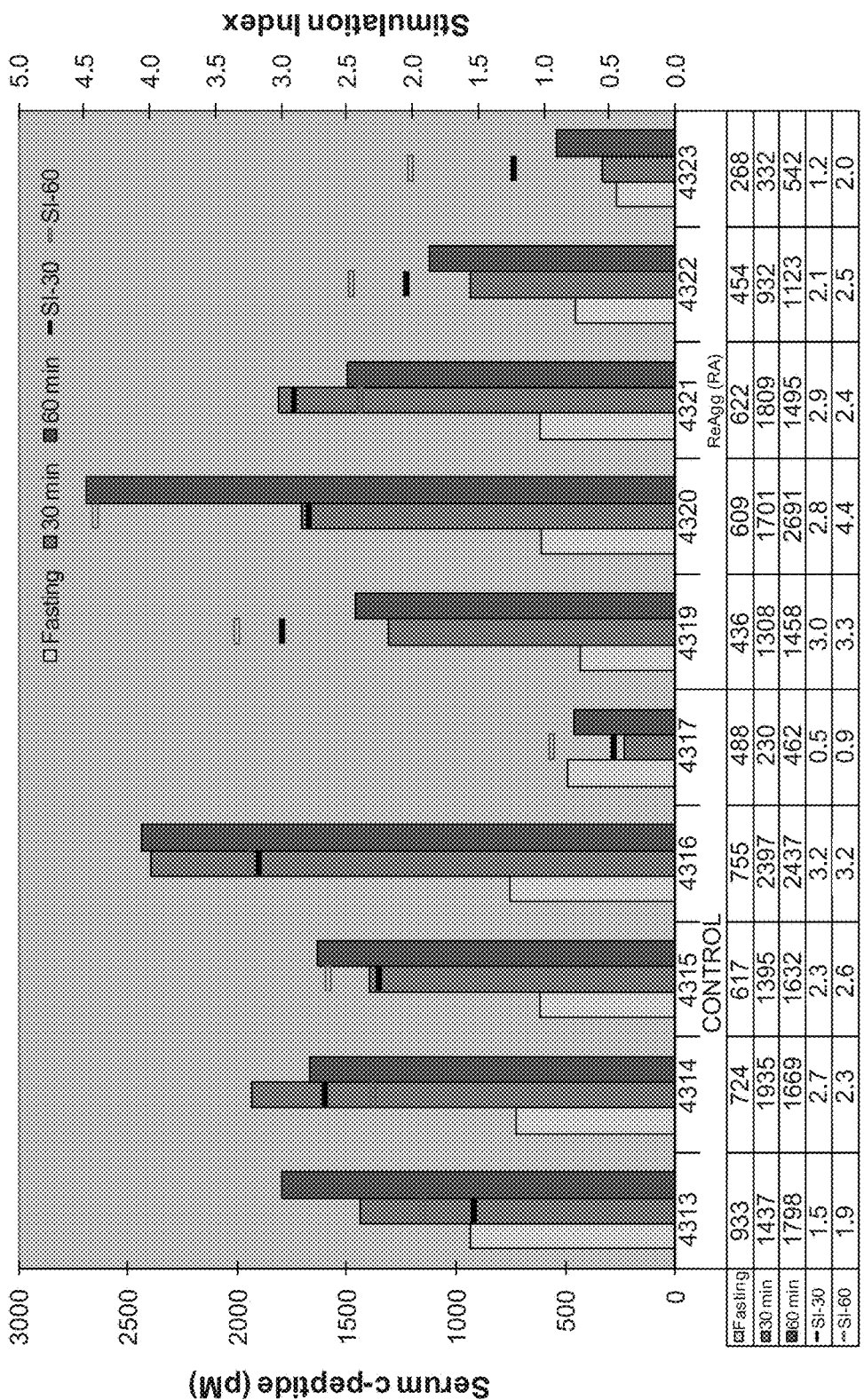
FIG. 34 is a graph showing the concentrations of human C-peptide in sera of mice implanted with encapsulated endocrine cells made as described in Example 18 whereby endocrine (CHGA+) cell types were enriched by dissociation and re-aggregation at the start of stage 7 (re-agg sample) and compared to cells differentiated in the same manner but not re-aggregated (control sample). Expression levels were analyzed 21 weeks post-engraftment at fasting, 30 min, and 60 min after intraperitoneal glucose administration. See Example 18.

FIG. 34 shows that after 21 weeks post-transplant, or in-life, the serum human C-peptide levels after fasting (first of three bars from the left for each animal), thirty-minutes (30'; second bar) and one hour (60'; third bar) following glucose administration or challenge. At 21 weeks post-implant, all but two animals (Animal No. 4317 and 4323; one from each cohort) produced robust levels of insulin as observed by mostly greater than 932 to 2691 pM of human sera C-peptide. However, when the stimulation indices are compared between the two groups (the difference between the 30' or 60' C-peptide serum level to that over the fasting serum C-peptide level) there was no significant difference in the in vivo function between the re-aggregated cell culture and Control cohorts. So, whether the transplanted cultures or grafts consisted of about 98% endocrine/CHGA+re-aggregated cell culture or about 87% endocrine/CHGA+(Control) both appear to have in vivo function. Thus, Applicants have demonstrated for the first time that an in vitro endocrine (CHGA+) cell population (a properly specified endocrine cell) can give rise to physiologically functional insulin secreting cells when implanted.

Thus, for the first time, Applicants have demonstrated that an in vitro population of properly specified endocrine cells, which when transplanted develop and mature to functional pancreatic islet cells that secrete insulin in response to blood glucose. Further, the in vivo function is similar to that previously described by Applicant for PEC and reported in Schulz et al. (2012), supra. Further, it appears that so long as the properly specified endocrine cells were made by the methods described herein via stages 1-7, additional enrichment of endocrine cells (or depletion of non-endocrine cells) via disassociation and re-aggregation is not necessary or required for in vivo function. These aspects of the invention have never been demonstrated up until now. Up until now, Applicants and others had only demonstrated in vivo function using a pancreatic progenitor population cell population and not an endocrine cell population. Indeed, as described in Kelly et al. (2011) supra shows that the endocrine (CHGA+) sub-populations of PEC or pancreatic progenitor preparations did not give rise to in vivo function.

Example 19

Complex Base Media for Culturing Endocrine Cells

Complex base media such as CMRL and RMPI are widely used for culturing islet cells and preserving islet cell mass. CMRL media is typically more complex (more components or ingredients) than RPMI. And both CMRL and RMPI are more complex than DMEM, a commonly used and less complex medium for cell culture. Thus, Applicants explored whether such complex base media would be beneficial to maintain endocrine cells during the later stages of differentiation, for example, stages 6 and 7.

Islet transplantation requires culturing and engraftment of islets with adequate islet cell mass and minimal toxicity. Short-term islet culture has been linked to rapid degradation, and loss of viability and glucose control. See, S. Matsumoto, et al. (2003), A comparative evaluation of culture conditions for short-term maintenance (<24 hr.) of human islets isolated using the Edmonton protocol, *Cell Tissue Banking*, 4, p. 85; and N. J. M. London, et al. (1998), Isolation, Culture and Functional Evaluation of Islets of Langerhans, *Diabetes & Metabolism*, 23, 200-207. In 1978, a study by Andersson et al. (1978) compared the effectiveness of TCM, RPMI, CMRL, DMEM and Hams F10 for culturing mouse islets. See Andersson A. (1978) Isolated mouse pancreatic islets in culture: Effects of serum and different culture media on the insulin production of the islets, *Diabetelogia*, 14, 397-404. Andersson's results showed that Ham's F10 provided for islet cultures with the most insulin content, but that RMPI provided for cultures with the best insulin biosynthesis rate; and that this was possibly due to the high glucose and nicotinamide in the media. Still other investigators such as Davalli et al. (1992) showed that TCM with adenosine phosphate and xanthine were better for culturing porcine islets than CMRL and RMPI. See Davalli, A. M. et al. (1992), In vitro function of adult pig islets: Effect of culture in different media, *Transplantation,* 60, 854-860. Davalii et al. further suggested that the high glucose found in Ham's F10 and RMPI were possibly toxic to the porcine islets. Hence, islets from different species may have different culture requirements and there is no one formula suitable for all endocrine and islet cells. See Andersson (1978), p. 4 supra.

Table 20 below describes only those components found in CMRL, RPMI and DMEM media which vary between each of the media types, i.e. Table 20 does not list those components shared in all 3 types of base media, but only listing those components which are contained in CMRL but not contained in RPMI and/or DMEM. Table 20 shows that CMRL is the most complex (greatest number of components) and DMEM is the least complex (the least number of components). Y, indicates presence of that component in that base media; and N, indicates the component is not present in the media. In brief, DMEM is lacking about 7 components (N, shaded boxes) which are present in CMRL and RPMI.

TABLE 20

Comparison of CMRL, RPMI and DMEM cell culture media

| CMRL (cb) | RPMI | DMEM (db) |
|---|---|---|
| Amino Acids | | |
| Hydroxy L-proline | Y | N |
| L-Alanine | N | N |
| L-Aspartic acid | Y | N |
| L-Cysteine hydrochloride-H2O | N | N |
| L-Glutamic Acid | Y | N |
| L-Proline | Y | N |
| Vitamins | | |
| Ascorbic Acid | N | N |
| Biotin | Y | N |
| Cholesterol | N | N |
| Nicotinic Acid (Niacin) | N | N |
| Para-Aminobenzoic Acid | Y | N |
| Pyridoxal hydrochloride | N | N |
| Inorganic Salts | | |
| Sodium Phosphaye monobasic (NaH2PO4—H2O) | N | Y |
| Other Components | | |
| 2'Deoxyadenosine | N | Y |
| 2'Deoxycytidine | N | N |
| 2'Deoxyguanosine | N | N |
| 5-Methyl-deoxycytidine | N | N |
| Co-carboxylase | N | N |
| Coenzyme A | N | N |
| Diphosphopyridine nucleotide (NAD) | N | N |
| FAD (flavin adenine dinucleotide) | N | N |
| Glutathione (reduced) | Y | N |
| Sodium acetate-3H2O | N | N |
| Sodium glucuronate-H2O | N | N |
| Thymidine | N | N |
| Triphosphopyridine Nucleotide (NADP) | N | N |
| Tween 80 ® | N | N |
| Uridine 5'-triphosphate | N | N |

Methods for making endocrine cell cultures were substantially similar to that described above except that during stage 6 (d15), or mid stage 7 (d23), or mid stage 7 (d26), or stages 6 and 7 (d15 to d25), DMEM or CMRL base media was used. In addition, some cultures received insulin like growth factor (IGF), nicotinamide (NC), glucose (Glc), and/or a rho-kinase inhibitor (Y-27632).

Figure 35A:
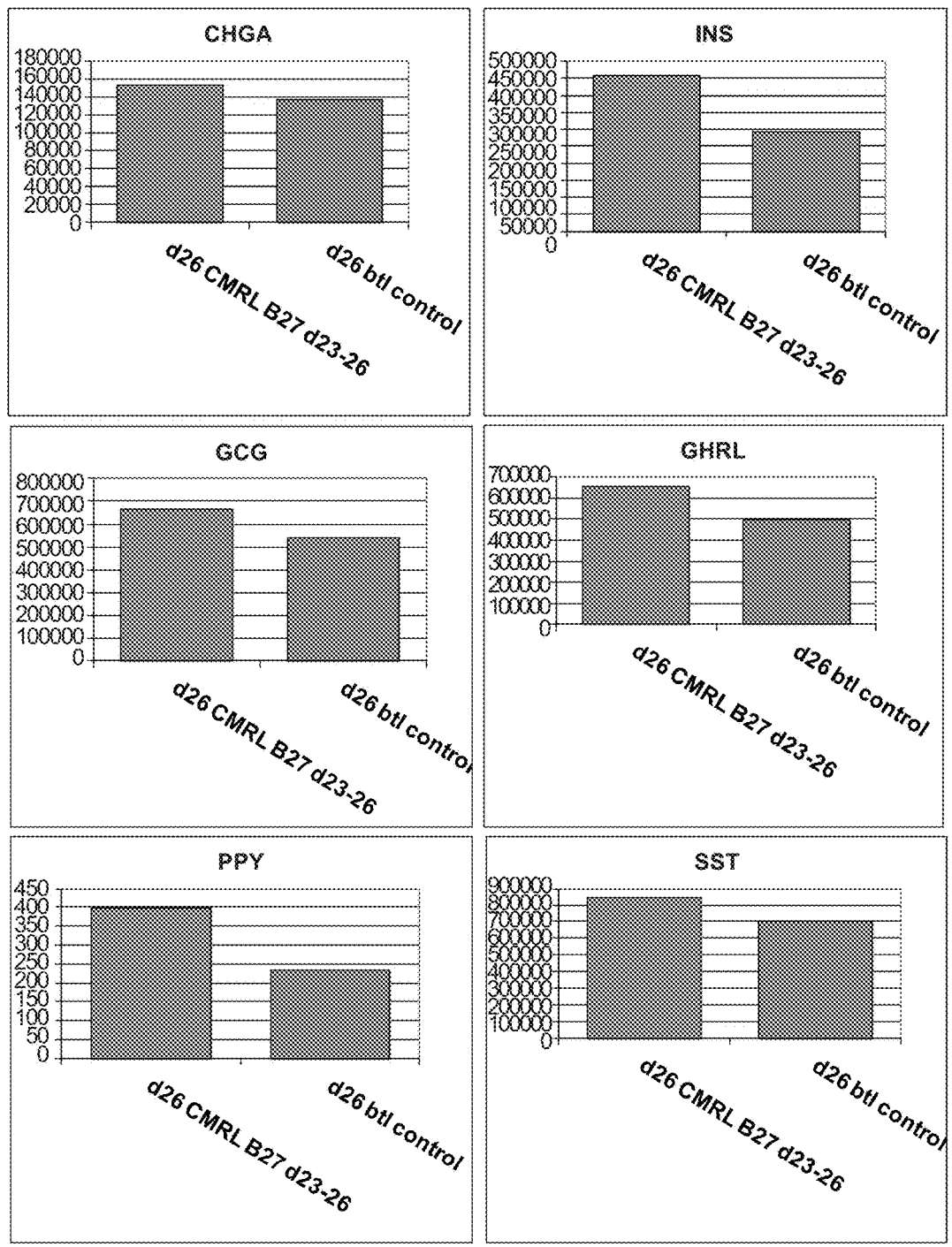
FIGS. 35A-35C are bar graphs showing Nanostring mRNA data of the relative gene expression levels of CHGA, INS, GCG, GHRL, PPY, SST (FIG. 35A); GCK, G6CP2, UCN3, PCSK1 (FIG. 35B); HNF1a, HNF4A, SLC30A8, CADH1 (FIG. 35C) describing the effect of DMEM and CMRL based media during stage 7. See Example 19.
Figure 35B:
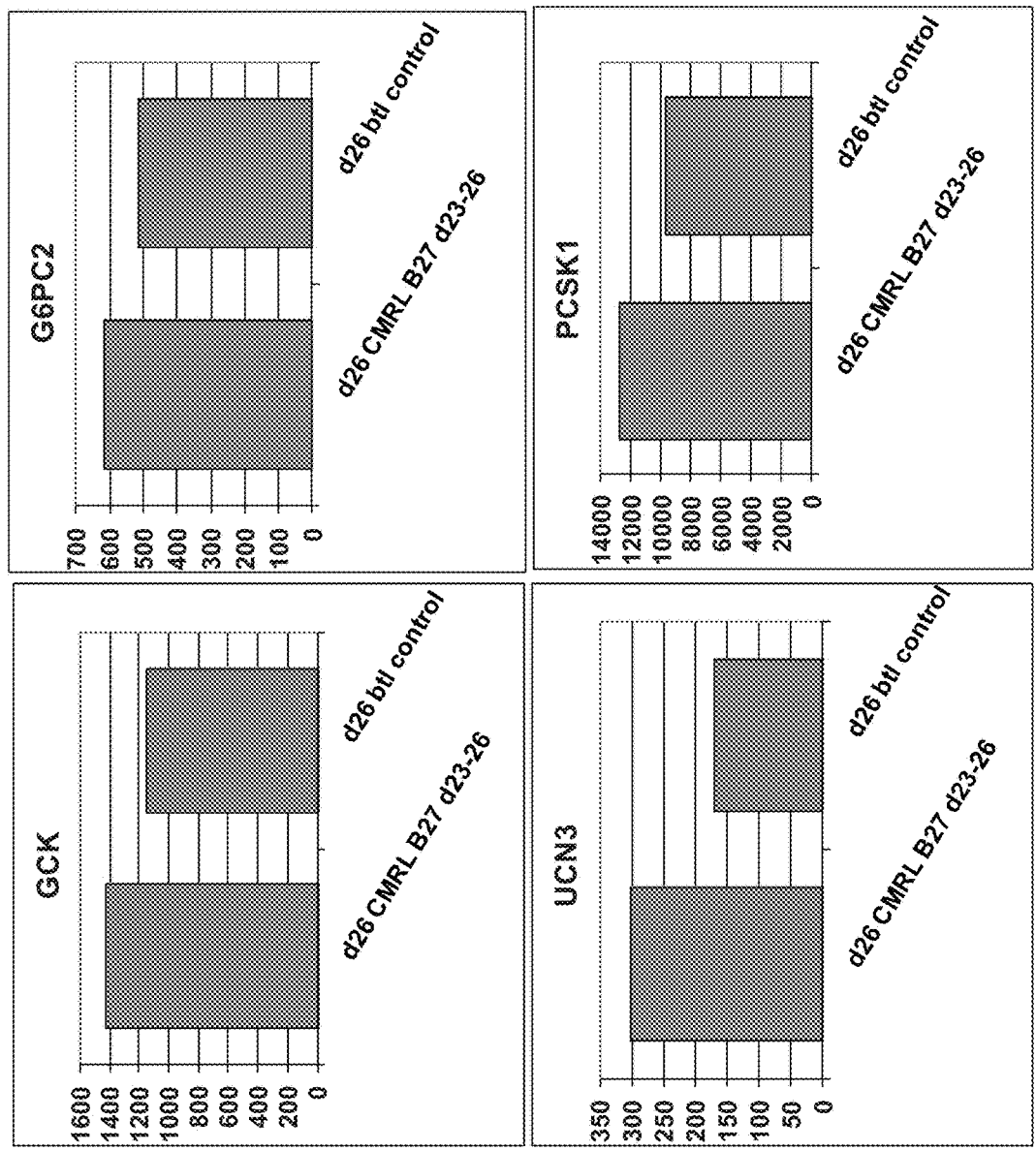
Figure 35C:
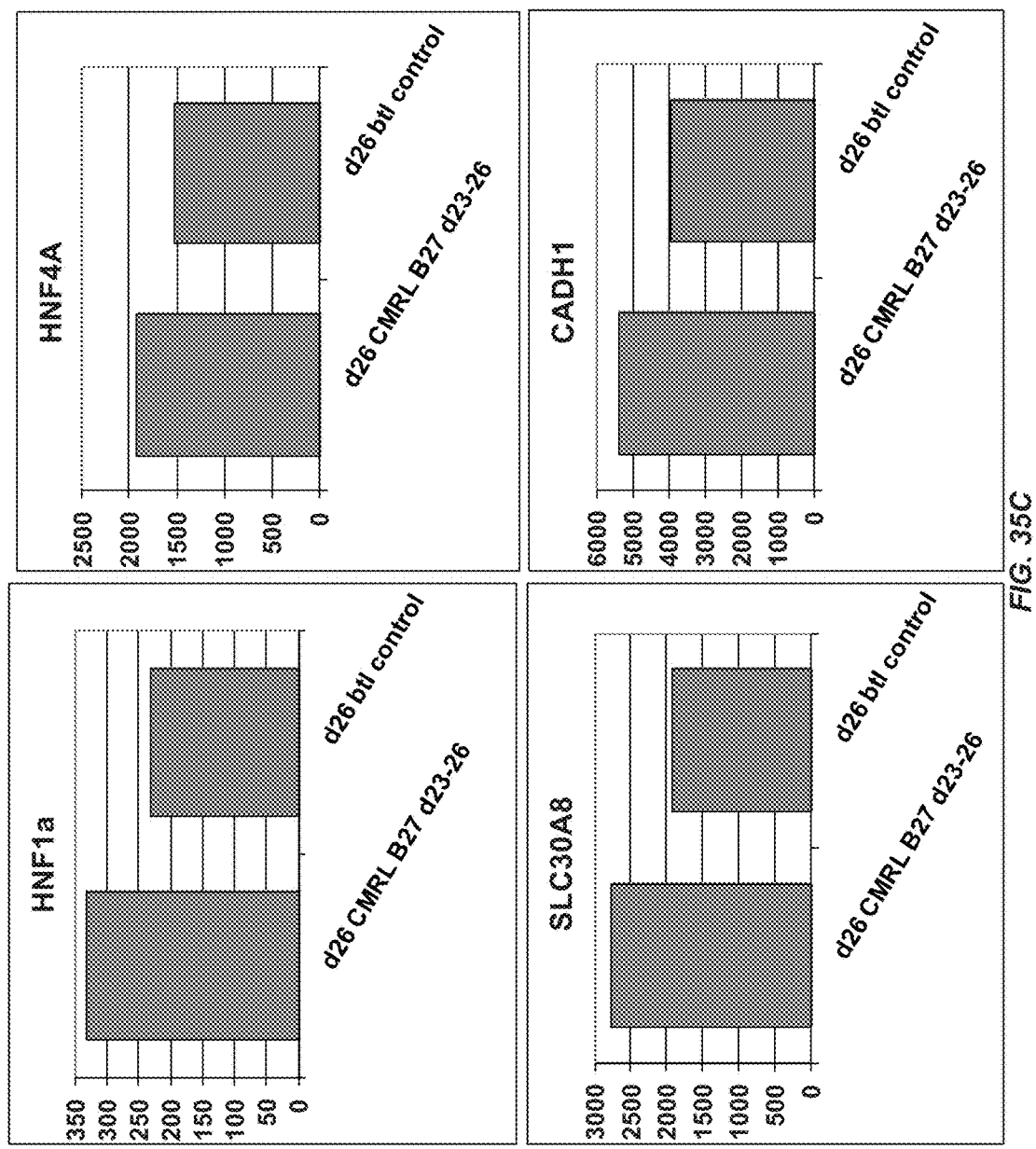

In one experiment, stage 7 cells, starting at about d23, were cultured in either CMRL or DMEM base media with B27 supplement, Matrigel, BMP, IGF and Y-27632. Nanostring analysis of d26 (stage 7) samples showed that, in general, stage 7 cells cultured in CMRL had increased non-specific gene expression of both hormone and pancreatic endocrine markers as compared to the same stage cells when cultured in DMEM. See FIGS. 35A-C. Thus, CMRL may be important for endocrine cell maintenance.

Corresponding studies were also performed using RPMI as compared to DMEM and CMRL-based media (data not shown). CMRL and RMPI medias had similar effects on the cell cultures and both were improved over that of DMEM, thus the component(s) which are not present in DMEM and present in both CMRL and RPMI may be important for endocrine cell maintenance during stage 6 and/or 7 including reduced glutathione, amino acids, hydroxyl-L-Proline, L-Proline, L-Aspartic Acid, L-Glutamic Acid and vitamins, biotin and para-aminobenzoic acid.

Example 20

Cryopreservation does not Reduce Endocrine Cell Numbers

A commercially viable cell therapy will require scale-up manufacturing of the cell product and a means to store the product long term for on-demand patient needs. Hence, any cell product, be it the cells alone or encapsulated cells, such as the ENCAPTRA® drug delivery device, may need to be cryopreserved or have other means for long-term storage without detrimental or toxic effects to the cells; and without affecting the cells' therapeutic effect or in this case in vivo production of insulin in response to blood glucose. Thus, Applicant's explored whether cryopreserved stage 7 endocrine cells maintain their ability to develop and function in vivo similar to that observed for fresh (non-cryopreserved) and cryopreserved PEC as described in detail in Applicant's U.S. Pat. Nos. 8,278,106 and 8,425,928, both titled, ENCAPSULATION OF PANCREATIC CELLS DERIVED FROM HUMAN PLURIPOTENT STEM CELLS, issued Oct. 2, 2012 and Apr. 23, 2013, respectively; and U.S. Application 61/775,480, titled CRYOPRESERVATION, HIBERNATION AND ROOM TEMPERATURE STORAGE OF ENCAPSULATED PANCREATIC ENDODERM CELL AGGREGATES, filed Mar. 7, 2013, and Kroon et al (2008) supra.

Methods for making endocrine cell cultures were substantially similar to that described above except cell cultures were all in CMRL based media during stage 7 and split into the following samples: 1) Not dissociated or re-aggregated but cryopreserved at about day 23 for several hours and then thawed and cultured for several days in CMRL base media with B27 supplement, BMP, TTNPB, and a rho-kinase inhibitor (No re-agg/Cryopreserved); 2) Not dissociated or re-aggregated and not cryopreserved (No-reagg/No cryopreserved); and 3) Dissociated and re-aggregated and not cryopreserved (Re-agg/No cryopreserved). All 3 samples above were cultured in the same stage 7 media conditions. Samples were analyzed by flow cytometry on day 27. See Table 21 below.

TABLE 21

Flow cytometry analysis of cryopreserved, fresh and re-aggregated stage 7 endocrine cells Stage 7 endocrine/non-Endocrine flow cytometry

| Total Endocrine (ChroA+) | ChroA+ Nkx6.1− INS− | ChroA+ NKx6.1− INS+ | ChroA+ NKx6.1+ INS− | ChroA+ Nkx6.1+ INS+ | Total ChroA− | ChroA− Nkx6.1+ INS− | ChroA− Nkx6.1+ INS+ | ChroA− Nkx6.1− INS+ | ChroA− Nkx6.1− INS− |
|---|---|---|---|---|---|---|---|---|---|
| 85.2 | 17.5 | 9.02 | 20.9 | 37.8 | 14.8 | 8.65 | 0.29 | 0.25 | 5.6 |

| Total Nkx6.1+ | ChroA− Nkx6.1+ INS− | ChroA− Nkx6.1+ INS+ | ChroA+ NKx6.1+ INS− | ChroA+ Nkx6.1+ INS+ | Total Nkx6.1− | ChroA+ Nkx6.1− INS− | ChroA− Nkx6.1− INS+ | ChroA− Nkx6.1− INS− | ChroA+ NKx6.1− INS+ |
|---|---|---|---|---|---|---|---|---|---|
| 67.6 | 8.65 | 0.29 | 20.9 | 37.8 | 32.3 | 17.5 | 0.25 | 5.6 | 9.02 |

| Total INS+ | ChroA− Nkx6.1− INS+ | ChroA− Nkx6.1+ INS+ | ChroA+ NKx6.1− INS+ | ChroA+ Nkx6.1+ INS+ | Total INS− | ChroA+ Nkx6.1− INS− | ChroA+ NKx6.1+ INS− | ChroA− Nkx6.1+ INS− | ChroA− Nkx6.1− INS− |
|---|---|---|---|---|---|---|---|---|---|
| 47.3 | 0.25 | 0.29 | 9.02 | 37.8 | 52.6 | 17.5 | 20.9 | 8.65 | 5.6 |

Stage 4 endocrine/non-endocrine flow cytometry

| Total Endocrine (ChroA+) | ChroA+ Nkx6.1− INS− | ChroA+ NKx6.1− INS+ | ChroA+ NKx6.1+ INS− | ChroA+ Nkx6.1+ INS+ | Total ChroA− | ChroA− Nkx6.1+ INS+ | ChroA− Nkx6.1+ INS− | ChroA− Nkx6.1− INS+ | ChroA− Nkx6.1− INS− |
|---|---|---|---|---|---|---|---|---|---|
| 39.4 | 15.0 | 7.74 | 8.78 | 7.85 | 60.1 | 0.57 | 46.1 | 0.23 | 13.2 |

| Total Nkx6.1+ | ChroA− Nkx6.1+ INS+ | ChroA− Nkx6.1+ INS− | ChroA+ NKx6.1+ INS− | ChroA+ Nkx6.1+ INS+ | Total Nkx6.1− | ChroA+ Nkx6.1− INS− | ChroA− Nkx6.1− INS− | ChroA− Nkx6.1− INS− | ChroA+ NKx6.1− INS+ |
|---|---|---|---|---|---|---|---|---|---|
| 63.3 | 0.57 | 46.1 | 8.78 | 7.85 | 36.2 | 15.0 | 0.23 | 13.2 | 7.74 |

| Total INS+ | ChroA− Nkx6.1− INS+ | ChroA− Nkx6.1+ INS+ | ChroA+ NKx6.1− INS+ | ChroA+ Nkx6.1+ INS+ | Total INS− | ChroA+ Nkx6.1− INS− | ChroA+ NKx6.1+ INS− | ChroA− Nkx6.1+ INS− | ChroA− Nkx6.1− INS− |
|---|---|---|---|---|---|---|---|---|---|
| 16.4 | 0.23 | 0.57 | 7.74 | 7.85 | 83.1 | 15.0 | 8.78 | 46.1 | 13.2 |

| Sample (d27) | Total Endocrine (CHGA+) | ChroA+ Nkx6.1+ PDX1-1−/+ | ChroA− NKx6.1− PDX1+ |
|---|---|---|---|
| 1. Cryopreserved, No re-agg. | 89.97 | 5.61 | 3.51 |
| 2. Fresh, No re-agg. (Control) | 88.57 | 5.71 | 4.39 |
| 3. Fresh, Re-agg. | 92.85 | 3.69 | 2.05 |

Based on the flow cytometry analysis in Table 21, for those cultures which were not dissociated or re-aggregated (samples 1 and 2), cryopreserving the cells (sample 2) does not reduce the total number of endocrine (CHGA+) cells as compared to the fresh cells (sample 1) (88.57 vs. 89.97). As expected, the total endocrine (CHGA+) population is higher in cultures that had been dissociated and re-aggregated, and not cryopreserved (92.85). Thus, dissociating and re-aggregating affects endocrine (CHGA+) cell numbers as described above in Example 17, but cryopreserving the stage 7 cultures does not appear to alter the cell composition.

Figure 36B:
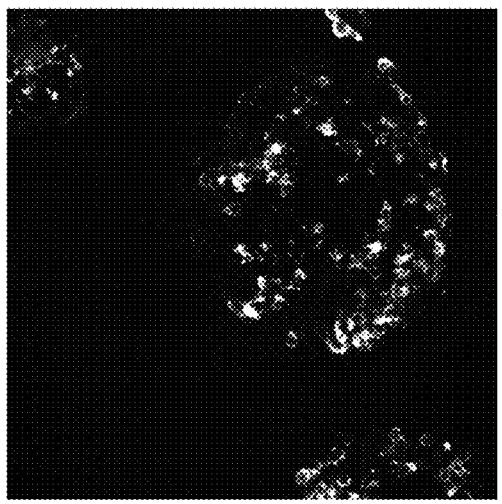
FIGS. 36A-36C are photo micrographs showing stage 7 endocrine cell aggregates as described in Example 20. The aggregates have not been re-aggregated at stage 7. The same field in FIG. 36A and FIG. 36B are stained for INS (cytoplasmic) and GCG (cytoplasmic), respectively.
Figure 36C:
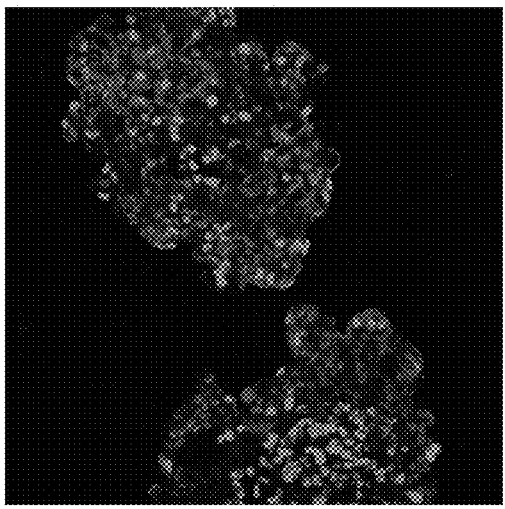
Figure 36A:
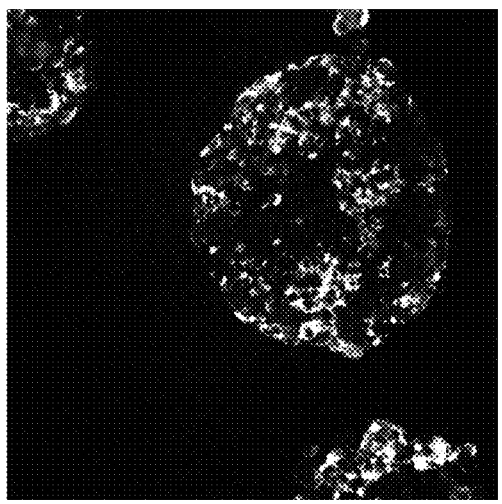
Figure 37A:
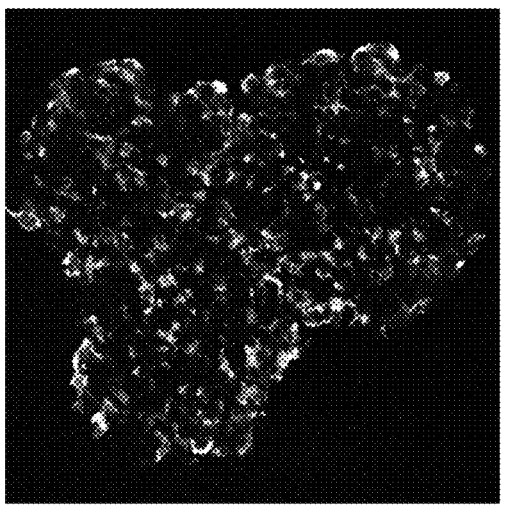
FIGS. 37A-37C are photo micrographs showing stage 7 endocrine cell aggregates as described in Example 20. The aggregates have been re-aggregated at stage 7. The same field in FIG. 37A and FIG. 37B are stained for INS (cytoplasmic) and GCG (cytoplasmic), respectively.
Figure 37B:
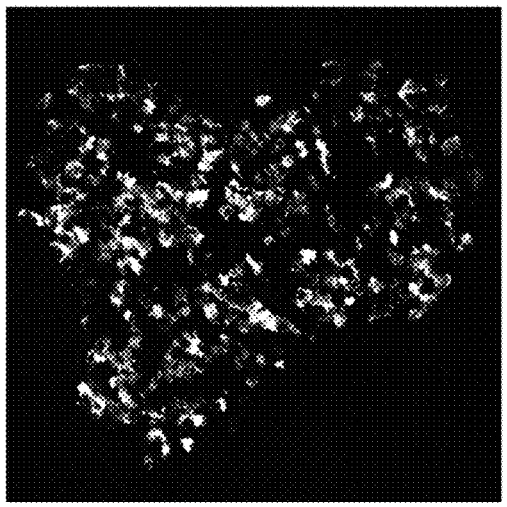
Figure 37C:
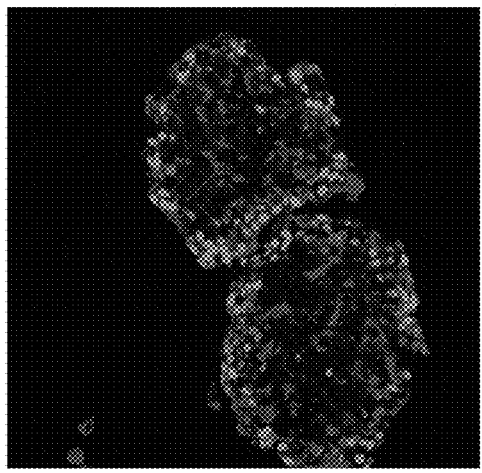
Figure 38:
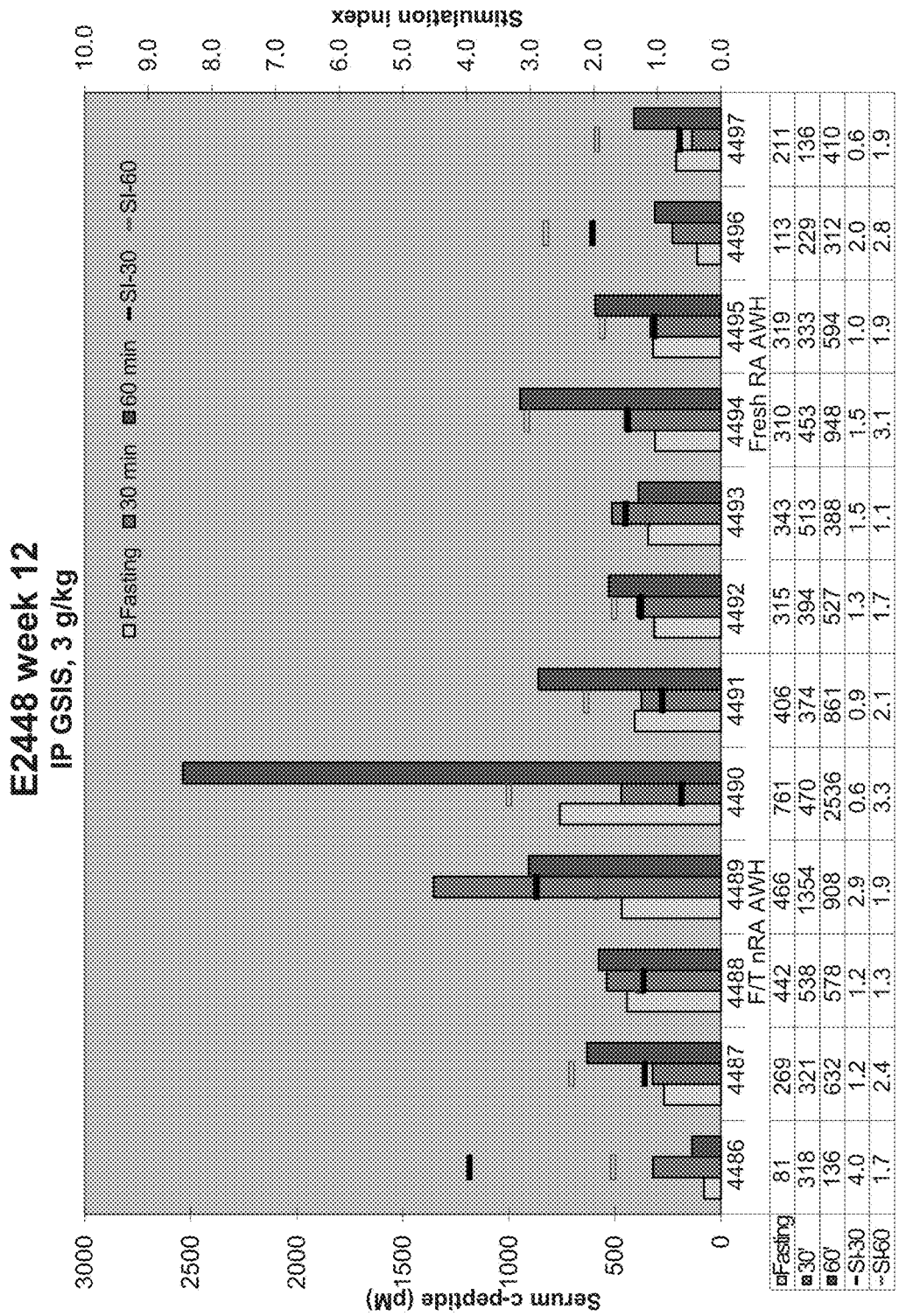
FIG. 38 is a graph showing the concentrations of human C-peptide in sera of mice implanted with encapsulated endocrine cells made as described in Example 20 whereby cell cultures were frozen (cryopreserved) and thawed (F/T) and not dissociated and re-aggregated (left side), or they were not frozen (Fresh) and dissociated and re-aggregated at the start of stage 7 (right side). Expression levels were analyzed 12 weeks post-engraftment at fasting, 30 min, and 60 min after intraperitoneal glucose administration. See Example 21.

Further, samples were analyzed using cell immunohistochemistry with NKX6.1, C-peptide, INS, and GCG staining. See FIGS. 36A-36B. The endocrine (CHGA+) cell aggregates from stage 7 (No re-agg/No cryopreserved; sample 2) showed NKX6.1 (nuclear) and C-peptide (cytoplasmic) co-expression or co-staining (FIG. 36A-36C). Co-staining was not observed in similar analysis of PEC from a stage 4 differentiation protocol. Cell cultures from stage 7 were also primarily singly hormonal, as can be seen in FIG. 36A-36C, which shows separate staining of INS (36A; cytoplasmic) and GCG (36B; cytoplasmic) cells, i.e. the majority of individual cells did not co-express INS and GCG as seen with endocrine (CHGA+) sub-populations of PEC from stage 4. FIG. 37 shows photomicrographs with similar staining patterns but from cell cultures which had been dissociated and re-aggregated at the start of stage 7.

FIG. 37 compares graft function from cell cultures 1 and 3 of Table 20 above. Analysis of the in vivo function of the transplanted stage 7 grafts of both cohorts of animals at 12 weeks showed that cultures which had been cryopreserved but not re-aggregated (Sample 1) had similar serum C-peptide levels at 30 and 60 minutes post glucose challenge as compared to those cultures which had not been cryopreserved but were re-aggregated (Sample 3). These C-peptide levels are comparable to those observed for weeks 10 and 15 in FIGS. 20 and 21 (e.g. at week 15, the average C-peptide level was 995 pM at sixty minutes post-glucose administration). So, it is expected and anticipated that a later analysis will show that C-peptide levels will increase to above 1000 pM at 30 and/or 60 minutes, in most of the animals, post glucose stimulation similar to that described in Example 18 and observed in FIG. 34. In fact, animal no. 4490, a Sample 1 graft, had serum C-peptide levels at 12 weeks that were comparable to animal no. 4320 in Example 18 (FIG. 34) after 21 weeks post implant.

Thus, cryopreserving stage 7 endocrine cells does not appear to affect their in vivo function.

Example 21

Increasing Glucose Concentrations Affects Hormone Expression

Glucose levels in cell culture formulations range from 1 g/L (5.5 mM) to 10 g/L (55 mM), with some media having about 5.5 mM glucose which approximates normal blood sugar levels in vivo. Glucose levels approaching 10 mM are pre-diabetic levels and those above 10 mM are analogous to a diabetic condition. Stated in another way, above 10 mM glucose mimics hyperglycemic conditions in vivo. High glucose can cause, for example, post-translational secondary modifications including glycation, glyoxidation and carbonyl stress. Since the reports of the effects of high-glucose on different cell types in vitro vary, Applicant's sought to study the effects of high glucose (i.e. 4.5 g/L or 24.98 mM glucose) on stage 6 and/or 7 endocrine cells.

Glucose is a soluble hexose sugar added to all cell culture media including Ames' Medium; Basal Medium Eagle (BME); BGJb Medium Fitton-Jackson Modification; Click's Medium; CMRL-1066 Medium; Dulbecco's Modified Eagle's Medium (DMEM); DMEM/Ham's Nutrient Mixture F-12 (50:50); F-12 Coon's Modification; Fischer's Medium; H-Y Medium (Hybri-Max®); Iscove's Modified Dulbecco's Medium (IMDM); McCoy's 5A Modified Medium; MCDB Media; Medium 199; Minimum Essential Medium Eagle (EMEM); NCTC Medium; Nutrient Mixture, Ham's F-10; Nutrient Mixture, Ham's F-12; Nutrient Mixture Ham's F-12 Kaighn's Modification (F12K); RPMI-1640; Serum-Free/Protein Free Hybridoma Medium; Waymouth Medium MB; Williams Medium E and various proprietary media. L-15 Medium contains galactose in place of glucose. See Sigma-Aldrich Media Expert, available on the world wide web at sigmaaldrich.com/life-science/cell-culture/learning-center/media-expert/glucose.html.

Media containing greater than 10 mM levels of glucose supplementation include at least DMEM/Ham's Nutrient Mixture F-12 (50:50) contains 17.5 mM of glucose; DMEM (Hi Glucose), GMEM and IMDM all contain 25 mM levels of glucose; and H-Y Medium (Hybri-Max®) and Serum-Free/Protein Free Hybridoma Medium contain 22.6 and 28.9 mM glucose, respectively. See Sigma-Aldrich Media Expert, available on the world wide web at sigmaaldrich.com/life-science/cell-culture/learning-center/media-expert/glucose.html. Because different cell culture media contain widely different levels of glucose, and the effects of glucose in general vary from one cell culture system to the next, the effects of high glucose on endocrine cells were studied.

Figure 39A:
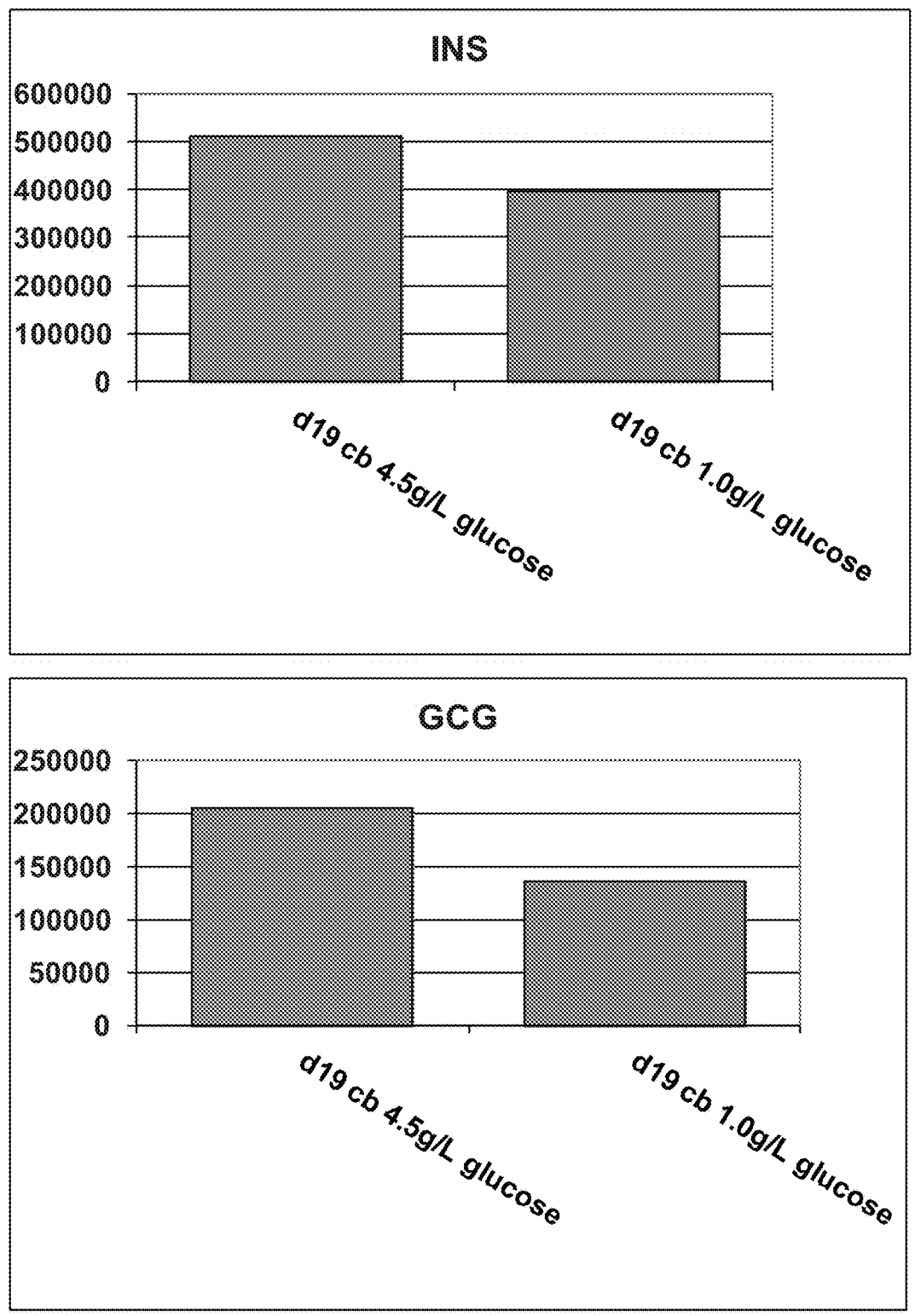
FIGS. 39A-39B are bar graphs showing Nanostring mRNA data of the relative gene expression levels of INS, GCG (FIG. 39A) and SST, GHRL (FIG. 39B) describing the effect of exogenous high-glucose during stage 6 on endocrine hormone expression. See Example 21.
Figure 39B:
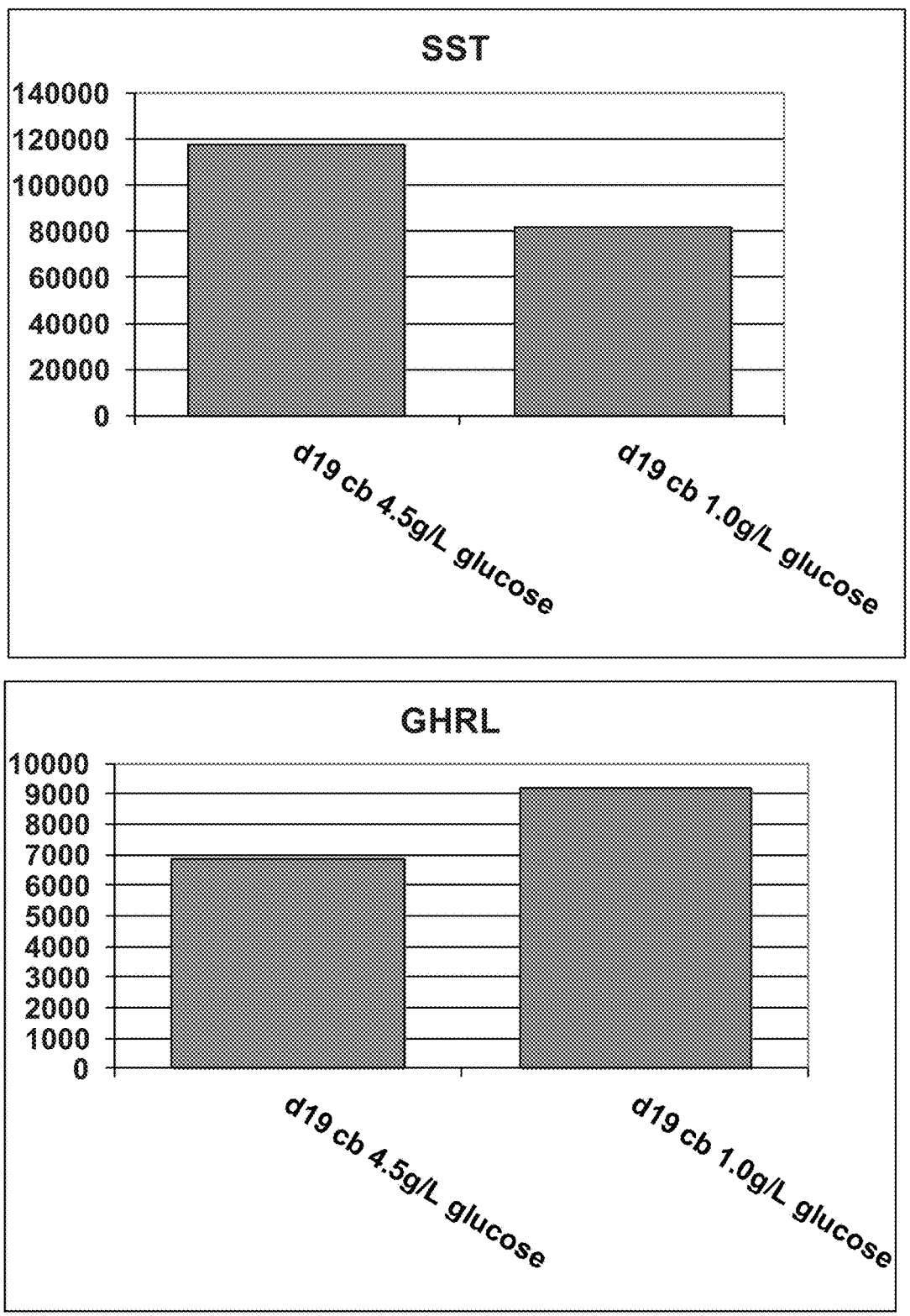

Again, methods for making endocrine cell cultures were substantially similar to that described above except during stages 6 and/or 7, cell cultures were treated with CMRL base medium with and without exogenous high-glucose (total glucose concentration 4.5 g/L, or 25 mM). So, this is 3.5 g/L in addition to the 1000 mg/L or 1 g/L (5.5 mM) of glucose already found in CMRL media. Both conditions with and without exogenous glucose were treated with the same growth factors including Nicotinamide, BMP, RA (or TTNPB) and alternatively a rho-kinase inhibitor and Matrigel. Nanostring analysis showed that when high-glucose was added at the start of stage 6, by the end of stage 6 there was increased expression of INS, GCG and SST and decreased expression of GHRL (FIG. 39A and FIG. 39B). Thus, increased exogenous glucose during stages 6 and 7, with the exception of Grehlin, increases hormone expression.

Example 22

Production of Immature Beta-Cells

Examples 8-21 describe various iterative methods for production of endocrine cells in vitro, including use of high Activin alone or combined with Wnt and/or Heregulin at stage 3; low Activin at stage 4 alone or combined with Heregulin; Noggin and a gamma secretase inhibitor with or without KGF, EGF and a rho-kinase inhibitor at stage 5; and one or more of the following nicotinamide, retinoic acid, BMP and Matrigel at stages 6-7. Endocrine cell populations produced from such methods are not only singly-hormonal (e.g. INS only, GCG only or SST only; see FIG. 39) but also co-express other immature endocrine cell markers including NKX6.1 and PDX1.

Flow cytometry analysis was performed on two different stage 7 cultures using INS, SST and GCG hormone staining (data set A and data set B). The one set of data (A) was performed after many iterations of stages 1-7 were examined and the other set of data (B) was performed earlier in time e.g., in the absence of nicotinamide, BMP, CMRL and the like. See Table 22 below. Table 22 shows total percentages of INS, SST and GCG positive staining (see 5 left columns), total INS, SST and GCG negative staining (see 5 right columns), and single hormone staining (see middle column). The hormone staining from these two data sets (A and B) is compared to that obtained from stage 4 PEC cultures that had been maintained in culture until about day 26.

TABLE 22

Comparison of Hormone Expressing Cells from Stage 7 and Stage 4 (PEC)

Stage 7 (d27) Hormone flow cytometry (A)

| Total INS+ | INS+ SST− GCG− | INS+ SST− GCG+ | INS+ SST+ GCG− | INS+ SST+ GCG+ | INS Only | Total INS− | INS− SST+ GCG− | INS− SST+ GCG+ | INS− SST− GCG+ | INS− SST− GCG− |
|---|---|---|---|---|---|---|---|---|---|---|
| 49.3 | 22.7 | 11.1 | 11.6 | 3.95 | 22.7 | 50.6 | 5.65 | 1.21 | 7.27 | 36.5 |

| Total SST+ | INS− SST+ GCG− | INS− SST+ GCG+ | INS+ SST+ GCG+ | INS+ SST+ GCG− | SST Only | Total SST− | INS− SST− GCG+ | INS− SST− GCG− | INS+ SST− GCG− | INS+ SST− GCG+ |
|---|---|---|---|---|---|---|---|---|---|---|
| 22.4 | 5.65 | 1.21 | 3.95 | 11.6 | 5.65 | 77.6 | 7.27 | 36.5 | 22.7 | 11.1 |

TABLE 22-continued

Comparison of Hormone Expressing Cells from Stage 7 and Stage 4 (PEC)

| Total GCG+ | INS−SST−GCG+ | INS+SST−GCG+ | INS+SST+GCG+ | INS−SST+GCG+ | GCG Only | Total GCG− | INS−SST+GCG− | INS+SST−GCG− | INS+SST+GCG− | INS−SST−GCG− |
|---|---|---|---|---|---|---|---|---|---|---|
| 23.5 | 7.27 | 11.1 | 3.95 | 1.21 | 7.27 | 76.5 | 5.65 | 22.7 | 11.6 | 36.5 |

Stage 7 (d29) Hormone flowcytometry (B)

| Total INS+ | INS+SST−GCG− | INS+SST−GCG+ | INS+SST+GCG− | INS+SST+GCG+ | INS Only | Total INS− | INS−SST+GCG− | INS−SST+GCG+ | INS−SST−GCG+ | INS−SST−GCG− |
|---|---|---|---|---|---|---|---|---|---|---|
| 22.7 | 12.9 | 4.3 | 4.3 | 1.08 | 12.9 | 77.3 | 1.68 | 0.46 | 2.57 | 72.6 |

| Total SST+ | INS−SST+GCG− | INS−SST+GCG+ | INS+SST+GCG+ | INS+SST+GCG− | SST Only | Total SST− | INS−SST−GCG+ | INS−SST−GCG− | INS+SST−GCG− | INS+SST−GCG+ |
|---|---|---|---|---|---|---|---|---|---|---|
| 7.5 | 1.68 | 0.46 | 1.08 | 4.3 | 1.68 | 92.4 | 2.57 | 72.6 | 12.9 | 4.3 |

| Total GCG+ | INS−SST−GCG+ | INS+SST−GCG+ | INS+SST+GCG+ | INS−SST+GCG+ | GCG Only | Total GCG− | INS−SST+GCG− | INS+SST−GCG− | INS+SST+GCG− | INS−SST−GCG− |
|---|---|---|---|---|---|---|---|---|---|---|
| 8.4 | 2.57 | 4.3 | 1.08 | 0.46 | 2.57 | 91.5 | 1.68 | 12.9 | 4.3 | 72.6 |

Stage 4 (d26) Hormone flow cytometry (PEC)

| Total INS+ | INS+SST−GCG− | INS+SST−GCG+ | INS+SST+GCG− | INS+SST+GCG+ | INS Only | Total INS− | INS−SST+GCG− | INS−SST+GCG+ | INS−SST−GCG+ | INS−SST−GCG− |
|---|---|---|---|---|---|---|---|---|---|---|
| 15.8 | 3.69 | 5.14 | 1.93 | 4.99 | 3.7 | 84.3 | 2.26 | 3.52 | 8.72 | 69.8 |

| Total SST+ | INS−SST+GCG− | INS−SST+GCG+ | INS+SST+GCG+ | INS+SST+GCG− | SST Only | Total SST− | INS−SST−GCG+ | INS−SST−GCG− | INS+SST−GCG− | INS+SST−GCG+ |
|---|---|---|---|---|---|---|---|---|---|---|
| 12.7 | 2.26 | 3.52 | 4.99 | 1.93 | 2.26 | 87.4 | 8.72 | 69.8 | 3.7 | 5.1 |

| Total GCG+ | INS−SST−GCG+ | INS+SST−GCG+ | INS+SST+GCG+ | INS−SST+GCG+ | GCG Only | Total GCG− | INS−SST+GCG− | INS+SST−GCG− | INS+SST+GCG− | INS−SST−GCG− |
|---|---|---|---|---|---|---|---|---|---|---|
| 22.4 | 8.72 | 5.1 | 4.99 | 3.52 | 8.72 | 77.7 | 2.26 | 3.7 | 1.9 | 69.8 |

In general, the total INS positive sub-population (the sum of singly INS-positive plus INS/SST co-positive plus INS/GCG co-positive plus INS/SST/GCG co-positive) are as much as 3-fold greater in stage 7 endocrine cultures than in stage 4 PEC cultures (49.3 vs. 22.7 vs. 15.8). Accordingly, the total INS only (no co-expression with SST or GCG) sub-population is also higher for stage 7 endocrine cultures than for stage 4 PEC cultures (22.7 vs. 12.9 vs. 3.7). Importantly, stage 7 cultures have more singly hormone expressing INS cells as a percentage of the total INS population (22.7/49.3=46% in A and 12.7/22.7=~57% in B) as compared to the stage 4 PEC cultures (3.7/15.8=23%). Hence, it appears that stage 7 endocrine cell cultures consist of more singly hormone expressing cells, particularly, INS only expressing cells, than stage 4 PEC cultures. And at least Examples 18 and 20 demonstrate that stage 7 endocrine cells, although still immature, do develop and mature to physiologically functional pancreatic islets capable of secreting insulin in response to blood glucose when transplanted; whereas the endocrine (CHGA+) sub-populations of stage 4 PEC cultures are not capable of the same in vivo. See FIG. 44 and FIG. 45 and Examples above for more detail.

Example 23

The Endocrine (CHGA+) Cells from Stage 7 and Stage 4 (PEC) are Distinguished from Each Other Although analysis of stage 7 (properly specified endocrine) and stage 4 (PEC) cultures use the same antibodies (e.g. CHGA, INS, NKX6.1) for cell staining and analysis, properly specified endocrine (CHGA+) cell sub-populations from stages 7 and 4 (PEC) are not the same.

Earlier, Applicants reported that the origin of the functional beta cells observed after transplantation of stage 4 PEC cultures was due to pancreatic progenitors or non-endocrine (CHGA−) cells and not from the primary endocrine (CHGA+) cells. Kelly et al. (2011), supra, demonstrated that when PEC cultures were enriched (purified) for endocrine (CHGA+) sub-populations and transplanted, they did not give rise to functional pancreatic islets or beta cells as compared to the un-enriched PEC cultures. See Kelly et al (2011), pp. 3-4, FIG. 4 and Supplementary Table 1; Schulz et al. (2012) supra; and U.S. Pat. Nos. 7,534,608; 7,695,965; 7,993,920; and 8,278,106. Examples 17 and 18 and Table 19 described a nearly pure (98.2%) endocrine (CHGA+) cell culture from stage 7 that when transplanted resulted in a robust functional graft in vivo (FIG. 34). In view of Examples 17 and 18 and other results described herein, the functional population of the stage 7 cultures is the endocrine (CHGA+) cells from stage 7 and not the significantly smaller percentage of non-endocrine (CHGA−) cells (2.08%). This is in contrast to the stage 4 PEC cultures, which Applicant's had reported in detail in prior disclosures, where the in vivo function is attributed to the non-endocrine (CHGA−) sub-populations. Therefore, in general, the endocrine sub-populations from stages 7 and 4 are not comparable or the same.

(37.8 vs. 7.8); and even though the stage 4 CHGA+/INS+/NKX6.1+ sub-populations may appear properly specified, as discussed above, these endocrine sub-populations from stage 4 do not function in vivo when transplanted, while the non-endocrine (CHGA−) sub-populations from stage 4 do mature and function in vivo. Thus, Applicant's refer to stage 7 endocrine cells as "immature endocrine cells" or "immature beta cells" and not endocrine progenitor/precursor cells since these cells are developmentally committed to becoming mature beta cells in vivo.

TABLE 23

Comparison of endocrine (CHGA+) and non-endocrine (CHGA−) cells from stage 7 and stage 4 (PEC)

Stage 7 endocrine/non-Endocrine flow cytometry

| Total Endocrine (ChroA+) | ChroA+ Nkx6.1− INS− | ChroA+ NKx6.1− INS+ | ChroA+ NKx6.1+ INS− | ChroA+ Nkx6.1+ INS+ | Total ChroA− | ChroA− Nkx6.1+ INS− | ChroA− Nkx6.1+ INS+ | ChroA− Nkx6.1− INS+ | ChroA− Nkx6.1− INS− |
|---|---|---|---|---|---|---|---|---|---|
| 85.2 | 17.5 | 9.02 | 20.9 | 37.8 | 14.8 | 8.65 | 0.29 | 0.25 | 5.6 |

| Total Nkx6.1+ | ChroA− Nkx6.1+ INS− | ChroA− Nkx6.1+ INS+ | ChroA+ NKx6.1+ INS− | ChroA+ Nkx6.1+ INS+ | Total Nkx6.1− | ChroA+ Nkx6.1− INS− | ChroA− Nkx6.1− INS+ | ChroA− Nkx6.1− INS− | ChroA+ NKx6.1− INS+ |
|---|---|---|---|---|---|---|---|---|---|
| 67.6 | 8.65 | 0.29 | 20.9 | 37.8 | 32.3 | 17.5 | 0.25 | 5.6 | 9.02 |

| Total INS+ | ChroA− Nkx6.1− INS+ | ChroA− Nkx6.1+ INS+ | ChroA+ NKx6.1− INS+ | ChroA+ Nkx6.1+ INS+ | Total INS− | ChroA+ Nkx6.1− INS− | ChroA+ NKx6.1+ INS− | ChroA− Nkx6.1+ INS− | ChroA− Nkx6.1− INS− |
|---|---|---|---|---|---|---|---|---|---|
| 47.3 | 0.25 | 0.29 | 9.02 | 37.8 | 52.6 | 17.5 | 20.9 | 8.65 | 5.6 |

Stage 4 endocrine/non-endocrine flow cytometry

| Total Endocrine (ChroA+) | ChroA+ Nkx6.1− INS− | ChroA+ NKx6.1− INS+ | ChroA+ NKx6.1+ INS− | ChroA+ Nkx6.1+ INS+ | Total ChroA− | ChroA− Nkx6.1+ INS− | ChroA− Nkx6.1+ INS+ | ChroA− Nkx6.1− INS+ | ChroA− Nkx6.1− INS− |
|---|---|---|---|---|---|---|---|---|---|
| 39.4 | 15.0 | 7.74 | 8.78 | 7.85 | 60.1 | 0.57 | 46.1 | 0.23 | 13.2 |

| Total Nkx6.1+ | ChroA− Nkx6.1+ INS+ | ChroA− Nkx6.1+ INS− | ChroA+ NKx6.1+ INS− | ChroA+ Nkx6.1+ INS+ | Total Nkx6.1− | ChroA+ Nkx6.1− INS− | ChroA− Nkx6.1− INS+ | ChroA− Nkx6.1− INS− | ChroA+ NKx6.1− INS+ |
|---|---|---|---|---|---|---|---|---|---|
| 63.3 | 0.57 | 46.1 | 8.78 | 7.85 | 36.2 | 15.0 | 0.23 | 13.2 | 7.74 |

| Total INS+ | ChroA− Nkx6.1− INS+ | ChroA− Nkx6.1+ INS+ | ChroA+ NKx6.1− INS+ | ChroA+ Nkx6.1+ INS+ | Total INS− | ChroA+ Nkx6.1− INS− | ChroA+ NKx6.1+ INS− | ChroA− Nkx6.1+ INS− | ChroA− Nkx6.1− INS− |
|---|---|---|---|---|---|---|---|---|---|
| 16.4 | 0.23 | 0.57 | 7.74 | 7.85 | 83.1 | 15.0 | 8.78 | 46.1 | 13.2 |

Table 23 shows flow cytometry data comparing total endocrine (CHGA+) and non-endocrine (CHGA−) sub-populations from stage 7 (properly specified endocrine) and stage 4 (PEC) and demonstrates that the sub-populations are not equivalent and are distinguished from each other. For example, the total percentage of CHGA+ sub-population was significantly higher for stage 7 as compared to the stage 4 cultures (85.2 vs. 39.4). Accordingly, the total percentage of CHGA− sub-population was significantly lower for stage 7 as compared to stage 4 cultures (14.8 vs. 60.1). Further, true endocrine cells, e.g. beta cells, not only express CHGA+ but also co-express at least INS and NKX6.1. Thus, a true endocrine cell expresses CHGA+/INS+/NKX6.1+ (triple positive) and is able to function in vivo. Table 23 shows that stage 7 cultures had almost 5-fold more CHGA+/INS+/NKX6.1+(triple positive) cells than stage 4 cultures Example 24

Purification of Endocrine Cells from Stage 7 Cell Populations Using a Zinc Sensor Beta cell secretory vesicles contain high concentrations of Zinc. Zinc is accumulated in the vesicles by at least the action of the Zinc transporter SLC30A8 (or ZnT8). Zinc-binding fluorescent probes have been used to visualize Zinc in cells by absorbing and emitting more light at specific wavelengths when bound with Zinc than without Zinc. Yet, reports show that most of the probes may not localize properly to detect Zinc within beta cell vesicles. Interestingly, PyDPy1 (or Py1; Chemical Communications, 2011, 47:7107-9) can get into vesicles, but has not been used with beta cells to date. Py1 increases fluorescence intensity 50-80× when bound to $Zn^{2+}$. For the first time, Applicants have demonstrated production of an endocrine cell, or immature beta cell, population capable of in vivo function. It is therefore advantageous to have a means for further enriching this population for purposes of further in vitro analysis, for use as a screening tool, or to provide an enriched immature beta cell population for transplant.

Stage 7 endocrine cells, or immature beta cells, were treated with Py1, and the cells were sorted via fluorescence for those containing high Zinc content. A Py1 zinc sensor (custom synthesized by ChemoGenics Biopharma, Research Triangle Park, N.C.) was resuspended at 10 mM in DMSO and diluted in DPBS(−/−)/0.25% BSA (Buffer A) to 5 micromolar final concentration (staining solution). Differentiated stage 7 cell aggregates were washed twice with DPBS(−/−) and dissociated with Accumax. The Accumax was quenched with addition of base medium containing B-27. The resulting cell suspension was filtered through a 40 micron mesh, centrifuged, washed in Buffer A and resuspended in staining solution. Staining was continued for 15 minutes, cells were centrifuged, washed in Buffer A and resuspended in Buffer A for sorting. Cells were sorted by flow cytometry into CMRL/50% FBS at 4° C. Following the sort, cells were centrifuged and resuspended in RNA isolation buffer.

Figure 40B:
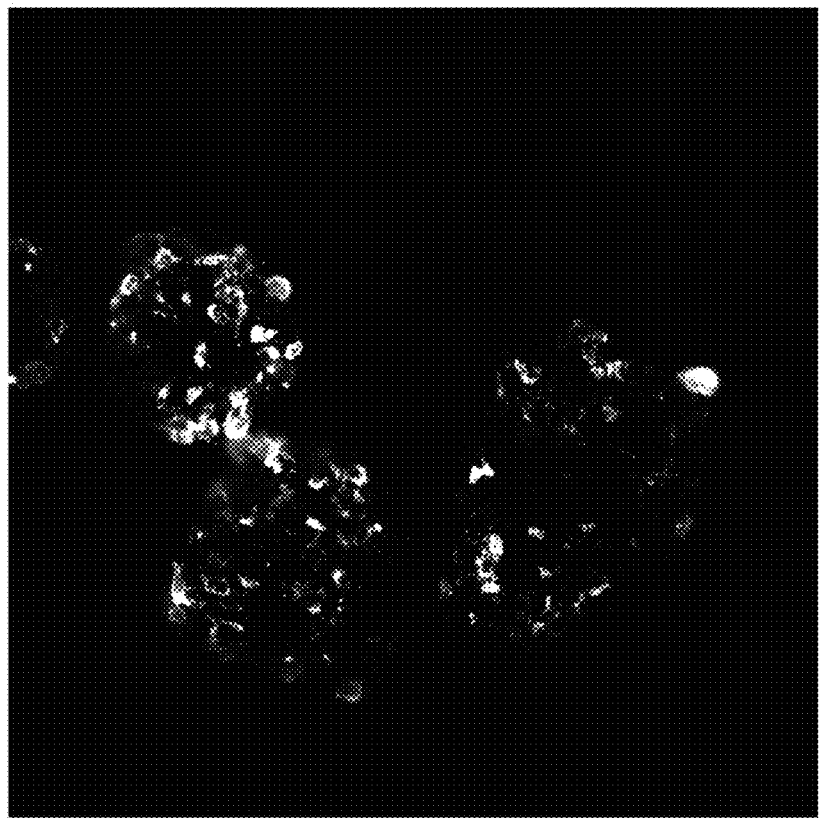
FIGS. 40A-40B is a photomicrograph showing stage 7 endocrine cell aggregates as described in Example 21 with exogenous high-glucose during stage 7.
Figure 40A:
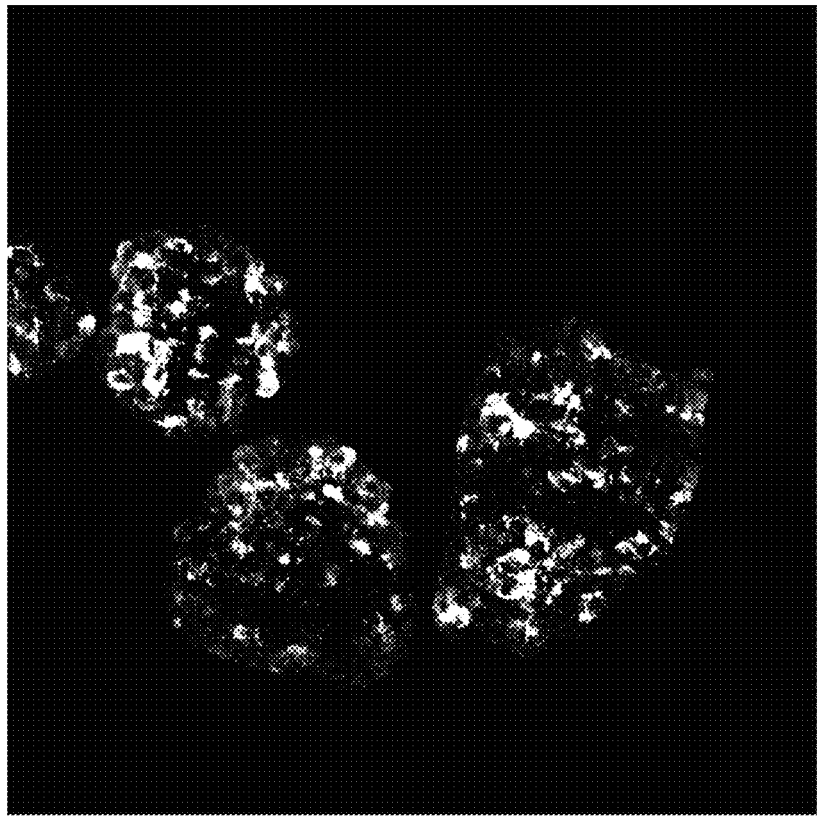

In the results shown in FIG. 40, the cells encompassed or gated by the polygon are live cells that have increased fluorescence due to the presence of Py1 sensor bound to Zinc. This cell population was further divided into two approximately equal gates and sorted into two tubes, designated Bright and Dim according to their fluorescence intensity. RNA was prepared from the cells and subjected to Nanostring analysis.

Figure 42A:
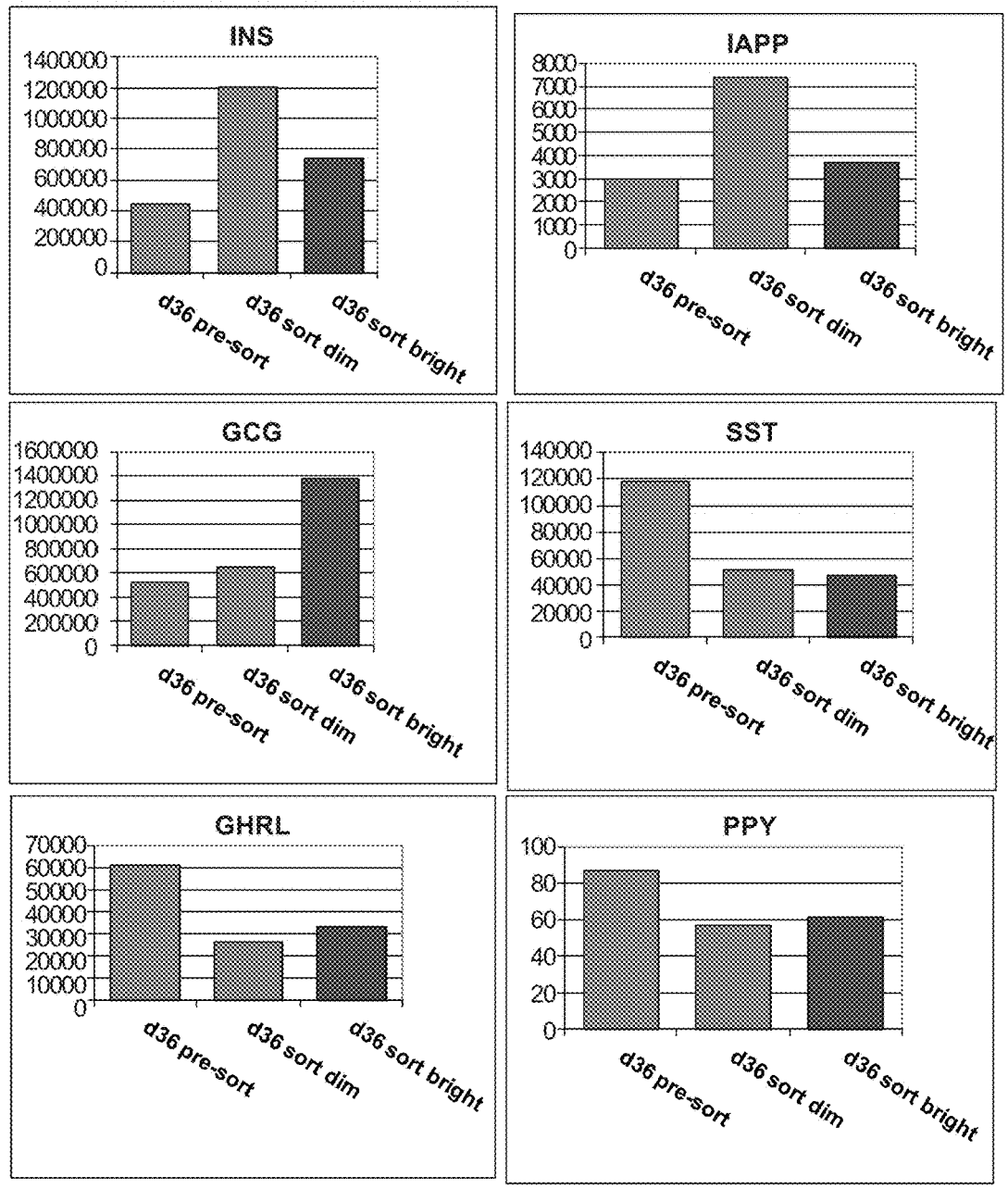
FIGS. 42A-42C are bar graphs showing Nanostring mRNA data of the relative gene expression levels of INS, GCG, GHRL, IAPP, SST and SST (FIG. 42A); PAX4, PDX1, ARX, NKX6.1 (FIG. 42B); and PCSK1, GCK, G6PC2 and SLC30A8 (FIG. 42C) characterizing and identifying the cells enriched from the zinc sort. See Example 24.
Figure 42B:
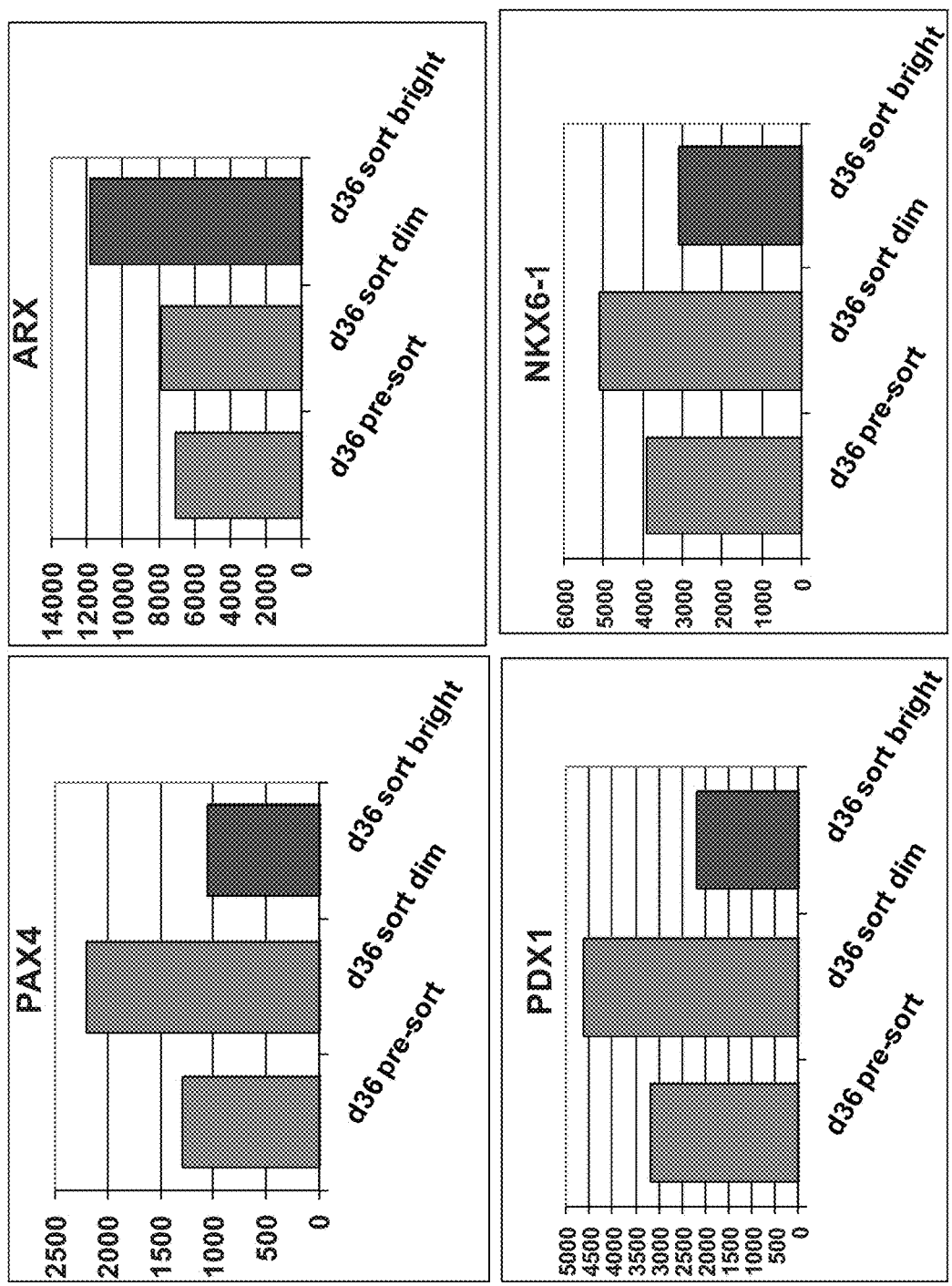
Figure 42C:
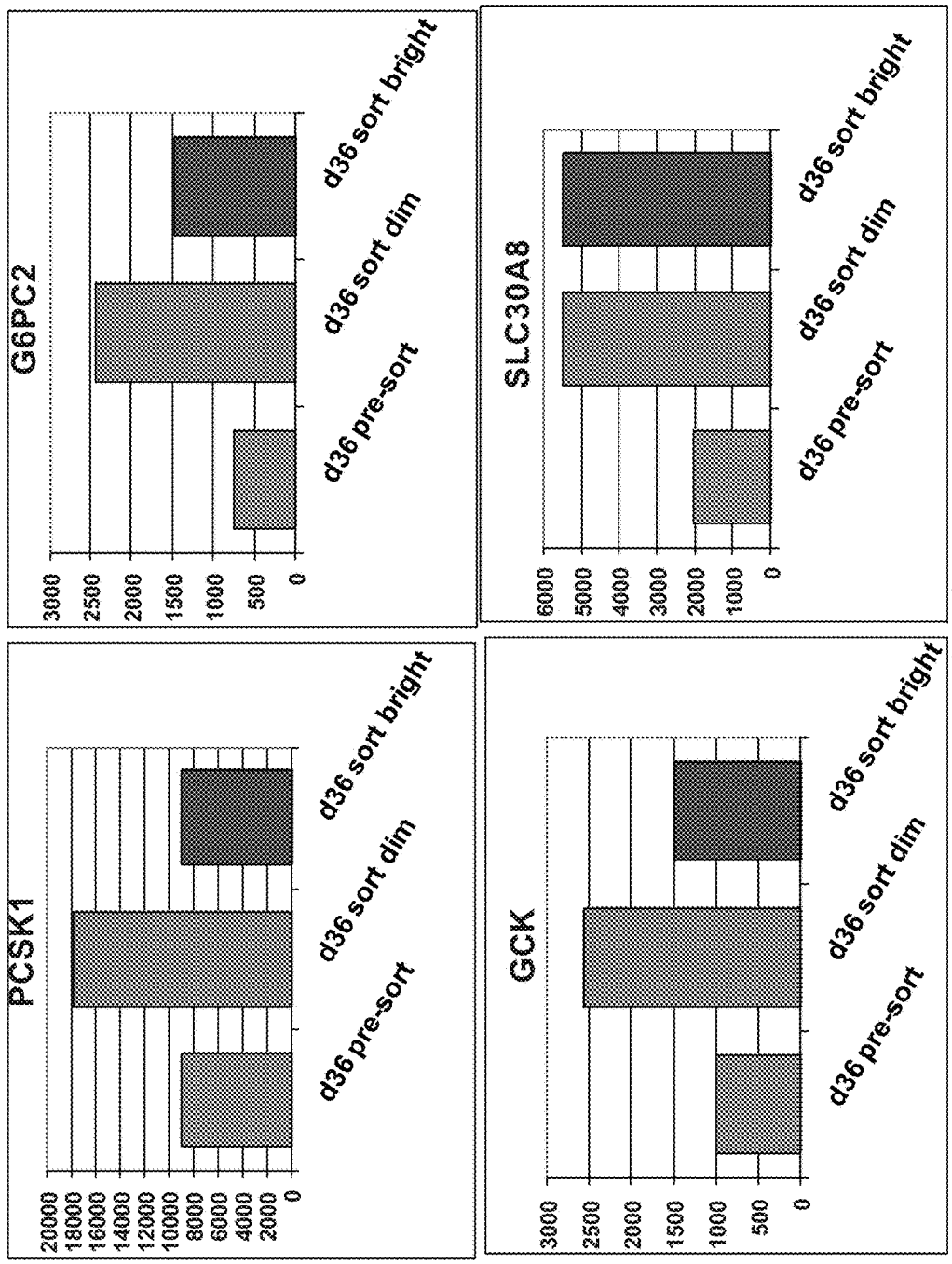

As seen in FIGS. 42A-C, the dim population is enriched for markers of the beta cell lineage such as INS, IAPP, PDX1, NKX6.1, PAX4, PCSK1, G6PC2, GCK and SLC30A8. This indicates that beta cells or immature beta cells can be purified from a stage 7 cell population using a Zinc sensor. A previous experiment determined that 630,000 INS mRNA units by Nanostring correspond to about 49% INS-positive cells by flow cytometry (data not shown). Thus a purified Dim population having an INS Nanostring value of 1,200,000, would correspond to about 93% INS-positive cells (1,200,000/630,000×49%).

Figure 41:
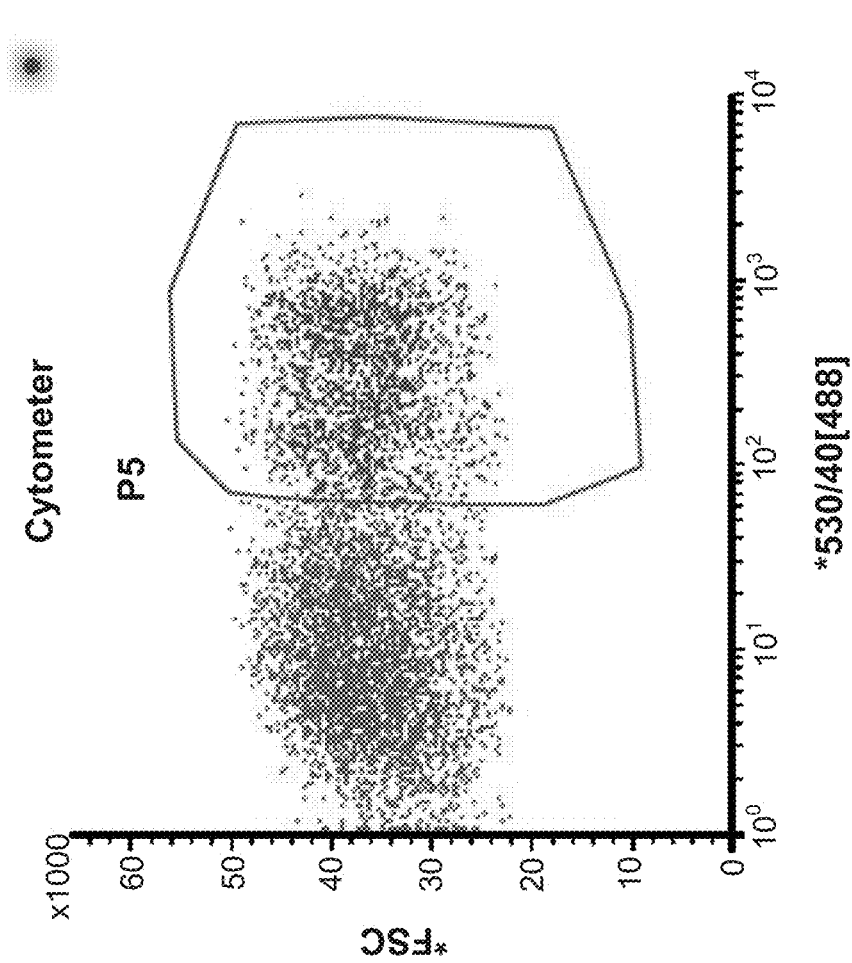
FIG. 41 Flow cytometry graph showing enrichment of immature endocrine beta cells from stage 7 first treated with Py1, a zinc binding agent, and sorted via fluorescence. See Example 24.
Figure 43:
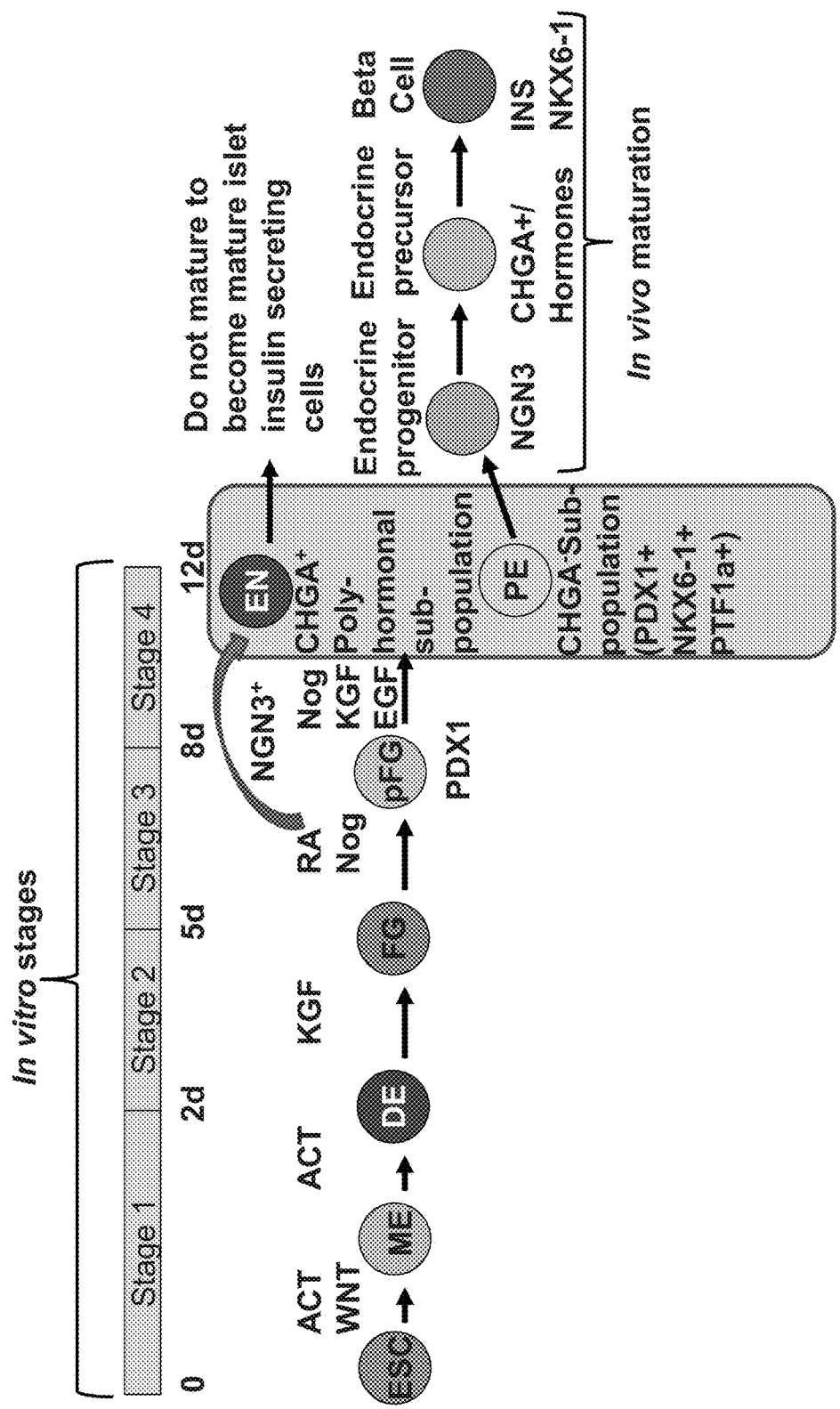
FIG. 43 is a schematic diagram of stages 1-4 for production of pancreatic endoderm cells (PEC) in vitro and development and maturation to insulin secreting beta cells in vivo. The diagram also depicts the two main sub-populations of PEC, endocrine (CHGA+) and non-endocrine (CHGA− cells. Embryonic stem cell (ESC), mesendoderm (ME), definitive endoderm (DE), foregut (FG), posterior foregut (pFG), and pancreatic epithelium or pancreatic endoderm (PE).

Conversely, the bright sorted population was enriched for markers of the alpha cell lineage such as GCG, ARX and SLC30A8 (FIGS. 41, 42, 43). And similar to beta cells, glucagon cells are also known to take up Zinc, So, Py 1 sensor can be used to bind Zinc in both beta and glucagon cells, but separated or sorted by their different levels of fluorescence.

Figure 44:
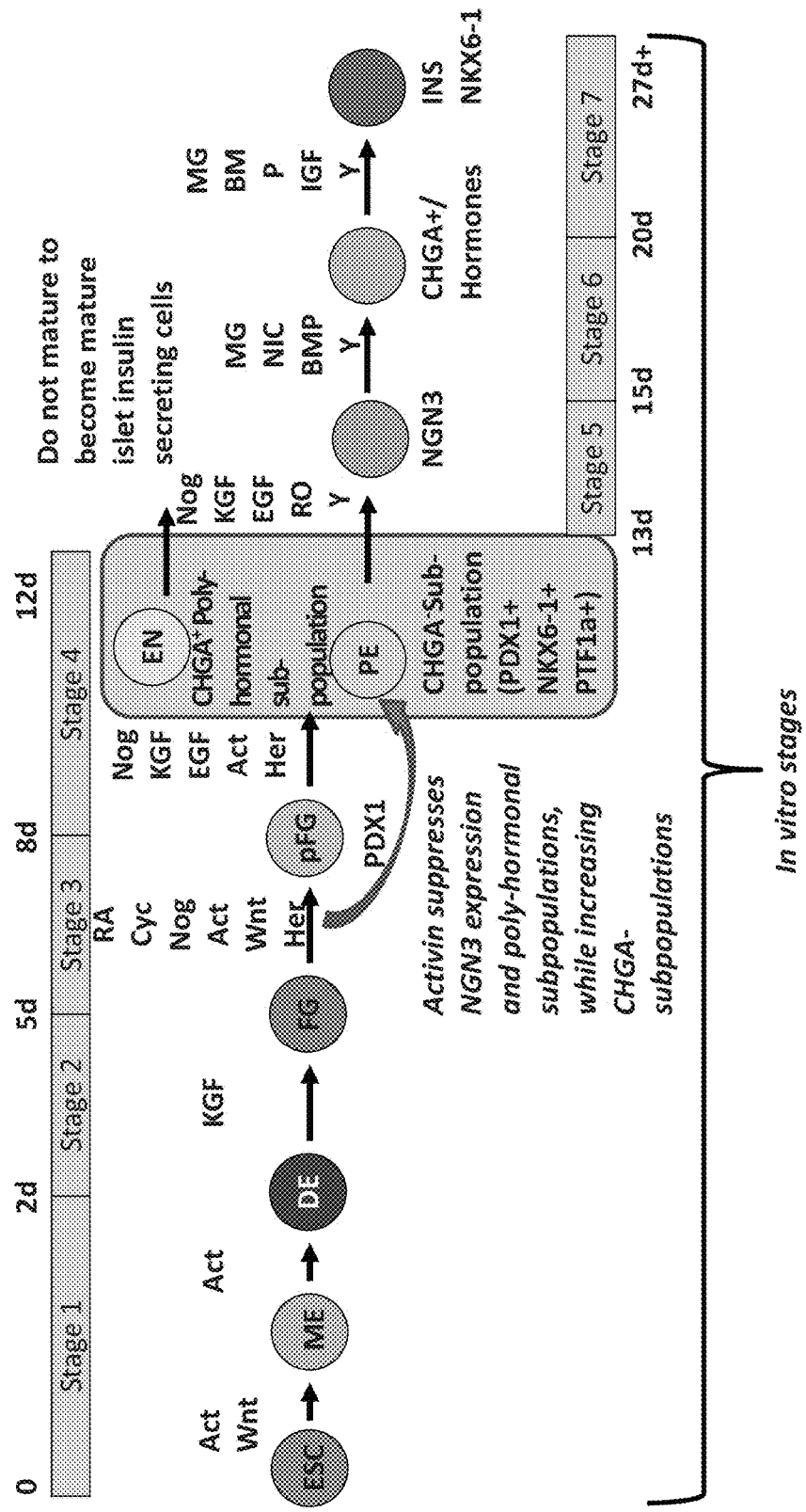
FIG. 44 is a schematic diagram of stages 1-7 for production of endocrine cells in vitro. The diagram also depicts that high levels of Activin (stage 3) followed by low-levels of Activin and removal of WNT (stage 4) represses or inhibits NGN3 expression, which is later expressed during stage 5 with addition of a gamma secretase inhibitor. Embryonic stem cell (ESC), mesendoderm (ME), definitive endoderm (DE), foregut (FG), posterior foregut (pFG), and pancreatic epithelium or pancreatic endoderm (PE).
Figure 45:
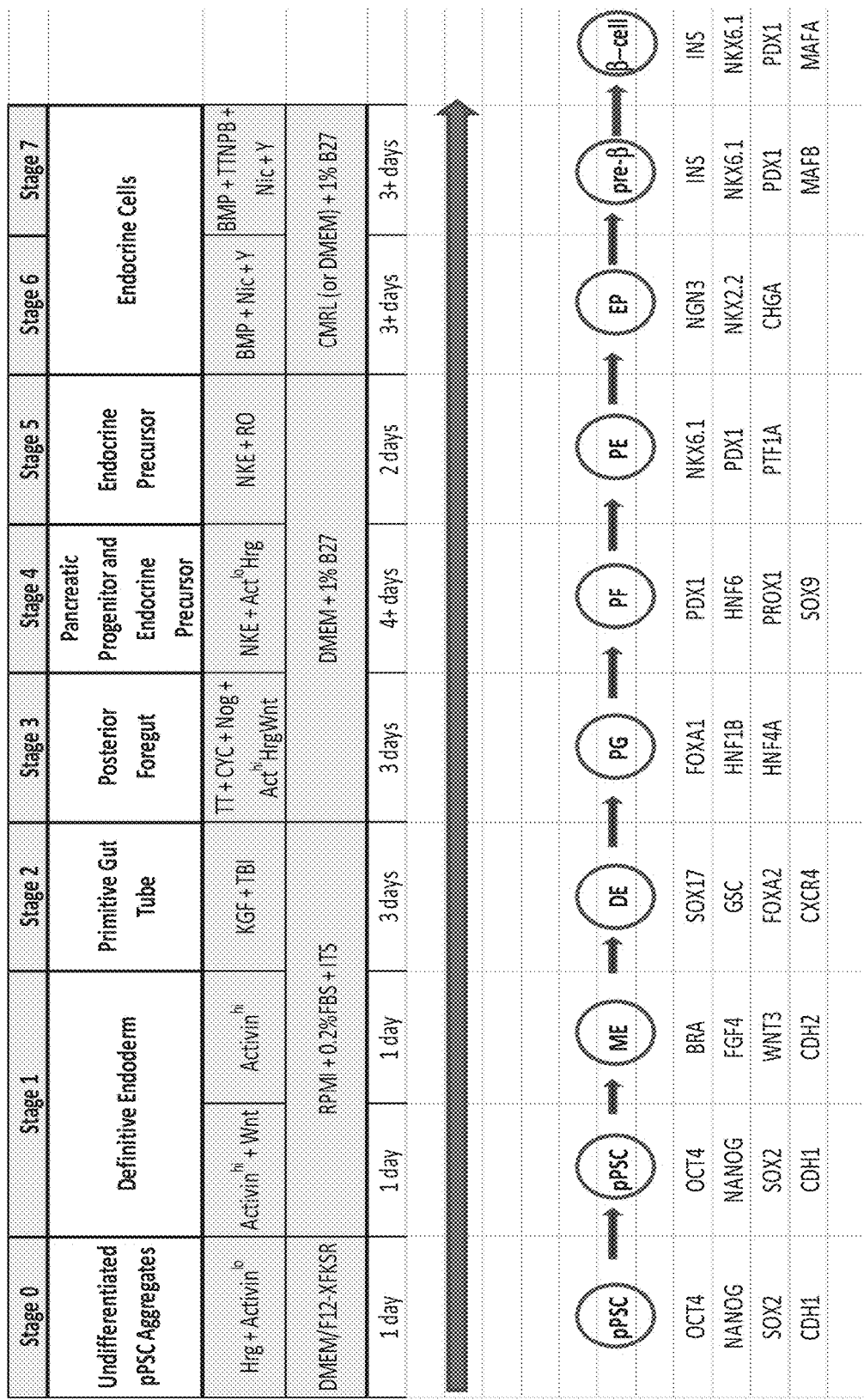
FIG. 45 is a schematic diagram of stages 1-7 for production of endocrine cells in vitro. The diagram also shows the stages, growth factors, cell types and signature markers of each cell type: embryonic stem cell (ESC), mesendoderm (ME), definitive endoderm (DE), foregut (FG), posterior foregut (pFG), pancreatic epithelium or pancreatic endoderm (PE), pre-beta cell (pre-B; or immature beta cell) and beta-cell (β-cell).

Summary of Methods for Making PEC (Stages 1-4) Endocrine Cell (Stages 1-7) Cultures In summary, the inventions described herein are directed to at least PEC and immature endocrine cells and methods for making such cells comprising at least stages 1-4 for production of PEC, and stages 1-7 for production of endocrine cells. FIGS. 43, 44 and 45 are diagrams summarizing certain aspects of Applicant's cell compositions and methods of production described herein.

Applicants have previously reported that endocrine (CHGA+) sub-populations following a stage 4 differentiation protocol do not develop into mature and functioning pancreatic islet cells when transplanted in vivo. Refer to the "EN" cell type after stage 4 in FIGS. 43 and 44. These endocrine (CHGA+) sub-populations had early or pre-mature NGN3 expression (NGN3 expression before PDX1 and NKX6.1 co-expression). See also Rukstalis et al. (2009), supra. In contrast, the non-endocrine (CHGA−) sub-populations of PEC that did not express NGN3 develop and mature into endocrine cells in vivo. This delayed NGN3 expression until after in vivo maturation of non-endocrine (CHGA−) sub-populations of PEC was shown in Example 10 (FIGS. 15-16) where the combination of Activin, Wnt and Heregulin effectively repressed NGN3 as compared to the control, and transplantation of this PEC as compared to the control gave rise to improve in vivo function. See FIGS. 15-16.

Applicant's then endeavored to obtain a properly specified endocrine cell culture that was capable of developing and maturing to pancreatic islets in vivo and make insulin in response to blood glucose levels similar to that observed in all the instances with PEC, specifically the non-endocrine (CHGA−) sub-population of PEC. To this end, Applicant's performed many iterative experiments to suppress or inhibit NGN3 expression at stages 3 and 4. Examples 8-11 describe in detail Applicant's use of Activin alone or in combination with other agents such as Wnt and Heregulin, and at various concentrations, to affect NGN3 expression or suppression. FIG. 44 also summarizes the effect of activin at stages 3 and 4.

Once it was demonstrated that NGN3 expression could be delayed and such did not affect the in vivo function, Applicant's explored methods for inducing expression of endocrine markers in stages after PEC (stage 4) formation. Examples 11-14 and 16-22 describe the many iterations and methods employed to optimize culture conditions to produce properly specified endocrine populations that could give rise to in vivo function. Specifically, Applicant used gamma secretase inhibitor at stage 5 to induce NGN3 expression and endocrine differentiation. Applicant used reagents such as CMRL at stages 6 and 7 to increase endocrine marker expression; BMP to increase INS and PDX1. FIGS. 44 and 45 summarize and describe these efforts.

It will be appreciated that initially the use of multiple methodologies are required to characterize and identify cells (e.g. Q-PCR, ICC, flow cytometry analysis, C-peptide assays and the like). After having fully characterized and identified such cells under certain cell differentiation culture conditions, Q-PCR and Nanostring multiplex RNA were often used as sole methods to analyze whether such a cell type was obtained.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements. Also, it will be appreciated that in embodiments where numerical values, such as amounts, concentrations, percentages, proportions or ranges, are recited the value that is referred to can be "at least about" the numerical value, "about" the numerical value or "at least" the numerical value.

What is claimed is:

1. A method for producing hormone secreting cells, said method comprising:
   maturing transplanted endocrine cells in vivo in a subject wherein the endocrine cells co-express INS+ and NKX6.1+, thereby producing hormone secreting cells.
2. The method of claim 1, wherein the endocrine cells are CHGA+.
3. The method of claim 1, wherein the hormone secreting cells secrete insulin and glucagon.
4. The method of claim 1, wherein the subject is a mammalian subject.
5. The method of claim 4, wherein the mammalian subject is a human subject.
6. The method of claim 5, wherein the human subject has been identified as having a condition which limits the ability of the subject to produce sufficient levels of insulin in response to physiologically high blood glucose concentrations.
7. The method of claim 1, further comprising detecting insulin secretion, wherein insulin secretion is detected by measuring C-peptide levels in a subject into whom the endocrine cells have been transplanted.
8. The method of claim 7, wherein C-peptide levels in the subject increase over time.
9. The method of claim 1, wherein the hormone secreting cells are insulin secreting cells that are responsive to blood glucose.
10. The method of claim 1, wherein the number of hormone-secreting cells increases over time.
11. The method of claim 1, wherein the hormone secreting cells are insulin secreting cells that form islet-like cell clusters.
12. The method of claim 1, wherein the endocrine cells are unipotent.
13. The method of claim 1, wherein the endocrine cells are aggregates.
14. The method of claim 13, wherein the aggregates are 50 to 300 microns in diameter.
15. The method of claim 1, wherein the endocrine cells are in a semipermeable encapsulation device.
16. The method of claim 1, wherein the endocrine cells do not substantially express NGN3.
17. A method for producing hormone secreting cells, said method comprising:
   maturing transplanted human cells in vivo, wherein the transplanted human cells comprise unipotent human immature beta cell suspension aggregates and wherein at least 10% of cells in the beta cell suspension aggregates are human immature beta cells that co-express INS and NKX6.1,
   thereby producing hormone secreting cells.
18. The method of claim 17, wherein the hormone secreting cells secrete insulin.

* * * * *